US 8,846,658 B2

(12) United States Patent
Veenstra

(10) Patent No.: US 8,846,658 B2
(45) Date of Patent: Sep. 30, 2014

(54) OXAZINE DERIVATIVES AND THEIR USE IN THE TREATMENT OF NEUROLOGICAL DISORDERS

(71) Applicant: Siem Jacob Veenstra, Lorrach (DE)

(72) Inventor: Siem Jacob Veenstra, Lorrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/136,679

(22) Filed: Dec. 20, 2013

(65) Prior Publication Data

US 2014/0113894 A1 Apr. 24, 2014

Related U.S. Application Data

(63) Continuation of application No. 13/940,354, filed on Jul. 12, 2013, which is a continuation of application No. 13/454,751, filed on Apr. 24, 2012, now abandoned, which is a continuation of application No. 12/842,360, filed on Jul. 23, 2010, now Pat. No. 8,207,164.

(60) Provisional application No. 61/363,702, filed on Jul. 13, 2010, provisional application No. 61/258,911, filed on Nov. 6, 2009, provisional application No. 61/228,472, filed on Jul. 24, 2009.

(51) Int. Cl.
| C07D 265/30 | (2006.01) |
| C07D 267/10 | (2006.01) |
| C07D 413/12 | (2006.01) |
| C07D 413/14 | (2006.01) |
| C07D 471/04 | (2006.01) |
| C07D 487/04 | (2006.01) |
| C07D 417/12 | (2006.01) |

(52) U.S. Cl.
USPC ................... 514/211.15; 514/228.8; 540/544; 540/98

(58) Field of Classification Search
None
See application file for complete search history.

(56) References Cited

U.S. PATENT DOCUMENTS

| 5,691,336 | A | 11/1997 | Dorn et al. |
| 7,642,272 | B2 | 1/2010 | Shankar et al. |
| 2004/0186148 | A1 | 9/2004 | Shankar et al. |
| 2006/0173050 | A1 | 8/2006 | Liu et al. |
| 2007/0225267 | A1 | 9/2007 | Broughton |
| 2009/0082560 | A1 | 3/2009 | Kobayashi et al. |
| 2009/0209755 | A1 | 8/2009 | Suzuki et al. |
| 2010/0075957 | A1 | 3/2010 | Tamura et al. |
| 2010/0197688 | A1 | 8/2010 | Nantermet et al. |
| 2011/0021520 | A1 | 1/2011 | Badiger et al. |
| 2012/0178745 | A1 | 7/2012 | Ramos |
| 2012/0184539 | A1 | 7/2012 | Badiger |

FOREIGN PATENT DOCUMENTS

| EP | 1942105 | 7/2008 |
| EP | 2151435 | 2/2010 |
| WO | 2005/079802 | 9/2005 |
| WO | 2006/034093 | 3/2006 |
| WO | 2007/049532 | 3/2007 |
| WO | 2008/106692 | 9/2008 |
| WO | 2008/133273 | 11/2008 |
| WO | 2008/133274 | 11/2008 |
| WO | 2009/010454 | 1/2009 |
| WO | 2009/091016 | 7/2009 |
| WO | 2009/151098 | 12/2009 |
| WO | 2010/007756 | 1/2010 |
| WO | 2010/047372 | 4/2010 |
| WO | 2010/070502 | 6/2010 |
| WO | 2010/128058 | 11/2010 |
| WO | 2011/009943 | 1/2011 |
| WO | 2011/020806 | 2/2011 |
| WO | 2011/058763 | 5/2011 |
| WO | 2011/069934 | 6/2011 |
| WO | 2011/070029 | 6/2011 |
| WO | 2011/071135 | 6/2011 |
| WO | 2011/138293 | 11/2011 |
| WO | 2011/154374 | 12/2011 |
| WO | 2011/154431 | 12/2011 |
| WO | 2012/095463 | 7/2012 |
| WO | 2012/095521 | 7/2012 |
| WO | 2013/054291 | 4/2013 |

OTHER PUBLICATIONS

Patani et al., Chem. Rev., 1996, 96, 3147-3176.*
U.S. Appl. No. 13/592,580, filed Aug. 23, 2012 (Lueoend).
Non-Final Rejection dated Jan. 30, 2013 in co-pending U.S. Appl. No. 13/518,907.
Patani et al., Bioisosterism: A Rational Approach in Drug Design, Chem. Rev., 96:3147-3176 (1996).
AlzheimersCure, 2012, http://www.alz.org/alzheimers_disease_treatments.asp.
AlzheimersCure, 2012, http://www.alz.org/research/science/alzheimers_prevention_and_risk.asp.
AlzheimersDrugs, 2012, http://www.alz.org/research/science/alzheimers_disease_treatments.asp.
Donezepil, 2012, http://en.wikipedia.org/wiki/Donepezil.
Galantamine, 2012, http://en.wikipedia.org/wiki/Galantamine.
Memantine, 2012, http://en.wikipedia.org/wiki/Memantine.
Rivastigmine, 2012, http://en.wikipedia.org/wiki/Rivastigmine.
Tacrine, 2012, http://en.wikipedia.org/wiki/Tacrine.
AlzheimersClinicalTrials, 2012, http://www.nature.com/nm/journal/v17/n8/full/nm0811-932.html.

* cited by examiner

*Primary Examiner* — Sun Jae Yoo
(74) *Attorney, Agent, or Firm* — Joshua Roth

(57) ABSTRACT

The invention relates to novel heterocyclic compounds of the formula (I)

in which all of the variables are as defined in the specification, in free form or in salt form, to their preparation, to their medical use and to medicaments comprising them.

8 Claims, 1 Drawing Sheet

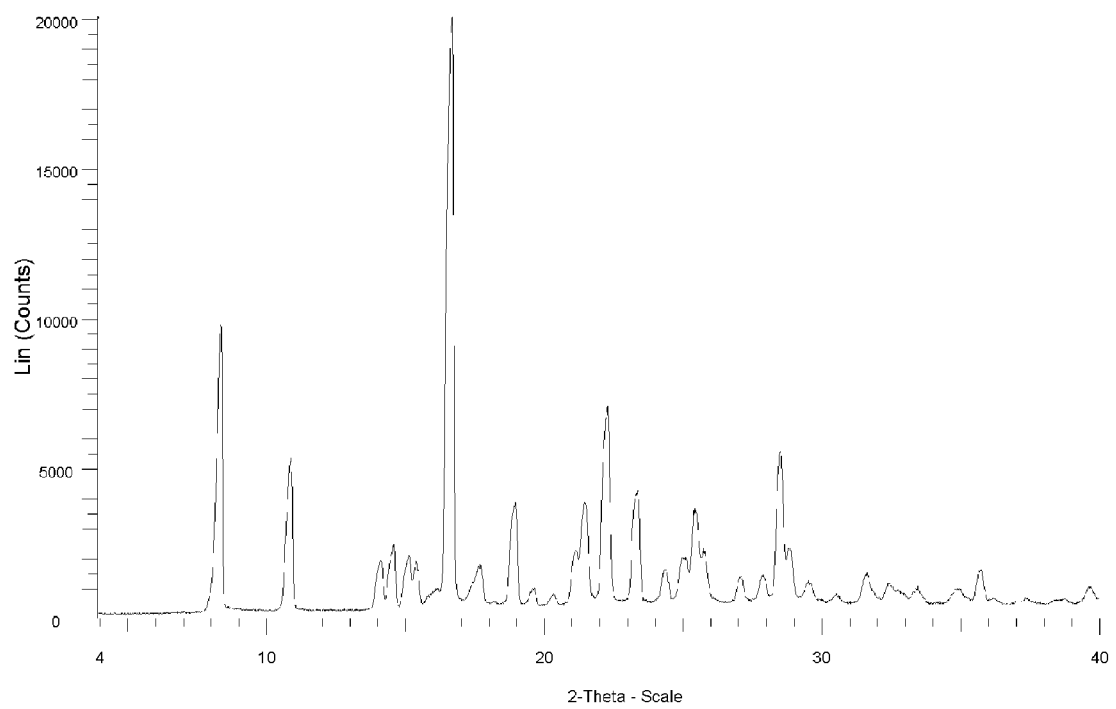

OXAZINE DERIVATIVES AND THEIR USE IN THE TREATMENT OF NEUROLOGICAL DISORDERS

This application is a US non-provisional filing of U.S. Provisional Applications 61/228,472 filed 24 Jul. 2009, 61/258,911 filed 6 Nov. 2009, and 61/363,702 filed 13 Jul. 2010, for which this application claims benefit, the contents of which are incorporated herein by reference in their entirety.

Alzheimer's Disease is a devastating neurodegenerative disorder. Its sporadic forms affect an elderly population (sharp increase in incidence at >75 years of age), in addition, there are various familial forms with an onset of the disease in the fourth or fifth decade of life. Pathologically, it is characterized by the presence of extracellular senile plaques, and intracellular neurofibrillar tangles in patient's brains. The core constituent of the senile plaques are small, 4 kDa amyloid peptides. They are generated by the proteolytic processing of a large transmembrane protein, amyloid precursor protein (APP). Cleavage of APP by beta-secretase (BACE-1) releases the soluble APP-beta fragment, while the 99-amino acid long C-terminus remains tethered to the membrane. This C-terminal fragment is subsequently proteolytically processed by gamma-secretase (an membrane multi-enzyme complex) to generate amyloid peptides of various length, predominantly 40 and 42 amino acids long (Hardy J, Selkoe D J (2002) Science; 297 (5580):353-356).

If, under pathologic conditions, the generation of these peptides occurs at an increased rate, or if their removal from the brain is disturbed, increased brain amyloid peptide concentrations leads to the formation of oligomers, fibrils and eventually plaques (Farris W, et al (2007) Am. J. Pathol.; 171 (1):241-251). It has been shown, that deposition of amyloid peptides and plaques in the brain is the first measurable event in the pathogenesis of Alzheimers Disease, and that it is the trigger for loss of synapses, synaptic contacts, and neurons (Grimmer T, et al (2009) Neurobiology of Aging; 30 (12): 1902-1909). Brain atrophy caused by massive neuron loss is followed by impairments in cognition, memory, orientation and the ability to perform the tasks of daily living, i.e. clinically manifest dementia (Okello A, et al (2009) Neurology; 73 (10):754-760).

BACE-1, also known as Asp2 or Memapsin 2, is a transmembrane aspartic protease highly expressed in neurons. It co-localizes with its substrate APP in Golgi and endocytic compartments (Willem M, Lammich S, Haass C (2009) Semin. Cell Dev. Biol; 20 (2):175-182). Knock-out studies in mice have demonstrated the absence of amyloid peptide formation, while the animals are healthy and fertile (Ohno M, et al (2007) Neurobiol. Dis.; 26 (1):134-145). Genetic ablation of BACE-1 in APP-overexpressing mice has demonstrated absence of plaque formation, and the reverse of cognitive deficits (Ohno M, et al (2004) Neuron; 41 (1):27-33). BACE-1 levels are elevated in the brains of sporadic Alzheimer's Disease patients (Hampel H, Shen Y (2009) Scand. J. Clin. Lab. Invest.; 69 (1):8-12).

Taken together, these findings suggest that the inhibition of BACE-1 may be a favourable therapeutic strategy for Alzheimer's Disease.

The present invention relates to novel oxazine derivatives having BACE inhibitory activity, to their preparation, to their medical use and to medicaments comprising them.

More particularly, in a first aspect, the invention relates to a compound of the formula

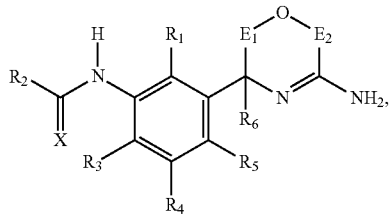

(I)

in which
X is O or S;
$R_1$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;

$R_2$ is an aryl, heteroaryl or non-aromatic heterocyclyl group $G_1$, which group $G_1$ is optionally substituted by 1, 2, 3 or 4 substituents independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3 or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

$R_3$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;

either
$R_4$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl; and $R_5$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;

or

R$_4$ and R$_5$, taken together, are —C(H)═C(H)—C(H)═C(H)— or a (C$_{1-8}$)alkylene group, in which (C$_{1-8}$)alkylene group 1 or 2 —CH$_2$— ring members are optionally replaced with hetero ring members independently selected from the group, consisting of —N(H)—, —N[(C$_{1-8}$)alkyl]-, —O—, —S—, —S(═O)— or —S(═O)$_2$—;

R$_6$ is hydrogen; (C$_{1-8}$)alkyl; halogen-(C$_{1-8}$)alkyl; hydroxy-(C$_{1-8}$)alkyl; (C$_{1-8}$)alkoxy-(C$_{1-8}$)alkyl; mercapto-(C$_{1-8}$)alkyl; (C$_{1-8}$)alkylthio-(C$_{1-8}$)alkyl; amino-(C$_{1-8}$)alkyl; N—(C$_{1-8}$)alkylamino-(C$_{1-8}$)alkyl; N,N-di-[(C$_{1-8}$)alkyl]amino-(C$_{1-8}$)alkyl with two identical or different (C$_{1-8}$)alkyl moieties in the N,N-di-[(C$_{1-8}$)alkyl]amino moiety; (C$_{2-8}$)alkenyl; or (C$_{2-8}$)alkynyl;

E$_1$ is —C(R$_7$)(R$_8$)—; or —C(R$_7$)(R$_8$)—C(R$_9$)(R$_{10}$)—;
E$_2$ is —C(R$_{11}$)(R$_{12}$)—; or —C(R$_{11}$)(R$_{12}$)—C(R$_{13}$)(R$_{14}$)—; either each of R$_7$ and R$_8$ is independently selected from the group, consisting of hydrogen, cyano, halogen, (C$_{1-8}$)alkyl, halogen-(C$_{1-8}$)alkyl, (C$_{1-8}$)alkoxy-(C$_{1-8}$)alkyl and (C$_{1-8}$)alkylthio-(C$_{1-8}$)alkyl;

or

R$_7$ and R$_8$, taken together, are oxo or —CH$_2$—CH$_2$—;
either each of R$_9$ and R$_{10}$ is independently selected from the group, consisting of hydrogen, cyano, halogen, (C$_{1-8}$)alkyl, halogen-(C$_{1-8}$)alkyl, (C$_{1-8}$)alkoxy-(C$_{1-8}$)alkyl and (C$_{1-8}$)alkylthio-(C$_{1-8}$)alkyl;

or

R$_9$ and R$_{10}$, taken together, are oxo or —CH$_2$—CH$_2$—;
either each of R$_{11}$ and R$_{12}$ is independently selected from the group, consisting of hydrogen, cyano, halogen, (C$_{1-8}$)alkyl, halogen-(C$_{1-8}$)alkyl, (C$_{1-8}$)alkoxy-(C$_{1-8}$)alkyl and (C$_{1-8}$)alkylthio-(C$_{1-8}$)alkyl;

or

R$_{11}$ and R$_{12}$, taken together, are oxo or —CH$_2$—CH$_2$—; and
either each of R$_{13}$ and R$_{14}$ is independently selected from the group, consisting of hydrogen, cyano, halogen, (C$_{1-8}$)alkyl, halogen-(C$_{1-8}$)alkyl; (C$_{1-8}$)alkoxy-(C$_{1-8}$)alkyl and (C$_{1-8}$)alkylthio-(C$_{1-8}$)alkyl;

or

R$_{13}$ and R$_{14}$, taken together, are oxo or —CH$_2$—CH$_2$—,
in free form or in salt form.

In a second aspect, the invention relates to a compound of the formula

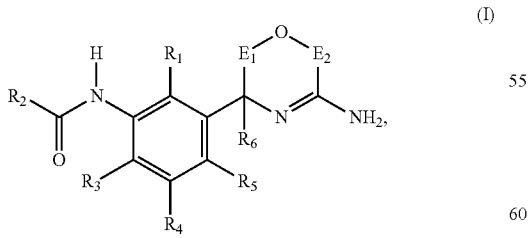

(I)

in which

R$_1$ is hydrogen; cyano; halogen; (C$_{1-8}$)alkyl; halogen-(C$_{1-8}$)alkyl; (C$_{1-8}$)alkoxy; halogen-(C$_{1-8}$)alkoxy; (C$_{1-8}$)alkylthio; halogen-(C$_{1-8}$)alkylthio; (C$_{1-8}$)alkoxy-(C$_{1-8}$)alkyl; (C$_{1-8}$)alkoxy-(C$_{1-8}$)alkoxy; (C$_{1-8}$)alkoxy-(C$_{1-8}$)alkylthio; (C$_{1-8}$)alkylthio-(C$_{1-8}$)alkyl; (C$_{1-8}$)alkylthio-(C$_{1-8}$)alkoxy; (C$_{1-8}$)alkylthio-(C$_{1-8}$)alkylthio; (C$_{2-8}$)alkenyl; or (C$_{2-8}$)alkynyl;

R$_2$ is a (C$_{3-8}$)cycloalkyl, aryl, heteroaryl or non-aromatic heterocyclyl group G$_1$, which group G$_1$ is optionally substituted by 1 to 4 substituents independently selected from the group, consisting of cyano, aminocarbonyl, halogen, (C$_{1-8}$)alkyl, halogen-(C$_{1-8}$)alkyl, hydroxy, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl and a (C$_{3-8}$)cycloalkyl, aryl, heteroaryl or non-aromatic heterocyclyl group G$_2$, which group G$_2$ is optionally substituted by 1 to 4 substituents independently selected from the group, consisting of cyano, aminocarbonyl, halogen, (C$_{1-8}$)alkyl, halogen-(C$_{1-8}$)alkyl, hydroxy, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl and (C$_{2-8}$)alkynyl;

R$_3$ is hydrogen; cyano; halogen; (C$_{1-8}$)alkyl; halogen-(C$_{1-8}$)alkyl; (C$_{1-8}$)alkoxy; halogen-(C$_{1-8}$)alkoxy; (C$_{1-8}$)alkylthio; halogen-(C$_{1-8}$)alkylthio; (C$_{1-8}$)alkoxy-(C$_{1-8}$)alkyl; (C$_{1-8}$)alkoxy-(C$_{1-8}$)alkoxy; (C$_{1-8}$)alkoxy-(C$_{1-8}$)alkylthio; (C$_{1-8}$)alkylthio-(C$_{1-8}$)alkyl; (C$_{1-8}$)alkylthio-(C$_{1-8}$)alkoxy; (C$_{1-8}$)alkylthio-(C$_{1-8}$)alkylthio; (C$_{2-8}$)alkenyl; or (C$_{2-8}$)alkynyl;

either

R$_4$ is hydrogen; cyano; halogen; (C$_{1-8}$)alkyl; halogen-(C$_{1-8}$)alkyl; (C$_{1-8}$)alkoxy; halogen-(C$_{1-8}$)alkoxy; (C$_{1-8}$)alkylthio; halogen-(C$_{1-8}$)alkylthio; (C$_{1-8}$)alkoxy-(C$_{1-8}$)alkyl; (C$_{1-8}$)alkoxy-(C$_{1-8}$)alkoxy; (C$_{1-8}$)alkoxy-(C$_{1-8}$)alkylthio; (C$_{1-8}$)alkylthio-(C$_{1-8}$)alkyl; (C$_{1-8}$)alkylthio-(C$_{1-8}$)alkoxy; (C$_{1-8}$)alkylthio-(C$_{1-8}$)alkylthio; (C$_{2-8}$)alkenyl; or (C$_{2-8}$)alkynyl; and R$_5$ is hydrogen; cyano; halogen; (C$_{1-8}$)alkyl; halogen-(C$_{1-8}$)alkyl; (C$_{1-8}$)alkoxy; halogen-(C$_{1-8}$)alkoxy; (C$_{1-8}$)alkylthio; halogen-(C$_{1-8}$)alkylthio; (C$_{1-8}$)alkoxy-(C$_{1-8}$)alkyl; (C$_{1-8}$)alkoxy-(C$_{1-8}$)alkoxy; (C$_{1-8}$)alkoxy-(C$_{1-8}$)alkylthio; (C$_{1-8}$)alkylthio-(C$_{1-8}$)alkyl; (C$_{1-8}$)alkylthio-(C$_{1-8}$)alkoxy; (C$_{1-8}$)alkylthio-(C$_{1-8}$)alkylthio; (C$_{2-8}$)alkenyl; or (C$_{2-8}$)alkynyl;

or

R$_4$ and R$_5$, taken together, are —C(H)═C(H)—C(H)═C(H)— or a (C$_{1-8}$)alkylene group, in which (C$_{1-8}$)alkylene group 1 or 2 —CH$_2$— ring members are optionally replaced with hetero ring members independently selected from the group, consisting of —N(H)—, —N[(C$_{1-8}$)alkyl]-, —O—, —S—, —S(═O)— or —S(═O)$_2$—;

R$_6$ is hydrogen; (C$_{1-8}$)alkyl; halogen-(C$_{1-8}$)alkyl; hydroxy-(C$_{1-8}$)alkyl; (C$_{1-8}$)alkoxy-(C$_{1-8}$)alkyl; mercapto-(C$_{1-8}$)alkyl; (C$_{1-8}$)alkylthio-(C$_{1-8}$)alkyl; amino-(C$_{1-8}$)alkyl; N—(C$_{1-8}$)alkylamino-(C$_{1-8}$)alkyl; N,N-di-[(C$_{1-8}$)alkyl]amino-(C$_{1-8}$)alkyl with two identical or different (C$_{1-8}$)alkyl moieties in the N,N-di-[(C$_{1-8}$)alkyl]amino moiety; (C$_{2-8}$)alkenyl; or (C$_{2-8}$)alkynyl;

E$_1$ is —C(R$_7$)(R$_8$)—; or —C(R$_7$)(R$_8$)—C(R$_9$)(R$_{10}$)—;
E$_2$ is —C(R$_{11}$)(R$_{12}$)—; or —C(R$_{11}$)(R$_{12}$)—C(R$_{13}$)(R$_{14}$)—;

either
each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_7$ and $R_8$, taken together, are oxo or —$CH_2$—$CH_2$—;
either
each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_9$ and $R_{10}$, taken together, are oxo or —$CH_2$—$CH_2$—;
either
each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{11}$ and $R_{12}$, taken together, are oxo or —$CH_2$—$CH_2$—; and
either
each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{13}$ and $R_{14}$, taken together, are oxo or —$CH_2$—$CH_2$—, in free form or in salt form.

In a third aspect, the invention relates to a compound of the formula

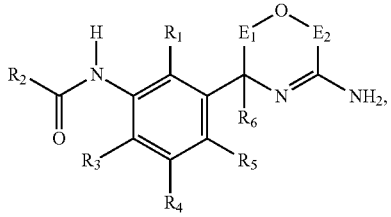

(I)

in which
$R_1$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio$(C_{1-8})$alkylthio; $(C_{2-8})$alkenyl; or $(C_{2-8})$alkynyl;

$R_2$ is a $(C_{3-8})$cycloalkyl, aryl, heteroaryl or non-aromatic heterocyclyl group $G_1$, which group $G_1$ is optionally substituted by 1 to 4 substituents independently selected from the group, consisting of cyano, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl and a $(C_{3-8})$cycloalkyl, aryl, heteroaryl or non-aromatic heterocyclyl group $G_2$, which group $G_2$ is optionally substituted by 1 to 4 substituents independently selected from the group, consisting of cyano, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

$R_3$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;
either
$R_4$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl; and
$R_5$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;
or
$R_4$ and $R_5$, taken together, are —C(H)=C(H)—C(H)=C(H)— or a $(C_{1-8})$alkylene group, in which $(C_{1-8})$alkylene group 1 or 2 —$CH_2$— ring members are optionally replaced with hetero ring members independently selected from the group, consisting of —N(H)—, —N[$(C_{1-8})$alkyl]-, —O—, —S—, —S(=O)— or —S(=O)$_2$—;
$R_6$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$alkyl; mercapto-$(C_{1-8})$alkyl; $(C_{1-8})$alkylthio-$(C_{1-8})$alkyl; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; $(C_{2-8})$alkenyl; or $(C_{2-8})$alkynyl;
$E_1$ is —C($R_7$)($R_8$)—; or —C($R_7$)($R_8$)—C($R_9$)($R_{10}$)—;
$E_2$ is —C($R_{11}$)($R_{12}$)—; or —C($R_{11}$)($R_{12}$)—C($R_{13}$)($R_{14}$)—;
either
each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_7$ and $R_8$, taken together, are oxo or —$CH_2$—$CH_2$—;
either
each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_9$ and $R_{10}$, taken together, are oxo or —$CH_2$—$CH_2$—;
either
each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;

or
R$_{11}$ and R$_{12}$, taken together, are oxo or —CH$_2$—CH$_2$—; and
either
each of R$_{13}$ and R$_{14}$ is independently selected from the group, consisting of hydrogen, cyano, halogen, (C$_{1-8}$)alkyl, halogen-(C$_{1-8}$)alkyl, (C$_{1-8}$)alkoxy-(C$_{1-8}$)alkyl and (C$_{1-8}$)alkylthio-(C$_{1-8}$)alkyl;
or
R$_{13}$ and R$_{14}$, taken together, are oxo or —CH$_2$—CH$_2$—,
in free form or in salt form.

Halogen denotes fluorine, chlorine, bromine or iodine.

A halogenated group or moiety, such as halogenalkyl, can be mono-, poly- or per-halogenated.

An aryl group, ring or moiety is a naphthyl or, preferably, phenyl group, ring or moiety.

A heteroaryl group, ring or moiety is a monocyclic aromatic 5- or 6-membered structure, in which structure 1, 2, 3 or 4 ring members are hetero ring members independently selected from the group, consisting of a nitrogen ring member, an oxygen ring member and a sulfur ring member, such as furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl; or a bicyclic aromatic 9- or 10- or membered structure, in which structure 1, 2, 3, 4 or 5 ring members are hetero ring members independently selected from the group, consisting of a nitrogen ring member, an oxygen ring member and a sulfur ring member. The fused rings completing the bicyclic groups may contain only carbon atoms and may be saturated, partially saturated, or unsaturated. Heteroaryl groups which are bicyclic include at least one fully aromatic ring but the other fused ring may be aromatic or non-aromatic. Examples of bicyclic heteroaryl groups include, benzofuranyl, benzothiophenyl, imidazopyridinyl, indazolyl, indolyl, isoquinolinyl, pyrazolopyridinyl and quinolinyl. The heteroaryl radical may be bonded via a carbon atom or heteroatom.

In one embodiment, the heteroaryl group is an aromatic 5- or 6-membered structure, in which structure 1, 2, 3 or 4 ring members are hetero ring members independently selected from the group, consisting of a nitrogen ring member, an oxygen ring member and a sulfur ring member.

A non-aromatic heterocyclyl group, ring or moiety is a non-aromatic 4-, 5-, 6- or 7-membered cyclic structure, in which cyclic structure 1, 2 or 3 ring members are hetero ring members independently selected from the group, consisting of a nitrogen ring member, an oxygen ring member and a sulfur ring member, such as azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

Any non-cyclic carbon containing group or moiety with more than 1 carbon atom is straight-chain or branched.

Unless defined otherwise, carbon containing groups, moieties or molecules contain 1 to 8, 1 to 6, 1 to 4 or 1 or 2 carbon atoms.

The terms "alkoxy", "alkenoxy" and "alkynoxy" respectively denote alkyl, alkenyl and alkynyl groups when linked by oxygen.

On account of one or more than one asymmetrical carbon atom, which may be present in a compound of the formula I, a corresponding compound of the formula I may exist in pure optically active form or in the form of a mixture of optical isomers, e.g. in the form of a racemic mixture. All of such pure optical isomers and all of their mixtures, including the racemic mixtures, are part of the present invention.

In one embodiment, the invention therefore relates to a compound of the formula

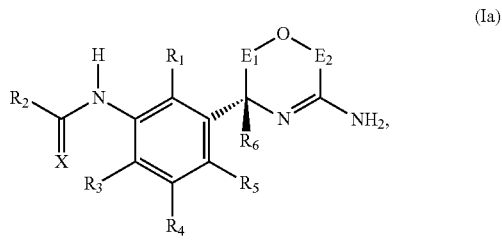

(Ia)

in which
X, E$_1$, E$_2$, R$_1$, R$_2$, R$_3$, R$_4$, R$_5$ and R$_6$ are as defined hereinbefore in relation to the formula I,
in free form or in salt form, In one embodiment, the invention therefore relates to a compound of the formula

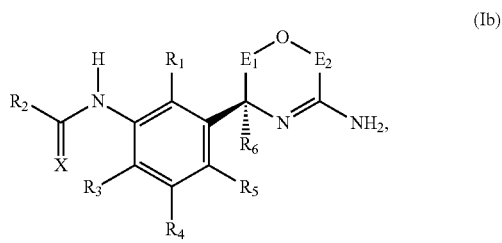

(Ib)

in which
X, E$_1$, E$_2$, R$_1$, R$_2$, R$_3$, R$_4$, R$_5$ and R$_6$ are as defined hereinbefore in relation to the formula I,
in free form or in salt form.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

A compound of the formula I may exist in tautomeric form. All such tautomers are part of the present invention.

A compound of the formula I may exist in free form or in salt form, for example a basic compound in acid addition salt form or an acidic compound in the form of a salt with a base. All of such free compounds and salts are part of the present invention.

In one embodiment, the invention relates to a compound of the formula I, Ia, Ib, Ic or Id as defined herein, in free form. In another embodiment, the invention relates to a compound of the formula I, Ia, Ib, Ic or Id, as defined herein, in salt form. In a further embodiment, the invention relates to a compound of the formula I, Ia, Ib, Ic or Id, as defined herein, in pharmaceutically acceptable salt form. In yet a further embodiment, the invention relates to a compound of the formula I, Ia, Ib, Ic or Id, as defined herein, in hydrochloride salt form. In yet a further embodiment, the invention relates to any one of the compounds of the Examples in free form. In yet a further embodiment, the invention relates to any one of the compounds of the Examples in pharmaceutically acceptable salt form. In yet a further embodiment, the invention relates to any one of the compounds of the Examples in hydrochloride salt form.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid and sulfosalicylic acid. Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines and basic ion exchange resins. Certain organic amines include isopropylamine, benzathine; cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the present invention may also form internal salts, e.g., zwitterionic molecules.

The present invention also provides pro-drugs of the compounds of the present invention that convert in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use. Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs. In one embodiment, the invention therefore relates to a compound of the formula I, Ia, Ib, Ic, Id, or Ie as defined herein, or a pharmaceutically acceptable salt thereof, in crystalline form.

The present invention includes all pharmaceutically acceptable isotope-labeled compounds of the formula I, wherein one or more than one atom is/are replaced by one or more than one atom having the same atomic number as, but an atomic mass different from, the one(s) usually found in nature. Examples of such isotopes are those of carbon, such as $^{11}C$, $^{13}C$ or $^{14}C$, chlorine, such as $^{36}Cl$, fluorine, such as $^{18}F$, bromine, such as $^{76}Br$, hydrogen, such as $^2H$ or $^3H$, iodine, such as $^{123}I$, $^{124}I$, $^{25}I$ or $^{131}I$, nitrogen, such as $^{13}N$ or $^{15}N$, oxygen, such as $^{15}O$, $^{17}O$ or $^{18}O$, phosphorus, such as $^{32}P$, or sulphur, such as $^{35}S$. An isotope-labeled compound of the formula I can be prepared by a process analogous to those described in the Examples or by a conventional technique known to those skilled in the art using an appropriate isotopically-labeled reagent or starting material. The incorporation of a heavier isotope, such as $^2H$ (D), may provide greater metabolic stability to a compound of the formula I, which may result in, for example, an increased in vivo-half-life of the compound or in reduced dosage requirements. Certain isotope-labeled compounds of the formula I, for example those incorporating a radioactive isotope, such as $^3H$ or $^{14}C$, may be used in drug or substrate-tissue distribution studies. Compounds of the formula I with a positron emitting isotope, such as $^{11}C$, $^{18}F$, $^{13}N$ or $^{15}O$, may be useful in positron emission tomography (PET) or single photon emission computed tomography (SPECT) studies, e.g. to examine substrate-receptor occupancies.

Pharmaceutically acceptable solvates in accordance with the invention include those wherein the solvent of crystallization may be isotopically substituted, e.g. D2O, d6-acetone, d6-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

In certain embodiments, the invention relates to a compound of the formula I, Ia, Ib, Ic or Id in free form or in salt form, in which:

(1) $R_1$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;

(2) $R_1$ is hydrogen;

(3) $R_2$ is an aryl, heteroaryl or non-aromatic heterocyclyl group $G_1$, which group $G_1$ is optionally substituted by 1, 2, 3 or 4 substituents independently selected from the group, consisting of cyano, nitro, amino, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3 or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

(4) $R_2$ is an aryl, heteroaryl or non-aromatic heterocyclyl group $G_1$, which group $G_1$ is optionally substituted by 1, 2, 3 or 4 substituents independently selected from the group, consisting of cyano, nitro, amino, aminocarbonyl, amino-$(C_{1-8})$alkyl, $(C_{1-14})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3 or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

(5) $R_2$ is an aryl or heteroaryl group $G_1$, which group $G_1$ is optionally substituted by 1, 2, 3 or 4 substituents independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy, $(C_{2-8})$alkynoxy and a $(C_{3-8})$cycloalkyl, aryl, heteroaryl or non-aromatic heterocyclyl group $G_2$, which group $G_2$ is optionally substituted by 1, 2, 3 or 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

(6) $R_2$ is a $(C_{3-8})$cycloalkyl, aryl, heteroaryl or non-aromatic heterocyclyl group $G_1$, which group $G_1$ is optionally substituted by 1 to 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl and a $(C_{3-8})$cycloalkyl, aryl, heteroaryl or non-aromatic heterocyclyl group $G_2$, which group $G_2$ is optionally substituted by 1 to 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

(7) $R_2$ is a $(C_{3-8})$cycloalkyl, aryl, heteroaryl or non-aromatic heterocyclyl group $G_1$, which group $G_1$ is optionally substituted by 1 to 4 substituents independently selected from the group, consisting of cyano, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl and a $(C_{3-8})$cycloalkyl, aryl, heteroaryl or non-aromatic heterocyclyl group $G_2$, which group $G_2$ is optionally substituted by 1 to 4 substituents independently selected from the group, consisting of cyano, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl and $(C_{2-8})$alkynyl;

(8) $R_2$ is a $(C_{3-8})$cycloalkyl, aryl or heteroaryl group $G_1$, which group $G_1$ is optionally substituted by 1 to 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl and a $(C_{3-8})$cycloalkyl, aryl or heteroaryl group $G_2$, which group $G_2$ is optionally substituted by 1 to 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio$(C_{1-8})$alkylthio, $(C_{2-8})$alkenyl and $(C_{2-8})$alkynyl;

(9) $R_2$ is a heteroaryl group $G_1$, which group $G_1$ is optionally substituted by 1 to 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl and a $(C_{3-8})$cycloalkyl, aryl or heteroaryl group $G_2$, which group $G_2$ is optionally substituted by 1 to 4 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{2-8})$alkenyl and $(C_{2-8})$alkynyl;

(10) $R_2$ is a heteroaryl group $G_1$, which group $G_1$ is optionally substituted by 1 or 2 substituents independently selected from the group, consisting of cyano, aminocarbonyl, halogen, $(C_{1-8})$alkyl, halogen-$(C_{1-8})$alkyl, hydroxy, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl and a $(C_{3-8})$cycloalkyl, aryl or heteroaryl group $G_2$, which group $G_2$ is unsubstituted;

(11) $R_2$ is a heteroaryl or aryl group which is optionally substituted by 1, 2, 3 or 4 substituents independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy and $(C_{2-8})$alkynoxy;

(12) $R_2$ is a heteroaryl group which is optionally substituted by 1, 2, 3 or 4 substituents independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen- (C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy and (C$_{2-8}$)alkynoxy;

(13) R$_2$ is a heteroaryl group which is optionally substituted by 1, 2, 3 or 4 substituents independently selected from the group, consisting of deuterium, cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, deuterated (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy and (C$_{2-8}$)alkynoxy;

(14) R$_2$ is a heteroaryl group which contains 1, 2 or 3 nitrogen atom ring members and is optionally substituted by 1, 2, 3 or 4 substituents independently selected from the group, consisting of deuterium, cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, deuterated (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy and (C$_{2-8}$)alkynoxy;

(15) R$_2$ is a monocyclic 6-membered heteroaryl group which contains 1, 2 or 3 nitrogen atom ring members and which is optionally substituted by 1, 2, 3 or 4 substituents independently selected from the group, consisting of cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy and (C$_{2-8}$)alkynoxy;

(16) R$_2$ is a 6-membered heteroaryl group which contains 1, 2 or 3 nitrogen atom ring members and which is substituted by 1, 2, 3 or 4 substituents and wherein one of the substituents is located at the para position of the heteroaryl group relative to the amide linker and wherein the substituents are independently selected from the group, consisting of cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy and (C$_{2-8}$)alkynoxy;

(17) R$_2$ is a 6-membered heteroaryl group which contains 1, 2 or 3 nitrogen atom ring members and which is substituted by 1, 2, 3 or 4 substituents and wherein one of the substituents is located at the para position of the heteroaryl group relative to the amide linker and wherein the substituents are independently selected from the group, consisting of cyano, halogen (C$_{1-6}$)alkyl, (C$_{1-6}$)alkoxy, (C$_{1-6}$)alkoxy-(C$_{1-6}$)alkyl, halogen-(C$_{1-6}$)alkyl and (C$_{2-8}$)alkynoxy;

(18) R$_2$ is a 6-membered heteroaryl group which contains 1, 2 or 3 nitrogen atom ring members and which is optionally substituted by 1, 2, 3 or 4 substituents independently selected from the group, consisting of cyano, halogen (C$_{1-6}$)alkyl, (C$_{1-6}$)alkoxy, (C$_{1-6}$)alkoxy-(C$_{1-6}$)alkyl, halogen-(C$_{1-6}$)alkyl and (C$_{2-8}$)alkynoxy;

(19) R$_2$ is a pyridyl or pyrazinyl group which is optionally substituted by 1, 2, 3 or 4 substituents independently selected from the group, consisting of cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy, (C$_{2-8}$)alkynoxy and a (C$_{3-8}$)cycloalkyl, aryl, heteroaryl or non-aromatic heterocyclyl group G$_2$, which group G$_2$ is optionally substituted by 1, 2, 3 or 4 substituents independently selected from the group, consisting of cyano, aminocarbonyl, halogen, (C$_{1-8}$)alkyl, halogen-(C$_{1-8}$)alkyl, hydroxy, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl and (C$_{2-8}$)alkynyl;

(20) R$_2$ is a pyridyl or pyrazinyl group which is optionally substituted by 1, 2, 3 or 4 substituents independently selected from the group, consisting of cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy, (C$_{2-8}$)alkynoxy and a (C$_{3-8}$)cycloalkyl, aryl or heteroaryl group G$_2$, which group G$_2$ is unsubstituted;

(21) R$_2$ is a pyridyl or pyrazinyl group which is optionally substituted by 1, 2, 3 or 4 substituents independently selected from the group, consisting of cyano, nitro, amino, aminocarbonyl, amino-(C$_{1-8}$)alkyl, (C$_{1-4}$)alkyl-amino-(C$_{1-8}$)alkyl, di(C$_{1-4}$)alkyl-amino-(C$_{1-8}$)alkyl, halogen, (C$_{1-8}$)alkyl, halogen-(C$_{1-8}$)alkyl, hydroxy, oxo, (C$_{1-8}$)alkoxy, halogen-(C$_{1-8}$)alkoxy, (C$_{1-8}$)alkylthio, halogen-(C$_{1-8}$)alkylthio, (C$_{1-8}$)alkoxy-(C$_{1-8}$)alkyl, (C$_{1-8}$)alkoxy-(C$_{1-8}$)alkoxy, (C$_{1-8}$)alkoxy-(C$_{1-8}$)alkylthio, (C$_{1-8}$)alkylthio-(C$_{1-8}$)alkyl, (C$_{1-8}$)alkylthio-(C$_{1-8}$)alkoxy, (C$_{1-8}$)alkylthio-(C$_{1-8}$)alkylthio, (C$_{2-8}$)alkenyl, (C$_{2-8}$)alkynyl, (C$_{2-8}$)alkenoxy and (C$_{2-8}$)alkynoxy;

(22) R$_2$ is a pyridyl or pyrazinyl group which is optionally substituted by 1, 2, 3 or 4 substituents independently selected from the group, consisting of cyano, halogen (C$_{1-6}$)alkyl, (C$_{1-6}$)alkoxy, (C$_{1-6}$)alkoxy-(C$_{1-6}$)alkoxy, halogen-(C$_{1-6}$)alkyl and (C$_{2-8}$)alkynoxy;

(23) R$_2$ is a pyridyl or pyrazinyl group which is optionally substituted by 1, 2, 3 or 4 substituents independently selected from the group, consisting of deuterium, cyano, halogen, (C$_{1-6}$)alkyl, deuterated (C$_{1-6}$)alkyl, (C$_{1-6}$)alkoxy, (C$_{1-6}$)alkoxy-(C$_{1-6}$)alkoxy, halogen-(C$_{1-6}$)alkyl and (C$_{2-8}$)alkynoxy;

(24) R$_2$ is a pyridyl group which is optionally substituted by 1, 2, 3 or 4 substituents independently selected from the group, consisting of cyano, halogen $(C_{1-6})$alkyl, $(C_{1-6})$alkoxy, $(C_{1-6})$alkoxy-$(C_{1-6})$alkoxy, halogen-$(C_{1-6})$alkyl and $(C_{2-8})$alkynoxy;

(25) $R_2$ is a pyrazinyl group which is optionally substituted by 1, 2, 3 or 4 substituents independently selected from the group, consisting of cyano, halogen $(C_{1-6})$alkyl, $(C_{1-6})$alkoxy, $(C_{1-6})$alkoxy-$(C_{1-6})$alkoxy, halogen-$(C_{1-6})$alkyl and $(C_{2-8})$alkynoxy;

(26) $R_2$ is a pyridyl or pyrazinyl group which is substituted by 1, 2, 3 or 4 substituents and wherein one of the substituents is located at the para position of the pyridyl or pyrazinyl group relative to the amide linker and wherein the substituents are independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy and $(C_{2-8})$alkynoxy;

(27) $R_2$ is a pyridyl or pyrazinyl group which is substituted by 1, 2, 3 or 4 substituents and wherein one of the substituents is located at the para position of the pyridyl or pyrazinyl group relative to the amide linker and wherein the substituents are independently selected from the group, consisting of deuterium, cyano, halogen, $(C_{1-6})$alkyl, deuterated $(C_{1-6})$alkyl, $(C_{1-6})$alkoxy, $(C_{1-6})$alkoxy-$(C_{1-6})$alkoxy, halogen-$(C_{1-6})$alkyl and $(C_{2-6})$alkynoxy;

(28) $R_2$ is a pyridyl or pyrazinyl group which is substituted by 1, 2, 3 or 4 substituents and wherein one of the substituents is located at the para position of the pyridyl or pyrazinyl group relative to the amide linker and wherein the substituents are independently selected from the group, consisting of cyano, halogen $(C_{1-6})$alkyl, $(C_{1-6})$alkoxy, $(C_{1-6})$alkoxy-$(C_{1-6})$alkoxy, halogen-$(C_{1-6})$alkyl and $(C_{2-6})$alkynoxy;

(29) $R_2$ is a pyridyl or pyrazinyl group which is substituted by 2, 3 or 4 substituents and wherein one of the substituents is located at the para position and one of the substituents is located at the ortho position of the pyridyl or pyrazinyl group relative to the amide linker and wherein the substituents are independently selected from the group, consisting of cyano, halogen $(C_{1-6})$alkyl, $(C_{1-6})$alkoxy, $(C_{1-6})$alkoxy-$(C_{1-6})$alkoxy, halogen-$(C_{1-6})$alkyl and $(C_{2-6})$alkynoxy;

(30) $R_2$ is a pyridyl or pyrazinyl group which is substituted by 2 substituents and wherein one of the substituents is located at the para position and one of the substituents is located at the ortho position of the pyridyl or pyrazinyl group relative to the amide linker and wherein the substituents are independently selected from the group, consisting of cyano, halogen $(C_{1-6})$alkyl, $(C_{1-6})$alkoxy, $(C_{1-6})$alkoxy-$(C_{1-6})$alkoxy, halogen-$(C_{1-6})$alkyl and $(C_{2-6})$alkynoxy;

(31) $R_2$ is a pyridyl or pyrazinyl group which is substituted by 2 substituents and wherein one of the substituents is located at the para position and one of the substituents is located at the ortho position of the pyridyl or pyrazinyl group relative to the amide linker and wherein the substituents are independently selected from the group, consisting of deuterium, cyano, chloro, bromo, $(C_{1-6})$alkyl, deuterated $(C_{1-6})$alkyl, $(C_{1-6})$alkoxy, $(C_{1-3})$alkoxy-$(C_{1-3})$alkoxy, trifluoromethyl and $(C_{2-4})$alkynoxy;

(32) $R_2$ is a pyridyl or pyrazinyl group which is substituted by 2 substituents and wherein one of the substituents is located at the para position and one of the substituents is located at the ortho position of the pyridyl or pyrazinyl group relative to the amide linker and wherein the substituents are independently selected from the group, consisting of cyano, chloro, bromo, $(C_{1-6})$alkyl, $(C_{1-6})$alkoxy, $(C_{1-3})$alkoxy-$(C_{1-3})$alkoxy, trifluoromethyl and $(C_{2-4})$alkynoxy;

(33) $R_3$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;

(34) $R_3$ is hydrogen;

(35) either
$R_4$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl; and
$R_5$ is hydrogen; cyano; halogen; $(C_{1-8})$alkyl; halogen-$(C_{1-8})$alkyl; $(C_{1-8})$alkoxy; halogen-$(C_{1-8})$alkoxy; $(C_{1-8})$alkylthio; halogen-$(C_{1-8})$alkylthio; $(C_{1-8})$alkoxy-$(C_{1-8})$alkyl; $(C_{1-8})$alkoxy-$(C_{1-8})$alkoxy; $(C_{1-8})$alkoxy-$(C_{1-8})$alkylthio; $(C_{1-8})$alkylthio-$(C_{1-8})$alkyl; $(C_{1-8})$alkylthio-$(C_{1-8})$alkoxy; $(C_{1-8})$alkylthio-$(C_{1-8})$alkylthio; $(C_{2-8})$alkenyl; or $(C_{2-8})$alkynyl;
or
$R_4$ and $R_5$, taken together, are —C(H)=C(H)—C(H)=C(H)— or a $(C_{1-8})$alkylene group, in which $(C_{1-8})$alkylene group 1 or 2 —CH$_2$— ring members are optionally replaced with hetero ring members independently selected from the group, consisting of —N(H)—, —N[$(C_{1-8})$alkyl]-, —O—, —S—, —S(=O)— or —S(=O)$_2$—;

(36) $R_4$ is hydrogen; or halogen; and
$R_5$ is hydrogen; or halogen;

(37) $R_4$ is hydrogen; and
$R_5$ is halogen;

(38) $R_4$ is halogen; and
$R_5$ is hydrogen;

(39) each of $R_4$ and $R_5$ is hydrogen;

(40) $R_4$ is hydrogen; and
$R_5$ is fluoro or chloro;

(41) $R_6$ is hydrogen; $(C_{1-8})$alkyl; halogen-$(C_{1-8})$alkyl; hydroxy-$(C_{1-8})$alkyl; $(C_{1-8})$alkoxy-$(C_{1-8})$alkyl; mercapto-$(C_{1-8})$alkyl; $(C_{1-8})$alkylthio-$(C_{1-8})$alkyl; amino-$(C_{1-8})$alkyl; N—$(C_{1-8})$alkylamino-$(C_{1-8})$alkyl; N,N-di-[$(C_{1-8})$alkyl]amino-$(C_{1-8})$alkyl with two identical or different $(C_{1-8})$alkyl moieties in the N,N-di-[$(C_{1-8})$alkyl]amino moiety; $(C_{2-8})$alkenyl; or $(C_{2-8})$alkynyl;

(42) $R_6$ is $(C_{1-8})$alkyl; or halogen-$(C_{1-8})$alkyl;

(43) $R_6$ is $(C_{1-3})$alkyl; or halogen-$(C_{1-3})$alkyl;

(44) $R_6$ is $(C_{1-8})$alkyl; or fluorine-substituted $(C_{1-8})$alkyl;

(45) $R_6$ is $(C_{1-3})$alkyl; or fluorine-substituted $(C_{1-3})$alkyl;

(46) $R_6$ is methyl, fluoromethyl or di-fluoromethyl;

(47) $R_6$ is di-fluoromethyl;

(48) $E_1$ is —C($R_7$)($R_8$)—; or —C($R_7$)(R)—C($R_9$)($R_{10}$)—;

(49) $E_1$ is —C($R_7$)($R_8$)—;

(50) $E_2$ is —C($R_{11}$)($R_{12}$)—; or —C($R_{11}$)($R_{12}$)—C($R_{13}$)($R_{14}$)—;

(51) $E_2$ is —C($R_{11}$)($R_{12}$)—;

(52) either
each of $R_7$ and $R_8$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_7$ and $R_8$, taken together, are oxo or —CH$_2$—CH$_2$—;

(53) each of $R_7$ and $R_8$ is independently selected from hydrogen and fluoro;

(54) each of $R_7$ and $R_8$ is hydrogen;
(55) either
each of $R_9$ and $R_{10}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_9$ and $R_{10}$, taken together, are oxo or —$CH_2$—$CH_2$—;
(56) each of $R_9$ and $R_{10}$ is hydrogen;
(57) either
each of $R_{11}$ and $R_{12}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{11}$ and $R_{12}$, taken together, are oxo or —$CH_2$—$CH_2$—;
(58) each of $R_{11}$ and $R_{12}$ is independently selected from the group, consisting of hydrogen, halogen, $(C_{1-8})$alkyl and halogen-$(C_{1-8})$alkyl;
(59) each of $R_{11}$ and $R_{12}$ is independently selected from the group, consisting of hydrogen, $(C_{1-8})$alkyl and halogen-$(C_{1-8})$alkyl;
(60) $R_{11}$ is $(C_{1-8})$alkyl, and $R_{12}$ is halogen-$(C_{1-8})$alkyl;
(61) each of $R_{11}$ and $R_{12}$ is independently selected from the group, consisting of hydrogen, $(C_{1-3})$alkyl and halogen-$(C_{1-3})$alkyl;
(62) each of $R_{11}$ and $R_{12}$ is independently selected from the group, consisting of hydrogen, methyl, fluoromethyl, difluoromethyl and trifluoromethyl;
(63) each of $R_{11}$ and $R_{12}$ is independently selected from the group, consisting of hydrogen, methyl and trifluoromethyl;
(64) each of $R_{11}$ and $R_{12}$ is hydrogen;
(65) either
each of $R_{13}$ and $R_{14}$ is independently selected from the group, consisting of hydrogen, cyano, halogen, $(C_{1-8})$alkyl, halogen-$(C_{1-8})$alkyl, $(C_{1-8})$alkoxy-$(C_{1-8})$alkyl and $(C_{1-8})$alkylthio-$(C_{1-8})$alkyl;
or
$R_{13}$ and $R_{14}$, taken together, are oxo or —$CH_2$—$CH_2$—.
(66) X is O;
(67) X is S.

The skilled person would understand that the embodiments (1) to (67) may be used independently, collectively or in any combination or sub-combination to the limit the scope of the invention as described hereinbefore in relation to compounds of the formula I, Ia, Ib, Ic or Id.

In one embodiment, the invention relates to a compound of the formula (Ic)

in which
$R_2$ is a heteroaryl group which is optionally substituted by 1, 2, 3 or 4 substituents independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy and $(C_{2-8})$alkynoxy;
$R_4$ is hydrogen; or halogen;
$R_5$ is hydrogen; or halogen;
$R_6$ is $(C_{1-8})$alkyl; or halogen-$(C_{1-8})$alkyl; and
each of $R_{11}$ and $R_{12}$ is independently selected from the group, consisting of hydrogen, methyl, fluoromethyl, difluoromethyl and trifluoromethyl;
in free form or in salt form.

In another embodiment, the invention relates to a compound of the formula (Id)

in which
$R_2$ is a pyridyl or pyrazinyl group which is optionally substituted by 1, 2, 3 or 4 substituents independently selected from the group, consisting of cyano, nitro, amino, aminocarbonyl, amino-$(C_{1-8})$alkyl, $(C_{1-4})$alkyl-amino-$(C_{1-8})$alkyl, di$(C_{1-4})$alkyl-amino-$(C_{1-8})$alkyl, halogen, $(C_{1-8})$alkyl, halogen-$(C_{1-8})$alkyl, hydroxy, oxo, $(C_{1-8})$alkoxy, halogen-$(C_{1-8})$alkoxy, $(C_{1-8})$alkylthio, halogen-$(C_{1-8})$alkylthio, $(C_{1-8})$alkoxy-$(C_{1-8})$alkyl, $(C_{1-8})$alkoxy-$(C_{1-8})$alkoxy, $(C_{1-8})$alkoxy-$(C_{1-8})$alkylthio, $(C_{1-8})$alkylthio-$(C_{1-8})$alkyl, $(C_{1-8})$alkylthio-$(C_{1-8})$alkoxy, $(C_{1-8})$alkylthio-$(C_{1-8})$alkylthio, $(C_{2-8})$alkenyl, $(C_{2-8})$alkynyl, $(C_{2-8})$alkenoxy and $(C_{2-8})$alkynoxy;
$R_4$ is hydrogen; or halogen;
$R_5$ is hydrogen; or halogen;
$R_6$ is $(C_{1-8})$alkyl; or halogen-$(C_{1-8})$alkyl; and
each of $R_{11}$ and $R_{12}$ is independently selected from the group, consisting of hydrogen, methyl, fluoromethyl, difluoromethyl and trifluoromethyl;
in free form or in salt form.

In yet another embodiment, the invention relates to a compound of the formula Id
in which
$R_2$ is a pyridyl or pyrazinyl group which is substituted by 1, 2, 3 or 4 substituents and wherein one of the substituents is located at the para position of the pyridyl or pyrazinyl group relative to the amide linker and wherein the substituents are independently selected from the group, consisting of cyano, halogen $(C_{1-6})$alkyl, $(C_{1-6})$alkoxy, $(C_{1-6})$alkoxy-$(C_{1-6})$alkoxy, halogen-$(C_{1-6})$alkyl and $(C_{2-6})$alkynoxy;
$R_4$ is hydrogen; or halogen;
$R_5$ is hydrogen; or halogen;
$R_6$ is methyl, fluoromethyl or di-fluoromethyl; and
each of $R_{11}$ and $R_{12}$ is independently selected from the group, consisting of hydrogen, methyl, fluoromethyl, difluoromethyl and trifluoromethyl;
in free form or in salt form.

In particular embodiments, the invention relates to one or more than one, e.g. all, of the compounds of the formula I mentioned in the Examples hereinafter, in free form or in salt form. In one embodiment, the invention relates to one of the compounds of the formula I mentioned in the Examples hereinafter, in free form. In another embodiment, the invention relates to one of the compounds of the formula I mentioned in the Examples hereinafter, in salt form. In a further embodiment, the invention relates to one of the compounds of the formula I mentioned in the Examples hereinafter, in pharmaceutically acceptable salt form. In yet a further embodiment, the invention relates to one of the compounds of the formula I mentioned in the Examples hereinafter, in hydrochloride salt form.

In another embodiment, the invention relates to a compound of the invention, or a pharmaceutically acceptable salt thereof, which is selected from:

Furan-2-carboxylic acid [3-(5-amino-3-methyl-3,6-dihydro-2H-[1,4]oxazin-3-yl)-phenyl]-amide;
5-Bromo-pyridine-2-carboxylic acid [3-(5-amino-3-methyl-3,6-dihydro-2H-[1,4]oxazin-3-yl)-phenyl]-amide;
5-Bromo-pyridine-2-carboxylic acid [3-(5-amino-3-methyl-3,6-di-hydro-2H-[1,4]oxazin-3-yl)-phenyl]-amide;
5-Bromo-pyridine-2-carboxylic acid [3-(5-amino-3-methyl-3,6-di-hydro-2H-[1,4]oxazin-3-yl)-phenyl]-amide;
2-Methyl-oxazole-4-carboxylic acid [3-(5-amino-3-methyl-3,6-dihydro-2H-[1,4]oxazin-3-yl)-phenyl]-amide;
5-Methyl-pyrazine-2-carboxylic acid [3-(5-amino-3-methyl-3,6-dihydro-2H-[1,4]oxazin-3-yl)-phenyl]-amide;
5-Bromo-pyrimidine-2-carboxylic acid [3-(5-amino-3-methyl-3,6-dihydro-2H-[1,4]oxazin-3-yl)-phenyl]-amide;
Imidazo[1,2-a]pyridine-2-carboxylic acid [3-(5-amino-3-methyl-3,6-dihydro-2H-[1,4]oxazin-3-yl)-phenyl]-amide;
3-Fluoro-pyridine-2-carboxylic acid [3-(5-amino-3-methyl-3,6-dihydro-2H-[1,4]oxazin-3-yl)-phenyl]-amide;
2,5-Dimethyl-oxazole-4-carboxylic acid [3-(5-amino-3-methyl-3,6-dihydro-2H-[1,4]oxazin-3-yl)-phenyl]-amide;
2-Methyl-thiazole-4-carboxylic acid [3-(5-amino-3-methyl-3,6-dihydro-2H-[1,4]oxazin-3-yl)-phenyl]-amide;
6-Hydroxy-pyridazine-3-carboxylic acid [3-(5-amino-3-methyl-3,6-dihydro-2H-[1,4]oxazin-3-yl)-phenyl]-amide;
Pyridine-2-carboxylic acid [3-(5-amino-3-methyl-3,6-dihydro-2H-[1,4]oxazin-3-yl)-phenyl]-amide;
5-Cyano-pyridine-2-carboxylic acid [3-(5-amino-3-methyl-3,6-dihydro-2H-[1,4]oxazin-3-yl)-phenyl]-amide;
5-(3-Trifluoromethyl-pyrazol-1-yl)-pyrazine-2-carboxylic acid [3-(5-amino-3-methyl-3,6-dihydro-2H-[1,4]oxazin-3-yl)-phenyl]-amide;
5-(3-Methyl-pyrazol-1-yl)-pyrazine-2-carboxylic acid [3-(5-amino-3-methyl-3,6-dihydro-2H-[1,4]oxazin-3-yl)-phenyl]-amide;
3-Chloro-5-trifluoromethyl-pyridine-2-carboxylic acid [3-(5-amino-3-methyl-3,6-dihydro-2H-[1,4]oxazin-3-yl)-phenyl]-amide;
5-Methoxy-pyrazine-2-carboxylic acid [3-(5-amino-3-methyl-3,6-dihydro-2H-[1,4]oxazin-3-yl)-phenyl]-amide;
5-Hydroxy-pyrazine-2-carboxylic acid [3-(5-amino-3-methyl-3,6-dihydro-2H-[1,4]oxazin-3-yl)-phenyl]-amide;
4-Bromo-furan-2-carboxylic acid [3-(5-amino-3-methyl-3,6-dihydro-2H-[1,4]oxazin-3-yl)-phenyl]-amide;
5-Chloro-pyridine-2-carboxylic acid [3-(5-amino-3-methyl-3,6-dihydro-2H-[1,4]oxazin-3-yl)-phenyl]-amide;
5-Trifluoromethyl-pyridine-2-carboxylic acid [3-(5-amino-3-methyl-3,6-dihydro-2H-[1,4]oxazin-3-yl)-phenyl]-amide;
5-Trifluoromethyl-furan-3-carboxylic acid [3-(5-amino-3-methyl-3,6-dihydro-2H-[1,4]oxazin-3-yl)-phenyl]-amide;
N-[3-(5-Amino-3-methyl-3,6-dihydro-2H-[1,4]oxazin-3-yl)-phenyl]-4-bromo-benzamide;
5-Methyl-pyridine-2-carboxylic acid [3-(5-amino-3-methyl-3,6-dihydro-2H-[1,4]oxazin-3-yl)-phenyl]-amide;
N-[3-(5-Amino-3-methyl-3,6-dihydro-2H-[1,4]oxazin-3-yl)-phenyl]-nicotinamide;
5-Bromo-3-methyl-pyridine-2-carboxylic acid [3-(5-amino-3-methyl-3,6-dihydro-2H-[1,4]oxazin-3-yl)-phenyl]-amide;
5-Methoxy-pyridine-2-carboxylic acid [3-(5-amino-3-methyl-3,6-dihydro-2H-[1,4]oxazin-3-yl)-phenyl]-amide;
5-Bromo-pyridine-2-carboxylic acid [3-(5-amino-3-fluoromethyl-3,6-dihydro-2H-[1,4]oxazin-3-yl)-phenyl]-amide;
5-Bromo-pyridine-2-carboxylic acid [3-(5-amino-3-fluoromethyl-3,6-dihydro-2H-[1,4]oxazin-3-yl)-5-chlorophenyl]-amide;
5-Bromo-pyridine-2-carboxylic acid [3-(5-amino-3-fluoromethyl-3,6-dihydro-2H-[1,4]oxazin-3-yl)-phenyl]-amide;
5-Bromo-pyridine-2-carboxylic acid [3-(5-amino-3-difluoromethyl-3,6-dihydro-2H-[1,4]oxazin-3-yl)-phenyl]-amide;
5-Chloro-pyridine-2-carboxylic acid [3-(5-amino-3-difluoromethyl-3,6-dihydro-2H-[1,4]oxazin-3-yl)-phenyl]-amide;
5-Cyano-pyridine-2-carboxylic acid [3-(5-amino-3-difluoromethyl-3,6-dihydro-2H-[1,4]oxazin-3-yl)-phenyl]-amide;
5-Bromo-3-methyl-pyridine-2-carboxylic acid [3-(5-amino-3-difluoromethyl-3,6-dihydro-2H-[1,4]oxazin-3-yl)-phenyl]-amide;
5-Methyl-pyrazine-2-carboxylic acid [3-(5-amino-3-difluoromethyl-3,6-dihydro-2H-[1,4]oxazin-3-yl)-phenyl]-amide;
5-Trifluoromethyl-pyridine-2-carboxylic acid [3-(5-amino-3-difluoromethyl-3,6-dihydro-2H-[1,4]oxazin-3-yl)-phenyl]-amide;
3-Chloro-5-trifluoromethyl-pyridine-2-carboxylic acid [3-(5-amino-3-difluoromethyl-3,6-dihydro-2H-[1,4]oxazin-3-yl)-phenyl]-amide;
5-Chloro-3-methyl-pyridine-2-carboxylic acid [3-(5-amino-3-difluoromethyl-3,6-dihydro-2H-[1,4]oxazin-3-yl)-phenyl]-amide;
5-Bromo-pyridine-2-carboxylic acid [3-(5-amino-3-difluoromethyl-3,6-dihydro-2H-[1,4]oxazin-3-yl)-4-fluorophenyl]-amide;
5-Chloro-pyridine-2-carboxylic acid [3-(5-amino-3-difluoromethyl-3,6-dihydro-2H-[1,4]oxazin-3-yl)-4-fluorophenyl]-amide;
5-Chloro-3-methyl-pyridine-2-carboxylic acid [3-(5-amino-3-difluoromethyl-3,6-dihydro-2H-[1,4]oxazin-3-yl)-4-fluoro-phenyl]-amide;
5-Bromo-3-methyl-pyridine-2-carboxylic acid [3-(5-amino-3-difluoromethyl-3,6-dihydro-2H-[1,4]oxazin-3-yl)-4-fluoro-phenyl]-amide;
3-Chloro-5-trifluoromethyl-pyridine-2-carboxylic acid [3-(5-amino-3-difluoromethyl-3,6-dihydro-2H-[1,4]oxazin-3-yl)-4-fluoro-phenyl]-amide;
5-Trifluoromethyl-pyridine-2-carboxylic acid [3-(5-amino-3-difluoromethyl-3,6-dihydro-2H-[1,4]oxazin-3-yl)-4-fluoro-phenyl]-amide;
5-Methyl-pyrazine-2-carboxylic acid [3-(5-amino-3-difluoromethyl-3,6-dihydro-2H-[1,4]oxazin-3-yl)-4-fluoro-phenyl]-amide;

5-Methoxy-pyridine-2-carboxylic acid [3-(5-amino-3-difluoromethyl-3,6-dihydro-2H-[1,4]oxazin-3-yl)-4-fluoro-phenyl]-amide;
5-Chloro-pyridine-2-carboxylic acid [3-(5-amino-3-trifluoromethyl-3,6-dihydro-2H-[1,4]oxazin-3-yl)-4-fluoro-phenyl]-amide;
5-Bromo-pyrimidine-2-carboxylic acid [3-(5-amino-3-methyl-3,6-dihydro-2H-[1,4]oxazin-3-yl)-5-bromo-phenyl]-amide;
5-Bromo-pyridine-2-carboxylic acid [3-(5-amino-3-methyl-3,6-dihydro-2H-[1,4]oxazin-3-yl)-5-bromo-phenyl]-amide;
5-Cyano-pyridine-2-carboxylic acid [3-(5-amino-3-methyl-3,6-dihydro-2H-[1,4]oxazin-3-yl)-5-bromo-phenyl]-amide;
5-Trifluoromethyl-pyridine-2-carboxylic acid [3-(5-amino-3-methyl-3,6-dihydro-2H-[1,4]oxazin-3-yl)-5-bromo-phenyl]-amide;
5-Bromo-3-methyl-pyridine-2-carboxylic acid [3-(5-amino-3-methyl-3,6-dihydro-2H-[1,4]oxazin-3-yl)-5-bromo-phenyl]-amide;
5-Chloro-pyridine-2-carboxylic acid [3-(5-amino-3-methyl-3,6-dihydro-2H-[1,4]oxazin-3-yl)-5-bromo-phenyl]-amide;
5-Methyl-pyrazine-2-carboxylic acid [3-(5-amino-3-methyl-3,6-dihydro-2H-[1,4]oxazin-3-yl)-5-bromo-phenyl]-amide;
2,5-Dimethyl-oxazole-4-carboxylic acid [3-(5-amino-3-methyl-3,6-dihydro-2H-[1,4]oxazin-3-yl)-5-bromo-phenyl]-amide;
2-Methyl-oxazole-4-carboxylic acid [3-(5-amino-3-methyl-3,6-dihydro-2H-[1,4]oxazin-3-yl)-5-bromo-phenyl]-amide;
5-Bromo-pyridine-2-carboxylic acid [3-(5-amino-3-methyl-3,6-dihydro-2H-[1,4]oxazin-3-yl)-4-fluoro-phenyl]-amide;
5-Methyl-pyrazine-2-carboxylic acid [3-(5-amino-3-methyl-3,6-dihydro-2H-[1,4]oxazin-3-yl)-4-fluoro-phenyl]-amide;
5-Cyano-pyridine-2-carboxylic acid [3-(5-amino-3-methyl-3,6-dihydro-2H-[1,4]oxazin-3-yl)-4-fluoro-phenyl]-amide;
5-Chloro-pyridine-2-carboxylic acid [3-(5-amino-3-methyl-3,6-dihydro-2H-[1,4]oxazin-3-yl)-4-fluoro-phenyl]-amide;
5-Bromo-3-methyl-pyridine-2-carboxylic acid [3-(5-amino-3-methyl-3,6-dihydro-2H-[1,4]oxazin-3-yl)-4-fluoro-phenyl]-amide;
Pyridine-2,5-dicarboxylic acid 5-amide 2-{[3-(5-amino-3-methyl-3,6-dihydro-2H-[1,4]oxazin-3-yl)-4-fluoro-phenyl]-amide};
5-Bromo-pyridine-2-carboxylic acid [3-(5-amino-3,6-dimethyl-6-trifluoromethyl-3,6-dihydro-2H-[1,4]oxazin-3-yl)-phenyl]-amide;
5-Methoxy-pyridine-2-carboxylic acid [3-(5-amino-3,6-dimethyl-6-trifluoromethyl-3,6-dihydro-2H-[1,4]oxazin-3-yl)-phenyl]-amide;
5-Bromo-pyridine-2-carboxylic acid [3-(5-amino-3,6-dimethyl-6-trifluoromethyl-3,6-di-hydro-2H-[1,4]oxazin-3-yl)-4-fluoro-phenyl]-amide;
5-Methoxy-pyridine-2-carboxylic acid [3-(5-amino-3,6-dimethyl-6-trifluoromethyl-3,6-di-hydro-2H-[1,4]oxazin-3-yl)-4-fluoro-phenyl]-amide;
5-Cyano-pyrimidine-2-carboxylic acid [3-(5-amino-3,6-dimethyl-6-trifluoromethyl-3,6-di-hydro-2H-[1,4]oxazin-3-yl)-4-fluoro-phenyl]-amide;
5-Bromo-pyrimidine-2-carboxylic acid [3-(5-amino-3,6-dimethyl-6-trifluoromethyl-3,6-dihydro-2H-[1,4]oxazin-3-yl)-4-fluoro-phenyl]-amide;
5-Cyano-3-methyl-pyridine-2-carboxylic acid [3-((5-amino-3,6-dimethyl-6-trifluoro-methyl-3,6-dihydro-2H-[1,4]oxazin-3-yl)-4-fluoro-phenyl]-amide;
5-Cyano-pyridine-2-carboxylic acid [3-(5-amino-3,6-dimethyl-6-trifluoro-methyl-3,6-dihydro-2H-[1,4]oxazin-3-yl)-4-fluoro-phenyl]-amide;
5-(2-Methoxy-ethoxy)-pyrazine-2-carboxylic acid [3-(5-amino-3,6-dimethyl-6-trifluoromethyl-3,6-dihydro-2H-[1,4]oxazin-3-yl)-4-fluoro-phenyl]-amide;
Cyano-pyridine-2-carboxylic acid [3-(5-amino-3-difluoromethyl-6-methyl-3,6-dihydro-2H-[1,4]oxazin-3-yl)-4-fluoro-phenyl]-amide;
Cyano-pyridine-2-carboxylic acid [3-(5-amino-3-difluoromethyl-6-methyl-3,6-dihydro-2H-[1,4]oxazin-3-yl)-4-fluoro-phenyl]-amide;
5-Bromo-pyridine-2-carboxylic acid [3-(5-amino-3-difluoromethyl-6-methyl-3,6-dihydro-2H-[1,4]oxazin-3-yl)-4-fluoro-phenyl]-amide;
5-Bromo-pyridine-2-carboxylic acid[3-(5-amino-3-difluoromethyl-6-methyl-3,6-dihydro-2H-[1,4]oxazin-3-yl)-4-fluoro-phenyl]-amide;
5-Cyano-pyridine-2-carboxylic acid [3-(5-amino-3-difluoromethyl-6,6-dimethyl-3,6-dihydro-2H-[1,4]oxazin-3-yl)-4-fluoro-phenyl]-amide;
5-Bromo-pyridine-2-carboxylic acid [3-(5-amino-3-difluoromethyl-6,6-dimethyl-3,6-dihydro-2H-[1,4]oxazin-3-yl)-4-fluoro-phenyl]-amide;
5-Bromo-pyridine-2-carboxylic acid [5-(5-amino-3-difluoromethyl-3,6-dihydro-2H-[1,4]oxazin-3-yl)-2,4-difluoro-phenyl]-amide;
5-Cyano-pyridine-2-carboxylic acid [5-(5-amino-3-difluoromethyl-3,6-dihydro-2H-[1,4]oxazin-3-yl)-2,4-difluoro-phenyl]-amide;
5-Bromo-3-methoxy-pyridine-2-carboxylic acid [5-(5-amino-3-difluoromethyl-3,6-dihydro-2H-[1,4]oxazin-3-yl)-2,4-difluoro-phenyl]-amide;
5-Bromo-3-hydroxy-pyridine-2-carboxylic acid [5-(5-amino-3-difluoromethyl-3,6-dihydro-2H-[1,4]oxazin-3-yl)-2,4-difluoro-phenyl]-amide;
5-Chloro-pyridine-2-carboxylic acid [3-(5-amino-3-fluoromethyl-3,6-dihydro-2H-[1,4]oxazin-3-yl)-4-fluoro-phenyl]-amide;
5-Bromo-pyridine-2-carboxylic acid [3-(5-amino-3-fluoromethyl-3,6-dihydro-2H-[1,4]oxazin-3-yl)-4-fluoro-phenyl]-amide;
5-Chloro-pyridine-2-carboxylic acid [3-(5-amino-3-fluoromethyl-3,6-dihydro-2H-[1,4]oxazin-3-yl)-4-fluoro-phenyl]-amide;
3,5-Dichloro-pyridine-2-carboxylic acid [3-(5-amino-3-fluoromethyl-3,6-dihydro-2H-[1,4]oxazin-3-yl)-4-fluoro-phenyl]-amide;
5-Cyano-pyridine-2-carboxylic acid [3-(5-amino-3-fluoromethyl-3,6-dihydro-2H-[1,4]oxazin-3-yl)-4-fluoro-phenyl]-amide;
5-Bromo-3-methyl-pyridine-2-carboxylic acid [3-(5-amino-3-fluoromethyl-3,6-dihydro-2H-[1,4]oxazin-3-yl)-4-fluoro-phenyl]-amide;
5-Bromo-3-methyl-pyridine-2-carboxylic acid [3-(5-amino-3-fluoromethyl-3,6-dihydro-2H-[1,4]oxazin-3-yl)-4-fluoro-phenyl]-amide;
5-Chloro-3-methyl-pyridine-2-carboxylic acid [3-(5-amino-3-fluoromethyl-3,6-dihydro-2H-[1,4]oxazin-3-yl)-4-fluoro-phenyl]-amide;

5-Chloro-4,6-dideutero-3-trideuteromethyl-pyridine-2-carboxylic acid [3-(5-amino-3-fluoromethyl-3,6-dihydro-2H-[1,4]oxazin-3-yl)-4-fluoro-phenyl]-amide;
5-Bromo-3-hydroxy-pyridine-2-carboxylic acid [3-(5-amino-3-fluoromethyl-3,6-dihydro-2H-[1,4]oxazin-3-yl)-4-fluoro-phenyl]-amide;
5-Bromo-3-methoxy-pyridine-2-carboxylic acid [3-(5-amino-3-fluoromethyl-3,6-dihydro-2H-[1,4]oxazin-3-yl)-4-fluoro-phenyl]-amide;
5-Bromo-pyridine-2-carboxylic acid[3-(3-amino-5-difluoromethyl-2,5,6,7-tetrahydro-[1,4]oxazepin-5-yl)-4-fluoro-phenyl]-amide;
5-Bromo-pyridine-2-carboxylic acid[3-(3-amino-5-difluoromethyl-2,5,6,7-tetrahydro-[1,4]oxazepin-5-yl)-4-fluoro-phenyl]-amide;
5-Cyano-pyridine-2-carboxylic acid [3-(3-amino-5-trifluoromethyl-2,5,6,7-tetrahydro-[1,4]oxazepin-5-yl)-4-fluoro-phenyl]-amide;
5-Bromo-pyridine-2-carboxylic acid [3-(3-amino-5-trifluoromethyl-2,5,6,7-tetrahydro-[1,4]oxazepin-5-yl)-4-fluoro-phenyl]-amide;
N-(3-(3-amino-6,6-difluoro-5-methyl-2,5,6,7-tetrahydro-1,4-oxazepin-5-yl)-4-fluorophenyl)-5-chloropicolinamide;
5-Bromo-pyridine-2-carboxylic acid [3-(3-amino-6,6-difluoro-5-methyl-2,5,6,7-tetrahydro-[1,4]oxazepin-5-yl)-4-fluoro-phenyl]-amide;
4-Bromo-furan-2-carboxylic acid [3-(5-amino-3-difluoromethyl-3,6-dihydro-2H-[1,4]oxazin-3-yl)-phenyl]-amide;
6-Hydroxy-pyridazine-3-carboxylic acid [3-(5-amino-3-difluoromethyl-3,6-dihydro-2H-[1,4]oxazin-3-yl)-phenyl]-amide;
2-Methyl-oxazole-4-carboxylic acid [3-(5-amino-3-difluoromethyl-3,6-dihydro-2H-[1,4]oxazin-3-yl)-phenyl]-amide;
2-Ethyl-oxazole-4-carboxylic acid [3-(5-amino-3-difluoromethyl-3,6-dihydro-2H-[1,4]oxazin-3-yl)-phenyl]-amide;
2,5-Dimethyl-oxazole-4-carboxylic acid [3-(5-amino-3-difluoromethyl-3,6-dihydro-2H-[1,4]oxazin-3-yl)-phenyl]-amide;
5-Bromo-3-methoxy-pyridine-2-carboxylic acid [3-(5-amino-3-difluoromethyl-3,6-dihydro-2H-[1,4]oxazin-3-yl)-phenyl]-amide;
5-Bromo-3-hydroxy-pyridine-2-carboxylic acid [3-(5-amino-3-difluoromethyl-3,6-dihydro-2H-[1,4]oxazin-3-yl)-phenyl]-amide;
5-(2-Methoxy-ethoxy)-pyridine-2-carboxylic acid [3-(5-amino-3-difluoromethyl-3,6-dihydro-2H-[1,4]oxazin-3-yl)-phenyl]-amide;
5-Difluoromethyl-pyrazine-2-carboxylic acid [3-(5-amino-3-difluoromethyl-3,6-dihydro-2H-[1,4]oxazin-3-yl)-phenyl]-amide;
3,5-Dichloro-pyridine-2-carboxylic acid [3-(5-amino-3-difluoromethyl-3,6-dihydro-2H-[1,4]oxazin-3-yl)-4-fluoro-phenyl]-amide;
5-Cyano-pyridine-2-carboxylic acid [3-(5-amino-3-difluoromethyl-3,6-dihydro-2H-[1,4]oxazin-3-yl)-4-fluoro-phenyl]-amide;
3,5-Difluoro-pyridine-2-carboxylic acid [3-(5-amino-3-difluoromethyl-3,6-dihydro-2H-[1,4]oxazin-3-yl)-4-fluoro-phenyl]-amide;
5-Bromo-3-methyl-benzofuran-2-carboxylic acid [3-(5-amino-3-difluoromethyl-3,6-dihydro-2H-[1,4]oxazin-3-yl)-4-fluoro-phenyl]-amide;
5-Chloro-4,6-dideutero-3-trideuteromethyl-pyridine-2-carboxylic acid [3-(5-amino-3-difluoromethyl-3,6-dihydro-2H-[1,4]oxazin-3-yl)-4-fluoro-phenyl]-amide;
5-Bromo-4,6-dideutero-3-trideuteromethyl-pyridine-2-carboxylic acid [3-(5-amino-3-difluoromethyl-3,6-dihydro-2H-[1,4]oxazin-3-yl)-4-fluoro-phenyl]-amide;
5-Bromo-3-chloro-pyridine-2-carboxylic acid [3-(5-amino-3-difluoromethyl-3,6-dihydro-2H-[1,4]oxazin-3-yl)-4-fluoro-phenyl]-amide;
5-Bromo-pyridine-2-carboxylic acid [3-(5-amino-3-difluoromethyl-3,6-dihydro-2H-[1,4]oxazin-3-yl)-4-fluoro-phenyl]-amide;
5-Bromo-3-hydroxy-pyridine-2-carboxylic acid [3-(5-amino-3-difluoromethyl-3,6-dihydro-2H-[1,4]oxazin-3-yl)-4-fluoro-phenyl]-amide;
5-Ethoxy-pyridine-2-carboxylic acid [3-(5-amino-3-difluoromethyl-3,6-dihydro-2H-[1,4]oxazin-3-yl)-4-fluoro-phenyl]-amide;
5-Chloro-pyrimidine-2-carboxylic acid [3-(5-amino-3-difluoromethyl-3,6-dihydro-2H-[1,4]oxazin-3-yl)-4-fluoro-phenyl]-amide;
5-Difluoromethyl-pyrazine-2-carboxylic acid [3-(5-amino-3-difluoromethyl-3,6-dihydro-2H-[1,4]oxazin-3-yl)-4-fluoro-phenyl]-amide;
5-(2,2-Difluoro-ethoxy)-pyrazine-2-carboxylic acid [3-(5-amino-3-difluoromethyl-3,6-dihydro-2H-[1,4]oxazin-3-yl)-4-fluoro-phenyl]-amide;
5-(2,2,2-Trifluoro-ethoxy)-pyrazine-2-carboxylic acid [3-(5-amino-3-difluoromethyl-3,6-dihydro-2H-[1,4]oxazin-3-yl)-4-fluoro-phenyl]-amide;
4-Bromo-furan-2-carboxylic acid [3-(5-amino-3-difluoromethyl-3,6-dihydro-2H-[1,4]oxazin-3-yl)-4-fluoro-phenyl]-amide;
Pyrazolo[1,5-a]pyridine-2-carboxylic acid [3-(5-amino-3 difluoromethyl-3,6-dihydro-2H [1,4]oxazin-3-yl)-4-fluoro-phenyl]-amide;
2-Methyl-oxazole-4-carboxylic acid [3-(5-amino-3-difluoromethyl-3,6-dihydro-2H-[1,4]oxazin-3-yl)-4-fluoro-phenyl]-amide;
2,5-Dimethyl-oxazole-4-carboxylic acid [3-(5-amino-3-difluoromethyl-3,6-dihydro-2H-[1,4]oxazin-3-yl)-4-fluoro-phenyl]-amide;
Imidazo[1,2-a]pyridine-2-carboxylic acid [3-(5-amino-3-difluoromethyl-3,6-dihydro-2H-[1,4]oxazin-3-yl)-4-fluoro-phenyl]-amide;
5-Bromo-3-methoxy-pyridine-2-carboxylic acid [3-(5-amino-3-difluoromethyl-3,6-dihydro-2H-[1,4]oxazin-3-yl)-4-fluoro-phenyl]-amide;
2-Ethyl-oxazole-4-carboxylic acid [3-(5-amino-3-difluoromethyl-3,6-dihydro-2H-[1,4]oxazin-3-yl)-4-fluoro-phenyl]-amide;
5-Difluoromethyl-pyridine-2-carboxylic acid [3-(5-amino-3-difluoromethyl-3,6-dihydro-2H-[1,4]oxazin-3-yl)-4-fluoro-phenyl]-amide;
1-Methyl-1H-imidazole-2 carboxylic acid [3-(5-amino-3 difluoromethyl-3,6-dihydro-2H [1,4]oxazin-3-yl)-4-fluoro-phenyl]-amide;
6-Hydroxy-pyridazine-3-carboxylic acid [3-(5-amino-3-difluoromethyl-3,6-dihydro-2H-[1,4]oxazin-3-yl)-4-fluoro-phenyl]-amide;
5-(2-Methoxy-ethoxy)-pyrazine-2-carboxylic acid [3-(5-amino-3-difluoromethyl-3,6-dihydro-2H-[1,4]oxazin-3-yl)-4-fluoro-phenyl]-amide;
5-(2-Fluoro-ethoxy)-pyrazine-2-carboxylic acid [3-(5-amino-3-difluoromethyl-3,6-dihydro-2H-[1,4]oxazin-3-yl)-4-fluoro-phenyl]-amide;
5-Chloro-pyridine-2-carboxylic acid [3-(5-amino-3-difluoromethyl-3,6-dihydro-2H-[1,4]oxazin-3-yl)-4-fluoro-phenyl]-amide;

5-Difluoromethoxy-pyridine-2-carboxylic acid [3-(5-amino-3-difluoromethyl-3,6-dihydro-2H-[1,4]oxazin-3-yl)-4-fluoro-phenyl]-amide;

5-Fluoromethoxy-pyridine-2-carboxylic acid [3-(5-amino-3-difluoromethyl-3,6-dihydro-2H-[1,4]oxazin-3-yl)-4-fluoro-phenyl]-amide;

5-Chloro-3-fluoro-pyridine-2-carboxylic acid [3-(5-amino-3-difluoromethyl-3,6-dihydro-2H-[1,4]oxazin-3-yl)-4-fluoro-phenyl]-amide;

5-Chloro-pyrazine-2-carboxylic acid [3-(5-amino-3-difluoromethyl-3,6-dihydro-2H-[1,4]oxazin-3-yl)-4-fluoro-phenyl]-amide;

5-Methyl-1H-pyrazole-3-carboxylic acid [3-(5-amino-3-difluoromethyl-3,6-dihydro-2H-[1,4]oxazin-3-yl)-4-fluoro-phenyl]-amide;

5-Methyl-pyridine-2-carboxylic acid [3-(5-amino-3-difluoromethyl-3,6-dihydro-2H-[1,4]oxazin-3-yl)-4-fluoro-phenyl]-amide;

5-Cyano-3-methyl-pyridine-2-carboxylic acid [3-(5-amino-3-difluoromethyl-3,6-dihydro-2H-[1,4]oxazin-3-yl)-4-fluoro-phenyl]-amide;

5-Hydroxy-pyrazine-2-carboxylic acid [3-(5-amino-3-difluoromethyl-3,6-dihydro-2H-[1,4]oxazin-3-yl)-4-fluoro-phenyl]-amide;

5-Methoxy-pyrazine-2-carboxylic acid [3-(5-amino-3-difluoromethyl-3,6-dihydro-2H-[1,4]oxazin-3-yl)-4-fluoro-phenyl]-amide;

5-Cyano-4,6-dideutero-3-trideuteromethyl-pyridine-2-carboxylic acid [3-(5-amino-3-difluoromethyl-3,6-dihydro-2H-[1,4]oxazin-3-yl)-4-fluoro-phenyl]-amide;

2-Methyl-thiazole-4-carboxylic acid [3-(5-amino-3-difluoromethyl-3,6-dihydro-2H-[1,4]oxazin-3-yl)-4-fluoro-phenyl]-amide;

5-Methyl-thiazole-2-carboxylic acid [3-(5-amino-3-difluoromethyl-3,6-dihydro-2H-[1,4]oxazin-3-yl)-4-fluoro-phenyl]-amide;

1-Methyl-1H-pyrazole-3-carboxylic acid [3-(5-amino-3-difluoromethyl-3,6-dihydro-2H-[1,4]oxazin-3-yl)-4-fluoro-phenyl]-amide;

1-Methyl-4-nitro-1H-pyrazole-3-carboxylic acid [3-(5-amino-3-difluoromethyl-3,6-dihydro-2H-[1,4]oxazin-3-yl)-4-fluoro-phenyl]-amide;

3-Amino-5-chloro-pyridine-2-carboxylic acid [3-(5-amino-3,6-dimethyl-6-trifluoromethyl-3,6-dihydro-2H-[1,4]oxazin-3-yl)-4-fluoro-phenyl]-amide;

3-Chloro-5-trifluoromethyl-pyridine-2-carboxylic acid [3-(3-amino-6,6-difluoro-5-methyl-2,5,6,7-tetrahydro-[1,4]oxazepin-5-yl)-4-fluoro-phenyl]-amide;

5-Bromo-3-methoxy-pyridine-2-carboxylic acid [3-(3-amino-6,6 difluoro-5-methyl-2,5,6,7 tetrahydro-[1,4]oxazepin-5-yl)-4 fluoro-phenyl]-amide;

5-Cyano-pyridine-2-carboxylic acid [3-(3-amino-6,6-difluoro-5 methyl-2,5,6,7-tetrahydro[1,4]oxazepin-5-yl)-4 fluoro-phenyl]-amide;

7H-Pyrrolo[2,3-d]pyrimidine-6-carboxylic acid [3-(5-amino-3-difluoromethyl-3,6-dihydro-2H-[1,4]oxazin-3-yl)-4-fluoro-phenyl]-amide;

3-Amino-5-(2-methoxy-ethoxy)-pyrazine-2-carboxylic acid [3-(5-amino-3-difluoromethyl-3,6-dihydro-2H-[1,4]oxazin-3-yl)-4-fluoro-phenyl]-amide;

(5-Difluoromethyl-5-{5-[(5-ethyl-pyridine-2-carbonyl)-amino]-2-fluoro-phenyl}-5,6-dihydro-2H-[1,4]oxazin-3-yl)-carbamic acid tert-butyl ester;

3-Amino-5-chloro-pyridine-2-carboxylic acid [3-(5-amino-3-difluoromethyl-3,6-dihydro-2H-[1,4]oxazin-3-yl)-4-fluoro-phenyl]-amide;

3-Chloro-5-methoxy-pyridine-2-carboxylic acid [3-(5-amino-3-difluoromethyl-3,6-dihydro-2H-[1,4]oxazin-3-yl)-4-fluoro-phenyl]-amide;

6-Oxo-1,6-dihydro-pyridine-3-carboxylic acid [3-(5-amino-3-difluoromethyl-3,6-dihydro-2H-[1,4]oxazin-3-yl)-4-fluoro-phenyl]-amide;

Pyrrolo[1,2-c]pyrimidine-3-carboxylic acid [3-(5-amino-3-difluoromethyl-3,6-dihydro-2H-[1,4]oxazin-3-yl)-4-fluoro-phenyl]-amide;

5-But-2-ynyloxy-pyrazine-2-carboxylic acid [3-(5-amino-3-difluoromethyl-3,6-dihydro-2H-[1,4]oxazin-3-yl)-4-fluoro-phenyl]-amide;

3-Amino-5-bromo-pyridine-2-carboxylic acid [3-(5-amino-3-difluoromethyl-3,6-dihydro-2H-[1,4]oxazin-3-yl)-4-fluoro-phenyl]-amide;

1-Ethyl-1H-imidazole-2-carboxylic acid [3-(5-amino-3-difluoromethyl-3,6-dihydro-2H-[1,4]oxazin-3-yl)-4-fluoro-phenyl]-amide;

5-Prop-2-ynyloxy-pyrazine-2-carboxylic acid [3-(5-amino-3-difluoromethyl-3,6-dihydro-2H-[1,4]oxazin-3-yl)-4-fluoro-phenyl]-amide;

5-Amino-2-methyl-oxazole-4-carboxylic acid [3-(5-amino-3-difluoromethyl-3,6-dihydro-2H-[1,4]oxazin-3-yl)-4-fluoro-phenyl]-amide;

5-Chloro-3-hydroxy-pyridine-2-carboxylic acid [3-(5-amino-3-difluoromethyl-3,6-dihydro-2H-[1,4]oxazin-3-yl)-4-fluoro-phenyl]-amide;

5-Isopropoxy-pyrazine-2-carboxylic acid [3-(5-amino-3-difluoromethyl-3,6-dihydro-2H-[1,4]oxazin-3-yl)-4-fluoro-phenyl]-amide;

5-Ethoxy-pyrazine-2-carboxylic acid [3-(5-amino-3-difluoromethyl-3,6-dihydro-2H-[1,4]oxazin-3-yl)-4-fluoro-phenyl]-amide;

5-Dimethylaminomethyl-3-methyl-benzofuran-2-carboxylic acid [3-(5-amino-3-difluoromethyl-3,6-dihydro-2H-[1,4]oxazin-3-yl)-4-fluoro-phenyl]-amide;

1,5-Dimethyl-1H-[1,2,3]triazole-4-carboxylic acid [3-(5-amino-3-difluoromethyl-3,6-dihydro-2H-[1,4]oxazin-3-yl)-4-fluoro-phenyl]-amide;

5-Methoxy-3-methyl-pyrazine-2-carboxylic acid [3-(5-amino-3-difluoromethyl-3,6-dihydro-2H-[1,4]oxazin-3-yl)-4-fluoro-phenyl]-amide;

3-Amino-5-methoxy-pyrazine-2-carboxylic acid [3-(5-amino-3-difluoromethyl-3,6-dihydro-2H-[1,4]oxazin-3-yl)-4-fluoro-phenyl]-amide;

5-Difluoromethoxy-3-methyl-pyridine-2-carboxylic acid [3-(5-amino-3-difluoromethyl-3,6-dihydro-2H-[1,4]oxazin-3-yl)-4-fluoro-phenyl]-amide;

5-Fluoromethoxy-3-methyl-pyridine-2-carboxylic acid [3-(5-amino-3-difluoromethyl-3,6-dihydro-2H-[1,4]oxazin-3-yl)-4-fluoro-phenyl]-amide;

5-(2-Methoxy-ethoxy)-3-methyl-pyrazine-2-carboxylic acid [3-(5-amino-3-difluoromethyl-3,6-dihydro-2H-[1,4]oxazin-3-yl)-4-fluoro-phenyl]-amide;

3,5-Dimethoxy-pyridine-2-carboxylic acid [3-(5-amino-3-difluoromethyl-3,6-dihydro-2H-[1,4]oxazin-3-yl)-4-fluoro-phenyl]-amide;

5-(2-Methoxy-ethoxy)-pyridine-2-carboxylic acid [3-(5-amino-3-difluoromethyl-3,6-dihydro-2H-[1,4]oxazin-3-yl)-4-fluoro-phenyl]-amide;

3-Fluoro-5-(2-methoxy-ethoxy)-pyridine-2-carboxylic acid [3-(5-amino-3-difluoromethyl-3,6-dihydro-2H-[1,4]oxazin-3-yl)-4-fluoro-phenyl]-amide;

5-But-2-ynyloxy-3-methyl-pyrazine-2-carboxylic acid [3-(5-amino-3-difluoromethyl-3,6-dihydro-2H-[1,4]oxazin-3-yl)-4-fluoro-phenyl]-amide;

3-Chloro-5-methoxymethyl-pyridine-2-carboxylic acid [3-(5-amino-3-difluoromethyl-3,6-dihydro-2H-[1,4]oxazin-3-yl)-4-fluoro-phenyl]-amide;
3-Chloro-5-fluoromethoxy-pyridine-2-carboxylic acid [3-(5-amino-3-difluoromethyl-3,6-dihydro-2H-[1,4]oxazin-3-yl)-4-fluoro-phenyl]-amide; and
3-Chloro-5-difluoromethoxy-pyridine-2-carboxylic acid [3-(5-amino-3-difluoromethyl-3,6-dihydro-2H-[1,4]oxazin-3-yl)-4-fluoro-phenyl]-amide.

In another embodiment, the invention relates to a compound of the invention, or a pharmaceutically acceptable salt thereof, which is selected from:

Furan-2-carboxylic acid [3-(5-amino-3-methyl-3,6-dihydro-2H-[1,4]oxazin-3-yl)-phenyl]-amide;
5-Bromo-pyridine-2-carboxylic acid [3-(5-amino-3-methyl-3,6-dihydro-2H-[1,4]oxazin-3-yl)-phenyl]-amide;
5-Bromo-pyridine-2-carboxylic acid [3-((R)-5-amino-3-methyl-3,6-dihydro-2H-[1,4]oxazin-3-yl)-phenyl]-amide;
5-Bromo-pyridine-2-carboxylic acid [3-((S)-5-amino-3-methyl-3,6-dihydro-2H-[1,4]oxazin-3-yl)-phenyl]-amide;
2-Methyl-oxazole-4-carboxylic acid [3-(5-amino-3-methyl-3,6-dihydro-2H-[1,4]oxazin-3-yl)-phenyl]-amide;
5-Methyl-pyrazine-2-carboxylic acid [3-(5-amino-3-methyl-3,6-dihydro-2H-[1,4]oxazin-3-yl)-phenyl]-amide;
5-Bromo-pyrimidine-2-carboxylic acid [3-(5-amino-3-methyl-3,6-dihydro-2H-[1,4]oxazin-3-yl)-phenyl]-amide;
Imidazo[1,2-a]pyridine-2-carboxylic acid [3-(5-amino-3-methyl-3,6-dihydro-2H-[1,4]oxazin-3-yl)-phenyl]-amide;
3-Fluoro-pyridine-2-carboxylic acid [3-(5-amino-3-methyl-3,6-dihydro-2H-[1,4]oxazin-3-yl)-phenyl]-amide;
2,5-Dimethyl-oxazole-4-carboxylic acid [3-(5-amino-3-methyl-3,6-dihydro-2H-[1,4]oxazin-3-yl)-phenyl]-amide;
2-Methyl-thiazole-4-carboxylic acid [3-(5-amino-3-methyl-3,6-dihydro-2H-[1,4]oxazin-3-yl)-phenyl]-amide;
6-Hydroxy-pyridazine-3-carboxylic acid [3-(5-amino-3-methyl-3,6-dihydro-2H-[1,4]oxazin-3-yl)-phenyl]-amide;
Pyridine-2-carboxylic acid [3-(5-amino-3-methyl-3,6-dihydro-2H-[1,4]oxazin-3-yl)-phenyl]-amide;
5-Cyano-pyridine-2-carboxylic acid [3-(5-amino-3-methyl-3,6-dihydro-2H-[1,4]oxazin-3-yl)-phenyl]-amide;
5-(3-Trifluoromethyl-pyrazol-1-yl)-pyrazine-2-carboxylic acid [3-(5-amino-3-methyl-3,6-dihydro-2H-[1,4]oxazin-3-yl)-phenyl]-amide;
5-(3-Methyl-pyrazol-1-yl)-pyrazine-2-carboxylic acid [3-(5-amino-3-methyl-3,6-dihydro-2H-[1,4]oxazin-3-yl)-phenyl]-amide;
3-Chloro-5-trifluoromethyl-pyridine-2-carboxylic acid [3-(5-amino-3-methyl-3,6-dihydro-2H-[1,4]oxazin-3-yl)-phenyl]-amide;
5-Methoxy-pyrazine-2-carboxylic acid [3-(5-amino-3-methyl-3,6-dihydro-2H-[1,4]oxazin-3-yl)-phenyl]-amide;
5-Hydroxy-pyrazine-2-carboxylic acid [3-(5-amino-3-methyl-3,6-dihydro-2H-[1,4]oxazin-3-yl)-phenyl]-amide;
4-Bromo-furan-2-carboxylic acid [3-(5-amino-3-methyl-3,6-dihydro-2H-[1,4]oxazin-3-yl)-phenyl]-amide;
5-Chloro-pyridine-2-carboxylic acid [3-(5-amino-3-methyl-3,6-dihydro-2H-[1,4]oxazin-3-yl)-phenyl]-amide;
5-Trifluoromethyl-pyridine-2-carboxylic acid [3-(5-amino-3-methyl-3,6-dihydro-2H-[1,4]oxazin-3-yl)-phenyl]-amide;
5-Trifluoromethyl-furan-3-carboxylic acid [3-(5-amino-3-methyl-3,6-dihydro-2H-[1,4]oxazin-3-yl)-phenyl]-amide;
N-[3-(5-Amino-3-methyl-3,6-dihydro-2H-[1,4]oxazin-3-yl)-phenyl]-4-bromo-benzamide;
5-Methyl-pyridine-2-carboxylic acid [3-(5-amino-3-methyl-3,6-dihydro-2H-[1,4]oxazin-3-yl)-phenyl]-amide;
N-[3-(5-Amino-3-methyl-3,6-dihydro-2H-[1,4]oxazin-3-yl)-phenyl]-nicotinamide;
5-Bromo-3-methyl-pyridine-2-carboxylic acid [3-((R)-5-amino-3-methyl-3,6-dihydro-2H-[1,4]oxazin-3-yl)-phenyl]-amide;
5-Methoxy-pyridine-2-carboxylic acid [3-((R)-5-amino-3-methyl-3,6-dihydro-2H-[1,4]oxazin-3-yl)-phenyl]-amide;
5-Bromo-pyridine-2-carboxylic acid [3-(5-amino-3-fluoromethyl-3,6-dihydro-2H-[1,4]oxazin-3-yl)-phenyl]-amide;
5-Bromo-pyridine-2-carboxylic acid [3-(5-amino-3-fluoromethyl-3,6-dihydro-2H-[1,4]oxazin-3-yl)-5-chloro-phenyl]-amide;
5-Bromo-pyridine-2-carboxylic acid [3-((R)-5-amino-3-fluoromethyl-3,6-dihydro-2H-[1,4]oxazin-3-yl)-phenyl]-amide;
5-Bromo-pyridine-2-carboxylic acid [3-(5-amino-3-difluoromethyl-3,6-dihydro-2H-[1,4]oxazin-3-yl)-phenyl]-amide;
5-Chloro-pyridine-2-carboxylic acid [3-(5-amino-3-difluoromethyl-3,6-dihydro-2H-[1,4]oxazin-3-yl)-phenyl]-amide;
5-Cyano-pyridine-2-carboxylic acid [3-(5-amino-3-difluoromethyl-3,6-dihydro-2H-[1,4]oxazin-3-yl)-phenyl]-amide;
5-Bromo-3-methyl-pyridine-2-carboxylic acid [3-(5-amino-3-difluoromethyl-3,6-dihydro-2H-[1,4]oxazin-3-yl)-phenyl]-amide;
5-Methyl-pyrazine-2-carboxylic acid [3-(5-amino-3-difluoromethyl-3,6-dihydro-2H-[1,4]oxazin-3-yl)-phenyl]-amide;
5-Trifluoromethyl-pyridine-2-carboxylic acid [3-(5-amino-3-difluoromethyl-3,6-dihydro-2H-[1,4]oxazin-3-yl)-phenyl]-amide;
3-Chloro-5-trifluoromethyl-pyridine-2-carboxylic acid [3-(5-amino-3-difluoromethyl-3,6-dihydro-2H-[1,4]oxazin-3-yl)-phenyl]-amide;
5-Chloro-3-methyl-pyridine-2-carboxylic acid [3-(5-amino-3-difluoromethyl-3,6-dihydro-2H-[1,4]oxazin-3-yl)-phenyl]-amide;
5-Bromo-pyridine-2-carboxylic acid [3-(5-amino-3-difluoromethyl-3,6-dihydro-2H-[1,4]oxazin-3-yl)-4-fluoro-phenyl]-amide;
5-Chloro-pyridine-2-carboxylic acid [3-(5-amino-3-difluoromethyl-3,6-dihydro-2H-[1,4]oxazin-3-yl)-4-fluoro-phenyl]-amide;
5-Chloro-3-methyl-pyridine-2-carboxylic acid [3-((R)-5-amino-3-difluoromethyl-3,6-dihydro-2H-[1,4]oxazin-3-yl)-4-fluoro-phenyl]-amide;
5-Bromo-3-methyl-pyridine-2-carboxylic acid [3-((R)-5-amino-3-difluoromethyl-3,6-dihydro-2H-[1,4]oxazin-3-yl)-4-fluoro-phenyl]-amide;
3-Chloro-5-trifluoromethyl-pyridine-2-carboxylic acid [3-((R)-5-amino-3-difluoromethyl-3,6-dihydro-2H-[1,4]oxazin-3-yl)-4-fluoro-phenyl]-amide;
5-Trifluoromethyl-pyridine-2-carboxylic acid [3-((R)-5-amino-3-difluoromethyl-3,6-dihydro-2H-[1,4]oxazin-3-yl)-4-fluoro-phenyl]-amide;
5-Methyl-pyrazine-2-carboxylic acid [3-((R)-5-amino-3-difluoromethyl-3,6-dihydro-2H-[1,4]oxazin-3-yl)-4-fluoro-phenyl]-amide;
5-Methoxy-pyridine-2-carboxylic acid [3-((R)-5-amino-3-difluoromethyl-3,6-dihydro-2H-[1,4]oxazin-3-yl)-4-fluoro-phenyl]-amide;
5-Chloro-pyridine-2-carboxylic acid [3-(5-amino-3-trifluoromethyl-3,6-dihydro-2H-[1,4]oxazin-3-yl)-4-fluoro-phenyl]-amide;

5-Bromo-pyrimidine-2-carboxylic acid [3-((R)-5-amino-3-methyl-3,6-dihydro-2H-[1,4]oxazin-3-yl)-5-bromo-phenyl]-amide;

5-Bromo-pyridine-2-carboxylic acid [3-((R)-5-amino-3-methyl-3,6-dihydro-2H-[1,4]oxazin-3-yl)-5-bromo-phenyl]-amide;

5-Cyano-pyridine-2-carboxylic acid [3-((R)-5-amino-3-methyl-3,6-dihydro-2H-[1,4]oxazin-3-yl)-5-bromo-phenyl]-amide;

5-Trifluoromethyl-pyridine-2-carboxylic acid [3-((R)-5-amino-3-methyl-3,6-dihydro-2H-[1,4]oxazin-3-yl)-5-bromo-phenyl]-amide;

5-Bromo-3-methyl-pyridine-2-carboxylic acid [3-((R)-5-amino-3-methyl-3,6-dihydro-2H-[1,4]oxazin-3-yl)-5-bromo-phenyl]-amide;

5-Chloro-pyridine-2-carboxylic acid [3-((R)-5-amino-3-methyl-3,6-dihydro-2H-[1,4]oxazin-3-yl)-5-bromo-phenyl]-amide;

5-Methyl-pyrazine-2-carboxylic acid [3-((R)-5-amino-3-methyl-3,6-dihydro-2H-[1,4]oxazin-3-yl)-5-bromo-phenyl]-amide;

2,5-Dimethyl-oxazole-4-carboxylic acid [3-((R)-5-amino-3-methyl-3,6-dihydro-2H-[1,4]oxazin-3-yl)-5-bromo-phenyl]-amide;

2-Methyl-oxazole-4-carboxylic acid [3-((R)-5-amino-3-methyl-3,6-dihydro-2H-[1,4]oxazin-3-yl)-5-bromo-phenyl]-amide;

5-Bromo-pyridine-2-carboxylic acid [3-(5-amino-3-methyl-3,6-dihydro-2H-[1,4]oxazin-3-yl)-4-fluoro-phenyl]-amide;

5-Methyl-pyrazine-2-carboxylic acid [3-(5-amino-3-methyl-3,6-dihydro-2H-[1,4]oxazin-3-yl)-4-fluoro-phenyl]-amide;

5-Cyano-pyridine-2-carboxylic acid [3-(5-amino-3-methyl-3,6-dihydro-2H-[1,4]oxazin-3-yl)-4-fluoro-phenyl]-amide;

5-Chloro-pyridine-2-carboxylic acid [3-(5-amino-3-methyl-3,6-dihydro-2H-[1,4]oxazin-3-yl)-4-fluoro-phenyl]-amide;

5-Bromo-3-methyl-pyridine-2-carboxylic acid [3-(5-amino-3-methyl-3,6-dihydro-2H-[1,4]oxazin-3-yl)-4-fluoro-phenyl]-amide;

Pyridine-2,5-dicarboxylic acid 5-amide 2-{[3-(5-amino-3-methyl-3,6-dihydro-2H-[1,4]oxazin-3-yl)-4-fluoro-phenyl]-amide};

5-Bromo-pyridine-2-carboxylic acid [3-((3R,6R)-5-amino-3,6-dimethyl-6-trifluoromethyl-3,6-dihydro-2H-[1,4]oxazin-3-yl)-phenyl]-amide;

5-Methoxy-pyridine-2-carboxylic acid [3-((3R,6R)-5-amino-3,6-dimethyl-6-trifluoromethyl-3,6-dihydro-2H-[1,4]oxazin-3-yl)-phenyl]-amide;

5-Bromo-pyridine-2-carboxylic acid [3-((3R,6R)-5-amino-3,6-di-methyl-6-trifluoromethyl-3,6-di-hydro-2H-[1,4]oxazin-3-yl)-4-fluoro-phenyl]-amide;

5-Methoxy-pyridine-2-carboxylic acid [3-((3R,6R)-5-amino-3,6-di-methyl-6-trifluoromethyl-3,6-di-hydro-2H-[1,4]oxazin-3-yl)-4-fluoro-phenyl]-amide;

5-Cyano-pyrimidine-2-carboxylic acid [3-((3R,6R)-5-amino-3,6-di-methyl-6-trifluoromethyl-3,6-di-hydro-2H-[1,4]oxazin-3-yl)-4-fluoro-phenyl]-amide;

5-Bromo-pyrimidine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide;

5-Cyano-3-methyl-pyridine-2-carboxylic acid [3-((3R,6R)-5-amino-3,6-dimethyl-6-trifluoro-methyl-3,6-dihydro-2H-[1,4]oxazin-3-yl)-4-fluoro-phenyl]-amide;

5-Cyano-pyridine-2-carboxylic acid [3-((3R,6R)-5-amino-3,6-dimethyl-6-trifluoro-methyl-3,6-*dihydro-2H-[1,4]oxazin-3-yl)-4-fluoro-phenyl]-amide;

5-(2-Methoxy-ethoxy)-pyrazine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide;

Cyano-pyridine-2-carboxylic acid [3-((3R,6R)-5-amino-3-difluoromethyl-6-methyl-3,6-dihydro-2H-[1,4]oxazin-3-yl)-4-fluoro-phenyl]-amide;

Cyano-pyridine-2-carboxylic acid [3-((3R,6S)-5-amino-3-difluoromethyl-6-methyl-3,6-dihydro-2H-[1,4]oxazin-3-yl)-4-fluoro-phenyl]-amide;

5-Bromo-pyridine-2-carboxylic acid[3-((3R,6R)-5-amino-3-difluoromethyl-6-methyl-3,6-dihydro-2H-[1,4]oxazin-3-yl)-4-fluoro-phenyl]-amide;

5-Bromo-pyridine-2-carboxylic acid [3-((3S,6R)-5-amino-3-difluoromethyl-6-methyl-3,6-dihydro-2H-[1,4]oxazin-3-yl)-4-fluoro-phenyl]-amide;

5-Cyano-pyridine-2-carboxylic acid[3-(5-amino-3-difluoromethyl-6,6-dimethyl-3,6-dihydro-2H-[1,4]oxazin-3-yl)-4-fluoro-phenyl]-amide;

5-Bromo-pyridine-2-carboxylic acid [3-(5-amino-3-difluoromethyl-6,6-dimethyl-3,6-dihydro-2H-[1,4]oxazin-3-yl)-4-fluoro-phenyl]-amide;

5-Bromo-pyridine-2-carboxylic acid [5-(5-amino-3-difluoromethyl-3,6-dihydro-2H-[1,4]oxazin-3-yl)-2,4-difluoro-phenyl]-amide;

5-Cyano-pyridine-2-carboxylic acid [5-(5-amino-3-difluoromethyl-3,6-dihydro-2H-[1,4]oxazin-3-yl)-2,4-difluoro-phenyl]-amide;

5-Bromo-3-methoxy-pyridine-2-carboxylic acid [5-(5-amino-3-difluoromethyl-3,6-dihydro-2H-[1,4]oxazin-3-yl)-2,4-difluoro-phenyl]-amide;

5-Bromo-3-hydroxy-pyridine-2-carboxylic acid [5-(5-amino-3-difluoromethyl-3,6-dihydro-2H-[1,4]oxazin-3-yl)-2,4-difluoro-phenyl]-amide;

5-Chloro-pyridine-2-carboxylic acid [3-((R)-5-amino-3-fluoromethyl-3,6-dihydro-2H-[1,4]oxazin-3-yl)-4-fluoro-phenyl]-amide;

5-Bromo-pyridine-2-carboxylic acid [3-(5-amino-3-fluoromethyl-3,6-dihydro-2H-[1,4]oxazin-3-yl)-4-fluoro-phenyl]-amide;

5-Chloro-pyridine-2-carboxylic acid [3-(5-amino-3-fluoromethyl-3,6-dihydro-2H-[1,4]oxazin-3-yl)-4-fluoro-phenyl]-amide;

3,5-Dichloro-pyridine-2-carboxylic acid [3-(5-amino-3-fluoromethyl-3,6-dihydro-2H-[1,4]oxazin-3-yl)-4-fluoro-phenyl]-amide;

5-Cyano-pyridine-2-carboxylic acid [3-(5-amino-3-fluoromethyl-3,6-dihydro-2H-[1,4]oxazin-3-yl)-4-fluoro-phenyl]-amide;

5-Bromo-3-methyl-pyridine-2-carboxylic acid [3-(5-amino-3-fluoromethyl-3,6-dihydro-2H-[1,4]oxazin-3-yl)-4-fluoro-phenyl]-amide;

5-Bromo-3-methyl-pyridine-2-carboxylic acid [3-((R)-5-amino-3-fluoromethyl-3,6-dihydro-2H-[1,4]oxazin-3-yl)-4-fluoro-phenyl]-amide;

5-Chloro-3-methyl-pyridine-2-carboxylic acid [3-((R)-5-amino-3-fluoromethyl-3,6-dihydro-2H-[1,4]oxazin-3-yl)-4-fluoro-phenyl]-amide;

5-Chloro-4,6-dideutero-3-trideuteromethyl-pyridine-2-carboxylic acid [3-((R)-5-amino-3-fluoromethyl-3,6-dihydro-2H-[1,4]oxazin-3-yl)-4-fluoro-phenyl]-amide;

5-Bromo-3-hydroxy-pyridine-2-carboxylic acid [3-((R)-5-amino-3-fluoromethyl-3,6-dihydro-2H-[1,4]oxazin-3-yl)-4-fluoro-phenyl]-amide;

5-Bromo-3-methoxy-pyridine-2-carboxylic acid [3-((R)-5-amino-3-fluoromethyl-3,6-dihydro-2H-[1,4]oxazin-3-yl)-4-fluoro-phenyl]-amide;

5-Bromo-pyridine-2-carboxylic acid[3-((S)-3-amino-5-difluoromethyl-2,5,6,7-tetrahydro-[1,4]oxazepin-5-yl)-4-fluoro-phenyl]-amide;

5-Bromo-pyridine-2-carboxylic acid[3-((S)-3-amino-5-difluoromethyl-2,5,6,7-tetrahydro-[1,4]oxazepin-5-yl)-4-fluoro-phenyl]-amide;

5-Cyano-pyridine-2-carboxylic acid [3-(3-amino-5-trifluoromethyl-2,5,6,7-tetrahydro-[1,4]oxazepin-5-yl)-4-fluoro-phenyl]-amide;

5-Bromo-pyridine-2-carboxylic acid [3-(3-amino-5-trifluoromethyl-2,5,6,7-tetrahydro-[1,4]oxazepin-5-yl)-4-fluoro-phenyl]-amide;

N-(3-(3-amino-6,6-difluoro-5-methyl-2,5,6,7-tetrahydro-1,4-oxazepin-5-yl)-4-fluorophenyl)-5-chloropicolinamide;

5-Bromo-pyridine-2-carboxylic acid [3-(3-amino-6,6-difluoro-5-methyl-2,5,6,7-tetrahydro-[1,4]oxazepin-5-yl)-4-fluoro-phenyl]-amide;

4-Bromo-furan-2-carboxylic acid [3-(5-amino-3-difluoromethyl-3,6-dihydro-2H-[1,4]oxazin-3-yl)-phenyl]-amide;

6-Hydroxy-pyridazine-3-carboxylic acid [3-(5-amino-3-difluoromethyl-3,6-dihydro-2H-[1,4]oxazin-3-yl)-phenyl]-amide;

2-Methyl-oxazole-4-carboxylic acid [3-(5-amino-3-difluoromethyl-3,6-dihydro-2H-[1,4]oxazin-3-yl)-phenyl]-amide;

2-Ethyl-oxazole-4-carboxylic acid [3-(5-amino-3-difluoromethyl-3,6-dihydro-2H-[1,4]oxazin-3-yl)-phenyl]-amide;

2,5-Dimethyl-oxazole-4-carboxylic acid [3-(5-amino-3-difluoromethyl-3,6-dihydro-2H-[1,4]oxazin-3-yl)-phenyl]-amide;

5-Bromo-3-methoxy-pyridine-2-carboxylic acid [3-(5-amino-3-difluoromethyl-3,6-dihydro-2H-[1,4]oxazin-3-yl)-phenyl]-amide;

5-Bromo-3-hydroxy-pyridine-2-carboxylic acid [3-(5-amino-3-difluoromethyl-3,6-dihydro-2H-[1,4]oxazin-3-yl)-phenyl]-amide;

5-(2-Methoxy-ethoxy)-pyridine-2-carboxylic acid [3-(5-amino-3-difluoromethyl-3,6-dihydro-2H-[1,4]oxazin-3-yl)-phenyl]-amide;

5-Difluoromethyl-pyrazine-2-carboxylic acid [3-(5-amino-3-difluoromethyl-3,6-dihydro-2H-[1,4]oxazin-3-yl)-phenyl]-amide;

3,5-Dichloro-pyridine-2-carboxylic acid [3-((R)-5-amino-3-difluoromethyl-3,6-dihydro-2H-[1,4]oxazin-3-yl)-4-fluoro-phenyl]-amide;

5-Cyano-pyridine-2-carboxylic acid [3-((R)-5-amino-3-difluoromethyl-3,6-dihydro-2H-[1,4]oxazin-3-yl)-4-fluoro-phenyl]-amide;

3,5-Difluoro-pyridine-2-carboxylic acid [3-((R)-5-amino-3-difluoromethyl-3,6-dihydro-2H-[1,4]oxazin-3-yl)-4-fluoro-phenyl]-amide;

5-Bromo-3-methyl-benzofuran-2-carboxylic acid [3-((R)-5-amino-3-difluoromethyl-3,6-dihydro-2H-[1,4]oxazin-3-yl)-4-fluoro-phenyl]-amide;

5-Chloro-4,6-dideutero-3-trideuteromethyl-pyridine-2-carboxylic acid [3-((R)-5-amino-3-difluoromethyl-3,6-dihydro-2H-[1,4]oxazin-3-yl)-4-fluoro-phenyl]-amide;

5-Bromo-4,6-dideutero-3-trideuteromethyl-pyridine-2-carboxylic acid [3-((R)-5-amino-3-difluoromethyl-3,6-dihydro-2H-[1,4]oxazin-3-yl)-4-fluoro-phenyl]-amide;

5-Bromo-3-chloro-pyridine-2-carboxylic acid [3-((R)-5-amino-3-difluoromethyl-3,6-dihydro-2H-[1,4]oxazin-3-yl)-4-fluoro-phenyl]-amide;

5-Bromo-pyridine-2-carboxylic acid [3-((R)-5-amino-3-difluoromethyl-3,6-dihydro-2H-[1,4]oxazin-3-yl)-4-fluoro-phenyl]-amide;

5-Bromo-3-hydroxy-pyridine-2-carboxylic acid [3-((R)-5-amino-3-difluoromethyl-3,6-dihydro-2H-[1,4]oxazin-3-yl)-4-fluoro-phenyl]-amide;

5-Ethoxy-pyridine-2-carboxylic acid [3-((R)-5-amino-3-difluoromethyl-3,6-dihydro-2H-[1,4]oxazin-3-yl)-4-fluoro-phenyl]-amide;

5-Chloro-pyrimidine-2-carboxylic acid [3-((R)-5-amino-3-difluoromethyl-3,6-dihydro-2H-[1,4]oxazin-3-yl)-4-fluoro-phenyl]-amide;

5-Difluoromethyl-pyrazine-2-carboxylic acid [3-((R)-5-amino-3-difluoromethyl-3,6-dihydro-2H-[1,4]oxazin-3-yl)-4-fluoro-phenyl]-amide;

5-(2,2-Difluoro-ethoxy)-pyrazine-2-carboxylic acid [3-((R)-5-amino-3-difluoromethyl-3,6-dihydro-2H-[1,4]oxazin-3-yl)-4-fluoro-phenyl]-amide;

5-(2,2,2-Trifluoro-ethoxy)-pyrazine-2-carboxylic acid [3-((R)-5-amino-3-difluoromethyl-3,6-dihydro-2H-[1,4]oxazin-3-yl)-4-fluoro-phenyl]-amide;

4-Bromo-furan-2-carboxylic acid [3-((R)-5-amino-3-difluoromethyl-3,6-dihydro-2H-[1,4]oxazin-3-yl)-4-fluoro-phenyl]-amide;

Pyrazolo[1,5-a]pyridine-2-carboxylic acid [3-((R)-5-amino-3 difluoromethyl-3,6-dihydro-2H [1,4]oxazin-3-yl)-4-fluoro-phenyl]-amide;

2-Methyl-oxazole-4-carboxylic acid [3-((R)-5-amino-3-difluoromethyl-3,6-dihydro-2H-[1,4]oxazin-3-yl)-4-fluoro-phenyl]-amide;

2,5-Dimethyl-oxazole-4-carboxylic acid [3-((R)-5-amino-3-difluoromethyl-3,6-dihydro-2H-[1,4]oxazin-3-yl)-4-fluoro-phenyl]-amide;

Imidazo[1,2-a]pyridine-2-carboxylic acid [3-((R)-5-amino-3-difluoromethyl-3,6-dihydro-2H-[1,4]oxazin-3-yl)-4-fluoro-phenyl]-amide;

5-Bromo-3-methoxy-pyridine-2-carboxylic acid [3-((R)-5-amino-3-difluoromethyl-3,6-dihydro-2H-[1,4]oxazin-3-yl)-4-fluoro-phenyl]-amide;

2-Ethyl-oxazole-4-carboxylic acid [3-((R)-5-amino-3-difluoromethyl-3,6-dihydro-2H-[1,4]oxazin-3-yl)-4-fluoro-phenyl]-amide;

5-Difluoromethyl-pyridine-2-carboxylic acid [3-((R)-5-amino-3-difluoromethyl-3,6-dihydro-2H-[1,4]oxazin-3-yl)-4-fluoro-phenyl]-amide;

1-Methyl-1H-imidazole-2 carboxylic acid [3-((R)-5-amino-3 difluoromethyl-3,6-dihydro-2H[1,4]oxazin-3-yl)-4-fluoro-phenyl]-amide;

6-Hydroxy-pyridazine-3-carboxylic acid [3-((R)-5-amino-3-difluoromethyl-3,6-dihydro-2H-[1,4]oxazin-3-yl)-4-fluoro-phenyl]-amide;

5-(2-Methoxy-ethoxy)-pyrazine-2-carboxylic acid [3-((R)-5-amino-3-difluoromethyl-3,6-dihydro-2H-[1,4]oxazin-3-yl)-4-fluoro-phenyl]-amide;

5-(2-Fluoro-ethoxy)-pyrazine-2-carboxylic acid [3-((R)-5-amino-3-difluoromethyl-3,6-dihydro-2H-[1,4]oxazin-3-yl)-4-fluoro-phenyl]-amide;

5-Chloro-pyridine-2-carboxylic acid [3-((R)-5-amino-3-difluoromethyl-3,6-dihydro-2H-[1,4]oxazin-3-yl)-4-fluoro-phenyl]-amide;

5-Difluoromethoxy-pyridine-2-carboxylic acid [3-((R)-5-amino-3-difluoromethyl-3,6-dihydro-2H-[1,4]oxazin-3-yl)-4-fluoro-phenyl]-amide;

5-Fluoromethoxy-pyridine-2-carboxylic acid [3-((R)-5-amino-3-difluoromethyl-3,6-dihydro-2H-[1,4]oxazin-3-yl)-4-fluoro-phenyl]-amide;

5-Chloro-3-fluoro-pyridine-2-carboxylic acid [3-((R)-5-amino-3-difluoromethyl-3,6-dihydro-2H-[1,4]oxazin-3-yl)-4-fluoro-phenyl]-amide;

5-Chloro-pyrazine-2-carboxylic acid [3-((R)-5-amino-3-difluoromethyl-3,6-dihydro-2H-[1,4]oxazin-3-yl)-4-fluoro-phenyl]-amide;

5-Methyl-1H-pyrazole-3-carboxylic acid [3-((R)-5-amino-3-difluoromethyl-3,6-dihydro-2H-[1,4]oxazin-3-yl)-4-fluoro-phenyl]-amide;

5-Methyl-pyridine-2-carboxylic acid [3-((R)-5-amino-3-difluoromethyl-3,6-dihydro-2H-[1,4]oxazin-3-yl)-4-fluoro-phenyl]-amide;

5-Cyano-3-methyl-pyridine-2-carboxylic acid [3-((R)-5-amino-3-difluoromethyl-3,6-dihydro-2H-[1,4]oxazin-3-yl)-4-fluoro-phenyl]-amide;

5-Hydroxy-pyrazine-2-carboxylic acid [3-((R)-5-amino-3-difluoromethyl-3,6-dihydro-2H-[1,4]oxazin-3-yl)-4-fluoro-phenyl]-amide;

5-Methoxy-pyrazine-2-carboxylic acid [3-((R)-5-amino-3-difluoromethyl-3,6-dihydro-2H-[1,4]oxazin-3-yl)-4-fluoro-phenyl]-amide;

5-Cyano-4,6-dideutero-3-trideuteromethyl-pyridine-2-carboxylic acid [3-((R)-5-amino-3-difluoromethyl-3,6-dihydro-2H-[1,4]oxazin-3-yl)-4-fluoro-phenyl]-amide;

2-Methyl-thiazole-4-carboxylic acid [3-((R)-5-amino-3-difluoromethyl-3,6-dihydro-2H-[1,4]oxazin-3-yl)-4-fluoro-phenyl]-amide;

5-Methyl-thiazole-2-carboxylic acid [3-((R)-5-amino-3-difluoromethyl-3,6-dihydro-2H-[1,4]oxazin-3-yl)-4-fluoro-phenyl]-amide;

1-Methyl-1H-pyrazole-3-carboxylic acid [3-((R)-5-amino-3-difluoromethyl-3,6-dihydro-2H-[1,4]oxazin-3-yl)-4-fluoro-phenyl]-amide;

1-Methyl-4-nitro-1H-pyrazole-3-carboxylic acid [3-((R)-5-amino-3-difluoromethyl-3,6-dihydro-2H-[1,4]oxazin-3-yl)-4-fluoro-phenyl]-amide;

3-Amino-5-chloro-pyridine-2-carboxylic acid [3-((3R,6R)-5-amino-3,6-dimethyl-6-trifluoro-methyl-3,6-dihydro-2H-[1,4]oxazin-3-yl)-4-fluoro-phenyl]-amide;

3-Chloro-5-trifluoromethyl-pyridine-2-carboxylic acid [3-(3-amino-6,6-difluoro-5-methyl-2,5,6,7-tetrahydro-[1,4]oxazepin-5-yl)-4-fluoro-phenyl]-amide;

5-Bromo-3-methoxy-pyridine-2-carboxylic acid [3-(3-amino-6,6 difluoro-5-methyl-2,5,6,7 tetrahydro-[1,4]oxazepin-5-yl)4 fluoro-phenyl]-amide;

5-Cyano-pyridine-2-carboxylic acid [3-(3-amino-6,6-difluoro-5 methyl-2,5,6,7-tetrahydro[1,4]oxazepin-5-yl)-4 fluoro-phenyl]-amide;

7H-Pyrrolo[2,3-d]pyrimidine-6-carboxylic acid [3-((R)-5-amino-3-difluoromethyl-3,6-dihydro-2H-[1,4]oxazin-3-yl)-4-fluoro-phenyl]-amide;

3-Amino-5-(2-methoxy-ethoxy)-pyrazine-2-carboxylic acid [3-((R)-5-amino-3-difluoromethyl-3,6-dihydro-2H-[1,4]oxazin-3-yl)-4-fluoro-phenyl]-amide;

((R)-5-Difluoromethyl-5-{5-[(5-ethyl-pyridine-2-carbonyl)-amino]-2-fluoro-phenyl}-5,6-dihydro-2H-[1,4]oxazin-3-yl)-carbamic acid tert-butyl ester;

3-Amino-5-chloro-pyridine-2-carboxylic acid [3-((R)-5-amino-3-difluoromethyl-3,6-dihydro-2H-[1,4]oxazin-3-yl)-4-fluoro-phenyl]-amide;

3-Chloro-5-methoxy-pyridine-2-carboxylic acid [3-((R)-5-amino-3-difluoromethyl-3,6-dihydro-2H-[1,4]oxazin-3-yl)-4-fluoro-phenyl]-amide;

6-Oxo-1,6-dihydro-pyridine-3-carboxylic acid [3-((R)-5-amino-3-difluoromethyl-3,6-dihydro-2H-[1,4]oxazin-3-yl)-4-fluoro-phenyl]-amide;

Pyrrolo[1,2-c]pyrimidine-3-carboxylic acid [3-((R)-5-amino-3-difluoromethyl-3,6-dihydro-2H-[1,4]oxazin-3-yl)-4-fluoro-phenyl]-amide;

5-But-2-ynyloxy-pyrazine-2-carboxylic acid [3-((R)-5-amino-3-difluoromethyl-3,6-dihydro-2H-[1,4]oxazin-3-yl)-4-fluoro-phenyl]-amide;

3-Amino-5-bromo-pyridine-2-carboxylic acid [3-((R)-5-amino-3-difluoromethyl-3,6-dihydro-2H-[1,4]oxazin-3-yl)-4-fluoro-phenyl]-amide;

1-Ethyl-1H-imidazole-2-carboxylic acid [3-((R)-5-amino-3-difluoromethyl-3,6-dihydro-2H-[1,4]oxazin-3-yl)-4-fluoro-phenyl]-amide;

5-Prop-2-ynyloxy-pyrazine-2-carboxylic acid [3-((R)-5-amino-3-difluoromethyl-3,6-dihydro-2H-[1,4]oxazin-3-yl)-4-fluoro-phenyl]-amide;

5-Amino-2-methyl-oxazole-4-carboxylic acid [3-((R)-5-amino-3-difluoromethyl-3,6-dihydro-2H-[1,4]oxazin-3-yl)-4-fluoro-phenyl]-amide;

5-Chloro-3-hydroxy-pyridine-2-carboxylic acid [3-((R)-5-amino-3-difluoromethyl-3,6-dihydro-2H-[1,4]oxazin-3-yl)-4-fluoro-phenyl]-amide;

5-Isopropoxy-pyrazine-2-carboxylic acid [3-((R)-5-amino-3-difluoromethyl-3,6-dihydro-2H-[1,4]oxazin-3-yl)-4-fluoro-phenyl]-amide;

5-Ethoxy-pyrazine-2-carboxylic acid [3-((R)-5-amino-3-difluoromethyl-3,6-dihydro-2H-[1,4]oxazin-3-yl)-4-fluoro-phenyl]-amide;

5-Dimethylaminomethyl-3-methyl-benzofuran-2-carboxylic acid [3-((R)-5-amino-3-difluoromethyl-3,6-dihydro-2H-[1,4]oxazin-3-yl)-4-fluoro-phenyl]-amide;

1,5-Dimethyl-1H-[1,2,3]triazole-4-carboxylic acid [3-((R)-5-amino-3-difluoromethyl-3,6-dihydro-2H-[1,4]oxazin-3-yl)-4-fluoro-phenyl]-amide;

5-Methoxy-3-methyl-pyrazine-2-carboxylic acid [3-((R)-5-amino-3-difluoromethyl-3,6-dihydro-2 H-[1,4]oxazin-3-yl)-4-fluoro-phenyl]-amide;

3-Amino-5-methoxy-pyrazine-2-carboxylic acid [3-((R)-5-amino-3-difluoromethyl-3,6-dihydro-2H-[1,4]oxazin-3-yl)-4-fluoro-phenyl]-amide;

5-Difluoromethoxy-3-methyl-pyridine-2-carboxylic acid [3-((R)-5-amino-3-difluoromethyl-3,6-dihydro-2H-[1,4]oxazin-3-yl)-4-fluoro-phenyl]-amide;

5-Fluoromethoxy-3-methyl-pyridine-2-carboxylic acid [3-((R)-5-amino-3-difluoromethyl-3,6-dihydro-2H-[1,4]oxazin-3-yl)-4-fluoro-phenyl]-amide;

5-(2-Methoxy-ethoxy)-3-methyl-pyrazine-2-carboxylic acid [3-((R)-5-amino-3-difluoromethyl-3,6-dihydro-2H-[1,4]oxazin-3-yl)-4-fluoro-phenyl]-amide;

3,5-Dimethoxy-pyridine-2-carboxylic acid [3-((R)-5-amino-3-difluoromethyl-3,6-dihydro-2H-[1,4]oxazin-3-yl)-4-fluoro-phenyl]-amide;

5-(2-Methoxy-ethoxy)-pyridine-2-carboxylic acid [3-((R)-5-amino-3-difluoromethyl-3,6-dihydro-2H-[1,4]oxazin-3-yl)-4-fluoro-phenyl]-amide;

3-Fluoro-5-(2-methoxy-ethoxy)-pyridine-2-carboxylic acid [3-((R)-5-amino-3-difluoromethyl-3,6-dihydro-2H-[1,4]oxazin-3-yl)-4-fluoro-phenyl]-amide;

5-But-2-ynyloxy-3-methyl-pyrazine-2-carboxylic acid [3-((R)-5-amino-3-difluoromethyl-3,6-dihydro-2H-[1,4]oxazin-3-yl)-4-fluoro-phenyl]-amide;

3-Chloro-5-methoxymethyl-pyridine-2-carboxylic acid [3-((R)-5-amino-3-difluoromethyl-3,6-dihydro-2H-[1,4]oxazin-3-yl)-4-fluoro-phenyl]-amide;

3-Chloro-5-fluoromethoxy-pyridine-2-carboxylic acid [3-((R)-5-amino-3-difluoromethyl-3,6-dihydro-2H-[1,4]oxazin-3-yl)-4-fluoro-phenyl]-amide; and 3-Chloro-5-difluoromethoxy-pyridine-2-carboxylic acid [3-((R)-5-amino-3-difluoromethyl-3,6-dihydro-2H-[1,4]oxazin-3-yl)-4-fluoro-phenyl]-amide.

In one embodiment, the invention relates to 5-cyano-pyridine-2-carboxylic acid [3-(5-amino-3-difluoromethyl-3,6-dihydro-2H-[1,4]oxazin-3-yl)-4-fluoro-phenyl]-amide, or a pharmaceutically acceptable salt thereof. In another embodiment, the invention relates to 5-cyano-pyridine-2-carboxylic acid [3-((R)-5-amino-3-difluoromethyl-3,6-d i hydro-2H-[1,4]oxazin-3-yl)-4-fluoro-phenyl]-amide, or a pharmaceutically acceptable salt thereof. In yet another embodiment, the invention relates to 5-cyano-pyridine-2-carboxylic acid [3-((S)-5-amino-3-difluoromethyl-3,6-dihydro-2H-[1,4]oxazin-3-yl)-4-fluoro-phenyl]-amide, or a pharmaceutically acceptable salt thereof.

In a more focused aspect, the invention relates to a crystalline form of 5-cyano-pyridine-2-carboxylic acid [3-((R)-5-amino-3-difluoromethyl-3,6-dihydro-2H-[1,4]oxazin-3-yl)-4-fluoro-phenyl]-amide, or a pharmaceutically acceptable salt thereof. In another embodiment, the invention relates to a crystalline form of 5-cyano-pyridine-2-carboxylic acid [3-((R)-5-amino-3-difluoromethyl-3,6-dihydro-2H-[1,4]oxazin-3-yl)-4-fluoro-phenyl]-amide which has an X-ray powder diffraction pattern with at least one, two or three peaks having angle of refraction 2 theta (θ) values selected from 8.3, 10.8, 16.6, 18.9, 21.5, 22.2, 23.3, 25.4 and 28.5 when measured using $CuK_\alpha$ radiation, more particularly wherein said values may be plus or minus 0.2° 2θ. In a further embodiment, the invention relates to a crystalline form of 5-cyano-pyridine-2-carboxylic acid [3-((R)-5-amino-3-difluoromethyl-3,6-dihydro-2H-[1,4]oxazin-3-yl)-4-fluoro-phenyl]-amide which has an X-ray powder diffraction pattern substantially the same as the X-ray powder diffraction pattern shown in FIG. 1 when measured using $CuK_\alpha$ radiation. For details see Example 152.

In a further aspect, the invention relates to a process for the preparation of a compound of the formula I, in free form or in salt form, comprising
a) the reaction of a compound of the formula

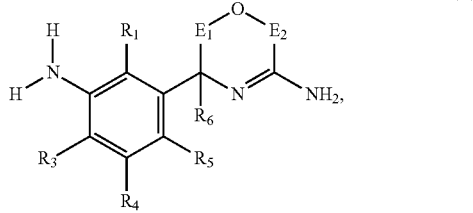

(II)

in which $R_1$, $R_3$, $R_4$, $R_5$, $R_6$, $E_1$ and $E_2$ are as defined for the formula I, in free form or in salt form, with a compound of the formula

(III)

in which $R_2$ is as defined for the formula I and L is a leaving group, in free form or in salt form,
b) the optional reduction, oxidation or other functionalisation of the resulting compound,
c) the cleavage of any protecting group(s) optionally present and
d) the recovery of the so obtainable compound of the formula I in free form or in salt form.

The reactions can be effected according to conventional methods, for example as described in the Examples.

The working-up of the reaction mixtures and the purification of the compounds thus obtainable may be carried out in accordance with known procedures.

Salts may be prepared from free compounds in known manner, and vice-versa.

Compounds of the formula I can also be prepared by further conventional processes, which processes are further aspects of the invention, e.g. as described in the Examples.

The starting materials of the formulae II and III are known, may be prepared according to conventional procedures starting from known compounds, may be prepared from known compounds as described in the Examples or may be prepared using procedures analogous to those described in the Examples.

Compounds of the formula I, in free form or in pharmaceutically acceptable salt form, hereinafter often referred to as "agents of the invention", exhibit valuable pharmacological properties, when tested in vitro or in vivo, and are, therefore, useful in medicaments.

E. g., agents of the invention are inhibitors of aspartic proteases and can be used for the treatment or prevention of a condition, disease or disorder involving processing by such enzymes. Particularly, agents of the invention inhibit beta-secretase and, thus, the generation of beta-amyloid and the subsequent aggregation into oligomers and fibrils.

The inhibiting properties of an agent of the invention towards proteases can be evaluated in tests as described hereinafter.

Test 1: Inhibition of Human BACE-1

Recombinant BACE-1 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic fluorescence-quenched peptide substrate, derived from the sequence of APP and containing a suitable fluorophore-quencher pair, is added to a final concentration of 1 to 5 μM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-1 activity as a function of the test compound concentration.

Test 2: Inhibition of Human BACE-2

Recombinant BACE-2 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic peptide substrate, derived from the sequence of APP and containing a suitable fluorophore-quencher pair, is added to a final concentration of 1 to 5 μM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-2 activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0 to 5.0. Synthetic peptide substrate Mca-Gly-Lys-Pro-Il e-Leu-Phe-Phe-Arg-Leu-Lys(DNP)-D-Arg-NH$_2$ is added to a final concentration of 1 to 5 µM, and the increase in fluorescence is recorded at excitation of 325 nm and emission at 400 nm in a microplate spectro-fluorimeter for 5 to 30 minutes in 1-minute intervals. IC$_{50}$ values are calculated from the percentage of inhibition of cathepsin D-activity as a function of the test compound concentration.

Test 4: Inhibition of Cellular Release of Amyloid Peptide 1-40

Chinese hamster ovary cells are transfected with the gene for amyloid precursor protein. The cells are plated at a density of 8000 cells/well into 96-well microtiter plates and cultivated for 24 hours in DMEM cell culture medium containing 10% FCS. The test compound is added to the cells at various concentrations, and the cells are cultivated for 24 hours in the presence of the test compound. The supernatants are collected, and the concentration of amyloid peptide 1-40 is determined using state of the art immunoassay techniques, for example sandwich ELISA, homogenous time-resolved fluorescence (HTRF) immunoassay, or electro-chemiluminescence immunoassay. The potency of the compound is calculated from the percentage of inhibition of amyloid peptide release as a function of the test compound concentration.

Agents of the invention were tested in at least one of the above-described tests. Specific activities of agents of the invention are described in Example 186.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by BACE-1 or (ii) associated with BACE-1 activity, or (iii) characterized by activity (normal or abnormal) of BACE-1; or (2) reducing or inhibiting the activity of BACE-1. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of BACE-1. The meaning of the term "a therapeutically effective amount" as illustrated in the above embodiments for BACE-1 also applies by the same means to any other relevant proteins/peptides/enzymes, such as BACE-2, or cathepsin D.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term an "agent" of the invention is used interchangeably with the term a "compound" of the invention and has no difference in meaning therefrom.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

Due to their inhibiting properties towards proteases, agents of the invention may be useful in the treatment or prevention of a variety of disabilitating psychiatric, psychotic, neurological or vascular states, such as a condition, disease or disorder of the vascular system or of the nervous system, in which beta-amyloid generation or aggregation plays a role, or, based on the inhibition of BACE-2 (beta-site APP-cleaving enzyme 2) or cathepsin D, which are close homologues of the pepsin-type aspartyl proteases and beta-secretase, and the correlation of the BACE-2 or cathepsin D expression with a more tumorigenic or metastatic potential of tumor cells, as anti-cancer medicaments, such as in the suppression of the metastasis process associated with tumor cells. The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e.g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e.g. neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile X syndrome; scrapie; cerebral amyloid angiopathy; an encephalopathy, e.g. transmissible spongiform encephalopathy; stroke; an attention disorder, e.g. attention deficit hyperactivity disorder; Tourette's syndrome; a speech disorder, including stuttering; a disorder of the circadian rhythm, e.g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e.g. in paraplegic patients; a hearing disorder, e.g. tinnitus or age-related hearing impairment; urinary incontinence; glaucoma; inclusion-body myositis; or a substance-related disorder, including substance abuse or dependency, including a substance, such as alcohol, withdrawal disorder. Agents of the invention may also be useful in enhancing cognition, e.g. in a subject suffering from a dementing condition, such as Alzheimer's disease; as premedication prior to anaesthesia or a minor medical intervention, such as endoscopy, including gastric endoscopy; or as ligands, e.g. radioligands or positron emission tomography (PET) ligands.

For the above-mentioned indications, the appropriate dosage will vary depending on, for example, the compound employed as active pharmaceutical ingredient, the host, the mode of administration, the nature and severity of the condition, disease or disorder or the effect desired. However, in general, satisfactory results in animals may be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e.g. in the form of a tablet or capsule, or parenterally, e.g. in the form of an injectable solution or suspension.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e.g. grapefruit juice, ketoconazole or, preferably, ritonavir. Such a composition may be manufactured in conventional manner, e.g. by mixing its components. Unit dosage forms contain, e.g., from about 0.1 to about 1000, preferably from about 1 to about 500, mg of an agent of the invention.

For example, for preclinical animal studies a compound of the invention, such as 5-cyano-pyridine-2-carboxylic acid [3-((R)-5-amino-3-difluoromethyl-3,6-dihydro-2H-[1,4]oxazin-3-yl)-4-fluoro-phenyl]-amide, could be formulated as a suspension in a 0.5% methylcellulose solution with 0.1% Tween80.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to an agent of the invention for use as a medicament, e.g. for the treatment or prevention of a neurological or vascular condition, disease or disorder, in which beta-amyloid generation or aggregation plays a role, or for the suppression of the metastasis process associated with tumor cells. In a further embodiment, the invention relates to an agent of the invention for use in the treatment of a disease or disorder mediated by BACE-1, BACE-2 or cathepsin D activity. In one embodiment, the invention relates to an agent of the invention for use in the treatment of Alzheimer's Disease.

In a further aspect, the invention relates to the use of an agent of the invention as an active pharmaceutical ingredient in a medicament, e.g. for the treatment or prevention of a neurological or vascular condition, disease or disorder, in which beta-amyloid generation or aggregation plays a role, or for the suppression of the metastasis process associated with tumor cells. In a further embodiment, the invention relates to the use of an agent of the invention as an active pharmaceutical ingredient in a medicament for the treatment or prevention of a disease or disorder mediated by BACE-1, BACE-2 or cathepsin D activity. In one embodiment, the invention relates to the use of an agent of the invention as an active pharmaceutical ingredient in a medicament for the treatment or prevention of Alzheimer's Disease.

In a further aspect, the invention relates to the use of an agent of the invention for the manufacture of a medicament for the treatment or prevention of a neurological or vascular condition, disease or disorder, in which beta-amyloid generation or aggregation plays a role, or for the suppression of the metastasis process associated with tumor cells. In a further embodiment, the invention relates to the use of an agent of the invention for the manufacture of a medicament for the treatment or prevention of a disease or disorder mediated by BACE-1, BACE-2 or cathepsin D activity. In one embodiment, the invention relates to the use of an agent of the invention for the manufacture of a medicament for the treatment or prevention of Alzheimer's Disease.

In a further aspect, the invention relates to a method for the treatment or prevention of a neurological or vascular condition, disease or disorder, in which beta-amyloid generation or aggregation plays a role, or for the suppression of the metastasis process associated with tumor cells, in a subject in need of such treatment, prevention or suppression, which method comprises administering to such subject an effective amount of an agent of the invention. In one embodiment, the invention relates to a method of modulating BACE-1, BACE-2 or cathepsin D activity in a subject, wherein the method comprises administering to the subject a therapeutically effective amount of an agent of the invention. In another embodiment, the invention relates to a method for the treatment or prevention of a disease mediated by BACE-1, BACE-2 or cathepsin D activity, in a subject in need of such treatment or prevention, which method comprises administering to such subject an effective amount of an agent of the invention. In yet another embodiment, the invention relates to a method for the treatment or prevention of Alzheimer's Disease, in a subject in need of such treatment or prevention, which method comprises administering to such subject an effective amount of an agent of the invention.

An agent of the invention can be administered as sole active pharmaceutical ingredient or as a combination with at least one other active pharmaceutical ingredient effective, e.g., in the treatment or prevention of a neurological or vascular condition, disease or disorder, in which beta-amyloid generation or aggregation plays a role, or in the suppression of the metastasis process associated with tumor cells. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e.g. a pack or dispenser-device adapted for the concomitant or separate administration of the at least two active components, in which these active components are separately arranged. In a further aspect, the invention relates to such pharmaceutical combinations.

In a further aspect, the invention therefore relates to a pharmaceutical combination comprising a therapeutically effective amount of an agent of the invention and a second drug substance, for simultaneous or sequential administration.

In one embodiment, the invention provides a product comprising a compound of an agent of the invention and at least one other therapeutic agent as a combined preparation for simultaneous, separate or sequential use in therapy. In one embodiment, the therapy is the treatment of a disease or condition mediated by BACE-1, BACE-2 or cathepsin D activity.

In one embodiment, the invention provides a pharmaceutical composition comprising an agent of the invention and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition mediated by BACE-1, BACE-2 or cathepsin D activity, wherein the medicament is prepared for administration with another therapeutic agent. The invention also provides the use of another therapeutic agent for treating a disease or condition mediated by BACE-1, BACE-2 or cathepsin D activity, wherein the medicament is administered with an agent of the invention.

The invention also provides an agent of the invention for use in a method of treating a disease or condition mediated by BACE-1, BACE-2 or cathepsin D activity, wherein the agent of the invention is prepared for administration with another therapeutic agent. The invention also provides another therapeutic agent for use in a method of treating a disease or condition mediated by BACE-1, BACE-2 or cathepsin D activity, wherein the other therapeutic agent is prepared for administration with an agent of the invention. The invention also provides an agent of the invention for use in a method of treating a disease or condition mediated by BACE-1, BACE-2 or cathepsin D activity, wherein the agent of the invention is administered with another therapeutic agent. The invention also provides another therapeutic agent for use in a method of treating a disease or condition mediated by BACE-1, BACE-2 or cathepsin D activity, wherein the other therapeutic agent is administered with an agent of the invention.

The invention also provides the use of an agent of the invention for treating a disease or condition mediated by BACE-1, BACE-2 or cathepsin D activity, wherein the patient has previously (e.g. within 24 hours) been treated with another therapeutic agent. The invention also provides the use of another therapeutic agent for treating a disease or condition mediated by BACE-1, BACE-2 or cathepsin D activity, wherein the patient has previously (e.g. within 24 hours) been treated with an agent of the invention.

In one embodiment, the invention relates to a compound of the invention in combination with another therapeutic agent wherein the other therapeutic agent is selected from:

(a) acetylcholinesterase inhibitors, such as donepezil (Aricept™), rivastigmine (Exelon™) and galantamine (Razadyne™);
(b) glutamate antagonists, such as memantine (Namenda™);
(c) antidepressant medications for low mood and irritability, such as citalopram (Celexa™), fluoxetine (Prozac™), paroxeine (Paxil™), sertraline (Zoloft™) and trazodone (Desyrel™);
(d) anxiolytics for anxiety, restlessness, verbally disruptive behavior and resistance, such as lorazepam (Ativan™) and oxazepam (Serax™);
(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers, such as carbamazepine (Tegretol™) and divalproex (Depakote™);
(g) nicotinic apha-7 agonists;
(h) mGluR5 antagonists;
(i) H3 agonists; and
(j) amyloid therapy vaccines.

The following Examples illustrate the invention, but do not limit it.

EXAMPLES

Abbreviations

ACN acetonitrile
AcOH acetic acid
Boc tert-butoxycarbonyl
t-Bu tert-butyl
t-BuOH tert-butanol
DAST diethylaminosulfurtrifluoride $(Et_2N)_2SF_3$
DCM dichloromethane
DIAD diisopropyl azodicarboxylate
DIPEA diisopropylethylamine
DMSO dimethylsulfoxide
DPPF 1,1'-bis(diphenylphosphino)ferrocene
ee enantiomeric excess
EDC 1-(3-dimethylaminopropyl)-3-ethylcarbodiimide hydrochloride eq equivalent(s)
Et$_3$N triethylamine
Et$_2$O diethylether
EtOAc ethyl acetate
EtOH ethanol
h hour(s)
Hex hexane
HOAt 1-hydroxy-7-aza-benztriazole
HOBT hydroxy-benztriazole
HPLC high performance liquid chromatography
LCMS liquid chromatography with mass spectrometry
LDA lithium diisopropylamide
MeOH methanol
min minute(s)
MS mass spectrometry
NMR nuclear magnetic resonance spectrometry
NP normal phase
PE petrolether
PPh3 triphenylphosphine
$R_f$ retention factor (TLC)
RP reverse phase
Rt retention time
rt room temperature
SMB simulated moving bed
TBME tert-butyl-methyl-ether
TFA trifluoroacetic acid
THF tetrahydrofuran
TLC thin layer chromatography
UPLC ultra performance liquid chromatography
General Chromatography Information
 HPLC Method H1 (Rt$_{H1}$):
 HPLC-column dimensions: 3.0×30 mm
 HPLC-column type: Zorbax SB-C18, 1.8 μm
 HPLC-eluent: A) water+0.05 Vol.-% TFA; B) ACN+0.05 Vol.-% TFA
 HPLC-gradient: 30-100% B in 3.25 min, flow=0.7 ml/min
 HPLC Method H2 (Rt$_{H2}$):
 HPLC-column dimensions: 3.0×30 mm
 HPLC-column type: Zorbax SB-C18, 1.8 μm
 HPLC-eluent: A) water+0.05 Vol.-% TFA; B) ACN+0.05 Vol.-% TFA
 HPLC-gradient: 0-100% B in 3.25 min, flow=0.7 ml/min
 LCMS Method H3 (Rt$_{H3}$):
 HPLC-column dimensions: 3.0×30 mm
 HPLC-column type: Zorbax SB-C18, 1.8 μm
 HPLC-eluent: A) water+0.05 Vol.-% TFA, B) ACN+0.05 Vol.-% TFA
 HPLC-gradient: 10-100% B in 3.25 min, flow=0.7 ml/min
 LCMS Method H4 (Rt$_{H4}$):
 HPLC-column dimensions: 3.0×30 mm
 HPLC-column type: Zorbax SB-C8, 1.8 μm
 HPLC-eluent: A) water+0.05 Vol.-% TFA, B) ACN+0.05 Vol.-% TFA
 HPLC-gradient: 10-95% B in 2.00 min, 95% B 2.00 min, flow=0.7 ml/min
 UPLC Method H5 (Rt$_{H5}$):
 HPLC-column dimensions: 2.1×50 mm
 HPLC-column type: Acquity UPLC HSS T3 C18, 1.7 μm
 HPLC-eluent: A) water+0.1 Vol.-% TFA, B) ACN+0.1 Vol.-% TFA
 HPLC-gradient: 5-100% B in 1.5 min, flow=1.0 ml/min
 LCMS Method H6 (Rt$_{H6}$):
 HPLC-column dimensions: 3.0×30 mm
 HPLC-column type: Zorbax SB-C18, 1.8 μm
 HPLC-eluent: A) water+0.05 Vol.-% TFA, B) ACN+0.05 Vol.-% TFA
 HPLC-gradient: 40-100% B in 3.25 min, flow=0.7 ml/min
 LCMS Method H7 (Rt$_{H7}$):
 HPLC-column dimensions: 3.0×30 mm
 HPLC-column type: Zorbax SB-C18, 1.8 μm
 HPLC-eluent: A) water+0.05 Vol.-% TFA; B) ACN+0.05 Vol.-% TFA
 HPLC-gradient: 50-100% B in 3.25 min, flow=0.7 ml/min
 LCMS Method H8 (Rt$_{H8}$):
 HPLC-column dimensions: 4.0×20 mm
 HPLC-column type: Mercury MS Synergi, 2 μm
 HPLC-eluent: A) water+0.1 Vol.-% formic acid, B) ACN
 HPLC-gradient: 0.5 min 30% B, 30-95% B in 1 min, 0.9 min 95% B,
 flow=2.0 ml/min
 HPLC-column temperature: 30° C.
 LCMS Method H9 (Rt$_{H9}$):
 HPLC-column dimensions: 4.0×20 mm
 HPLC-column type: Mercury MS Synergi, 2 μm
 HPLC-eluent: A) water+0.1 Vol.-% formic acid, B) ACN
 HPLC-gradient: 0.5 min 70% B, 70-100% B in 1 min, 0.6 min 70% B,
 flow=2.0 ml/min
 HPLC-column temperature: 30° C.
 UPLC Method H10 (Rt$_{H10}$):
 HPLC-column dimensions: 2.1×50 mm
 HPLC-column type: Acquity UPLC HSS T3, 1.8 μm
 HPLC-eluent: A) water+0.05 Vol.-% formic acid+3.75 mM ammonium acetate B) ACN+0.04 Vol.-% formic acid
 HPLC-gradient: 2-98% B in 1.7 min, 98% B 0.45 min, flow=1.2 ml/min
 LCMS Method H11 (Rt$_{H11}$):
 HPLC-column dimensions: 2.1×30 mm
 HPLC-column type: Ascentis Express C18, 2.8 μm
 HPLC-eluent: A) water+0.05 Vol.-% formic acid+3.75 mM ammonium acetate, B) ACN+0.04 Vol.-% formic acid
 HPLC-gradient: 2-98% B in 1.4 min, 0.75 min 98% B, flow=1.2 ml/min
 HPLC-column temperature: 50° C.

Example 1

Furan-2-carboxylic acid [3-(5-amino-3-methyl-3,6-dihydro-2H-[1,4]oxazin-3-yl)-phenyl]-amide hydrochloride

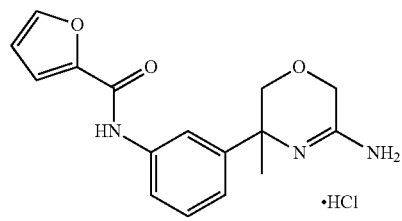 [SMILES: CC1(c2cccc(NC(=O)c3ccco3)c2)COCC(N)=N1 ; Cl]

a) 2-Amino-2-(3-bromo-phenyl)-propionitrile

A mixture of 1-(3-bromo-phenyl)-ethanone (10 g, 50 mmol), NH$_4$Cl (6.4 g, 100 mmol) and KCN (6.5 g, 100 mmol)

was dissolved in ammonia (200 ml). The solution was stirred at room temperature for 3 days. The mixture was extracted with diethylether (3×300 ml). The organic phase was washed with water and brine, dried with $Na_2SO_4$ and concentrated in vacuo to yield the title compound (also containing some unreacted starting material). $^1$H-NMR (400 MHz, $CDCl_3$): 7.84 (s, 1H), 7.59 (d, 1H), 7.48 (d, 1H), 7.28 (m, 1H), 1.75 (s, 3H).

b) 2-Amino-2-(3-bromo-phenyl)-propionic acid hydrochloride

2-Amino-2-(3-bromo-phenyl)-propionitrile (10 g, 44 mmol) was added to concentrated hydrochloric acid (100 ml) at room temperature. The mixture was refluxed overnight and then concentrated in vacuo to give a crude product, which was washed with EtOAc to yield the pure title compound. $^1$H-NMR (400 MHz, $CD_3OD$): 7.62 (m, 2H), 7.48 (m, 2H), 1.82 (s, 3H).

c) 2-Amino-2-(3-bromo-phenyl)-propan-1-ol $NaBH_4$ (38 g, 1.125 mol) was added at room temperature to a slurry of 2-amino-2-(3-bromo-phenyl)-propionic acid hydrochloride (105 g, 375 mmol) in dry THF. At 0° C. $BF_3$—$O(C_2H_5)_2$ (158 g, 1.125 mol) was added dropwise. The mixture was allowed to warm to room temperature, stirred for three days, quenched with 1M aqueous NaOH solution, concentrated in vacuo to remove the THF and extracted with EtOAc (3×300 ml). The organic phase was washed with 1M aqueous NaOH solution, dried with sodium sulfate and concentrated in vacuo to yield the title compound, which was used in the next reaction step without further purification. $^1$H-NMR (400 MHz, $CDCl_3$): 7.61 (s, 1H), 7.35 (m, 2H), 7.21 (m, 1H), 3.58 (q, 2H), 1.42 (s, 3H).

d) N-[1-(3-Bromo-phenyl)-2-hydroxy-1-methyl-ethyl]-2-chloro-acetamide

2-Chloroacetyl chloride (2.24 g, 19.8 mmol) was added dropwise at 0° C. to a suspension of 2-amino-2-(3-bromo-phenyl)-propan-1-ol (3.8 g, 16.5 mmol), $K_2CO_3$ (4.55 g, 33 mmol) and dichloromethane (40 ml). The mixture was allowed to warm to room temperature over a period of approximately 3 h, washed with 1N hydrochloric acid and brine, dried with $Na_2SO_4$ and evaporated in vacuo to yield the crude title compound. $^1$H-NMR (400 MHz, $CDCl_3$): 7.43 (m, 2H), 7.23 (m, 2H), 4.10-4.03 (m, 4H), 1.71 (s, 3H).

e) 5-(3-Bromo-phenyl)-5-methyl-morpholin-3-one

The crude N-[1-(3-bromo-phenyl)-2-hydroxy-1-methyl-ethyl]-2-chloro-acetamide (70 g, 230 mmol) was dissolved in tert-butanol (1 l). The solution was treated with portions of potassium tert-butoxide (52 g, 460 mmol). The mixture was refluxed for 30 min, after cooling quenched with water and evaporated. The residue was dissolved in EtOAc (500 ml) and washed with water and brine. The organic phase was dried with $Na_2SO_4$ and concentrated in vacuo to yield the crude title compound. The crude product was purified by chromatography on silica gel (PE/EtOAc=20:1 to 1:1) to give the title compound in the form of a grey solid. $^1$H-NMR (400 MHz, DMSO-$d_6$): 8.66 (s, 1H), 7.60 (s, 1H), 7.48 (d, 1H), 7.44 (d, 1H), 7.34 (t, 1H), 4.02 (s, 2H), 3.92 (d, 1H), 3.68 (d, 1H), 1.38 (s, 3H).

f) 5-(3-Bromo-phenyl)-5-methyl-morpholine-3-thione

A solution of 5-(3-bromo-phenyl)-5-methyl-morpholin-3-one (18 g, 67 mmol) in dry THF was treated with Lawesson's reagent (27 g, 67 mmol) in one portion at room temperature. The mixture was refluxed for 2 h. The title compound was obtained by chromatography on silica gel (PE/EtOAc=30:1 to 10:1). $^1$H-NMR (400 MHz, DMSO-$d_6$): 11.08 (s, 1H), 7.50 (m, 2H), 7.35 (m, 2H), 4.36 (s, 2H), 4.00 (m, 1H), 3.73 (m, 1H), 1.51 (s, 3H).

g) 5-(3-Bromo-phenyl)-5-methyl-5,6-dihydro-2H-[1,4]oxazin-3-ylamine

To a solution of 5-(3-bromo-phenyl)-5-methyl-morpholine-3-thione (5 g, 17.5 mmol) in MeOH/$NH_3$ (110 ml) were added at room temperature t-BuOOH (28 ml, 65%) and $NH_4OH$ (47 ml, 25%). The mixture was stirred overnight, quenched with aqueous $Na_2S_2O_3$ solution, concentrated in vacuo to remove the methanol solution and extracted with EtOAc (3×30 ml). The organic phase was dried with $Na_2SO_4$ and concentrated in vacuo to give the crude product, which was purified by preparative HPLC [column: Venusil XBP-C18, 250×21.2 mm, 10 μm; injection volume: 10 ml/injection; mobile phase: $CH_3CN/H_2O$=10 to 35% (0.1% formic acid) gradient for 15 min, washed with 95% $CH_3CN$ for 4 min, back to 10% balance for 4 min] to give the title compound in the form of a formic acid salt. $^1$H-NMR (300 MHz, DMSO-$d_6$): 9.99 (s, 1H), 8.39 (s, 1H), 7.65 (s, 1H), 7.55 (d, 1H), 7.47 (d, 1H), 7.39 (t, 1H), 4.46 (s, 2H), 4.05 (d, 1H), 3.85 (d, 1H), 1.55 (s, 3H).

h) [5-(3-Bromo-phenyl)-5-methyl-5,6-dihydro-2H-[1,4]oxazin-3-yl]-carbamic acid tert-butyl ester A mixture of 5-(3-bromo-phenyl)-5-methyl-5,6-dihydro-2H-[1,4]oxazin-3-ylamine (4.73 g, 15 mmol) and dichloromethane was cooled to 0° C., treated with $(Boc)_2O$ (4.26 g, 19.5 mmol) and DIPEA (2.91 g, 22.5 mmol) and stirred for 17 h at room temperature. 300 ml of water were added dropwise, the phases were separated, the aqueous phase was extracted twice with dichloromethane, and the combined organic phases were washed with 1M aqueous HCl solution and water, dried with $Na_2SO_4$ and evaporated under reduced pressure to yield the title compound. $^1$H-NMR (500 MHz, DMSO-$d_6$): 9.58 (br, 1H), 7.62 (s, 1H), 7.40-7.25 (m, 3H), 4.50-4.30 (m, 2H), 3.75-3.35 (m, 2H), 1.45 (s, 3H), 1.41 (s, 9H); MS: 369, 371 [(M+H)$^+$].

i) [5-(3-Azido-phenyl)-5-methyl-5,6-dihydro-2H-[1,4]oxazin-3-yl]-carbamic acid tert-butyl ester

[5-(3-Bromo-phenyl)-5-methyl-5,6-dihydro-2H-[1,4]oxazin-3-yl]-carbamic acid tert-butyl ester (5.03 g, 12.67 mmol), sodium azide (1.647 g, 25.3 mmol), sodium ascorbate (0.125 g, 0.63 mmol), copper iodide (0.241 g, 1.27 mmol) and (1R,2R)—N,N'-dimethyl-cyclohexane-1,2-diamine (0.270 g, 1.90 mmol) were dissolved in ethanol (17.7 ml) and water (7.6 ml). The mixture was stirred under $N_2$ at 90° C. for 4 h and then poured into 1M aqueous $KHCO_3$ solution. The mixture was extracted with EtOAc, and the organic phase was washed with brine, dried with $Na_2SO_4$ and evaporated under reduced pressure. The residue was purified by chromatography on silica gel (cyclohexane/EtOAc=7:3) to yield the title compound.

$^1$H-NMR (500 MHz, DMSO-$d_6$): 9.57 (br, 1H), 7.38 (m, 1H), 7.24 (d, 1H), 7.18 (br, 1H), 7.0 (br, 1H), 4.50-4.30 (m, 2H), 3.75-3.35 (m, 2H), 1.41 (s, 9H), 1.36 (s, 3H); MS: 332 [(M+H)$^+$].

j) [5-(3-Amino-phenyl)-5-methyl-5,6-dihydro-2H-[1, 4]oxazin-3-yl]-carbamic acid tert-butyl ester A solution of [5-(3-azido-phenyl)-5-methyl-5,6-dihydro-2H-[1,4]oxazin-3-yl]-carbamic acid tert-butyl ester (497 mg, 1.50 mmol) in EtOAc (37 ml) was hydrogenated using Lindlar catalyst (10 h, room temperature). The mixture was filtered through Celite, and the filtrate was evaporated under reduced pressure yielding the title compound in the form of a colourless solid. $^1$H-NMR (500 MHz, DMSO-$d_6$): 9.57 (br, 1H), 6.97 (br, 1H), 6.55 (s, 1H), 6.52 (d, 1H), 6.45 (br, 1H), 5.08 (br, 2H), 4.40-4.30 (m, 2H), 3.75-3.45 (m, 2H), 1.47 (s, 3H), 1.39 (s, 9H); MS: 306 [(M+H)$^+$].

k) (5-{3-[(Furan-2-carbonyl)-amino]-phenyl}-5-methyl-6,6-dihydro-2H-[1,4]oxazin-3-yl)-carbamic acid tert-butyl ester

[5-(3-Amino-phenyl)-5-methyl-5,6-dihydro-2H-[1,4]oxazin-3-yl]-carbamic acid tert-butyl ester (264 mg, 0.865 mmol), furan-2-carboxylic acid (107 mg, 0.951 mmol) and HOBT (172 mg, 1.124 mmol) were dissolved in dichloromethane under $N_2$ at 0° C. DIPEA (112 mg, 0.865 mmol) and EDC (182 mg, 0.951 mmol) were added. The mixture was stirred at 0° C. for 10 min, then allowed to warm to room temperature, stirred for 17 h at room temperature, quenched with 1M aqueous $KHCO_3$ solution and extracted with dichloromethane. The organic phase was washed with water and brine, dried with $Na_2SO_4$ and concentrated under reduced pressure. The residue was purified by chromatography on silica gel (cyclohexane/EtOAc) to yield the title compound in the form of a colourless solid. $^1$H-NMR (400 MHz, DMSO-$d_6$): 9.86 (br, 1H), 9.27 (br, 1H), 7.83 (d, 1H), 7.69 (m, 2H), 7.30 (m, 2H), 7.15 (dd, 1H), 6.65 (m, 1H), 4.40-4.30 (m, 2H), 3.75-3.55 (m, 2H), 1.52 (s, 3H), 1.44 (s, 9H); MS: 400 [(M+H)$^+$].

l) Furan-2-carboxylic acid [3-(5-amino-3-methyl-3, 6-dihydro-2H-[1,4]oxazin-3-yl)-phenyl]-amide hydrochloride A solution of (5-{3-[(furan-2-carbonyl)-amino]-phenyl}-5-methyl-5,6-dihydro-2H-[1,4]oxazin-3-yl)-carbamic acid tert-butyl ester (39.9 mg, 0.1 mmol) in dichloromethane was treated with 4M HCl in dioxane (40 eq). The mixture was warmed to 40° C. for 10 h and then evaporated under reduced pressure to yield the title compound (hydrochloride salt) in the form of a colourless solid. $^1$H-NMR (500 MHz, DMSO-$d_6$): 10.65 (1H, NH), 10.31 (s, 1H), 9.14 (br, 1H), 8.52 (br, 1H), 7.95 (s, 1H), 7.82 (s, 1H), 7.77 (d, 1H), 7.40 (m, 2H), 7.18 (d, 1H), 6.72 (m, 1H), 4.59 (s, 2H), 3.87 (dd, 2H), 1.64 (s, 3H); MS: 300 [(M+H)$^+$].

Example 2

5-Bromo-pyridine-2-carboxylic acid [3-(5-amino-3-methyl-3,6-dihydro-2H-[1,4]oxazin-3-yl)-phenyl]-amide hydrochloride

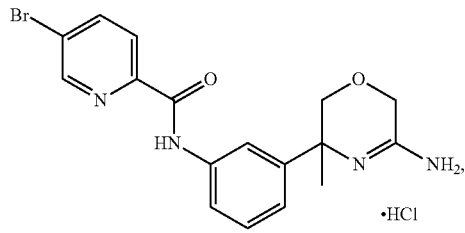 [SMILES: CC1(c2cccc(NC(=O)c3ccc(Br)cn3)c2)COCC(N)=N1 ; Cl]

a) (5-{3-[(5-Bromo-pyridine-2-carbonyl)-amino]-phenyl}-5-methyl-5,6-dihydro-2H-[1,4]oxazin-3-yl)-carbamic acid tert-butyl ester

[5-(3-Amino-phenyl)-5-methyl-5,6-dihydro-2H-[1,4]oxazin-3-yl]-carbamic acid tert-butyl ester (264 mg, 0.865 mmol), 5-bromo-pyridine-2-carboxylic acid (192 mg, 0.951 mmol) and HOBT (172 mg, 1.124 mmol) were dissolved in dichloromethane under $N_2$ at 0° C. DIPEA (112 mg, 0.865 mmol) and EDC (182 mg, 0.951 mmol) were added. The mixture was stirred at 0° C. for 10 min, then allowed to warm to room temperature, stirred for 17 h at room temperature, quenched with 1M aqueous $KHCO_3$ solution and extracted with dichloromethane. The organic phase was washed with water and brine, dried with $Na_2SO_4$ and concentrated under reduced pressure. The residue was purified by chromatography on silica gel (cyclohexane/EtOAc) to yield the title compound in the form of a colourless solid. $^1$H-NMR (400 MHz, DMSO-$d_6$, 81° C.): 10.32 (1H, NH), 9.30 (br, 1H), 8.81 (s, 1H), 8.29 (dd, 1H), 8.08 (d, 1H), 7.81 (m, 2H), 7.33 (m, 1H), 7.19 (d, 1H), 4.40-4.30 (m, 2H), 3.75-3.55 (m, 2H), 1.53 (s, 3H), 1.45 (s, 9H); MS: 489 [(M+H)$^+$].

b) 5-Bromo-pyridine-2-carboxylic acid [3-(5-amino-3-methyl-3,6-dihydro-2H-[1,4]oxazin-3-yl)-phenyl]-amide hydrochloride A solution of (5-{3-[(5-bromo-pyridine-2-carbonyl)-amino]-phenyl}-5-methyl-5,6-dihydro-2H-[1,4]oxazin-3-yl)-carbamic acid tert-butyl ester (44.4 mg, 0.1 mmol) in dichloromethane was treated with 4M HCl in dioxane (40 eq). The mixture was warmed to 40° C. for 10 h and then evaporated under reduced pressure to yield the title compound (hydrochloride salt) in the form of a colourless solid. $^1$H-NMR (500 MHz, DMSO-$d_6$): 10.70 (s, 1H), 10.62 (s, 1H), 9.14 (s, 1H), 8.87 (d, 1H), 8.52 (s, 1H), 8.34 (dd, 1H), 8.11 (d, 1H), 7.96 (m, 2H), 7.43 (t, 1H), 7.21 (d, 1H), 4.59 (s, 2H), 3.88 (m, 2H), 1.65 (s, 3H); MS: 389 [(M+H)$^+$].

Examples 3 to 30

The compounds listed in Table 1 were prepared by procedures analogous to those used in examples 1 and 2.

TABLE 1

| Example | Compound | ¹H-NMR (δ; DMSO-d₆) | MS [m/z; (M + 1)⁺] |
|---------|----------|---------------------|---------------------|
| 3 | 5-Bromo-pyridine-2-carboxylic acid [3-((R)-5-amino-3-methyl-3,6-dihydro-2H-[1,4]oxazin-3-yl)-phenyl]-amide hydrochloride | 10.73 (s, 1H), 10.65 (s, 1H), 9.18 (s, 1H), 8.87 (d, 1H), 8.57 (s, 1H), 8.34 (dd, 1H), 8.11 (d, 1H), 7.96 (m, 2H), 7.43 (t, 1H), 7.22 (d, 1H), 4.59 (s, 2H), 3.88 (m, 2H), 1.65 (s, 3H) | 389 |
| 4 | 5-Bromo-pyridine-2-carboxylic acid [3-((S)-5-amino-3-methyl-3,6-dihydro-2H-[1,4]oxazin-3-yl)-phenyl]-amide hydrochloride | 10.73 (s, 1H), 10.65 (s, 1H), 9.18 (s, 1H), 8.87 (d, 1H), 8.57 (s, 1H), 8.34 (dd, 1H), 8.11 (d, 1H), 7.96 (m, 2H), 7.43 (t, 1H), 7.22 (d, 1H), 4.59 (s, 2H), 3.88 (m, 2H), 1.64 (s, 3H) | 389 |
| 5 | 2-Methyl-oxazole-4-carboxylic acid [3-(5-amino-3-methyl-3,6-dihydro-2H-[1,4]oxazin-3-yl)-phenyl]-amide hydrochloride | 9.91 (s, 1H), 8.61 (s, 1H), 7.76 (s, 1H), 7.65 (d, 1H), 7.23 (t, 1H), 7.16 (d, 1H), 5.57 (br, 2H), 4.00-3.85 (m, 2H), 3.60-3.40 (m, 2H), 1.34 (s, 3H) | 315 |
| 6 | 5-Methyl-pyrazine-2-carboxylic acid [3-(5-amino-3-methyl-3,6-dihydro-2H-[1,4]oxazin-3-yl)-phenyl]-amide hydrochloride | 10.51 (s, 1H), 9.16 (s, 1H), 8.70 (s, 1H), 7.87 (s, 1H), 7.76 (d, 1H), 7.29 (t, 1H), 7.21 (d, 1H), 5.76 (br, 2H), 4.00-3.85 (m, 2H), 3.63-3.48 (m, 2H), 1.37 (s, 3H) | 326 |

TABLE 1-continued

| Example | Compound | ¹H-NMR (δ; DMSO-d₆) | MS [m/z; (M + 1)⁺] |
|---|---|---|---|
| 7 | 5-Bromo-pyrimidine-2-carboxylic acid [3-(5-amino-3-methyl-3,6-dihydro-2H-[1,4]oxazin-3-yl)-phenyl]-amide hydrochloride | 10.85 (s, 1H), 10.65 (s, 1H), 9.24 (s, 2H), 9.16 (s, 1H), 8.55 (s, 1H), 7.90 (m, 2H), 7.44 (t, 1H), 7.23 (d, 1H), 4.59 (s, 2H), 3.91 (m, 2H), 1.65 (s, 3H) | 390 |
| 8 | Imidazo[1,2-a]pyridine-2-carboxylic acid [3-(5-amino-3-methyl-3,6-dihydro-2H-[1,4]oxazin-3-yl)-phenyl]-amide hydrochloride | 10.70 (s, 2H), 9.19 (s, 1H), 8.77 (m, 2H), 8.57 (s, 1H), 7.94 (m, 2H), 7.73 (d, 1H), 7.60 (t, 1H), 7.43 (t, 1H), 7.21 (d, 2H), 4.59 (s, 2H), 3.89 (m, 2H), 1.65 (s, 3H) | 350 |
| 9 | 3-Fluoro-pyridine-2-carboxylic acid [3-(5-amino-3-methyl-3,6-dihydro-2H-[1,4]oxazin-3-yl)-phenyl]-amide hydrochloride | 10.69 (s, 1H), 10.65 (s, 1H), 9.15 (s, 1H), 8.57 (d, 1H), 8.53 (s, 1H), 7.95 (t, 1H), 7.87 (m, 2H), 7.76 (m, 1H), 7.43 (t, 1H), 7.22 (d, 1H), 4.59 (s, 2H), 3.91 (m, 2H), 1.64 (s, 3H) | 329 |
| 10 | 2,5-Dimethyl-oxazole-4-carboxylic acid [3-(5-amino-3-methyl-3,6-dihydro-2H-[1,4]oxazin-3-yl)-phenyl]-amide hydrochloride | 10.60 (s, 1H), 9.98 (s, 1H), 9.12 (s, 1H), 8.49 (s, 1H), 7.87 (m, 2H), 7.37 (t, 1H), 7.16 (d, 1H), 4.58 (s, 2H), 3.88 (m, 2H), 2.59 (s, 3H), 2.46 (s, 3H), 1.63 (s, 3H) | 329 |

TABLE 1-continued

| Example | Compound | ¹H-NMR (δ; DMSO-d₆) | MS [m/z; (M + 1)⁺] |
|---|---|---|---|
| 11 | 2-Methyl-thiazole-4-carboxylic acid [3-(5-amino-3-methyl-3,6-dihydro-2H-[1,4]oxazin-3-yl)-phenyl]-amide hydrochloride | 10.63 (s, 1H), 10.24 (s, 1H), 9.13 (s, 1H), 8.51 (s, 1H), 8.29 (s, 1H), 7.89 (m, 1H), 7.40 (t, 1H), 7.18 (d, 1H), 4.58 (s, 2H), 3.88 (m, 2H), 2.77 (s, 3H), 1.64 (s, 3H) | 331 |
| 12 | 6-Hydroxy-pyridazine-3-carboxylic acid [3-(5-amino-3-methyl-3,6-dihydro-2H-[1,4]oxazin-3-yl)-phenyl]-amide hydrochloride | 13.57 (s, 1H), 10.60 (s, 1H), 10.38 (s, 1H), 9.14 (s, 1H), 8.52 (s, 1H), 7.92 (d, 1H), 7.83 (m, 2H), 7.41 (t, 1H), 7.20 (d, 1H), 7.04 (d, 1H), 4.58 (s, 2H), 3.89 (m, 2H), 1.63 (s, 3H) | 328 |
| 13 | Pyridine-2-carboxylic acid [3-(5-amino-3-methyl-3,6-dihydro-2H-[1,4]oxazin-3-yl)-phenyl]-amide hydrochloride | 10.71 (s, 1H), 10.65 (s, 1H), 9.16 (s, 1H), 8.75 (d, 1H), 8.54 (s, 1H), 8.17 (d, 1H), 8.09 (t, 1H), 7.97 (m, 2H), 7.70 (m, 1H), 7.43 (t, 1H), 7.21 (d, 1H), 4.59 (s, 2H), 3.91 (m, 2H), 1.65 (s, 3H) | 311 |
| 14 | 5-Cyano-pyridine-2-carboxylic acid [3-(5-amino-3-methyl-3,6-dihydro-2H-[1,4]oxazin-3-yl)-phenyl]-amide hydrochloride | 10.88 (s, 1H), 10.62 (s, 1H), 9.22 (s, 1H), 9.14 (s, 1H), 8.59 (m, 1H), 8.53 (s, 1H), 8.31 (d, 1H), 7.96 (m, 2H), 7.44 (t, 1H), 7.23 (d, 1H), 4.59 (s, 2H), 3.88 (m, 2H), 1.65 (s, 3H) | 336 |

TABLE 1-continued

| Example | Compound | ¹H-NMR (δ; DMSO-d₆) | MS [m/z; (M + 1)⁺] |
|---|---|---|---|
| 15 | 5-(3-Trifluoromethyl-pyrazol-1-yl)-pyrazine-2-carboxylic acid [3-(5-amino-3-methyl-3,6-dihydro-2H-[1,4]oxazin-3-yl)-phenyl]-amide hydrochloride | 10.90 (s, 1H), 10.60 (s, 1H), 9.28 (s, 1H), 9.20 (s, 1H), 9.10 (s, 1H), 8.96 (s, 1H), 8.50 (s, 1H), 7.94 (m, 2H), 7.40 (t, 1H), 7.21 (m, 2H), 4.59 (s, 2H), 3.88 (m, 2H), 1.64 (s, 3H) | 446 |
| 16 | 5-(3-Methyl-pyrazol-1-yl)-pyrazine-2-carboxylic acid [3-(5-amino-3-methyl-3,6-dihydro-2H-[1,4]oxazin-3-yl)-phenyl]-amide hydrochloride | 10.80 (s, 1H), 10.60 (s, 1H), 9.12 (m, 3H), 8.60 (s, 1H), 8.50 (s, 1H), 7.94 (m, 2H), 7.45 (t, 1H), 7.21 (d, 1H), 6.55 (s, 1H), 4.59 (s, 2H), 3.88 (m, 2H), 2.35 (s, 3H), 1.64 (s, 3H) | 392 |
| 17 | 3-Chloro-5-trifluoromethyl-pyridine-2-carboxylic acid [3-(5-amino-3-methyl-3,6-dihydro-2H-[1,4]oxazin-3-yl)-phenyl]-amide hydrochloride | 10.91 (s, 1H), 10.60 (br, 1H), 9.11 (br, 1H), 9.07 (s, 1H), 8.72 (s, 1H), 8.50 (br, 1H), 7.76 (m, 2H), 7.46 (t, 1H), 7.26 (d, 1H), 4.58 (s, 2H), 3.89 (m, 2H), 1.64 (s, 3H) | 413 |
| 18 | 5-Methoxy-pyrazine-2-carboxylic acid [3-(5-amino-3-methyl-3,6-dihydro-2H-[1,4]oxazin-3-yl)-phenyl]-amide hydrochloride | 10.60 (s, 1H), 9.16 (s, 1H), 8.90 (s, 1H), 8.50 (s, 1H), 8.42 (s, 1H), 7.94 (m, 2H), 7.40 (t, 1H), 7.21 (d, 1H), 4.59 (s, 2H), 4.05 (s, 3H), 3.88 (m, 2H), 1.64 (s, 3H) | 342 |
| 19 | 5-Hydroxy-pyrazine-2-carboxylic acid [3-(5-amino-3-methyl-3,6-dihydro-2H-[1,4]oxazin-3-yl)-phenyl]-amide hydrochloride | 13.00 (s, 1H), 10.60 (s, 1H), 10.25 (s, 1H), 9.16 (s, 1H), 8.48 (s, 1H), 8.10 (br, 1H), 8.05 (s, 1H), 7.91 (d, 1H), 7.85 (s, 1H), 7.38 (t, 1H), 7.15 (d, 1H), 4.59 (s, 2H), 3.88 (m, 2H), 1.64 (s, 3H) | 328 |

TABLE 1-continued

| Example | Compound | ¹H-NMR (δ; DMSO-d₆) | MS [m/z; (M + 1)⁺] |
|---|---|---|---|
| 20 | 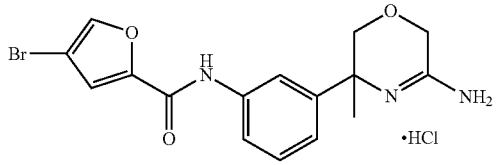<br>4-Bromo-furan-2-carboxylic acid [3-(5-amino-3-methyl-3,6-dihydro-2H-[1,4]oxazin-3-yl)-phenyl]-amide hydrochloride | 10.65 (s, 1H), 10.42 (s, 1H), 9.14 (s, 1H), 8.52 (s, 1H), 8.22 (s, 1H), 7.80 (s, 1H), 7.75 (d, 1H), 7.56 (s, 1H), 7.40 (m, 2H), 7.18 (d, 1H), 4.59 (s, 2H), 3.87 (m, 2H), 1.64 (s, 3H) | 379 |
| 21 | 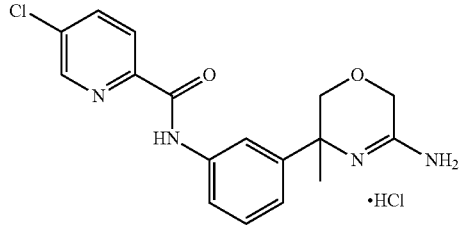 [SMILES: CC1(c2cccc(NC(=O)c3ccc(Cl)cn3)c2)COCC(N)=N1 ; Cl]<br>5-Chloro-pyridine-2-carboxylic acid [3-(5-amino-3-methyl-3,6-dihydro-2H-[1,4]oxazin-3-yl)-phenyl]-amide hydrochloride | 10.71 (s, 1H), 10.60 (s, 1H), 9.25 (s, 1H), 8.79 (s, 1H), 8.52 (s, 1H), 8.18 (m, 2H), 7.96 (m, 2H), 7.42 (t, 1H), 7.20 (d, 1H), 4.58 (s, 2H), 3.89 (m, 2H), 1.64 (s, 3H) | 345 |
| 22 | 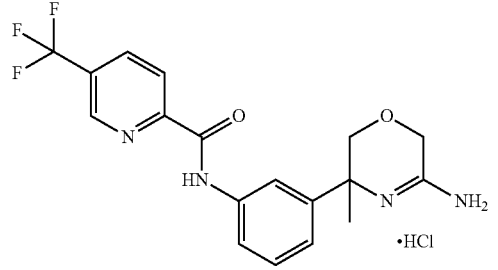 [SMILES: CC1(c2cccc(NC(=O)c3ccc(C(F)(F)F)cn3)c2)COCC(N)=N1 ; Cl]<br>5-Trifluoromethyl-pyridine-2-carboxylic acid [3-(5-amino-3-methyl-3,6-dihydro-2H-[1,4]oxazin-3-yl)-phenyl]-amide hydrochloride | 10.81 (s, 1H), 10.60 (br, 1H), 9.11 (s, 1H), 8.51 (d, 1H), 8.34 (d, 1H), 7.95 (m, 2H), 7.44 (m, 2H), 7.22 (d, 1H), 4.58 (s, 2H), 3.89 (m, 2H), 1.64 (s, 3H) | 379 |
| 23 | 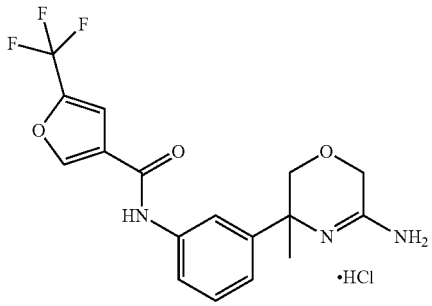 [SMILES: CC1(c2cccc(NC(=O)c3coc(C(F)(F)F)c3)c2)COCC(N)=N1 ; Cl]<br>5-Trifluoromethyl-furan-3-carboxylic acid [3-(5-amino-3-methyl-3,6-dihydro-2H-[1,4]oxazin-3-yl)-phenyl]-amide hydrochloride | 10.60 (s, 1H), 10.35 (s, 1H), 9.11 (s, 1H), 8.72 (s, 1H), 8.48 (s, 1H), 7.80 (s, 2H), 7.70 (d, 1H), 7.43 (m, 2H), 7.21 (d, 1H), 4.58 (s, 2H), 3.88 (m, 2H), 1.64 (s, 3H) | 368 |

TABLE 1-continued

| Example | Compound | ¹H-NMR (δ; DMSO-d$_6$) | MS [m/z; (M + 1)$^+$] |
|---|---|---|---|
| 24 | N-[3-(5-Amino-3-methyl-3,6-dihydro-2H-[1,4]oxazin-3-yl)-phenyl]-4-bromo-benzamide hydrochloride | 10.60 (s, 1H), 10.44 (s, 1H), 9.12 (s, 1H), 8.50 (s, 1H), 7.91 (m, 2H), 7.84 (s, 1H), 7.77 (m, 3H), 7.42 (t, 1H), 7.20 (d, 1H), 4.59 (s, 2H), 3.88 (m, 2H), 1.64 (s, 3H) | 388 |
| Reference Example 25 | Cyclohexanecarboxylic acid [3-(5-amino-3-methyl-3,6-dihydro-2H-[1,4]oxazin-3-yl)-phenyl]-amide hydrochloride | 10.60 (s, 1H), 9.96 (s, 1H), 9.15 (s, 1H), 8.53 (s, 1H), 7.72 (s, 1H), 7.56 (m, 1H), 7.33 (t, 1H), 7.09 (d, 1H), 4.57 (s, 2H), 3.86 (m, 2H), 2.34 (m, 1H), 1.80-1.15 (m, 10H), 1.60 (s, 3H) | 316 |
| Reference Example 26 | 4,4-Difluoro-cyclohexanecarboxylic acid [3-(5-amino-3-methyl-3,6-dihydro-2H-[1,4]oxazin-3-yl)-phenyl]-amide hydrochloride | 10.55 (s, 1H), 10.11 (s, 1H), 9.09 (s, 1H), 8.46 (d, 1H), 7.73 (s, 1H), 7.54 (d, 1H), 7.35 (t, 1H), 7.12 (d, 1H), 4.57 (s, 2H), 3.85 (m, 2H), 2.09 (m, 2H), 1.91 (m, 4H), 1.82 (m, 2H), 1.69 (m, 2H), 1.61 (s, 3H) | 352 |
| 27 | 5-Methyl-pyridine-2-carboxylic acid [3-(5-amino-3-methyl-3,6-dihydro-2H-[1,4]oxazin-3-yl)-phenyl]-amide hydrochloride | 10.70 (s, 1H), 10.65 (s, 1H), 9.18 (s, 1H), 8.57 (m, 2H), 8.07 (m, 1H), 7.98 (d, 1H), 7.95 (s, 1H), 7.90 (m, 1H), 7.42 (t, 2H), 7.20 (d, 1H), 4.59 (s, 2H), 3.88 (m, 2H), 2.43 (s, 3H), 1.65 (s, 3H) | 325 |

TABLE 1-continued

| Example | Compound | ¹H-NMR (δ; DMSO-d$_6$) | MS [m/z; (M + 1)⁺] |
|---|---|---|---|
| 28 | N-[3-(5-Amino-3-methyl-3,6-dihydro-2H-[1,4]oxazin-3-yl)-phenyl]-nicotinamide hydrochloride | 10.74 (s, 1H), 9.22 (s, 1H), 9.20 (s, 1H), 8.85 (d, 1H), 8.58 (s, 1H), 8.49 (d, 1H), 7.86 (s, 1H), 7.79 (m, 1H), 7.72 (m, 1H), 7.44 (t, 1H), 7.23 (d, 1H), 4.59 (s, 2H), 3.91 (m, 2H), 1.65 (s, 3H) | 311 |
| 29 | 5-Bromo-3-methyl-pyridine-2-carboxylic acid [3-((R)-5-amino-3-methyl-3,6-dihydro-2H-[1,4]oxazin-3-yl)-phenyl]-amide hydrochloride | 10.74 (s, 1H), 10.63 (s, 1H), 9.20 (s, 1H), 8.68 (1 s, 1H), 8.59 (s, 1H), 8.18 (s, 1H), 7.88 (d, 1H), 7.81 (s, 1H), 7.41 (t, 1H), 7.19 (d, 1H), 4.59 (s, 2H), 3.88 (m, 2H(AB-sytem)), 2.58 (s, 3H), 1.65 (s, 3H) | 403 |
| 30 | 5-Methoxy-pyridine-2-carboxylic acid [3-((R)-5-amino-3-methyl-3,6-dihydro-2H-[1,4]oxazin-3-yl)-phenyl]-amide hydrochloride | 10.69 (s, 1H), 10.55 (br, 1H), 9.15 (s, 1H), 8.55 (d, 1H), 8.39 (d, 1H), 8.14 (d, 1H), 7.96 (d, 1H), 7.92 (s, 1H), 7.64 (dd, 1H), 7.41 (t, 1H), 7.17 (d, 1H), 4.58 (s, 2H), 3.96 (s, 3H), 3.90 (m, 2H), 1.64 (s, 3H) | 341 |

The racemic (5-{3-[(5-bromo-pyridine-2-carbonyl)-amino]-phenyl}-5-methyl-5,6-dihydro-2H-[1,4]oxazin-3-yl)-carbamic acid tert-butyl ester was separated into the pure enantiomers by preparative chiral HPLC (column: CHIRACEL OD-PREP; solvent: heptane/ethanol/methanol=90:5:5; flow: 1 ml/min; detection at 210 nm). These enantiomers were treated with 4M HCl in dioxane to obtain the enantiomerically pure compounds 3 and 4. Example 3: [α]$_D$=−50.0°, c=0.519% (MeOH). Example 4: [α]$_D$=+58.1°, c=0.498% (MeOH). Examples 29 and 30 can be obtained by a similar procedure.

Example 31

5-Bromo-pyridine-2-carboxylic acid [3-(5-amino-3-fluoromethyl-3,6-dihydro-2H-[1,4]oxazin-3-yl)-phenyl]-amide

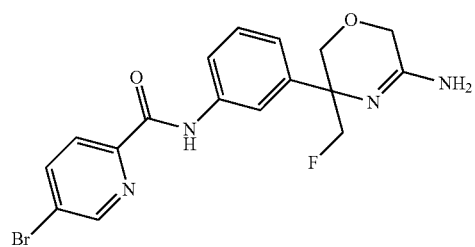 [SMILES: NC1=NC(CF)(c2cccc(NC(=O)c3ccc(Br)cn3)c2)COC1]

a) 2-(3-Bromo-phenyl)-2-nitro-propane-1,3-diol

A mixture of 1-bromo-3-nitromethyl-benzene (6.82 g, 31.6 mmol), formaline (35%, 5.22 ml, 66.3 mmol) and Et$_3$N (2.2 ml, 15.78 mmol) was heated at 50° C. for 1 h, diluted with water and extracted with TBME. The organic phase was washed with brine, dried with MgSO$_4$ and evaporated. The residue was crystallized from TBME/hexane to yield the title compound in the form of a colourless solid. TLC (hexane/EtOAc=2:1): R$_f$=0.2; HPLC: Rt$_{H2}$=3.117 min; $^{11}$H-NMR (400 MHz, CD$_3$OD): 7.61-7.54 (m, 2H), 7.39-7.34 (m, 2H), 4.40 (d, 2H), 4.35 (d, 2H); MS: 298, 300 [(M+Na)$^+$].

b) 2-Amino-2-(3-bromo-phenyl)-propane-1,3-diol

A solution of 2-(3-bromo-phenyl)-2-nitro-propane-1,3-diol (6.79 g, 24.59 mmol) in 100 ml of EtOH was hydrogenated in the presence of 5 g of Raney-Ni. When the take-up of hydrogen had ceased, the mixture was filtered through Celite, and the filtrate was chromatographed on silica gel (EtOAc/MeOH/25% aqueous NH$_3$, 5%) to give the title compound in the form of a colourless solid. TLC (EtOAc/MeOH/25% aqueous NH$_3$, 5%): R$_f$=0.24; HPLC: Rt$_{H2}$=2.354 min; $^1$H-NMR (400 MHz, CD$_3$OD): 7.73 (s, 1H), 7.50 (d, 1H), 7.44 (d, 1H), 7.29 (t, 1H), 3.79 (d, 2H), 3.72 (d, 2H); MS: 246, 248 [(M+H)$^+$].

c) N-[1-(3-Bromo-phenyl)-2-hydroxy-1-hydroxymethyl-ethyl]-2-chloro-acetamide To a stirred suspension of 2-amino-2-(3-bromo-phenyl)-propane-1,3-diol (3.5 g, 14.22 mmol), 30 ml of THF and 30 ml of 10% aqueous Na$_2$CO$_3$ solution was added dropwise chloroacetyl chloride (1.472 ml, 18.5 mmol) at 0° C. over a period of 10 min. The mixture was stirred for 1 h, diluted with water and extracted with EtOAc. The organic phase was washed with 1N aqueous NaOH solution, 10% aqueous Na$_2$CO$_3$ solution and brine. Chromatography on silica gel (EtOAc/hexane 50-30%) gave the title compound in the form of a colourless solid. TLC (hexane/EtOAc=1:1): R$_f$=0.21; HPLC: Rt$_{H2}$=2.926 min; $^1$H-NMR (400 MHz, CD$_3$OD): 7.58 (s, 1H), 7.44 (d, 1H), 7.37 (d, 1H), 7.29 (t, 1H), 4.91 (s, 2H), 4.07 (d, 2H), 4.00 (d, 2H); MS: 322, 324, 326 [(M+H)$^+$].

d) 5-(3-Bromo-phenyl)-5-hydroxymethyl-morpholin-3-one

A suspension of N-[1-(3-bromo-phenyl)-2-hydroxy-1-hydroxymethyl-ethyl]-2-chloro-acetamide (3.24 g, 10.04 mmol) and 35 ml of t-BuOH was treated with potassium tert-butoxide (1.127 g, 10.04 mmol). The mixture was heated at reflux for 1 h and neutralized with 10 ml of 1N HCl. Water and TBME were added, and the precipitate was filtered off. The organic phase of the filtrate was separated, dried with sodium sulfate and chromatographed on silica gel (EtOAc/MeOH 1-2%) to give the title compound in the form of a colourless solid. TLC (EtOAc/MeOH 1%): R$_f$=0.23, HPLC: Rt$_{H2}$=2.839 min; $^1$H-NMR (400 MHz, CD$_3$OD): 7.70 (s, 1H), 7.53-7.47 (m, 2H), 7.35 (t, 1H), 4.17 (s, 2H), 4.08 (d, 1H), 3.98 (d, 1H), 3.91 (d, 1H), 3.87 (d, 1H); MS: 287, 289 [(M+H)$^+$].

e) 5-(3-Bromo-phenyl)-5-fluoromethyl-morpholin-3-one

A suspension of 5-(3-bromo-phenyl)-5-hydroxymethyl-morpholin-3-one (2.6 g, 9.09 mmol) and 120 ml of dichloromethane was cooled to 0° C. DAST (1.26 ml) was added dropwise. The mixture was stirred overnight, poured onto 50 ml of 10% aqueous Na$_2$CO$_3$ solution and ice and extracted with dichloromethane. The extract was dried with sodium sulfate and evaporated. Chromatography on silica gel (EtOAc/hexane=1:1) gave the title compound in the form of a colourless solid. TLC (hexane/EtOAc=1:1): R$_f$=0.31; HPLC: Rt$_{H2}$=3.13 min; $^1$H-NMR (400 MHz, CD$_3$OD): 7.71 (s, 1H), 7.56 (d, 1H), 7.52 (d, 1H), 7.38 (t, 1H), 4.77 (d, 2H), 4.20 (s, 2H), 4.11 (d, 1H), 3.95 (d, 1H); MS: 289, 291 [(M+H)$^+$].

f) 5-(3-Bromo-phenyl)-5-fluoromethyl-morpholine-3-thione

A mixture of 5-(3-bromo-phenyl)-5-fluoromethyl-morpholin-3-one (1.52 g, 5.28 mmol) and Lawesson's reagent (2.14 g, 5.28 mmol) in 21 ml of THF was heated at 50° C. for 1 h and then evaporated. The residue was chromatographed on silica gel (cyclohexane/EtOAc=15:1) to give the title compound in the form of a colourless foam. TLC (hexane/EtOAc=3:1): R$_f$=0.21; HPLC: Rt$_{H2}$=3.49 min; $^1$H-NMR (400 MHz, CD$_3$OD): 7.65 (s, 1H), 7.58 (d, 1H), 7.47 (d, 1H), 7.39 (t, 1H), 4.87 (s, 2H), 4.63 (d, 1H), 4.50 (s, 2H), 4.02 (d, 1H); MS: 304, 306 [(M+H)$^+$].

g) [5-(3-Bromo-phenyl)-6-fluoromethyl-5,6-dihydro-2H-[1,4]oxazin-3-yl]-carbamic acid tert-butyl ester To a solution of 5-(3-bromo-phenyl)-5-fluoromethyl-morpholine-3-thione (200 mg, 0.658 mmol) in 5 ml of 7M NH$_3$/MeOH were added t-butyl hydroperoxide (80%, 0.818 ml, 6.58 mmol) and then 1.7 ml of 25% aqueous NH$_4$OH. After 2 h, the mixture was quenched with a saturated aqueous solution of Na$_2$S$_2$O$_3$ and extracted with EtOAc. The extract was washed with brine, dried with sodium sulfate and evaporated. The crude 5-(3-bromo-phenyl)-5-fluoromethyl-5,6-dihydro-2H-[1,4]oxazin-3-ylamine (189 mg, 0.658 mmol) was dissolved in 4 ml of dichloromethane. The solution was treated with DIPEA (0.172 ml, 0.987 mmol) and Boc$_2$O (187 mg, 0.855 mmol). After 14 h, the mixture was diluted with dichloromethane and washed with water, 1N HCl and brine. The organic phase was dried with sodium sulfate and evaporated. The residue was chromatographed on silica gel (cyclohexane/EtOAc=6:1) to yield the title compound. TLC (hexane/EtOAc=6:1): R$_f$=0.20; HPLC: Rt$_{H1}$=2.380 min; $^1$H-NMR (400 MHz, CDCl$_3$): 7.56-6.98 (m, 4H; broad signals due to rotamers), 4.80-3.60 (m, 6H), 1.42 (br, 9H); MS: 387, 389 [(M+H)$^+$].

h) [5-(3-Azido-phenyl)-5-fluoromethyl-5,6-dihydro-2H-[1,4]oxazin-3-yl]-carbamic acid tert-butyl ester A suspension of [5-(3-bromo-phenyl)-5-fluoromethyl-5,6-dihydro-2H-[1,4]oxazin-3-yl]-carbamic acid tert-butyl ester (114 mg, 0.295 mmol), NaN$_3$ (77 mg, 1.18 mmol), CuI (11 mg, 0.059 mmol), sodium ascorbate (12 mg, 0.059 mmol), N,N'-dimethyl-cyclohexane-1,2-diamine (13 mg, 0.089 mmol), 1.5 ml of EtOH and 0.6 ml of water was stirred under N$_2$ at 90° C. for 1 h. The mixture was filtered through Celite, and the filtrate was chromatographed on silica gel (cyclohexane/EtOAc=6:1) to yield the title compound in the form of a colourless foam. TLC (hexane/EtOAc=3:1): R$_f$=0.33; HPLC: Rt$_{H1}$=2.258 min; $^1$H-NMR (400 MHz, CDCl$_3$); 7.40-6.88 (m, 4H; broad signals due to rotamers), 4.75-3.60 (m, 6H), 1.42 (br, 9H); MS: 350 [(M+H)$^+$].

i) (5-{3-[(5-Bromo-pyridine-2-carbonyl)-amino]-phenyl}-5-fluoromethyl-5,6-dihydro-2H-[1,4]oxazin-3-yl)-carbamic acid tert-butyl ester A solution of [5-(3-azido-phenyl)-5-fluoromethyl-5,6-dihydro-2H-[1,4]oxazin-3-yl]-carbamic acid tert-butyl ester (56 mg, 0.161 mmol) in 2 ml of EtOAc was hydrogenated in the presence of Lindlar catalyst (11 mg) for 3 h. The mixture was filtered through Celite, and the filtrate was evaporated. The crude [5-(3-amino-phenyl)-5-fluoromethyl-5,6-dihydro-2H-[1,4]oxazin-3-yl]-carbamic acid tert-butyl ester (50 mg, 0.155 mmol) was taken up in 2 ml of dichloromethane. A mixture of 5-bromo-pyridine-2-carboxylic acid (34.4 mg, 0.170 mmol), HOBT (30.9 mg, 0.17 mmol) and EDC (32.6 mg, 0.17 mmol) in 2 ml of dichloromethane was added, followed by the addition of triethylamine (0.054 ml). The mixture was stirred for 4 h, treated with 5% aqueous NaHCO$_3$ solution and extracted twice with dichloromethane. The organic phase was dried with MgSO$_4$ and evaporated. The residue was chromatographed on silica gel (EtOAc/cyclohexane=1:4) to yield the title compound. TLC (hexane/EtOAc=3:1): R$_f$=0.16; HPLC: Rt$_{H1}$=2.763 min; $^1$H-NMR (400 MHz, CDCl$_3$): 9.80 (br, 1H), 8.60 (d, 1H), 8.11 (d, 1H), 7.98 (d, 1H), 7.77 (d, 1H), 7.73 (d, 1H), 7.33 (br, 1H), 7.15 (d, 1H), 4.75-3.65 (m, 6H), 1.60 (br; minor rotamer tBu), 1.42 (br; major rotamer tBu); MS: 507, 509 [(M+H)$^+$].

j) 5-Bromo-pyridine-2-carboxylic acid [3-5-amino-3-fluoromethyl-3,6-dihydro-2H-[1,4]oxazin-3-yl)-phenyl]-amide A solution of (5-{3-[(5-bromo-pyridine-2-carbonyl)-amino]-phenyl}-5-fluoromethyl-5,6-dihydro-2H-[1,4]oxazin-3-yl)-carbamic acid tert-butyl ester (48 mg, 0.095 mmol) in 2 ml of 3N HCl in MeOH was stirred at 40° C. for 2 h. The mixture was evaporated, and the residue was purified by chromatography on silica gel with a gradient of dichloromethane and 2-10% MeOH/NH$_4$OH (0.5%), yielding the title compound in the form of a colorless foam. TLC (dichloromethane/MeOH/25% aqueous NH$_4$OH=90:9:1): R$_f$=0.28; HPLC: Rt$_{H1}$=2.755 min; $^1$H-NMR (400 MHz, CDCl$_3$): 8.58 (d, 1H), 8.10 (d, 1H), 7.96 (dd, 1H), 7.76 (s, 1H), 7.71 (d, 1H), 7.31 (t, 1H), 7.21 (d, 1H), 4.55-4.33 (m, 2H), 4.13-3.95 (m, 3H), 3.65 (d, 1H), 4.0-3.3 (br, NH$_2$); MS: 407, 409 [(M+H)$^+$].

Example 32

The compound listed in Table 2 was prepared by a procedure analogous to that used in example 31 starting from 1-bromo-3-chloro-5-nitromethyl-benzene.

TABLE 2

| Example | Compound | $^1$H-NMR (δ; CD$_3$OD) | MS [m/z; (M + 1)$^+$] |
|---|---|---|---|
| 32 | 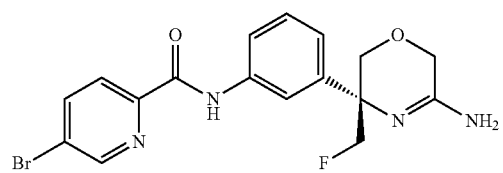 [SMILES: NC1=N[C@](CF)(c2cccc(NC(=O)c3ccc(Br)cn3)c2)COC1]<br>5-Bromo-pyridine-2-carboxylic acid [3-(5-amino-3-fluoromethyl-3,6-dihydro-2H-[1,4]oxazin-3-yl)-5-chloro-phenyl]-amide hydrochloride | 8.85 (d, 1H), 8.29 (m, 1H), 8.17 (d, 1H), 8.07 (m, 1H), 7.97 (s, 1H), 7.37 (s, 2H), 5.05 (m, 1H), 4.95 (m, 1H), 4.70 (s, 2H), 4.19 (m, 2H) | 442 |

Example 33

5-Bromo-pyridine-2-carboxylic acid [3-((R)-5-amino-3-fluoromethyl-3,6-dihydro-2H-[1,4]oxazin-3-yl)-phenyl]-amide a) (R)-[5-(3-Amino-phenyl)-5-fluoromethyl-5,6-dihydro-2H-[1,4]oxazin-3-yl]-carbamic acid tert-butyl ester A solution of 740 mg (2.118 mmol) [5-(3-azido-phenyl)-5-fluoromethyl-5,6-dihydro-2H-[1,4]oxazin-3-yl]-carbamic acid tert-butyl ester (Example 31h) in 5 ml THF and 5 ml EtOH was stirred in the presence of 35 mg 10% Pd—C under hydrogen. After 3 h the mixture was filtered over celite, concentrated and crystallized from EtOAc/hexane to give a beige solid. The racemic product was separated via prep HPLC on Chiralpak AD-H 250×4.6 mm column using heptan/EtOH 1:1 as an eluent. The desired compound was the slower eluting (R)-enantiomer. TLC: Rf (Hexane/EtOAc 2:1)=0.15. HPLC: Rt$_H$=1.764 min; ESIMS [M+H]$^+$=324. $^1$H-NMR (CDCl3, 360 MHz, broad signals due to hindered rotation): 10.5 (br, 1H), 7.12 (br, 1H), 6.69 (d, 1H), 6.59 (br d, 1H), 4.8-4.0 (m, 8H), 1.48 (br s, 9H).

b) ((R)-6-{3-[(5-Bromo-pyridine-2-carbonyl)-amino]-phenyl}-6-fluoromethyl-5,6-dihydro-2H-[1,4]oxazin-3-yl)-carbamic acid tert-butyl ester To an at 0° C. stirred solution of 105 mg (0.325 mmol) (R)-[5-(3-amino-phenyl)-5-fluoromethyl-5,6-dihydro-2H-[1,4]oxazin-3-yl]-carbamic acid tert-butyl ester, 72 mg (0.357 mmol) 5-bromo-pyridine-2-carboxylic acid, 57 mg (0.422 mmol) HOAt and 82 mg (0.812 mmol) Et$_3$N in 3 ml DCM were added 81 mg (0.422 mmol) EDC.HCl. After 18 h the mixture was diluted with EtOAc and washed with water, 5% aqueous NaHCO$_3$ and brine. Chromatography on silica gel (hexane/EtOAc 3:1) gave the desired product as a colorless solid.

TLC: Rf (Hexane/EtOAc 2:1)=0.31.
HPLC: Rt$_{H4}$=2.481 min; ESIMS [M+H]$^+$=507/509 (1Br);
$^1$H-NMR (360 MHz, CDCl$_3$, major rotamer only): 9.80 (br s, 1H), 8.61 (s, 1H), 8.13 (d, 1H), 7.87 (dd, 1H), 7.77 (br s, 1H), 7.73 (d, 1H), 7.35 (br, 1H), 7.15 (t, 1H), 4.90-4.20 (m, 5H), 4.15 (d, 1H), 3.75 (br, 1H), 1.45 (br s, 9H).

c) 5-Bromo-pyridine-2-carboxylic acid [3-((R)-amino-3-fluoromethyl-3,6-dihydro-2H-[1,4]oxazin-3-yl)-phenyl]-amide A solution of 117 mg (0.231 mmol) ((R)-5-{3-[(5-bromo-pyridine-2-carbonyl)-amino]-phenyl}-5-fluoromethyl-5,6-dihydro-2H-[1,4]oxazin-3-yl)-carbamic acid tert-butyl ester in 2 ml 4N HCl in dioxane was stirred at 45° C. overnight. The mixture was concentrated and crystallized from EtOAc/hexane to yield the title compound as colorless crystals.

Rf (DCM/[MeOH/NH3 aqueous, 25%; 9:1:0.1)=0.15
HPLC: Rt$_{H3}$=2.786 min; ESIMS [M+H]$^+$=407/409 (1Br);
$^1$H-NMR (600 MHz, DMSO-d6): δ 10.81 (s, 1H), 10.78 (s, 1H), 8.88 (s, 1H), 8.65 (s, 1H), 8.36 (d, 1H), 8.10 (d, 1H), 8.00 (d, 1H), 7.48 (t, 1H), 7.28 (d, 1H), 4.89 (d, 2H, CH2F), 4.62 (s, 2H), 4.10 (d, 1H), 4.01 (d, 1H).

Example 34

5-Bromo-pyridine-2-carboxylic acid [3-(5-amino-3-difluoromethyl-3,6-dihydro-2H-[1,4]oxazin-3-yl)-phenyl]-amide hydrochloride

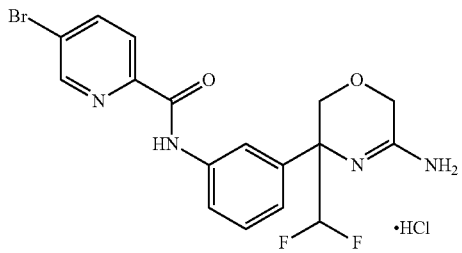 [SMILES: NC1=NC(c2cccc(NC(=O)c3ccc(Br)cn3)c2)(C(F)F)COC1 ; Cl]

a) 1-(3-Bromo-phenyl)-2,2-difluoro-ethanone

1-Bromo-3-iodo-benzene (22.5 g, 90 mmol, Aldrich) was dissolved in THF and cooled to −78° C. nBuLi (69.8 ml, 90 mmol) was added over 15 minutes and the reaction was stirred for 30 min. at −78° C. Difluoro-acetic acid ethyl ester (16.59 ml, 153 mmol, Aldrich) was added dropwise and stirring was continued for 3 hrs. After completion the reaction was quenched by the addition of 329 ml 2 M HCl solution and reaction was warmed to r.t. The phases were separated and the aqueous phases was extracted with Et$_2$O. The organic phases were washed with water and brine, dried over Na$_2$SO$_4$ and concentrated under reduced pressure. The residue was purified by automated column chromatography (cyclohexane/ethyl acetate) to yield the title compound as a yellow oil. $^1$H-NMR (360 MHz, DMSO-d$_6$): 8.18 (s, 1H), 8.02 (m, 2H), 7.61 (t, 1H), 7.21 (t, 1H, CHF$_2$); GC/MS: 234 [(M+H)$^+$].

b) [1-(3-Bromo-phenyl)-2,2-difluoro-ethylidene]-carbamic acid tert-butyl ester 1-(3-Bromo-phenyl)-2,2-difluoro-ethanone (15.36 g, 65.4 mmol) and N-boc-imino(triphenyl)phosphorane (27.1 g, 71.9 mmol) were heated for 75 hrs in toluene under N$_2$. After completion, volatiles were removed under reduced pressure and 457 ml hexane were added. The reaction was heated to reflux, cooled down and the formed precipitate was filtered off. The filtrate was evaporated yielding the crude product which was purified by column chromatography (cylcohexane/TBME). Yellow oil was obtained as product. $^1$H-NMR (360 MHz, DMSO-d$_6$): 8.02 (m, 1H), 7.85 (m, 1H), 7.55 (m, 2H), 7.20 (t, 1H, CHF$_2$); MS: 234 [(M+H-Boc)$^+$].

c) [1-(3-Bromo-phenyl)-1-difluoromethyl-allyl]-carbamic acid tert-butyl ester

[1-(3-Bromo-phenyl)-2,2-difluoro-ethylidene]-carbamic acid tert-butyl ester (9.09 g, 27.2 mmol) was dissolved in toluene and cooled to −20° C. under N$_2$. Using a syringe pump, vinylmagnesiumbromide (42.5 ml, 34.0 mmol) was added (1 eq. per hour). After 1.25 hrs no starting material was left and 218 ml half-saturated NH$_4$Cl solution was added to the reaction. The product was extracted with TBME. The organic phases were washed with water and brine, dried over Na$_2$SO$_4$ and concentrated under reduced pressure. The residue was purified by automated column chromatography (cyclohexane/TBME) to yield the title compound as a yellowish oil. $^1$H-NMR (600 MHz, DMSO-d$_6$): 7.81 (br, 1H, NH), 7.52 (m, 2H), 7.35 (m, 2H), 6.48 (t, 1H, CHF$_2$), 5.45 (d, 1H), 5.15 (d, 1H), 1.32 (s, 9H); MS: 362 [(M+H)$^+$].

d) [1-(3-Bromo-phenyl)-2,2-difluoro-1-hydroxymethyl-ethyl]-carbamic acid tert-butyl ester

[1-(3-Bromo-phenyl)-1-difluoromethyl-allyl]-carbamic acid tert-butyl ester (7.88 g, 21.76 mmol) was dissolved in 218 ml dichloromethane and 73 ml methanol. NaHCO3 (2.74 g, 32.6 mmol) was added and the reaction mixture was cooled to −78° C. The solution was treated with O$_3$ for 30 min. (until the reaction mixture turned blue). Gas was stopped and stirring was continued for 15 minutes. The reaction was flushed with oxygen and nitrogen until color disappeared. NaBH4 (2.47 g, 65.3 mmol) was added in three protions and stirring was continued for 30 min. at −78° C. The reaction was warmed to 0° C. and poured onto 435 ml 1 M HCl solution. The product was extracted with TBME. The organic phases were washed with water and brine, dried over Na$_2$SO$_4$ and concentrated under reduced pressure to yield the title compound as a greenish oil. $^1$H-NMR (600 MHz, DMSO-d$_6$): 7.49 (m, 2H), 7.38 (br, 1H, NH), 7.32 (m, 2H), 6.37 (t, 1H, CHF$_2$), 5.20 (br, 1H), 3.95 (m, 1H), 3.86 (br, 1H), 1.32 (s, 9H); MS: 366 [(M+H)$^+$].

e) 2-Amino-2-(3-bromo-phenyl)-3,3-difluoro-propan-1-ol hydrochloride

[1-(3-Bromo-phenyl)-2,2-difluoro-1-hydroxymethyl-ethyl]-carbamic acid tert-butyl ester (8.408 g, 22.96 mmol)

was dissolved in 105 ml 4 N HCl in dioxane. The reaction was stirred for 45 min. After completion volatiles were removed under reduced pressure to yield a white solid. $^1$H-NMR (360 MHz, DMSO-d$_6$): 9.30 (br, 3H, NH$_3^+$), 7.85 (s, 1H), 7.70 (d, 1H), 7.60 (d, 1H), 7.49 (t, 1H), 6.63 (t, 1H, CHF$_2$), 6.03 (br, 1H), 4.05 (m, 2H); MS: 266 [(M+H)$^+$].

f) N-[1-(3-Bromo-phenyl)-2,2-difluoro-1-hydroxymethyl-ethyl]-2-chloro-acetamide 2-Amino-2-(3-bromo-phenyl)-3,3-difluoro-propan-1-ol hydrochloride (6.5 g, 24.43 mmol) was put between 60 ml aqueous 2 M Na$_2$CO$_3$ solution and 60 ml dichloromethane and cooled to 0° C. under strong stirring. Then chloroacetylchloride (2.94 ml, 36.6 mmol), diluted in 8 ml dichloromethane, was added dropwise to the biphasic solution. After the complete addition, the reaction was stirred for 30 minutes at r.t. After completion 10 ml MeOH were added and stirring was continued for 10 minutes. Then TBME und water were added. The phases were separated, and the aqueous phase was extracted with TBME. The organic phases were washed with water and brine, dried over Na$_2$SO$_4$ and concentrated under reduced pressure to yield the title compound as off-white solid. $^1$H-NMR (360 MHz, DMSO-d$_6$): 8.72 (s, 1H), 7.53 (m, 2H), 7.35 (m, 2H), 6.48 (t, 1H, CHF$_2$), 5.39 (t, 1H), 4.18 (m, 2H), 3.10 (s, 2H); MS: 342 [(M+H)$^+$].

g) 5-(3-Bromo-phenyl)-5-difluoromethyl-morpholin-3-one

N-[1-(3-Bromo-phenyl)-2,2-difluoro-1-hydroxymethylethyl]-2-chloro-acetamide (8.10 g, 23.65 mmol) and potassium tert-butoxide (5.31 g, 47.3 mmol) were heated to 95° C. in 118 ml tert-butanol for 30 minutes. After completion water was added and the reaction was evaporated. The residue was put between ethyl acetate and water. The phases were separated and the aqueous phase was extracted twice with ethyl acetate. The organic phases were washed with water and brine, dried over Na$_2$SO$_4$ and concentrated under reduced pressure to yield the title compound as off-white solid. $^1$H-NMR (360 MHz, DMSO-d$_6$): 9.13 (s, 1H, NH), 7.78 (s, 1H), 7.59 (m, 2H), 7.42 (t, 1H), 6.48 (t, 1H, CHF$_2$), 4.28 (d, 1H), 4.10 (m, 2H), 3.92 (m, 1H); MS: 306 [(M+H)$^+$].

h) 5-(3-Bromo-phenyl)-5-difluoromethyl-morpholine-3-thione 5-(3-Bromo-phenyl)-5-difluoromethyl-morpholin-3-one (6.10 g, 19.93 mmol) was dissolved in 63 ml dry pyridine, and P$_2$S$_5$ (5.32 g, 23.91 mmol) was added. The mixture was heated to 80° V for 2 hrs. After completion, the mixture was put between ethyl acetate and 1 H HCl solution. Phases were separated and the organic phase was washed with 1 N HCl, saturated NaHCO$_3$ solution and brine. The organic phases were combined, dried over Na$_2$SO$_4$ and concentrated under reduced pressure to yield the title compound as off-white solid. $^1$H-NMR (360 MHz, DMSO-d$_6$): 8.60 (s, 1H, NH), 7.80-7.35 (m, 4H), 6.54 (t, 1H, CHF$_2$), 4.45 (m, 2H), 4.28 (d, 1H), 4.12 (d, 1H); MS: 322 [(M+H)$^+$].

i) 5-(3-Bromo-phenyl)-6-difluoromethyl-6,6-dihydro-2H-[1,4]oxazin-3-ylamine 5-(3-Bromo-phenyl)-5-difluoromethyl-morpholine-3-thione (7.49 g, 23.25 mmol) was dissolved in 36 ml 7N NH$_3$ in methanol and stirred at room temperature for 18 h. After completion, volatiles were removed under reduced pressure to yield the title compound. $^1$H-NMR (360 MHz, DMSO-d$_6$): 7.80 (s, 1H), 7.52 (m, 2H), 7.33 (m, 1H), 6.25 (br, 2H, NH$_2$), 6.04 (t, 1H, CHF$_2$), 4.15-3.90 (m, 2H), 3.72 (d, 1H), 3.45 (d, 1H); MS: 305 [(M+H)$^+$].

j) [5-(3-Bromo-phenyl)-5-difluoromethyl-5,6-dihydro-2H-[1,4]oxazin-3-yl]-carbamic acid tert-butyl ester 5-(3-Bromo-phenyl)-5-difluoromethyl-5,6-dihydro-2H-[1,4]oxazin-3-ylamine (6.12 g, 20.06 mmol) was dissolved in 100 ml ACN under N$_2$ at 0° C. Then Boc$_2$O (5.69 g, 26.1 mmol), DIPEA (5.25 ml, 30.1 mmol) and DMAP (0.25 g, 2.01 mmol) were added and the ice bath was removed. The reaction was stirred at room temperature for 90 min. After completion, the reaction was diluted with water and extracted with dichloromethane. The organic phases were washed with 1N HCl, saturated NaHCO$_3$ sol., water and brine, dried over Na$_2$SO$_4$ and concentrated under reduced pressure. The residue was purified by automated column chromatography (cyclohexane/TBME) to yield the title compound as a brownish solid. $^1$H-NMR (360 MHz, DMSO-d$_6$): 9.97 (s, 1H, NH), 7.80 (s, 1H), 7.55 (m, 2H), 7.35 (m, 1H), 6.17 (t, 1H, CHF$_2$), 4.62 (d, 1H), 4.41 (d, 1H), 4.22 (d, 1H), 3.75 (d, 1H), 1.45 (s, 9H); MS: 405 [(M+H)$^+$].

k) [5-(3-Azido-phenyl)-5-difluoromethyl-5,6-dihydro-2H-[1,4]oxazin-3-yl]-carbamic acid tert-butyl ester

[5-(3-Bromo-phenyl)-5-difluoromethyl-5,6-dihydro-2H-[1,4]oxazin-3-yl]-carbamic acid tert-butyl ester (2.25, 5.55 mmol), sodium azide (2.89 g, 44.4 mmol), sodium ascorbate (0.440 g, 2.22 mmol), copper iodide (0.423 g, 2.22 mmol) and rac-trans-N,N'-dimethyl-cyclohexane-1,2-diamine (0.790 g, 5.55 mmol) were dissolved in ethanol (76.6 ml) and water (33.0 ml). The mixture was stirred under N$_2$ at 70° C. for 30 minutes. After completion hexane/ethyl acetate 1/1 were added and the reaction mixture was filtered over silica gel. The filtrate was evaporated and the residue was purified by chromatography on silica gel (cyclohexane/TBME 9/1 to obtain azide, later hexane/ethyl acetate 2/1 to 1/1 to obtain aniline as side product) to yield the title compound. $^1$H-NMR (360 MHz, CDCl$_3$): 7.42 (m, 1H), 7.25 (m, 2H), 7.07 (m, 1H), 5.97 (t, 1H, CHF$_2$), 4.80 (d, 1H), 4.65 (d, 1H), 4.25 (d, 1H), 3.80 (d, 1H), 1.55 (s, 9H); MS: 368 [(M+H)$^+$].

l) [5-(3-Amino-phenyl)-5-difluoromethyl-5,6-dihydro-2H-[1,4]oxazin-3-yl]-carbamic acid tert-butyl ester A solution of [5-(3-azido-phenyl)-5-difluoromethyl-5,6-dihydro-2H-[1,4]oxazin-3-yl]-carbamic acid tert-butyl ester (1.71 g, 4.65 mmol) in 22 ml ethanol and 12 ml THF was hydrogenated with Pd/C (10%) (3 hrs, r.t.) The mixture was filtered through Celite, and the filtrate was evaporated and the residue was purified by chromatography on silica gel (cyclohexane/ethyl acetate) to yield the title compound as colorless solid.

$^1$H-NMR (360 MHz, CDCl$_3$): 7.22 (m, 1H), 6.92 (m, 1H), 6.84 (m, 1H), 6.70 (m, 1H), 5.95 (t, 1H, CHF$_2$), 4.92 (m, 1H), 4.73 (m, 1H), 4.32 (m, 1H), 3.95 (m, 1H), 1.53 (s, 9H); MS: 342 [(M+H)$^+$].

m) (5-{3-[(5-Bromo-pyridine-2-carbonyl)-amino]-phenyl}-5-difluoromethyl-5,6-dihydro-2H-[1,4]oxazin-3-yl)-carbamic acid tert-butyl ester

[5-(3-Amino-phenyl)-5-difluoromethyl-5,6-dihydro-2H-[1,4]oxazin-3-yl]-carbamic acid tert-butyl ester and 5-bromo-pyridine-2-carboxylic acid were coupled according the procedure described in example 51m). ¹H-NMR (360 MHz, CDCl₃): 9.92 (s, 1H, NH), 8.73 (s, 1H), 8.24 (d, 1H), 8.10 (d, 1H), 7.88 (m, 2H), 7.45 (m, 1H), 7.31 (m, 1H), 5.92 (t, 1H, CHF₂), 4.84 (d, 1H), 4.65 (d, 1H), 4.31 (d, 1H), 3.96 (d, 1H), 1.52 (s, 9H); MS: 525 [(M+H)⁺].

n) 5-Bromo-pyridine-2-carboxylic acid [3-(5-amino-3-difluoromethyl-3,6-dihydro-2H-[1,4]oxazin-3-yl)-phenyl]-amide hydrochloride (5-{3-[(5-Bromo-pyridine-2-carbonyl)-amino]-phenyl}-5-difluoromethyl-5,6-dihydro-2H-[1,4]oxazin-3-yl)-carbamic acid tert-butyl ester was deprotected according to the procedure described in example 51). ¹H-NMR (500 MHz, DMSO-d₆): 10.85 (s, 1H), 10.25 (s, 1H), 9.65 (br, 1H), 8.90 (s, 1H), 8.67 (br, 1H), 8.35 (m, 1H), 8.09 (d, 1H), 7.99 (m, 2H), 7.50 (t, 1H), 7.30 (d, 1H), 6.70 (t, 1H, CHF₂), 4.63 (m, 2H), 4.38 (m, 1H), 4.05 (m, 1H); MS: 425 [(M+H)⁺].

Examples 35 to 41

The compounds listed in Table 3 were prepared by a procedure analogous to that used in example 34.

TABLE 3

| Example | Compound | ¹H-NMR (δ; DMSO-d₆) | MS [m/z; (M + 1)⁺] |
|---|---|---|---|
| 35 | 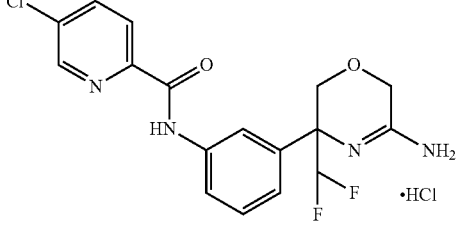<br>5-Chloro-pyridine-2-carboxylic acid [3-(5-amino-3-difluoromethyl-3,6-dihydro-2H-[1,4]oxazin-3-yl)-phenyl]-amide hydrochloride | 10.78 (s, 1H), 9.71 (s, 1H), 8.82 (s, 2H), 8.22 (m, 2H), 8.04 (m, 2H), 7.53 (t, 1H), 7.35 (d, 1H), 6.74 (t, 1H, CHF₂), 4.67 (m, 2H), 4.41 (m, 1H), 4.08 (m, 1H) | 381 |
| 36 | 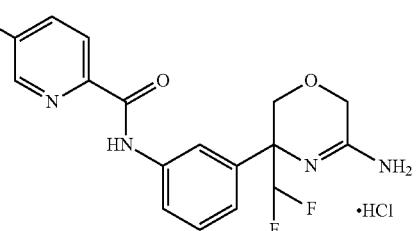<br>5-Cyano-pyridine-2-carboxylic acid [3-(5-amino-3-difluoromethyl-3,6-dihydro-2H-[1,4]oxazin-3-yl)-phenyl]-amide hydrochloride | 10.93 (s, 1H), 9.73 (s, 1H), 9.24 (s, 1H), 8.86 (s, 1H), 8.64 (d, 1H), 8.32 (d, 1H), 8.05 (m, 2H), 7.54 (t, 1H), 7.37 (d, 1H), 6.73 (t, 1H, CHF₂), 4.68 (m, 2H), 4.43 (m, 1H), 4.07 (m, 1H) | 372 |
| 37 | 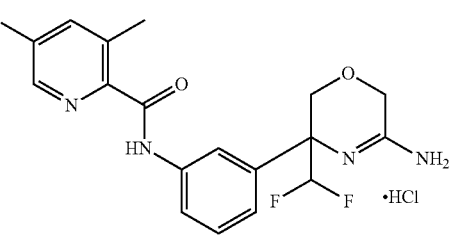<br>5-Bromo-3-methyl-pyridine-2-carboxylic acid [3-(5-amino-3-difluoromethyl-3,6-dihydro-2H-[1,4]oxazin-3-yl)-phenyl]-amide hydrochloride | 11.13 (s, 1H), 10.75 (s, 1H), 9.73 (s, 1H), 8.91 (s, 1H), 8.68 (s, 1H), 8.21 (s, 1H), 7.92 (m, 2H), 7.48 (t, 1H), 7.32 (d, 1H), 6.71 (t, 1H, CHF₂), 4.65 (m, 2H), 4.40 (m, 1H), 4.05 (m, 1H), 2.58 (s, 3H) | 439 |

TABLE 3-continued

| Example | Compound | ¹H-NMR (δ; DMSO-d₆) | MS [m/z; (M + 1)⁺] |
|---|---|---|---|
| 38 | 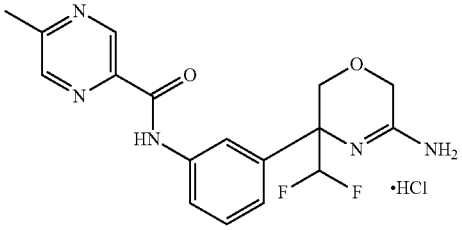 [SMILES: Cc1cnc(C(=O)Nc2cccc(C3(C(F)F)COCC(N)=N3)c2)cn1 ; Cl]<br>5-Methyl-pyrazine-2-carboxylic acid [3-(5-amino-3-difluoromethyl-3,6-dihydro-2H-[1,4]oxazin-3-yl)-phenyl]-amide hydrochloride | 11.13 (s, 1H), 10.80 (s, 1H), 9.71 (s, 1H), 9.16 (s, 1H), 8.89 (s, 1H), 8.72 (s, 1H), 8.05 (s, 1H), 7.99 (d, 1H), 7.30 (t, 1H), 7.35 (d, 1H), 6.71 (t, 1H, CHF₂), 4.65 (m, 2H), 4.40 (m, 1H), 4.05 (m, 1H), 2.58 (s, 3H) | 362 |
| 39 | 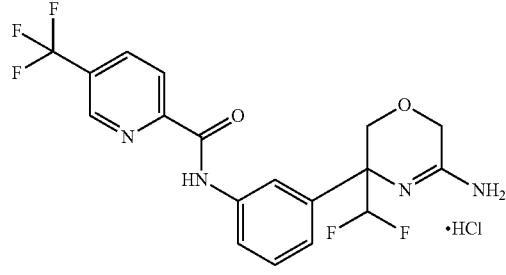 [SMILES: NC1=NC(c2cccc(NC(=O)c3ccc(C(F)(F)F)cn3)c2)(C(F)F)COC1 ; Cl]<br>5-Trifluoromethyl-pyridine-2-carboxylic acid [3-(5-amino-3-difluoromethyl-3,6-dihydro-2H-[1,4]oxazin-3-yl)-phenyl]-amide hydrochloride | 11.1 (s, 1H), 10.94 (s, 1H), 9.70 (s, 1H), 8.82 (s, 1H), 8.53 (d, 1H), 8.36 (d, 1H), 8.04 (m, 2H), 7.53 (t, 1H), 7.35 (d, 1H), 6.72 (t, 1H, CHF₂), 4.68 (m, 2H), 4.41 (m, 1H), 4.08 (m, 1H) | 415 |
| 40 | 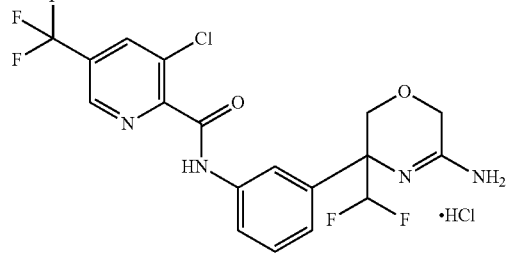<br>3-Chloro-5-trifluoromethyl-pyridine-2-carboxylic acid [3-(5-amino-3-difluoromethyl-3,6-dihydro-2H-[1,4]oxazin-3-yl)-phenyl]-amide hydrochloride | 11.1 (s, 1H), 11.02 (s, 1H), 9.70 (s, 1H), 9.10 (s, 1H), 8.77 (s, 1H), 8.73 (s, 1H), 7.87(s, 1H), 7.78 (d, 1H), 7.53 (t, 1H), 7.36 (d, 1H), 6.73 (t, 1H, CHF₂), 4.68 (m, 2H), 4.41 (m, 1H), 4.10 (m, 1H) | 449 |
| 41 | 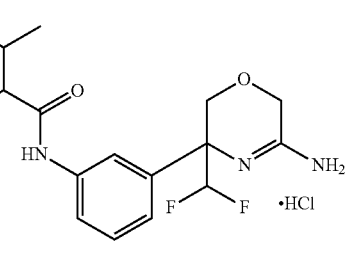<br>5-Chloro-3-methyl-pyridine-2-carboxylic acid [3-(5-amino-3-difluoromethyl-3,6-dihydro-2H-[1,4]oxazin-3-yl)-phenyl]-amide hydrochloride | 11.18 (s, 1H), 10.68 (s, 1H), 9.75 (s, 1H), 8.95 (s, 1H), 8.59 (s, 1H), 8.06 (s, 1H), 7.92 (m, 2H), 7.49 (t, 1H), 7.34 (d, 1H), 6.71 (t, 1H, CHF₂), 4.67 (m, 2H), 4.40 (m, 1H), 4.05 (m, 1H), 2.58 (s, 3H) | 395 |

Example 42

5-Bromo-pyridine-2-carboxylic acid [3-(5-amino-3-difluoromethyl-3,6-dihydro-2H-[1,4]oxazin-3-yl)-4-fluoro-phenyl]-amide hydrochloride

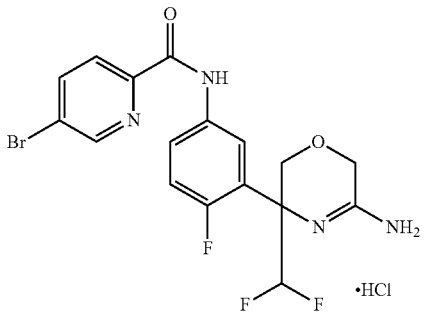 [SMILES: NC1=NC(c2cc(NC(=O)c3ccc(Br)cn3)ccc2F)(C(F)F)COC1 ; Cl]

a) 1-(5-Bromo-2-fluoro-phenyl)-ethanone

A solution of 17.78 ml (126 mmol) diisopropyl amine in 375 ml THF was cooled to −78° C. A 1.6 M solution of BuLi in hexanes (79 ml, 126 mmol) was added drop wise. After 15 minutes 20 g of 4-bromo-1-fluoro benzene (114 mmol) was added dropwise while keeping the temperature below −60° C. After stirring for 2.5 h at −70° C. 13.22 ml ethyl difluoro acetate were added. The mixture was warmed to −40° C. and then quenched by pouring the mixture onto 1M HCl. The mixture was extracted with ligroine, dried with $MgSO_4 \cdot H_2O$, concentrated and purified by column chromatography (silica gel; hexane/5-15% TBME) to give the desired product as a yellow liquid. $^1$H-NMR ($CDCl_3$, 360 MHz): 8.09 (dd, 1H), 7.82-7.77 (m, 1H), 7.17 (t, 1H), 6.45 (t, 1H, $CHF_2$)

b) 1-(5-Bromo-2-fluoro-phenyl)-1-difluoromethyl-allyl]-carbamic acid tert-butyl ester A mixture of 16 g (63.2 mmol) 1-(5-bromo-2-fluoro-phenyl)-ethanone and 26.3 g (69.6 mmol) N-tert-butyloxycarbonyl-triphenyliminophosphorane were heated at 90° C. in toluene for 18 h. The mixture was triturated with hexane and filtered to remove triphenyl phosphine oxide. The filtrate was purified by chromatography on silica gel (hexane/1-5% TBME) to give 11.37 g (32.3 mmol) of the desired product as a slightly impure yellow oil. TLC: Rf (Hexane/EtOAc 6:1)=0.65.

The product was dissolved in 100 ml THF and cooled to −78° C. Vinylmagnesium bromide (48 ml of a 1M solution in THF) was added dropwise, while the reaction temperature was not allowed to exceed −60° C. The mixture was stirred at −70° C. for 1 h before it was allowed to warm to 0° C. The reaction was quenched with 10% aqueous ammonium chloride and extracted with TBME. The organic layer was washed with brine, treated with activated charcoal and MgSO4.H2O and filtered over celite. The filtrated was concentrated and crystallized from hexane to give the desired product as colorless crystals.

HPLC: $Rt_{H1}$=3.575 min; ESIMS $[M+Na]^+$=402/404 (1Br);
$^1$H-NMR ($CDCl_3$, 360 MHz): 7.57 (dd, 1H), 7.51-7.45 (m, 1H), 7.00 (dd, 1H), 6.49 (t, 1H, $CHF_2$), 6.21 (dd, 1H), 5.59 (d, 1H), 5.40 (dd, 1H), 5.25 (br, 1H), 1.40 (br s, 9H).

c) [1-(5-Bromo-2-fluoro-phenyl)-2,2-difluoro-1-hydroxymethyl-ethyl]-carbamic acid tert-butyl ester A suspension of 10.99 g (28.9 mmol) 1-(5-bromo-2-fluoro-phenyl)-1-difluoromethyl-allyl]-carbamic acid tert-butyl ester and 3.84 g (43.4 mmol) sodium hydrogen carbonate in 200 ml DCM and 80 ml MeOH was cooled to −78° C. A mixture of $O_3$ in oxygen gas was introduced till the blue color persisted. The excess ozone was removed by bubbling through oxygen gas for 10 minutes. NaBH4 (2.187 g, 57.8 mmol) was added as a solid in three portions. The mixture was stirred 10 min at −78° C. and then allowed to warm to 0° C. After 30 min the mixture was poured onto ice-cold 1N HCl and extracted with TBME. The organic phase was washed with 1N HCl, brine, dried with MgSO4.H2O and evaporated. The crude product was crystallized from hexane to give the desired product as colorless crystals.

TLC: Rf (Hexane/EtOAc 4:1)=0.29.
HPLC: $Rt_{H1}$=3.000 min; ESIMS $[M+Na]^+$=406/408 (1Br);
$^1$H-NMR (DMSO-d6, 360 MHz): 7.60-7.49 (m, 2H), 7.42 (br s, 1H), 7.180 (dd, 1H), 6.49 (t, 1H, $CHF_2$), 5.27 (br s, 1H), 3.90 (br s, 2H), 1.35 (br s, 9H).

d) N-[1-(5-Bromo-2-fluoro-phenyl)-2,2-difluoro-1-hydroxymethyl-ethyl]-2-chloro-acetamide A suspension of 10.22 g (26.6 mmol) [1-(5-bromo-2-fluoro-phenyl)-2,2-difluoro-1-hydroxymethyl-ethyl]-carbamic acid tert-butyl ester in 133 ml 4N HCl in dioxane was stirred for two h at rt. The mixture was evaporated to give the hydrochloride salt of 2-amino-2-(5-bromo-2-fluoro-phenyl)-3,3-difluoro-propan-1-ol.

HPLC: $Rt_{H3}$=2.550 min; ESIMS $[M+H]^+$=284,286 (1Br);

The crude product was taken up in 63 ml DCM and 63 ml 10% aqueous soda and stirred vigorously with ice-cooling. A solution of 3.34 ml (42 mmol) chloroacetyl chloride in 10 ml DCM was added dropwise. The ice bath was taken away and stirring was continued for 1 h. The mixture was diluted with TBME and water. The organic phase was dried with MgSO4.H2O and purified via chromatography on silica gel (hexane/25-33% EtOAc) to give the desired product as a slightly impure resin.

HPLC: $Rt_{H3}$=3.336 min; ESIMS $[M+H]^+$=360/362/364 (1Br, 1Cl);
$^1$H-NMR (DMSO-d6, 360 MHz): 8.78 (s, 1H), 7.62-7.53 (m, 2H), 7.19 (dd, 1H), 6.53 (t, 1H, $CHF_2$), 5.43 (t, 1H), 4.27-4.02 (m, 4H).

e) 5-(5-Bromo-2-fluoro-phenyl)-6-difluoromethyl-morpholin-3-one

A solution of 9.59 g (26.2 mmol) N-[1-(5-Bromo-2-fluoro-phenyl)-2,2-difluoro-1-hydroxymethyl-ethyl]-2-chloro-acetamide in 134 ml t-butanol was treated with 3.58 g KOtBu. The mixture was heated at reflux for 3 h. After cooling down the mixture was diluted with EtOAc and 1N HCl. The organic phase was washed with brine, dried with MgSO4.H2O, filtered and evaporated. The product was obtained as colorless crystal (TBME/hexane).

TLC: Rf (Hexane/EtOAc 2:1)=0.29.
HPLC: $Rt_{H3}$=2.950 min; ESIMS $[M+H]^+$=324/326 (1Br);
$^1$H-NMR (CDCl3, 360 MHz): 7.61-7.55 (m, 2H), 7.09 (dd, 1H), 6.80 (br, 1H), 6.35 (t, 1H, CHF2), 4.37-4.17 (m, 4H).

f) 5-(5-Bromo-2-fluoro-phenyl)-5-difluoromethyl-morpholin-3-thione

A mixture of 7.34 g (22.65 mmol) 5-(5-bromo-2-fluoro-phenyl)-5-difluoromethyl-morpholin-3-one and 5.19 g (12.46 mmol) Lawesson's reagent in 73 ml of THF was refluxed for 1 h. The mixture was concentrated and crystallized from DCM/hexane and recrystallized from EtOH to yield the desired product as colorless crystals.

HPLC: $Rt_{H3}$=3.370 min; ESIMS [M+H]$^+$=340/342 (1Br);
$^1$H-NMR (DMSO-d6, 360 MHz): 11.40 (s, 1H), 7.77-7.70 (m, 1H), 7.63 (dd, 1H), 7.37 (dd, 1H), 6.35 (t, 1H, CHF2), 4.50 (d, 1H), 4.44 (d, 1H), 4.29 (d, 1H), 4.10 (d, 1H).

g) 5-(5-Bromo-2-fluoro-phenyl)-5-difluoromethyl-5,6-dihydro-2H-[1,4]oxazin-3-ylamine A solution of 6.14 g (18.05 mmol) 5-(5-bromo-2-fluoro-phenyl)-5-difluoromethyl-morpholine-3-thione in 77 ml 7M NH3/MeOH was stirred at rt for 6 h. The mixture was evaporated and purified chromatographed on silica gel (DCM/1-5% MeOH followed by DCM/MeOH/aqueous NH3 95:4.5:0.5) to give the desired product as yellowish resin.

HPLC: $Rt_{H3}$=2.477 min; ESIMS [M+H]$^+$=323/325 (1Br);
$^1$H-NMR (DMSO-d6, 360 MHz): 7.99 (dd, 1H), 7.62-7.56 (m, 1H), 7.22 (dd, 1H), 6.31 (br, 2H), 6.12 (t, 1H, CHF2), 4.25 (d, 1H), 4.05 (d, 1H), 3.94 (d, 1H), 3.75 (d, 1H).

h) [5-(5-Bromo-2-fluoro-phenyl)-5-difluoromethyl-5,6-dihydro-2H-[1,4]oxazin-3-yl]-carbamic acid tert-butyl ester To an ice-cold solution of 6.38 g (19.75 mmol) 5-(5-bromo-2-fluoro-phenyl)-5-difluoromethyl-5,6-dihydro-2H-[1,4]oxazin-3-ylamine in 100 ml THF were added 5.60 g (25.67 mmol) Boc$_{20}$ and 5.17 ml (29.6 mmol) DIPEA. The mixture was stirred for 4 h at rt. Then the mixture was diluted with TBME and washed with 5% aqueous NaHCO3. The organic phase was dried with MgSO4.H2O, filtered and concentrated. Purification by chromatography on silica gel (hexane/5-20% EtOAc) gave the desired product as a colorless solid.

TLC: Rf (Hexane/EtOAc 9:1)=0.27.
HPLC: $Rt_{H1}$=3.299 min; ESIMS [M+H]$^+$=423/425 (1Br);
$^1$H-NMR (CDCl3, 360 MHz): 7.81 (dd, 1H), 7.50-7.44 (m, 1H), 7.00 (dd, 1H), 6.12 (t, 1H, CHF2), 4.83 (d, 1H), 4.60 (d, 1H), 4.37 (dd, 1H), 3.94 (d, 1H), 1.52 (s, 9H).

i) [5-(5-Azido-2-fluoro-phenyl)-5-difluoromethyl-5,6-dihydro-2H-[1,4]oxazin-3-yl]-carbamic acid tert-butyl ester To a solution of 7.27 g (17.18 mmol) [5-(5-bromo-2-fluoro-phenyl)-5-difluoromethyl-5,6-dihydro-2H-[1,4]oxazin-3-yl]-carbamic acid tert-butyl ester and 2.443 g (17.18 mmol) trans-N,N'-dimethylcyclohexane-1,2-diamine in 237 ml EtOH was added a solution of 8.93 g (137 mmol) sodium azide and 1.361 g (6.87 mmol) sodium-ascorbate in 102 ml water. The mixture was degassed and brought under nitrogen atmosphere. CuI (1.309 g, 6.87 mmol) was added and the mixture was heated at 70° C. The initially formed suspension turned into a homogeneous blue solution. The mixture was cooled to rt, diluted with water and TBME. The organic phase was washed with brine and dried with MgSO4.H2O. The crude product was purified by chromatography on silica gel (hexane/5-8% TBME) to give the desired product as a colorless solid.

HPLC: $Rt_{H1}$=3.173 min; ESIMS [M+H]$^+$=386;
$^1$H-NMR (CDCl3, 360 MHz, signals broadened due to rotamers): 7.39-7.44 (m, 1H), 7.15-7.06 (m, 1H), 7.05-6.98 (m, 1H), 6.14 (t, 1H, CHF2), 4.80 (d, 1H), 4.60 (d, 1H), 4.39 (d, 1H), 3.97 (d, 1H), 1.52 (s, 9H).

j) [5-(5-Amino-2-fluoro-phenyl)-6-difluoromethyl-5,6-dihydro-2H-[1,4]oxazin-3-yl]-carbamic acid tert-butyl ester A solution of 4.89 g (12.69 mmol) [5-(5-azido-2-fluoro-phenyl)-5-difluoromethyl-5,6-dihydro-2H-[1,4]oxazin-3-yl]-carbamic acid tert-butyl ester in 64 ml EtOH and 17 ml THF was treated with 1.1 g 10% Pd—C and stirred under an atmosphere of hydrogen until the starting material had been consumed. The mixture was diluted with DCM and filtered over celite. The product was purified by chromatography on silica gel (hexane/25-50% EtOAc) to give the desired product as colorless foam.

HPLC: $Rt_{H3}$=2.778 min; ESIMS [M+H]$^+$=360;
$^1$H-NMR (CDCl3, 360 MHz, spectrum not interpretable due to rotamers): 7.1-6.1 (m, ~4H), 5.0-4.9 (m, ~4H), 1.52 (br s, 9H).

k) (5-{5-[(5-Bromo-pyridine-2-carbonyl)-amino]-2-fluoro-phenyl}-5-difluoromethyl-5,6-dihydro-2H-[1,4]oxazin-3-yl)-carbamic acid tert-butyl ester To a solution of 325 mg (0.952 mmol) [5-(5-amino-2-fluoro-phenyl)-5-difluoromethyl-5,6-dihydro-2H-[1,4]oxazin-3-yl]-carbamic acid tert-butyl ester, 212 mg (1.047 mmol) 5-bromo-pyridine-2-carboxylic acid, 168 mg (1.238 mmol) HOAt and 0.34 ml (2.38 mmol) Et$_3$N in 5 ml DCM were added 237 mg (1.24 mmol) EDC.HCl. The mixture was stirred overnight. The mixture was diluted with EtOAc and washed with water, 1N HCl, brine and 5% aqueous NaHCO$_3$. The organic phase was dried with MgSO4.H2O, filtered and purified by chromatography on silica gel (hexane/14-18% EtOAc) to give the desired product as colorless foam.

TLC: Rf (Hexane/EtOAc 3:1)=0.35.
HPLC: $Rt_{H1}$=3.127 min; ESIMS [M+H]$^+$=525/527 (1Br);
$^1$H-NMR (CDCl3, 360 MHz): 9.90 (br s, 1H), 8.72 (d, 1H), 8.23 (d, 1H), 8.09 (dd, 1H), 7.94-7.86 (m, 2H), 7.47 (t, 1H), 7.38-7.28 (m, 3H), 5.92 (t, 1H, CHF2), 4.87 (d, 1H), 4.67 (d, 1H), 4.6-4.45 (br, 1H), 4.34 (d, 1H), 4.00 (d, 1H), 1.56 (br s, 9H).

l) 5-Bromo-pyridine-2-carboxylic acid [3-(5-amino-3-difluoromethyl-3,6-dihydro-2H-[1,4]oxazin-3-yl)-4-fluoro-phenyl]-amide A solution of 100 mg (0.184 mmol) (5-{5-[(5-bromo-pyridine-2-carbonyl)-amino]-2-fluoro-phenyl}-5-difluoromethyl-5,6-dihydro-2H-[1,4]oxazin-3-yl)-carbamic acid tert-butyl ester in 1.4 ml 4N HCl in dioxane was stirred at 50° C. After 15 min 0.3 ml 3N HCl in MeOH were added and the now homogeneous solution was stirred for 3 h. The mixture was concentrated and crystallized from EtOH/TBME to yield the title compound.

HPLC: $Rt_{H3}$=2.857 min; ESIMS [M+H]$^+$=443/445;
$^1$H-NMR (600 MHz, DMSO-d6): δ 10.93 (s, 1H), 9.78 (s, 1H), 8.89 (s, 1H), 8.77 (s, 1H), 8.35 (d, 1H), 8.11-8-06 (m, 3H), 7.39 (t, 1H), 6.79 (t, 1H, CHF2), 4.70 (d, 1H), 4.64 (d, 1H), 4.34 (d, 1H), 4.17 (d, 1H).

Examples 43 to 49

The compounds listed in Table 4 were prepared by a procedure analogous to that used in example 42.

For enantiomerically pure compounds the racemic precursor [5-(5-amino-2-fluoro-phenyl)-5-difluoromethyl-5,6-dihydro-2H-[1,4]oxazin-3-yl]-carbamic acid tert-butyl ester (example 42j)) was separated via prep-HPLC on Chiralpak AD-H 250×4.6 mm column using supercritical CO2/EtOH 9:1 as an eluent. The desired compound was the slower eluting (R)-enantiomer. Enantiomeric excess=99.7%; $[\alpha]_D$= −109.7° (c=1, CHCl$_3$).

TABLE 4

| Example | Compound | $^1$H-NMR (δ; DMSO-d$_6$) | MS [m/z; (M + 1)$^+$] |
|---|---|---|---|
| 43 | 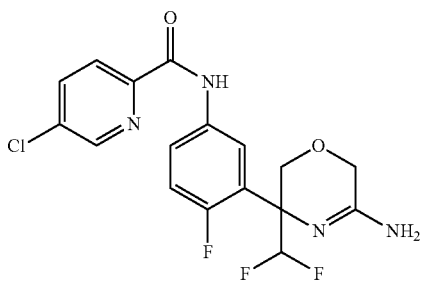 [SMILES: NC1=NC(c2cc(NC(=O)c3ccc(Cl)cn3)ccc2F)(C(F)F)COC1]<br>5-Chloro-pyridine-2-carboxylic acid [3-(5-amino-3-difluoromethyl-3,6-dihydro-2H-[1,4]oxazin-3-yl)-4-fluoro-phenyl]-amide | 10.95 (s, 1H), 9.77 (s, 1H), 8.80 (s and s, 2H), 8.22 (dd, 1H), 8.17 (d, 1H), 8.10-8.06 (m, 2H), 7.39 (t, 1H), 6.78 (t, 1H, CHF2), 4.72 (d, 1H), 4.65 (d, 1H), 4.32 (d, 1H), 4.18 (d, 1H). | 399 |
| 44 | 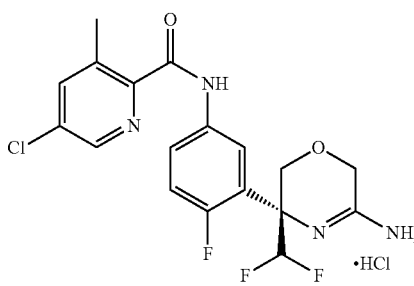<br>5-Chloro-3-methyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.78 (s, 1H), 9.78 (s, 1H), 8.78 (s, 1H), 8.62 (s, 1H), 8.01-7.94 (m, 2H), 7.39 (dd, 1H), 6.78 (t, 1H, CHF2), 4.72 (d, 1H), 4.68 (d, 1H), 4.39 (d, 1H), 4.21 (d, 1H). | 413 |
| 45 | 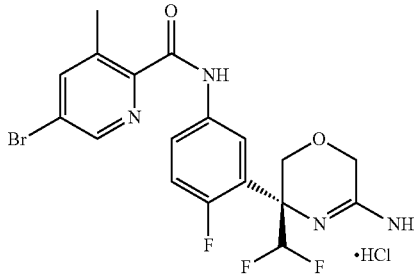<br>5-Bromo-3-methyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.64 (s, 1H), 9.78 (s, 1H), 8.67 (s, 1H), 8.19 (s, 1H), 8.01-7.94 (m, 2H), 7.38 (dd, 1H), 6.78 (t, 1H, CHF2), 4.75 (d, 1H), 4.65 (d, 1H), 4.34 (d, 1H), 4.17 (d, 1H). | 457 |

TABLE 4-continued

| Example | Compound | ¹H-NMR (δ; DMSO-d₆) | MS [m/z; (M + 1)⁺] |
|---|---|---|---|
| 46 | 3-Chloro-5-trifluoromethyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.05 (s, 1H), 9.74 (s, 1H), 9.08 (s, 1H), 8.80 (s, 1H), 8.74 (s, 1H), 8.90-8.84 (m, 2H), 7.41 (dd, 1H), 6.78 (t, 1H, CHF2), 4.69 (d, 1H), 4.64 (d, 1H), 4.35 (d, 1H), 4.17 (d, 1H). | 467 |
| 47 | 5-Trifluoromethyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.02 (s, 1H), 9.75 (s, 1H), 9.15 (s, 1H), 8.74 (s, 1H), 8.52 (d, 1H), 8.34 (d, 1H), 8.12-8.06 (m, 2H), 7.40 (dd, 1H), 6.78 (t, 1H, CHF2), 4.70 (d, 1H), 4.60 (d, 1H), 4.31 (d, 1H), 4.18 (d, 1H). | 433 |
| 48 | 5-Methyl-pyrazine-2-carboxylic acid [3-((R)-5-amino-3-difluoromethyl-3,6-dihydro-2H-[1,4]oxazin-3-yl)-4-fluoro-phenyl]-amide hydrochloride | 11.00 (s, 1H), 10.95 (s, 1H), 9.73 (s, 1H), 9.17 (s, 1H), 8.73 (d and d, 2H), 8.14-8.10 (m, 1H), 8.08-8.03 (m, 1H), 7.40 (dd, 1H), 6.78 (t, 1H, CHF2), 4.70 (d, 1H), 4.65 (d, 1H), 4.32 (d, 1H), 4.18 (d, 1H), 2.56 (s, 3H). | 380 |

TABLE 4-continued

| Example | Compound | $^1$H-NMR (δ; DMSO-$d_6$) | MS [m/z; $(M+1)^+$] |
|---|---|---|---|
| 49 | 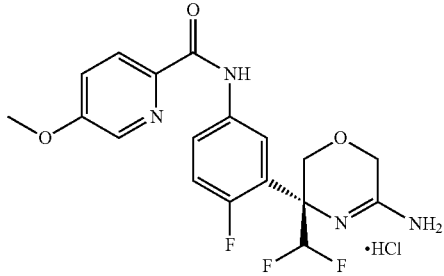 [SMILES: COc1ccc(C(=O)Nc2ccc(F)c([C@]3(C(F)F)COCC(N)=N3)c2)nc1 ; Cl]  5-Methoxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.99 (s, 1H), 10.74 (s, 1H), 9.75 (s, 1H), 8.71 (s, 1H), 8.39 (s, 1H), 8.15 (d, 1H), 8.10-8.14 (m, 2H), 7.40 (dd, 1H), 7.64 (d, 1H), 6.37 (dd, 1H), 6.78 (t, 1H, CHF2), 4.72 (d, 1H), 4.63 (d, 1H), 4.33 (d, 1H), 4.17 (d, 1H), 3.44 (s, 3H). | 395 |

Example 50

5-Chloro-pyridine-2-carboxylic acid [3-(5-amino-3-trifluoromethyl-3,6-dihydro-2H-[1,4]oxazin-3-yl)-4-fluoro-phenyl]-amide

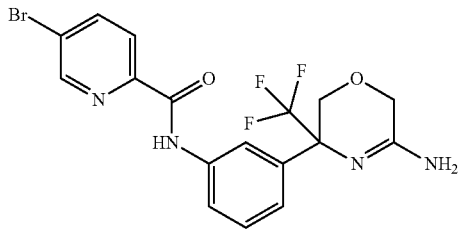 [SMILES: NC1=NC(c2cccc(NC(=O)c3ccc(Br)cn3)c2)(C(F)(F)F)COC1]

a) 2-(3-Bromo-phenyl)-2-tert-butoxycarbonylamino-3,3,3-trifluoro-propionic acid ethyl ester A solution of 5.66 g (20 mmol) 1-bromo-3-iodo-benzene in 25 ml THF was stirred at −20° C. A 1.82 M solution of isopropylmagnesium chloride (12.1 ml, 22.0 mmol) in THF was added and the mixture was stirred 1 h at 0° C. The mixture was cooled to −78° C. and a solution of 5.38 g (20 mmol) 2-[(E)-tert-butoxycarbonylimino]-3,3,3-trifluoro-propionic acid ethyl ester in 50 ml of THF was added over a period of 2 h. After 20 min the mixture was quenched with 5% aqueous NH₄Cl. The mixture was extracted with TBME. The organic phase was dried with Na2SO4, filtered and evaporated. Purification via chromatography on silica gel (c-hexane/0-14% EtOAc) gave the desired product as a colorless resin.

TLC: Rf (Hexane/EtOAc 6:1)=0.37.
HPLC: Rt$_{H1}$=3.704 min; ESIMS [M+Na]$^+$=448/450 (1Br);
$^1$H-NMR (CDCl3, 360 MHz): 7.69 (s, 1H), 7.57 (d, 1H), 7.49 (d, 1H), 7.31 (t, 1H), 5.70 (br s, 1H), 4.37 (q, 2H), 1.42 (br s, 9H), 1.30 (t, 3H).

b) [1-(3-Bromo-phenyl)-2,2,2-trifluoro-1-hydroxymethyl-ethyl]-carbamic acid tert-butyl ester To an at −7° C. stirred solution of 5 g (11.73 mmol) 2-(3-bromo-phenyl)-2-tert-butoxycarbonylamino-3,3,3-trifluoro-propionic acid ethyl ester in 50 ml toluene were added 58.7 ml of a 1.7M solution of DibalH in toluene. The mixture was stirred overnight at rt and quenched with an aqueous tartaric acid solution. The mixture was extracted with EtOAc and the organic phase was washed with brine, dried with MgSO4.H2O and evaporated. Purification via chromatography on silica gel (c-hexane/15-50% TBME) gave the desired product as a colorless resin.

TLC: Rf (Hexane/EtOAc 3:1)=0.35
HPLC: Rt$_{H1}$=3.155 min; ESIMS [M+Na]$^+$=406/408 (1Br);
$^1$H-NMR (CDCl3, 360 MHz): 7.54 (s, 1H), 7.45 (d, 1H), 7.35 (d, 1H), 7.23 (t, 1H), 5.38 (s, 1H), 4.28-4.12 (m, 3H), 1.38 (br s, 9H).

c) [2-(3-Bromo-phenyl)-2-tert-butoxycarbonylamino-3,3,3-trifluoro-propoxy]-acetic acid ethyl ester With the use of a syringe pump a solution of 1.87 ml (15.17 mmol) ethyl diazoacetate in 8 ml DCM were added to a stirred solution of 2.01 g (5.23 mmol) [1-(3-bromo-phenyl)-2,2,2-trifluoro-1-hydroxymethyl-ethyl]-carbamic acid tert-butyl ester and 46 mg (0.105 mmol) Rh₂(OAc)₂ in 34 ml DCM over a period of 3.5 h. After 30 min the mixture was evaporated and chromatographed on silica gel (c-hexane/0-20% TBME) to give the desired product contaminated with a diazo ester oligomer.

HPLC: Rt$_{H1}$=3.752 min; ESIMS [M+Na]$^+$=492/494 (1Br);
$^1$H-NMR (CDCl3, 360 MHz): 7.67 (s, 1H), 7.51 (d, 1H), 7.46 (d, 1H), 7.28 (t, 1H), 6.28 (s, impurity), 6.05 (br s, 1H), 4.35-4.10 (m, 5H), 3.85 (br, 1H), 1.40 (br s, 9H), 1.35 (t, 3H).

d) [2-Amino-2-(3-bromo-phenyl)-3,3,3-trifluoro-propoxy]-acetic acid ethyl ester A solution of 1.4 g (2.47 mmol) [2-(3-bromo-phenyl)-2-tert-butoxycarbonylamino-3,3,3-trifluoro-propoxy]-acetic acid ethyl ester in 5 ml DCM was treated with 3.74 ml 4N HCl/dioxane. After standing overnight the mixture was evaporated, taken up in EtOAc and washed with 10% aqueous NaHCO3. The organic phase was washed with brine, dried with Na2SO4 and purified via chromatography on silica gel (c-hexane/10-15% EtOAc) to give the desired product as a colorless resin.

TLC: Rf (Hexane/EtOAc 3:1)=0.30.
HPLC: Rt$_{H1}$=2.316 min; ESIMS [M+H]$^+$=370/372 (1Br);
$^1$H-NMR (CDCl3, 360 MHz): 7.77 (s, 1H), 7.51 (d, 1H), 7.43 (d, 1H), 7.19 (t, 1H), 4.16 (q, 2H), 4.05 (s, 2H), 3.98 (d, 1H), 3.79 (d, 1H), 1.21 (t, 3H).

e) 5-(3-Bromo-phenyl)-5-trifluoromethyl-morpholin-3-one

A solution of 598 mg (1.616 mmol) [2-Amino-2-(3-bromo-phenyl)-3,3,3-trifluoro-propoxy]-acetic acid ethyl ester in 5.4 ml toluene and 2.7 ml TFA was heated at reflux temperature for 5 h. The cooled down mixture was evaporated, taken up in EtOAc, washed with 5% aqueous NaHCO3, dried with Na2SO4 and evaporated to give the essentially pure title compound as a colorless solid.

TLC: Rf (Hexane/EtOAc 3:1)=0.13.
HPLC: Rt$_{H1}$=2.099 min; ESIMS [M+H]$^+$=324/326 (1Br);
$^1$H-NMR (CDCl3, 360 MHz): 7.68 (s, 1H), 7.63 (d, 1H), 7.48 (d, 1H), 7.39 (t, 1H), 6.70 (br s, 1H), 4.41 (d, 1H), 4.38 (d, 1H), 4.25 (d, 1H), 3.95 (d, 1H).

f) [5-(3-Amino-phenyl)-5-trifluoromethyl-5,6-dihydro-2H-[1,4]oxazin-3-yl]-carbamic acid tert-butyl ester The title compound was obtained by methods described for the conversions of 42e) to 42j).

TLC: Rf (Hexane/EtOAc 1:1)=0.16.
HPLC: Rt$_{H4}$=2.214 min; ESIMS [M+H]$^+$=360;
$^1$H-NMR (CD3OD, 360 MHz): 7.00 (t, 1H), 6.86 (s, 1H), 6.78 (d, 1H), 6.60 (d, 1H), 4.52 (d, 1H), 4.40 (d, 1H), 4.03 (d, 1H), 3.88 (d, 1H).

g) (5-{5-[(5-Chloro-pyridine-2-carbonyl)-amino]-2-fluoro-phenyl}-5-trifluoromethyl-5,6-dihydro-2H-[1,4]oxazin-3-yl)-carbamic acid tert-butyl ester To a solution of 56 mg (0.156 mmol) [5-(3-amino-phenyl)-5-trifluoromethyl-5,6-dihydro-2H-[1,4]oxazin-3-yl]-carbamic acid tert-butyl ester, 27 mg (0.171 mmol) 5-chloro-pyridine-2-carboxylic acid, 27.6 mg (0.203 mmol) HOAt and 0.054 ml (0.39 mmol) Et3N in 1 ml DCM were added 33 mg (0.171 mmol) EDC.HCl. After 18 h the mixture was diluted with EtOAc, washed with water, 1N HCl, brine and 5% aqueous NaHCO3. The organic phase was dried with MgSO4.H2O, filtered and purified by chromatography on silica gel (hexane/14-18% EtOAc) to give the desired product as colorless foam.

TLC: Rf (Hexane/EtOAc 3:1)=0.34.
HPLC: Rt$_{H4}$=2.871 min; ESIMS [M+Na]$^+$=521/523 (1Cl);
$^1$H-NMR (CDCl3, 360 MHz): 8.51 (d, 1H), 8.19 (d, 1H), 7.85-7.80 (m, 3H), 7.36 (t, 1H), 7.25 (d, 1H), 4.68 (d, 1H), 4.57 (d, 1H), 4.15 (d, 1H), 4.03 (d, 1H), 1.50 (br s, 9H).

h) 5-Chloro-pyridine-2-carboxylic acid [3-(5-amino-3-trifluoromethyl-3,6-dihydro-2H-[1,4]oxazin-3-yl)-4-fluoro-phenyl]-amide A solution of 68 mg (0.136 mmol) (5-{5-[(5-chloro-pyridine-2-carbonyl)-amino]-2-fluoro-phenyl}-5-trifluoromethyl-5,6-dihydro-2H-[1,4]oxazin-3-yl)-carbamic acid tert-butyl ester in 2 ml 4N HCl in dioxane was stirred at 40° C. overnight. The mixture was concentrated and crystallized from EtOAc/hexane to yield the title compound as colorless crystals.

HPLC: Rt$_{H3}$=2.927 min; ESIMS [M+H]$^+$=399/401 (1Cl);
$^1$H-NMR (400 MHz, DMSO-d6): δ 10.60 (s, 1H), 8.19 (dd, 1H), 8.14 (d, 1H), 8.10 (s, 1H), 7.87 (d, 1H), 7.38 (d, 1H), 7.33 (d, 1H), 6.27 (br s, 1H), 4.12 (d, 1H), 4.04 (d, 1H), 3.94 (d, 1H), 3.93 (d, 1H).

Example 51

5-Bromo-pyrimidine-2-carboxylic acid [3-((R)-5-amino-3-methyl-3,6-dihydro-2H-[1,4]oxazin-3-yl)-5-bromo-phenyl]-amide hydrochloride

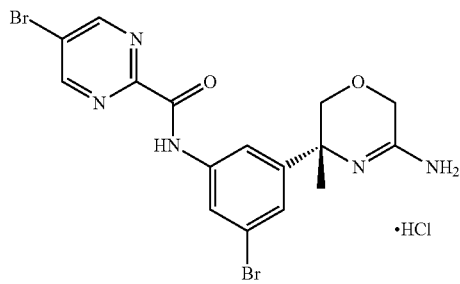 [SMILES: C[C@@]1(c2cc(Br)cc(NC(=O)c3ncc(Br)cn3)c2)COCC(N)=N1 ; Cl]

a) 1-(3-Bromo-5-nitro-phenyl)-ethanol

A solution of TiCl$_4$ (9.48 g, 50 mmol) and methylmagnesiumbromide (20.80 ml, 52 mmol, 2.5 M solution in THF) in THF (400 ml) was stirred at –30° C. when 3-bromo-5-nitro-benzaldehyde (9.20 g, 40 mmol) was added as solid. The mixture was stirred for 1 h at –30° C. As the reaction was not complete, the reaction was cooled to –78° C. and 0.65 eq. methylmagnesium bromide and 0.625 eq. TiCl$_4$ were added and stirring was continued at –30° C. This procedure was repeated again to add 0.325 eq. methylmagnesium bromide and 0.313 eq. TiCl$_4$. After complete conversion the reaction was cooled to –78° C. and quenched by addition of 500 ml cold water. 500 ml dichloromethane were added and the reaction was allowed to warm to r.t. The phases were separated and the aqueous phase was extracted twice with dichloromethane. The organic phases were washed with water and brine, combined and dried over Na$_2$SO$_4$. Volatiles were removed under reduced pressure. The crude product was purified by automated column chromatography (cyclohexane/ethyl acetate) yielding the title compound as yellowish oil.
$^1$H-NMR (360 MHz, CDCl$_3$): 8.20 (s, 1H), 8.10 (s, 1H), 7.78 (s, 1H), 4.95 (q, 1H), 1.45 (d, 3H).

b) 1-(3-Bromo-5-nitro-phenyl)-ethanone 1-(3-Bromo-5-nitro-phenyl)-ethanol (12.84 g, 52.2 mmol) was dissolved in dioxane (245 ml) and manganedioxide (31.8 g, 365 mmol) was added. The reaction was refluxed for 17 hrs. The reaction was filtered and solvent was removed under reduced pressure yielding the title compound as yellow solid.
$^1$H-NMR (500 MHz, DMSO-d$_6$): 8.64 (s, 1H), 8.58 (s, 1H), 8.53 (s, 1H), 2.70 (s, 3H); GC/MS: 243 [(M)$^+$].

c) 2-Methyl-propane-2-sulfinic acid [1-(3-bromo-5-nitro-phenyl)-eth-(E)-ylidene]-amide 1-(3-Bromo-5-nitro-phenyl)-ethanone (11.6 g, 47.5 mmol), (R)-(+)-tert-butanesulfinamide (6.34 g, 52.3 mmol)

and Ti(OEt)$_4$ (24.64 ml, 119 mmol) were mixed in 62 ml THF and refluxed for 2.5 hrs. The reaction was cooled and carefully quenched by addition of ice and water. The white precipitate was filtered off and the aqueous mixture was extracted with ethyl acetate. The organic phases were washed with water and brine, combined and dried over Na$_2$SO$_4$. Volatiles were removed under reduced pressure. The crude product was purified by automated column chromatography (cyclohexane/ethyl acetate) yielding the title compound as yellow oil. $^1$H-NMR (500 MHz, DMSO-d$_6$): 8.58 (s, 1H), 8.55 (s, 1H), 8.43 (s, 1H), 2.79 (s, 3H), 1.24 (s, 9H); MS: 347 [(M+H)$^+$]; [α]$^D$=+54.5° (c=0.481% in chloroform).

d) 2-Methyl-propane-2-sulfinic acid [(R)-(3-bromo-6-nitro-phenyl)-cyano-methyl-methyl]-amide The sulfoxiimine from the previous step (12.48 g, 35.9 mmol) and CsF (6.01 g, 39.5 mmol) were dissolved in hexane (287 ml) and THF (72 ml) and cooled to −50° C. TMSCN (3.92 g, 39.5 mmol) were added dropwise and the reaction was stirred at 0° C. for 4 h. The reaction was cooled to −78° C. and quenched by addition of 720 ml saturated NH$_4$Cl solution. The product was extracted with ethyl acetate. The organic phases were washed with water and brine, combined and dried over Na$_2$SO$_4$. Volatiles were removed under reduced pressure. The crude product was purified by automated column chromatography (cyclohexane/ethyl acetate) yielding the title compound as tan solid. $^1$H-NMR (500 MHz, CDCl$_3$): 8.43 (s, 2H), 8.13 (s, 1H), 4.19 (s, NH, 1H), 2.05 (s, 3H), 1.30 (s, 9H); MS: 374 [(M+H)$^+$]; [α]$^D$=+3.2° (c=0.497% in chloroform)

e) (R)-2-Amino-2-(3-bromo-nitro-phenyl)-propionic acid hydrochloride

2-Methyl-propane-2-sulfinic acid [(R)-(3-bromo-5-nitro-phenyl)-cyano-methyl-methyl]-amide (4.87 g, 13.0 mmol) was suspended in 215 ml conc. HCl (12.1 M) and refluxed for 4 hrs. Toluene was added twice and volatiles were removed under reduced pressure yielding a off-white solid. $^1$H-NMR (360 MHz, MeOD): 8.60 (s, 1H), 8.44 (s, 1H), 8.18 (s, 1H), 2.05 (s, 3H); MS: 289 [(M+H)$^+$].

f) (R)-2-Amino-2-(3-bromo-6-nitro-phenyl)-propan-1-ol (R)-2-Amino-2-(3-bromo-5-nitro-phenyl)-propionic acid (8.41 g, 25.8 mmol) was suspended in abs. THF (39 ml) and cooled to 0° C. BH$_3$ in THF (103 ml, 103 mmol, 1M in THF) was added and the reaction was stirred at r.t. for 1 hr. The reaction was poured onto NaHCO$_3$ (solid, 26 g, 12 eq.), 78 g ice and 155 ml ethyl acetate and stirred for 20 min. at r.t. Phases were separated. The organic phases were washed with water and brine, combined and dried over Na$_2$SO$_4$. Volatiles were removed under reduced pressure yielding the title compound as brown oil. $^1$H-NMR (360 MHz, DMSO-d$_6$): 8.40 (s, 1H), 8.25 (s, 1H), 8.18 (s, 1H), 4.95 (t, 1H), 3.55 (m, 1H), 3.38 (m, 1H), 1.33 (s, 3H); MS: 275 [(M+H)$^+$].

g) N—[(R)-1-(3-Bromo-6-nitro-phenyl)-2-hydroxy-1-methyl-ethyl]-2-chloro-acetamide (R)-2-Amino-2-(3-bromo-5-nitro-phenyl)-propan-1-ol (6.27 g, 22.79 mmol) was dissolved in DMF (230 ml) under N$_2$ and K$_2$CO$_3$ (7.87 g, 57 mmol) and DIPEA (3.98 ml, 22.79 mmol) were added. The mixture was cooled to 0° C. and chloro-acetylchloride (2.83 g, 25.07 mmol) was added dropwise. The reaction was stirred at 0° C. for 19 hrs. After completion, the reaction was put between water (2.3 liter) and toluene (2.3 l). The organic phases were washed with water and brine, combined and dried over Na$_2$SO$_4$. Volatiles were removed under reduced pressure. The crude product was purified by automated column chromatography (cyclohexane/ethyl acetate) yielding the title compound as colorless oil. $^1$H-NMR (360 MHz, DMSO-d$_6$): 8.51 (1H, NH), 8.28 (s, 1H), 8.12 (s, 1H), 7.93 (s, 1H), 5.25 (t, 1H), 4.15 (d, 2H), 3.62 (m, 2H), 1.62 (s, 3H); MS: 351 [(M+H)$^+$].

h) (R)-5-(3-Bromo-5-nitro-phenyl)-6-methyl-morpholin-3-one

N—[(R)-1-(3-Bromo-5-nitro-phenyl)-2-hydroxy-1-methyl-ethyl]-2-chloro-acetamide (4.45 g, 10.76 mmol) and KOtBu (2.414 g, 21.52 g) were suspended in 55 ml tert-butanol under N$_2$ and heated 100° C. for 30 min. After completion water was added to the reaction and tert-butanol was removed under reduced pressure. The product was extracted with ethyl acetate from the remaining aqueous phase. The organic phases were washed with water and brine, combined and dried over Na$_2$SO$_4$. Volatiles were removed under reduced pressure. The crude product was purified by automated column chromatography (cyclohexane/ethyl acetate) yielding the title compound as tan solid. $^1$H-NMR (360 MHz, DMSO-d$_6$): 8.88 (1H, NH), 8.35 (s, 1H), 8.28 (s, 1H), 8.14 (s, 1H), 4.16 (m, 1H), 4.06 (s, 2H), 3.74 (m, 1H), 1.50 (s, 3H); MS: 316 [(M+H)$^+$].

i) (R)-5-(3-Bromo-6-nitro-phenyl)-5-methyl-morpholine-3-thione (R)-5-(3-Bromo-5-nitro-phenyl)-5-methyl-morpholin-3-one (2.60 g, 7.84 mmol) and Lawesson's reagent (2.54 g, 6.27 mmol) were stirred at 80° C. for 2 hrs. Volatiles were removed under reduced pressure and the crude product mixture was purified by automated column chromatography (cyclohexane/ethyl acetate) yielding the title compound as yellow foam. $^1$H-NMR (360 MHz, DMSO-d$_6$): 11.28 (1H, NH), 8.38 (s, 1H), 8.22 (s, 1H), 8.17 (s, 1H), 4.44 (m, 1H), 4.22 (d, 1H), 3.81 (m, 1H), 1.60 (s, 3H); MS: 331 [(M+H)$^+$].

j) (R)-5-(3-Bromo-6-nitro-phenyl)-5-methyl-5,6-dihydro-2H-[1,4]oxazin-3-ylamine (R)-5-(3-Bromo-5-nitro-phenyl)-5-methyl-morpholine-3-thione (2.86 g, 7.77 mmol) was dissolved in 7M NH3 in methanol (50 ml). Tert-Butylhydroperoxide (9.41 ml, 78 mmol) and ammonia hydroxide (25% sol., 21.2 ml, 136 mmol) were added and the reaction was stirred at r.t. for 2 hrs. Upon completion, 50 ml half-saturated Na$_2$S$_2$O$_3$ solution was added to the reaction and the product was extracted with ethyl acetate. The organic phases were washed with water and brine, combined and dried over Na$_2$SO$_4$. Volatiles were removed under reduced pressure, yielding the title compound as yellowish solid. ¹H-NMR (360 MHz, DMSO-$d_6$): 8.34 (s, 1H), 8.25 (s, 1H), 8.12 (s, 1H), 5.85 (br, 2H), 4.01 (m, 1H), 3.80 (m, 1H), 3.55 (m, 1H), 1.38 (s, 3H); MS: 314 [(M+H)⁺].

k) [(R)-5-(3-Bromo-6-nitro-phenyl)-5-methyl-5,6-dihydro-2H-[1,4]oxazin-3-yl]-carbamic acid tert-butyl ester (R)-5-(3-Bromo-5-nitro-phenyl)-5-methyl-5,6-dihydro-2H-[1,4]oxazin-3-ylamine (1.74 g, 5.10 mmol) was dissolved in 40 ml dichloromethane under $N_2$ and cooled to 0° C. $Boc_2O$ (1.45 g, 6.63 mmol) and DIPEA (1.34 ml, 7.65 mmol) were added and the reaction was stirred at r.t for 18 hrs. 100 ml water was added to the reaction. The organic phases were washed with water and brine, combined and dried over $Na_2SO_4$. Volatiles were removed under reduced pressure. The crude product was purified by automated column chromatography (cyclohexane/ethyl acetate) yielding the title compound as white foam. ¹H-NMR (360 MHz, DMSO-$d_6$): 9.76 (s, 1H, NH), 8.32 (s, 1H), 8.27 (s, 1H), 8.17 (s, 1H), 4.60 (d, 1H), 4.38 (d, 1H), 3.94 (d, 1H), 3.48 (d, 1), 1.44 (s, 9H), 1.38 (s, 3H); MS: 414 [(M+H)⁺].

l) [(R)-(3-Amino-5-bromo-phenyl)-5-methyl-5,6-dihydro-2H-[1,4]oxazin-3-yl]-carbamic acid tert-butyl ester

[(R)-5-(3-Bromo-5-nitro-phenyl)-5-methyl-5,6-dihydro-2H-[1,4]oxazin-3-yl]-carbamic acid tert-butyl ester (930 mg, 2.13 mmol) was dissolved in 5 ml methanol. Raney-Nickel was added and the reaction was hydrogenated for 1.5 hrs at r.t. The reaction was filtered over Celite, washed with dichloromethane/methanol (9/1). Volatiles were removed under reduced pressure yielding the title compound as white solid.

¹H-NMR (360 MHz, DMSO-$d_6$): 9.60 (br, 1H), 6.72 (s, 1H), 6.64 (s, 1H), 6.55 (s, 1H), 5.40 (br, 2H), 4.38 (m, 2H), 3.65 (m, 2H), 1.44 (s, 12H); MS: 384 [(M+H)⁺]; $[\alpha]^D$= –172.9° (c=0.441% in methanol)

m) ((R)-5-{3-Bromo-6-[(5-bromo-pyrimidine-2-carbonyl)-amino]-phenyl}-5-methyl-5,6-dihydro-2H-[1,4]oxazin-3-yl)-carbamic acid tert-butyl ester

[(R)-5-(3-Amino-5-bromo-phenyl)-5-methyl-5,6-dihydro-2H-[1,4]oxazin-3-yl]-carbamic acid tert-butyl ester (33 mg, 0.082 mmol), 5-bromo-pyrimidine-2-carboxylic acid (18 mg, 0.090 mmol) and HOBT (16 mg, 0.106 mmol) were dissolved in dichloromethane under $N_2$ at 0° C. DIPEA (10.54 mg, 0.082 mmol) and EDC (17 mg, 0.090 mmol) were added. The mixture was stirred at 0° C. for 10 min, then allowed to warm to room temperature, stirred for 17 h at room temperature, quenched with 1M aqueous $KHCO_3$ solution and extracted with dichloromethane. The organic phase was washed with water and brine, dried over $Na_2SO_4$ and concentrated under reduced pressure. The residue was purified by automated column chromatography (cyclohexane/ethyl acetate) to yield the title compound as a tan foam. MS: 569 [(M+H)⁺].

n) 5-Bromo-pyrimidine-2-carboxylic acid [3-((R)-5-amino-3-methyl-3,6-dihydro-2H-[1,4]oxazin-3-yl)-5-bromo-phenyl]-amide hydrochloride A solution of ((R)-5-{3-bromo-5-[(5-bromo-pyrimidine-2-carbonyl)-amino]-phenyl}-5-methyl-5,6-dihydro-2H-[1,4]oxazin-3-yl)-carbamic acid tert-butyl ester (22 mg, 0.039 mmol) in 4 M HCl in dioxane (0.8 ml, 80 eq.) was warmed to 40° C. for 24 hrs in a closed reaction vial. After completion volatiles were removed under reduced pressure to yield the title compound (hydrochloride salt) in the form of a colourless solid. ¹H-NMR (500 MHz, DMSO-$d_6$): 11.05 (s, 1H), 10.61 (s, 1H, NH), 9.25 (s, 2H), 9.19 (s, 1H), 8.58 (s, 1H), 8.26 (s, 1H), 7.89 (s, 1H), 7.44 (s, 1H), 4.59 (m, 2H), 3.91 (m, 2H), 1.63 (s, 3H); MS: 470 [(M+H)⁺].

Examples 52 to 59

The compounds listed in Table 5 were prepared by a procedure analogous to that used in example 51.

TABLE 5

| Example | Compound | ¹H-NMR (δ; DMSO-$d_6$) | MS [m/z; (M + 1)⁺] |
|---|---|---|---|
| 52 | 5-Bromo-pyridine-2-carboxylic acid [3-((R)-5-amino-3-methyl-3,6-dihydro-2H-[1,4]oxazin-3-yl)-5-bromo-phenyl]-amide hydrochloride | 10.45 (s, 1H), 8.88 (s, 1H), 8.35 (m, 1H), 8.17 (d, 1H), 8.07 (m, 1H), 7.93 (s, 1H), 7.68 (m, 2H), 7.40 (s, 1H), 4.55 (m, 2H), 4.15 (m, 2H), 1.60 (s, 3H) | 467 |

TABLE 5-continued

| Example | Compound | $^1$H-NMR (δ; DMSO-$d_6$) | MS [m/z; $(M+1)^+$] |
|---|---|---|---|
| 53 | 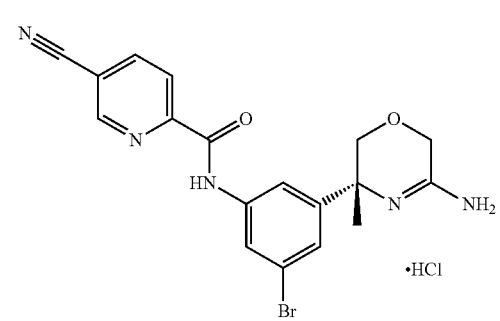 [SMILES: C[C@@]1(c2cc(Br)cc(NC(=O)c3ccc(C#N)cn3)c2)COCC(N)=N1 ; Cl] 5-Cyano-pyridine-2-carboxylic acid [3-((R)-5-amino-3-methyl-3,6-dihydro-2H-[1,4]oxazin-3-yl)-5-bromo-phenyl]-amide hydrochloride | 11.02 (s, 1H), 10.55 (s, 1H), 8.65 (s, 1H), 8.56 (m, 1H), 8.31 (s, 1H), 8.27 (m, 1H), 7.96 (s, 1H), 7.40 (s, 1H), 4.55 (m, 2H), 3.90 (m, 2H), 1.60 (s, 3H) | 414 |
| 54 | 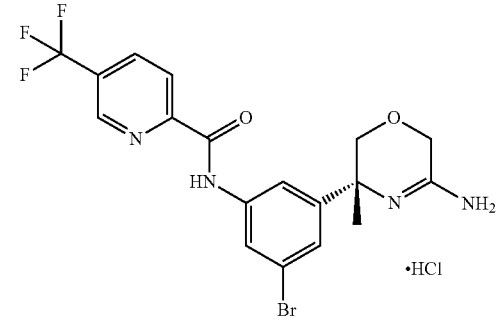 [SMILES: C[C@@]1(c2cc(Br)cc(NC(=O)c3ccc(C(F)(F)F)cn3)c2)COCC(N)=N1 ; Cl] 5-Trifluoromethyl-pyridine-2-carboxylic acid [3-((R)-5-amino-3-methyl-3,6-dihydro-2H-[1,4]oxazin-3-yl)-5-bromo-phenyl]-amide hydrochloride | free base: 10.95 (s, 1H), 9.15 (s, 1H), 8.53 (m, 1H), 8.36 (m, 1H), 8.18 (s, 1H), 7.92 (s, 1H), 7.44 (s, 1H), 6.15 (br, 2H), 4.10 (m, 2H), 3.60 (m, 2H), 1.42 (s, 3H) | 457 |
| 55 | 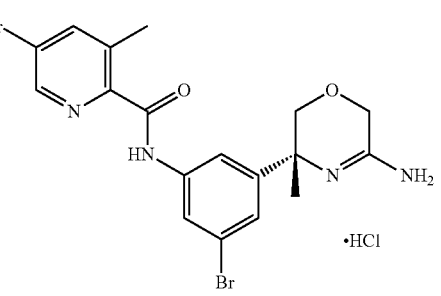 5-Bromo-3-methyl-pyridine-2-carboxylic acid [3-((R)-5-amino-3-methyl-3,6-dihydro-2H-[1,4]oxazin-3-yl)-5-bromo-phenyl]-amide hydrochloride | 10.80 (s, 1H), 8.69 (s, 1H), 8.22 (m, 2H), 7.81 (s, 1H), 7.42 (s, 1H), 4.55 (br, 2H), 3.90 (m, 2H), 2.58 (s, 3H), 1.62 (s, 3H) | 481 |

TABLE 5-continued

| Example | Compound | ¹H-NMR (δ; DMSO-d₆) | MS [m/z; (M + 1)⁺] |
|---|---|---|---|
| 56 | 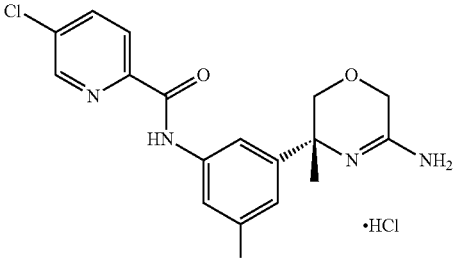<br>5-Chloro-pyridine-2-carboxylic [3-((R)-5-amino-3-methyl-3,6-dihydro-2H-[1,4]oxazin-3-yl)-5-bromo-phenyl]-amide hydrochloride | 10.90 (s, 1H), 8.82 (s, 1H), 8.30 (s, 1H), 8.25 (m, 1H), 8.18 (m, 1H), 7.96 (s, 1H), 7.42 (m, 2H), 4.55 (m, 2H), 3.90 (m, 2H), 1.63 (s, 3H) | 423 |
| 57 | 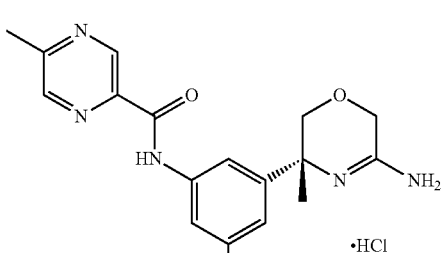<br>5-Methyl-pyrazine-2-carboxylic acid [3-((R)-5-amino-3-methyl-3,6-dihydro-2H-[1,4]oxazin-3-yl)-5-bromo-phenyl]-amide hydrochloride | 10.90 (s, 1H), 10.50 (br, 1H), 9.20 (s, 1H), 8.75 (s, 1H), 8.30 (s, 1H), 8.01 (s, 1H), 7.43 (s, 1H), 4.55 (m, 2H), 3.90 (m, 2H), 1.63 (s, 3H) | 405 |
| 58 | 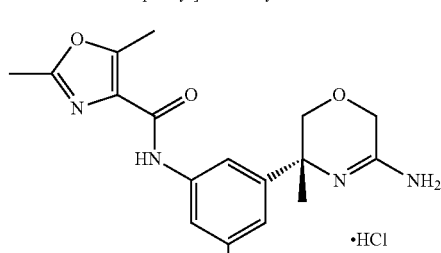<br>2,5-Dimethyl-oxazole-4-carboxylic acid [3-((R)-5-amino-3-methyl-3,6-dihydro-2H-[1,4]oxazin-3-yl)-5-bromo-phenyl]-amide hydrochloride | 10.22 (s, 1H), 8.22 (s, 1H), 7.86 (s, 1H), 7.38 (s, 1H), 4.54 (m, 2H), 3.85 (m, 2H), 2.61 (s, 3H), 2.45 (s, 3H), 1.61 (s, 3H) | 406 |
| 59 | 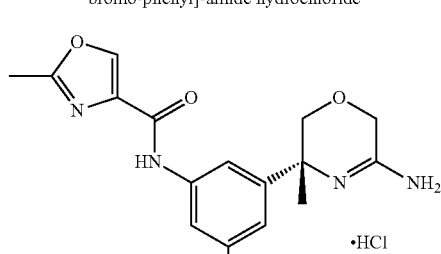<br>2-Methyl-oxazole-4-carboxylic acid [3-((R)-5-amino-3-methyl-3,6-dihydro-2H-[1,4]oxazin-3-yl)-5-bromo-phenyl]-amide hydrochloride | 10.40 (s, 1H), 8.71 (s, 1H), 8.21 (s, 1H), 7.89 (s, 1H), 7.38 (s, 1H), 4.52 (m, 2H), 3.86 (m, 2H), 3.27 (s, 3H), 1.59 (s, 3H) | 392 |

Examples 60 to 65

The compounds listed in Table 6 were prepared by procedures analogous to those used in examples 51 (steps a) and b)) and 1 (steps c) to I)). 5-Bromo-2-fluorobenzaldehyde was used instead of 3-bromo-5-nitro-benzaldehyde.

TABLE 6

| Example | Compound | $^1$H-NMR (δ; DMSO-$d_6$) | MS [m/z; (M + 1)$^+$] |
|---|---|---|---|
| 60 | 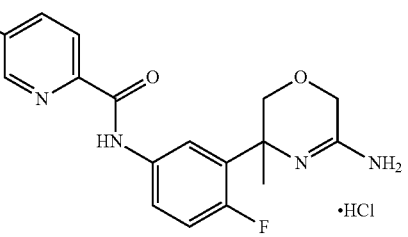<br>5-Bromo-pyridine-2-carboxylic acid [3-(5-amino-3-methyl-3,6-dihydro-2H-[1,4]oxazin-3-yl)-4-fluoro-phenyl]-amide hydrochloride | 10.85 (s, 1H), 10.20 (br, 1H), 8.88 (s, 1H), 8.35 (m, 1H), 8.09 (d, 1H), 7.95 (m, 2H), 7.26 (t, 1H), 4.52 (m, 2H), 4.10 (m, 1H), 3.85 (m, 1H), 1.60 (s, 3H) | 407 |
| 61 | 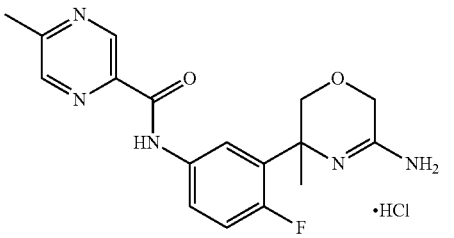 [SMILES: Cc1cnc(C(=O)Nc2ccc(F)c(C3(C)COCC(N)=N3)c2)cn1 ; Cl]<br>5-Methyl-pyrazine-2-carboxylic acid [3-(5-amino-3-methyl-3,6-dihydro-2H-[1,4]oxazin-3-yl)-4-fluoro-phenyl]-amide hydrochloride | 10.85 (s, 1H), 10.25 (br, 1H), 9.30 (br, 1H), 9.15 (s, 1H), 8.72 (s, 1H), 8.58 (br, 1H), 8.00 (m, 2H), 7.28 (m, 1H), 4.55 (m, 2H), 4.12 (m, 1H), 3.88 (m, 1H), 1.62 (s, 3H) | 344 |
| 62 | 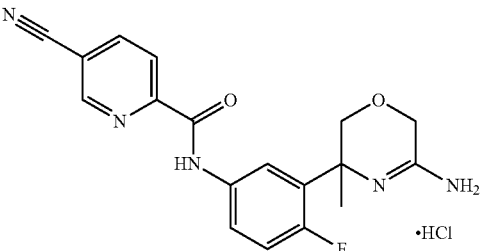<br>5-Cyano-pyridine-2-carboxylic acid [3-(5-amino-3-methyl-3,6-dihydro-2H-[1,4]oxazin-3-yl)-4-fluoro-phenyl]-amide hydrochloride | 11.02 (s, 1H), 10.70 (br, 1H), 9.20 (s, 1H), 8.59 (m, 1H), 8.31 (d, 1H), 7.98 (m, 2H), 7.27 (t, 1H), 4.52 (m, 2H), 4.06 (m, 1H), 3.87 (m, 1H), 1.64 (s, 3H) | 354 |
| 63 | 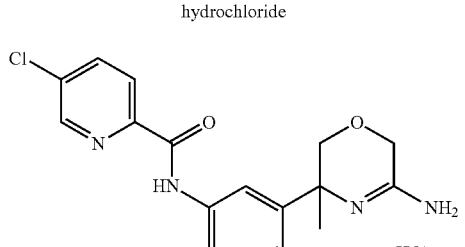<br>5-Chloro-pyridine-2-carboxylic acid [3-(5-amino-3-methyl-3,6-dihydro-2H-[1,4]oxazin-3-yl)-4-fluoro-phenyl]-amide hydrochloride | 10.95 (s, 1H), 10.80 (s, 1H), 9.32 (s, 1H), 8.80 (s, 1H), 8.62 (s, 1H), 8.20 (m, 1H), 8.14 (m, 1H), 8.03 (m, 1H), 7.95 (m, 1H), 7.26 (m, 1H), 4.58 (m, 2H), 4.12 (m, 1H), 3.88 (m, 1H), 1.67 (s, 3H) | 363 |

TABLE 6-continued

| Example | Compound | $^1$H-NMR (δ; DMSO-d$_6$) | MS [m/z; (M + 1)$^+$] |
|---|---|---|---|
| 64 | 5-Bromo-3-methyl-pyridine-2-carboxylic acid [3-(5-amino-3-methyl-3,6-dihydro-2H-[1,4]oxazin-3-yl)-4-fluoro-phenyl]-amide hydrochloride | 10.75 (s, 1H), 10.72 (s, 1H), 9.30 (s, 1H), 8.66 (s, 1H), 8.63 (s, 1H), 8.18 (s, 1H), 7.94 (m, 1H), 7.81 (m, 1H), 7.28 (dd, 1H), 4.55 (m, 2H(AB-system)), 4.0 (m, 2H(AB-system)), 2.55 (s, 3H), 1.65 (s, 3H) | 421 |
| 65 | Pyridine-2,5-dicarboxylic acid 5-amide 2-{[3-(5-amino-3-methyl-3,6-dihydro-2H-[1,4]oxazin-3-yl)-4-fluoro-phenyl]-amide} hydrochloride | 10.95 (s, 1H), 10.75 (s, 1H), 9.27 (s, 1H), 9.15 (s, 1H), 8.64 (s, 1H), 8.46 (m, 1H), 8.37 (m, 1H), 8.22 (m, 1H), 8.05 (m, 1H), 7.97 (m, 1H), 7.80 (s, 1H), 7.26 (m, 1H), 4.58 (m, 2H), 4.12 (m, 1H), 3.89 (m, 1H), 1.67 (s, 3H) | 372 |

Example 66

5-Bromo-pyridine-2-carboxylic acid [3-((3R*,6R*)-5-amino-3,6-dimethyl-6-trifluoromethyl-3,6-dihydro-2H-[1,4]oxazin-3-yl)-phenyl]-amide hydrochloride

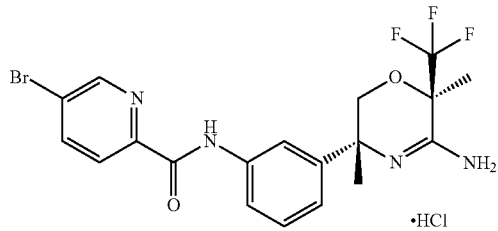 [SMILES: C[C@@]1(c2cccc(NC(=O)c3ccc(Br)cn3)c2)CO[C@@](C)(C(F)(F)F)C(N)=N1 ; Cl]

a) 2-[2-(3-Bromo-phenyl)-2-oxo-ethoxy]-3,3,3-trifluoro-2-methyl-propionic acid methyl ester To a solution of 3,3,3-trifluoro-2-hydroxy-2-methyl-propionic acid methyl ester (22.94 g, 133 mmol) in CH$_2$Cl$_2$ (400 ml) was added rhodium(II) trifluoroacetate dimer (0.439 g, 0.667 mmol). After cooling to 0° C. a solution of 1-(3-bromo-phenyl)-2-diazo-ethanone (15.0 g, 66.7 mmol) dissolved in CH$_2$Cl$_2$ (100 ml) was added over a period of 2 h. The reaction mixture was concentrated and the title compound was obtained after flash-chromatography on silica gel (toluene) as a yellow oil: TLC (toluene/EtOAc 10:1): Rf=0.45; HPLC Rt$_{H5}$=1.352 min; $^1$H NMR (360 MHz, CDCl$_3$): δ 8.15 (s, 1H), 7.94 (d, 1H), 7.76 (d, 1H), 7.40 (t, 1H), 4.87 (s, 2H), 3.89 (s, 3H), 1.72 (s, 3H); ESIMS: 386, 388 [(M+NH$_4$)$^+$].

b) 2-[2-(3-Bromo-phenyl)-2-hydroxy-propoxy]-3,3,3-trifluoro-2-methyl-propionic acid methyl ester To a solution of 2-[2-(3-bromo-phenyl)-2-oxo-ethoxy]-3,3,3-trifluoro-2-methyl-propionic acid methyl ester (6.6 g, 17 mmol) in toluene (120 ml) was added under argon at −78° C. a 2M solution of AlMe$_3$ in heptane (17 ml, 34 mmol) and after stirring for 0.5 h at −78° C. a 1.6 M solution of MeLi in Et$_2$O (21.3 ml, 34 mmol) over a period of 40 min. After stirring for 0.5 h at −78° C. the reaction mixture was added to a cold aqueous NaH$_2$PO$_4$ solution and was extracted with EtOAc. Combined organic layers were washed with brine, dried over MgSO$_4$, filtered and evaporated. The crude product was purified by flash-chromatography on silica gel (toluene to toluene/EtOAc 10:1) to provide a diastereomeric mixture of the title compound as a yellow oil: TLC (toluene/EtOAc 10:1): Rf=0.34 and 0.37; HPLC Rt$_{H5}$=1.359 min; $^1$H NMR (360 MHz, CDCl$_3$): δ 7.69 (m, 1H), 7.43 (m, 2H), 7.25 (t, 1H), 3.86 (s, 3H), 3.68 (m, 2H), 3.43 and 3.33 (s, 1H), 1.63 and 1.61 (s, 3H), 1.58 (s, 3H); ESIMS: 402, 404 [(M+NH$_4$)$^+$].

c) 2-[2-Azido-2-(3-bromo-phenyl)-propoxy]-3,3,3-trifluoro-2-methyl-propionic acid methyl ester To a solution of 2-[2-(3-bromo-phenyl)-2-hydroxy-propoxy]-3,3,3-trifluoro-2-methyl-propionic acid methyl ester (5.1 g, 11.92 mmol) in toluene (50 ml) was added trimethylsilyl azide (3.95 ml, 29.8 mmol) and at 0° C. BF$_3$-Et$_2$O (4.53 ml, 35.8 mmol). The reaction mixture was stirred for 2 days at 25° C. and for another day at 40° C. The reaction was carefully quenched by slow addition of the reaction mixture to a cold aqueous NH$_4$OH solution. The product was extracted with EtOAc and the combined organic layers were washed with brine, dried over MgSO$_4$, filtered and evaporated. The crude product was purified by flash-chromatography on silica gel (toluene to toluene/EtOAc 10:1) to provide a diastereomeric mixture of the title compound as a light yellow oil: TLC (toluene/EtOAc 10:1): Rf=0.69; HPLC Rt$_{H5}$=1.560 min; $^1$H NMR (360 MHz, CDCl$_3$): δ 7.65 (s, 1H), 7.48 (d, 1H), 7.41 (d, 1H), 7.27 (t, 1H), 3.87 and 3.85 (s, 3H), 3.76 (m, 2H), 1.78 and 1.75 (s, 3H), 1.65 and 1.61 (s, 3H); ESIMS: 427, 429 [(M+NH$_4$)$^+$].

d) 2-[2-amino-2-(3-bromo-phenyl)-propoxy]-3,3,3-trifluoro-2-methyl-propionic acid methyl ester To a solution of the 2-[2-azido-2-(3-bromo-phenyl)-propoxy]-3,3,3-trifluoro-2-methyl-propionic acid methyl ester (4.2 g, 9.22 mmol) in THF-H$_2$O 3:1 (48 ml) was added indium (2.116 g, 18.43 mmol) followed by 4N aqueous HCl over a period of 20 min and stirring for 1 h at 25° C. The reaction mixture was added to a 10% aqueous K$_2$CO$_3$ solution and the product was extracted with EtOAc. The combined organic layers were washed with brine, dried over MgSO$_4$, filtered and evaporated. The crude product was purified by flash-chromatography on NEt$_3$ deactivated silica gel (hexane/EtOAc 2:1 to EtOAc) to provide a diastereomeric mixture of the title compound as a yellow oil: TLC (EtOAc): Rf=0.46; HPLC Rt$_{H5}$5=0.999 min; $^1$H NMR (360 MHz, CDCl$_3$): δ 7.73 (s, 1H), 7.47 (d, 1H), 7.41 (d, 1H), 7.24 (t, 1H), 3.84 and 3.83 (s, 3H), 3.59 (s, 2H), 1.61 and 1.59 (s, 3H), 1.52 and 1.51 (s, 3H); ESIMS: 384, 386 [(M+H)$^+$].

e) (2R*,5R*)-5-(3-Bromo-phenyl)-2,5-dimethyl-2-trifluoromethyl-morpholin-3-one and (2S*,5R*)-5-(3-Bromo-phenyl)-2,5-dimethyl-2-trifluoromethyl-morpholin-3-one To a solution of 2-[2-amino-2-(3-bromo-phenyl)-propoxy]-3,3,3-trifluoro-2-methyl-propionic acid methyl ester (2.7 g, 6.89 mmol) in CH$_2$Cl$_2$ (40 ml) was added under argon at 0-5° C. a 2M solution of AlMe$_3$ in heptane (10.33 ml, 20.66 mmol). After stirring for 1 h at 25° C. the reaction mixture was cannulated into a cold 1N aqueous HCl. The product was extracted with CH$_2$Cl$_2$ and the combined organic layers were washed with 5% aqueous NaHCO$_3$ solution, dried over MgSO$_4$, filtered and evaporated. The crude product was purified by flash-chromatography on silica gel (hexane/EtOAc 4:1 to 1:1) to provide the (2R*,5R*)-diastereomer as white crystals: TLC (hexane/EtOAc 3:1): Rf=0.34; HPLC Rt$_{H5}$=1.262 min; $^1$H NMR (360 MHz, CDCl$_3$): δ 7.55 (s, 1H), 7.52 (m, 1H), 7.32 (m, 2H), 6.61 (s, 1H), 4.04 (s, 2H), 1.67 (s, 3H), 1.58 (s, 3H); ESIMS: 352, 354 [(M+H)$^+$] and the (2S*,5R*)-diastereomer as white crystals: TLC (hexane/EtOAc 3:1): Rf=0.16; HPLC Rt$_{H5}$=1.230 min; $^1$H NMR (360 MHz, CDCl$_3$): δ7.57 (s, 1H), 7.52 (d, 1H), 7.37 (d, 1H), 7.32 (t, 1H), 6.45 (s, 1H), 4.11 (dd, 1H), 3.83 (dd, 1H), 1.7 (s, 3H), 1.72 (s, 3H); ESIMS: 352, 354 [(M+H)$^+$].

f) (2S*,5R*)—(3-Bromo-phenyl)-2,5-dimethyl-2-trifluoromethyl-morpholine-3-thione To a solution of (2R*,5R*)-5-(3-bromo-phenyl)-2,5-dimethyl-2-trifluoromethyl-morpholin-3-one (2.48 g, 7.0 mmol) in toluene (25 ml) was added hexamethyldisiloxane (2.7 ml, 12.7 mmol) and phosphorouspentasulfide (1.878 g, 4.23 mmol) and the reaction mixture was heated at reflux for 16 h. To the cold reaction mixture was added acetone (10 ml) and 20% aqueous K$_2$CO$_3$ solution and the mixture was stirred for 1 h at 25° C. The product was extracted with EtOAc and the combined organic layers were washed with brine, dried over MgSO$_4$, filtered and concentrated. The crude product was crystallized from diisopropylether to provide the purified title compound as white crystals: TLC (hexane/EtOAc 3:1): Rf=0.55; HPLC Rt$_{H5}$=1.408 min; $^1$H NMR (360 MHz, CDCl$_3$): δ 8.51 (s, 1H), 7.53 (d, 1H), 7.48 (s, 1H), 7.34 (t, 1H), 7.28 (d, 1H), 4.07 (m, 2H), 1.79 (s, 3H), 1.71 (s, 3H); ESIMS: 368, 370 [(M+H)$^+$].

g) (2R*,5R*)-5-(3-Bromo-phenyl)-2,5-dimethyl-2-trifluoromethyl-5,6-dihydro-2H-[1,4]oxazin-3-ylamine To a solution of (2S*,5R*)-5-(3-bromo-phenyl)-2,5-dimethyl-2-trifluoromethyl-morpholine-3-thione (2.5 g, 6.79 mmol) in THF (25 ml) was added concentrated aqueous NH$_4$OH (10.7 ml, 170 mmol) and 80% tert-butylhydroperoxide in H$_2$O (4.25 ml, 33.9 mmol) and the reaction mixture was stirred for 3 h at 25° C. After addition of another 4.25 ml of 80% tert-butylhydroperoxide in H$_2$O the reaction mixture was stirred overnight at 25° C. The reaction mixture was slowly added to concentrated sodium metabisulfite solution at 0-10° C., and after addition of 20% aqueous K$_2$CO$_3$ solution the product was extracted with EtOAc. Combined organic layers were washed with brine, dried over MgSO$_4$, filtered and concentrated. The crude title product was used as such for the next transformation. A small amount was purified by flash-chromatography and transferred into the hydrochloride salt with 1N HCl in Et$_2$O to provide the title compound as a white solid: TLC (EtOAc/MeOH 9:1): Rf=0.60; HPLC Rt$_{H5}$=1.024 min; $^1$H NMR (600 MHz, DMSO-d$_6$): δ 11.55 (s, 1H), 9.54 (d, 2H), 7.74 (s, 1H), 7.60 (d, 1H), 7.51 (d, 1H), 7.42 (t, 1H), 4.15 (d, 1H), 4.06 (d, 1H), 1.75 (s, 3H), 1.66 (s, 3H); ESIMS: 351, 353 [(M+H)$^+$].

h) [(2R*,5R*)-5-(3-Bromo-phenyl-2,5-dimethyl-2-trifluoromethyl-5,6-dihydro-2H-[1,4]oxazin-3-yl]-carbamic acid tert-butyl ester To a solution of (2R*,5R*)-5-(3-bromo-phenyl)-2,5-dimethyl-2-trifluoromethyl-5,6-dihydro-2H-[1,4]oxazin-3-ylamine (1.5 g, 4.27 mmol) in acetonitrile (30 ml) was added Boc$_2$O (1.86 g, 8.54 mmol) and NEt$_3$ (1.79 ml, 12.8 mmol) and the reaction mixture was stirred for 4 h at 25° C. The reaction mixture was added to aqueous NaH$_2$PO$_4$ solution and extracted with EtOAc. Combined organic layers were washed with brine, dried over MgSO$_4$, filtered and concentrated. The crude product was purified by flash-chromatography on silica gel (hexane to hexane/EtOAc 1:1) to provide the title compound as a light yellow oil: TLC (hexane/EtOAc 3:1): Rf=0.57; HPLC Rt$_{H5}$=1.549 min; $^1$H NMR (360 MHz, CDCl$_3$): δ 7.50 (m, 2H), 7.30 (m, 2H), 4.04 (s, 2H), 1.69 (s, 3H), 1.64 (s, 3H), 1.57 (s, 9H); ESIMS: 451, 453 [(M+H)$^+$].

i) [(2R*,5R*)-5-(3-Azido-phenyl)-2,5-dimethyl-2-trifluoromethyl-5,6-dihydro-2H-[1,4]oxazin-3-yl]-carbamic acid tert-butyl ester To a solution of [(2R*,5R*)-5-(3-bromo-phenyl)-2,5-dimethyl-2-trifluoromethyl-5,6-dihydro-2H-[1,4]oxazin-3-yl]-carbamic acid tert-butyl ester (1.1 g, 2.39 mmol) in EtOH—H$_2$O 2:1 (15 ml) was added under argon NaN$_3$ (0.62 g, 9.5 mmol), trans-N,N-dimethylcyclohexan-1,2-diamine (0.075 ml, 0.48 mmol), sodium-ascorbate (0.084 g, 0.48 mmol) and CuI (0.091 g, 0.48 mmol) and the resulting reaction mixture was heated for 45 min at 70° C. The reaction mixture was added to saturated aqueous NH$_4$Cl solution and extracted with EtOAc. Combined organic layers were washed with 5% aqueous NaHCO$_3$ solution and brine, dried over MgSO$_4$, filtered and concentrated. The crude title product was obtained as a yellow oil and used as such in the next transformation: TLC (toluene/EtOAc 10:1): Rf=0.53; HPLC Rt$_{H5}$=1.532 min; $^1$H NMR (360 MHz, CDCl$_3$): δ 7.44 (t, 1H), 7.15 (d, 1H), 7.06 (d, 1H), 6.98. (s, 1H), 4.04 (m, 2H), 1.69 (s, 3H), 1.63 (s, 3H), 1.57 (s, 9H); ESIMS: 412, 414 [(M+H)$^+$].

j) [(2R*,5R*)-5-(3-Amino-phenyl)-2,5-dimethyl-2-trifluoromethyl-5,6-dihydro-2H-[1,4]-oxazin-3-yl]-carbamic acid tert-butyl ester A solution of [(2R*,5R*)-5-(3-azido-phenyl)-2,5-dimethyl-2-trifluoromethyl-5,6-dihydro-2H-[1,4]oxazin-3-yl]-carbamic acid tert-butyl ester (0.82 g, 1.92 mmol) in EtOH (10 ml) was stirred in the presence of 10% Pd—C (0.1 g) under an atmosphere of hydrogen at 25° C. for 1.5 h. The catalyst was filtered off over Celite, evaporated and the residual oil was purified by flash-chromatography on silica gel (hexane/EtOAc 10:1 to 1:2) to provide the title compound as a colorless foam: TLC (hexane/EtOAc 1:1): Rf=0.43; HPLC Rt$_{H5}$=1.082 min; $^1$H NMR (360 MHz, CDCl$_3$): δ 10.94 (s, 1H), 7.21 (t, 1H), 6.74 (d, 1H), 6.67 (d, 1H), 6.66 (s, 1H), 4.01 (s, 2H), 3.78 (broad s, 2H), 1.68 (s, 3H), 1.65 (s, 3H), 1.57 (s, 9H); ESIMS: 386, 388 [(M+H)$^+$].

k) ((2R*,5R*)-6-{3-[(5-bromo-pyridine-2-carbonyl)-amino]-phenyl}-2,5-dimethyl-2-trifluoromethyl-5,6-dihydro-2H-[1,4]oxazin-3-yl)-carbamic acid tert-butyl ester To a solution of [(2R*,5R*)-5-(3-amino-phenyl)-2,5-dimethyl-2-trifluoromethyl-5,6-dihydro-2H-[1,4]oxazin-3-yl]-carbamic acid tert-butyl ester (0.1 g, 0.253 mmol) in DMF (2.5 ml) was added 5-bromo-pyridine-2-carboxylic acid (78 mg, 0.379 mmol), EDC (0.074 g, 0.379 mmol), HOAt (0.053 g, 0.379 mmol) and DIPEA (0.083 g, 0.632 mmol) and the reaction mixture was stirred for 2 h at 25° C. After evaporation of the DMF the residue was taken up in NaH$_2$PO$_4$ solution and extracted with EtOAc. Combined organic layers were washed with 5% NaHCO$_3$ solution and brine, dried over MgSO$_4$, filtered and concentrated. The crude product was crystallized from diisopropylether to provide the title compound as a white crystalline solid: TLC (hexane/EtOAc 1:1): Rf=0.61; HPLC Rt$_{H5}$=1.565 min; $^1$H NMR (360 MHz, CDCl$_3$): ): δ 11.01 (s, 1H), 9.92 (s, 1H), 8.71 (dd, 1H), 8.21 (d, 1H), 8.10 (dd, 1H), 7.87 (s, 1H), 7.73 (d, 1H), 7.46 (t, 1H), 7.18 (d, 1H), 4.10 (m, 2H), 1.75 (s, 3H), 1.67 (s, 3H), 1.58 (s, 9H); ESIMS: 571, 573 [(M+H)$^+$].

l) 5-Bromo-pyridine-2-carboxylic acid [3-(3R*,6R*)-6-amino-3,6-dimethyl-6-trifluoromethyl-3,6-dihydro-2H-[1,4]oxazin-3-yl)-phenyl]-amide hydrochloride ((2R*,5R*)-5-{3-[(5-bromo-pyridine-2-carbonyl)-amino]-phenyl}-2,5-dimethyl-2-trifluoromethyl-5,6-dihydro-2H-[1,4]oxazin-3-yl)-carbamic acid tert-butyl ester (0.113 g, 0.194 mmol) was dissolved in THF (1 ml) and 4N HCl (5 ml) and the reaction mixture was stirred for 2 h at 25° C. and 3 h at 40° C. The solvents were removed under reduced pressure and the resulting residue was titurated with Et$_2$O to provide the title compound as a white amorphous solid: TLC (EtOAc/MeOH 9:1): Rf=0.56; HPLC Rt$_{H5}$=1.147 min; $^1$H NMR (600 MHz, DMSO-d$_6$): δ 11.45 (s, 1H), 10.81 (s, 1H), 9.74 (d, 2H), 8.88 (dd, 1H), 8.34 (dd, 1H), 8.10 (d, 1H), 8.01 (d, 1H), 7.95 (s, 1H), 7.46 (t, 1H), 7.27 (d, 1H), 4.13 (d, 1H), 4.05 (d, 1H), 1.81 (s, 3H), 1.69 (s, 3H); ESIMS: 471, 473 [(M+H)$^+$].

Example 67

The compound in Table 7 can be prepared by a procedure analogous to that used in example 66.

TABLE 7

| Example | Compound | $^1$H-NMR (δ; DMSO-d$_6$) | MS [m/z; (M + 1)$^+$] |
|---|---|---|---|
| 67 | 5-Methoxy-pyridine-2-carboxylic acid [3-((3R*,6R*)-5-amino-3,6-dimethyl-6-trifluoromethyl-3,6-dihydro-2H-[1,4]oxazin-3-yl)-phenyl]-amide hydrochloride | 11.65 (s, 1H), 10.65 (s, 1H), 9.55 (1, 1H), 9.51 (s, 1H), 8.40 (d, 1H), 8.14 (d, 1H), 8.01 (dd, 1H), 7.94 (s, 1H), 7.63 (dd, 1H), 7.44 (dd, 1H), 7.24 (dd, 1H), 4.18 (d, 1H), 4.07 (d, 1H), 3.90 (s, 3H), 1.78 (s, 3H), 1.58 (s, 3H) | 423 |

Examples 68 to 70

The compounds listed in Table 8 can be prepared by a procedure analogous to that used in example 66, starting from 5-bromo-2-fluoro-benzoyl chloride.

TABLE 8

| Example | Compound | $^1$H-NMR (δ; DMSO-$d_6$) | MS [m/z; (M + 1)$^+$] |
|---|---|---|---|
| 68 | 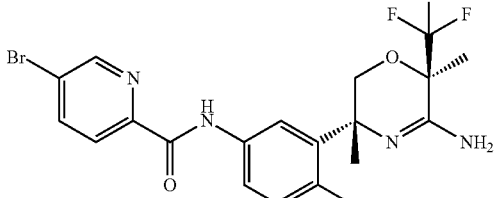<br>5-Bromo-pyridine-2-carboxylic acid [3-((3R*,6R*)-5-amino-3,6-dimethyl-6-trifluoromethyl-3,6-dihydro-2H-[1,4]oxazin-3-yl)-4-fluorophenyl]-amide hydrochloride | 11.65 (s, 1H), 11.00 (s, 1H), 9.60 (d, 2H), 8.84 (s, 1H), 8.34 (dd, 1H), 8.09 (d, 1H), 8.04 (m, 1H), 7.96 (dd, 1H), 7.33 (dd, 1H), 4.31 (d, 1H), 4.09 (d, 1H), 3.92 (s, 3H), 1.75 (s, 3H), 1.70 (s, 3H) | 489, 491 |
| 69 | 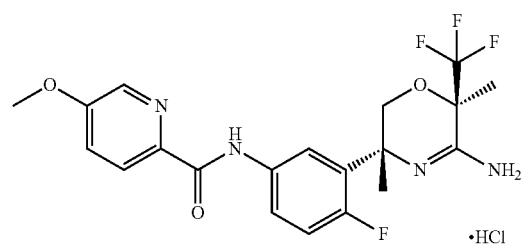 [SMILES: COc1ccc(C(=O)Nc2ccc(F)c([C@]3(C)CO[C@@](C)(C(F)(F)F)C(N)=N3)c2)nc1 ; Cl]<br>5-Methoxy-pyridine-2-carboxylic acid [3-((3R*,6R*)-5-amino-3,6-dimethyl-6-trifluoromethyl-3,6-dihydro-2H-[1,4]oxazin-3-yl)-4-fluorophenyl]-amide hydrochloride | 11.68 (s, 1H), 10.81 (s, 1H), 9.59 (d, 2H), 8.40 (d, 1H), 8.12 (d, 1H), 8.02 (m, 1H), 7.97 (d, 1H), 7.62 (dd, 1H), 7.31 (dd, 1H), 4.29 (d, 1H), 4.09 (d, 1H), 3.92 (s, 3H), 1.77 (s, 3H), 1.70 (s, 3H) | 441 |
| 70 | 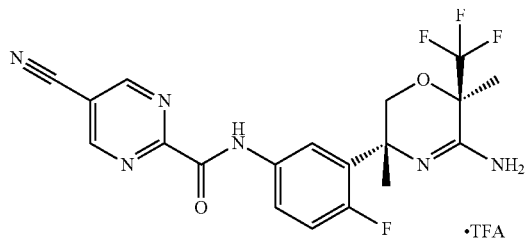 [SMILES: C[C@@]1(c2cc(NC(=O)c3ncc(C#N)cn3)ccc2F)CO[C@@](C)(C(F)(F)F)C(N)=N1 ; "·TFA"]<br>5-Cyano-pyrimidine-2-carboxylic acid [3-((3R*,6R*)-5-amino-3,6-dimethyl-6-trifluoromethyl-3,6-dihydro-2H-[1,4]oxazin-3-yl)-4-fluorophenyl]-amide trifluoroacetate | 9.92 (br s, 1H), 8.0-9.1 (m, 5H), 7.89 (m, 1H), 7.51 (m, 1H), 7.09 (dd, 1H), 4.43 (d, 1H), 4.02 (d, 1H), 1.71 (d, 3H), 1.64 (s, 3H) | 437 |

Example 71

5-Bromo-pyrimidine-2-carboxylic acid [3-((3R,6R)-6-amino-3,6-dimethyl-6-trifluoromethyl-3,6-dihydro-2H-[1,4]oxazin-3-yl)-4-fluoro-phenyl]-amide hydrochloride

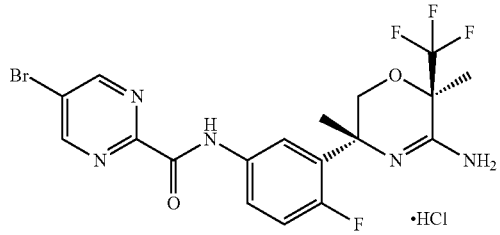 [SMILES: C[C@@]1(c2cc(NC(=O)c3ncc(Br)cn3)ccc2F)CO[C@@](C)(C(F)(F)F)C(N)=N1 ; Cl]

a) 2-(5-Bromo-2-fluoro-phenyl)-propan-2-ol

To a solution of diisopropyl amine (57.3 ml, 402 mmol) in THF (500 ml) was added under argon a 1.6 M solution of nBuLi in hexane (260 ml, 416 mmol) below −50° C. After stirring for 30 min at −75° C., 4-bromo-1-fluoro benzene (31.1 ml, 277 mmol) was added while keeping the temperature below −70° C. After stirring for 2 h at −75° C., acetone (41.2 ml, 554 mmol) was added below −65° C. and the reaction mixture was stirred for 1 h at −75° C., warmed up to −50° C. and poured onto 10% aqueous NH$_4$Cl solution. The mixture was extracted with TBME, organic phases were washed with aqueous KHSO$_4$ solution, saturated NaHCO$_3$ solution and brine, dried over MgSO$_4$, filtered and concentrated. The crude product was crystallized from hexane to provide the title compound as white crystals: TLC (hexane-EtOAc 3:1): Rf=0.45; HPLC Rt$_{H5}$=1.045 min; $^1$H NMR (360 MHz, CDCl$_3$): δ 7.74 (dd, 1H), 7.36 (m, 1H), 6.93 (dd, 1H), 2.04 (d, 1H), 1.63 (s, 6H).

b) 4-Bromo-1-fluoro-2-isopropenyl-benzene

To a solution of 2-(5-bromo-2-fluoro-phenyl)-propan-2-ol (119.7 g, 498 mmol) in CH$_2$Cl$_2$ (50 ml) was added hydrochinone (2.74 g, 24.9 mmol) and 250 ml 85% H$_3$PO$_4$. The resulting reaction mixture was stirred for 3.5 h at 50° C. The mixture was poured onto ice-water and extracted with CH$_2$Cl$_2$. The organic phases were washed with 2N aqueous NaOH and water, dried over MgSO$_4$, filtered and concentrated. The crude product was dissolved in hexane and filtered through a plough of silica gel to obtain after concentration at 600 mbar the title compound as a colorless oil: TLC (hexane): Rf=0.52; HPLC Rt$_{H5}$=1.416 min; $^1$H NMR (360 MHz, CDCl$_3$): δ 7.43 (dd, 1H), 7.37 (m, 1H), 6.94 (dd, 1H), 5.27 (d, 2H), 2.13 (s, 3H).

c) (S)-2-(5-Bromo-2-fluoro-phenyl)-propane-1,2-diol

To a suspension of K$_3$Fe(CN)$_6$ (186 g, 561 mmol), K$_2$CO$_3$ (78 g, 561 mmol), (DHQ)$_2$-PHAL (1.311 g, 1.674 mmol) and K$_2$OsO$_2$(OH)$_4$ (0.378 g, 1 mmol) in t-BuOH—H$_2$O 1:1 (1600 ml) was added 4-bromo-1-fluoro-2-isopropenyl-benzene (36 g, 167 mmol) at 0° C. and the reaction mixture was stirred for 14 h at 0° C. After careful addition of Na$_2$S$_2$O$_5$ (100 g) at 0-5° C. the reaction mixture was stirred for 1 h before extraction with EtOAc. Combined extracts were washed with 5% NaS$_3$O$_3$ solution and brine, dried over MgSO4, filtered and concentrated to give the title compound as a white solid: TLC (hexane-EtOAc 1:1): Rf=0.46; HPLC Rt$_{H5}$=0.767 min; ESIMS: 266, 268 [(M+NH$_4$)$^+$]; $^1$H NMR (360 MHz, CDCl$_3$): δ 7.71 (dd, 1H), 7.27 (m, 1H), 6.83 (dd, 1H), 3.85 (d, 1H), 3.62 (d, 1H), 2.94 (s, 3H), 2.01 (s, 1H), 1.43 (s, 3H).

d) (S)-2-(5-Bromo-2-fluoro-phenyl)-2-methyl-oxirane

To a solution of (S)-2-(5-bromo-2-fluoro-phenyl)-propane-1,2-diol (37.35 g, 150 mmol) in CH$_2$Cl$_2$ (400 ml) was added under argon NEt$_3$ (41.8 ml, 300 mmol) and dropwise mesyl chloride (12.8 ml, 165 mmol) at 0-5° C. After stirring for 0.5 h at 0-5° C. the reaction mixture was added to cold 1N HCl and extracted with CH$_2$Cl$_2$. Combined extracts were washed with 1N HCl, H$_2$O and saturated NaHCO$_3$ solution, dried over MgSO$_4$, filtered and concentrated. The crude mesylate was dissolved in TBME (500 ml) and 200 ml 2N aqueous NaOH and after stirring for 2 h at 25° C. the mixture was extracted with TBME. Combined extracts were washed with NaH$_2$PO$_4$ solution and brine, dried over MgSO$_4$, filtered and concentrated to provide the (S)-enantiomer as a colorless oil: 78% ee (Chiralpak AS-H 1218, hexane-EtOH 97:3, 0.4 mL/min); TLC (hexane-EtOAc 3:1): Rf=0.69; HPLC Rt$_{H5}$=1.186 min; $^1$H NMR (360 MHz, CDCl$_3$): δ 7:46 (dd, 1H), 7.30 (m, 1H), 6.83 (dd, 1H), 2.88 (d, 1H), 2.72 (d, 1H), 1.59 (s, 3H).

e) (S)-1-Azido-2-(5-bromo-2-fluoro-phenyl)-propan-2-ol

To a solution of (S)-2-(5-bromo-2-fluoro-phenyl)-2-methyl-oxirane (51.85 g, 224 mmol) in EtOH (800 ml) was added NaN$_3$ (36.8 g, 531 mmol), NH$_4$Cl (60.6 g, 1122 mmol) and 18-crown-6 (59.8 g, 224 mmol) and the reaction mixture was heated at reflux for 6 h. The reaction mixture was filtered and concentrated to half of its volume. The residual oil was extracted with EtOAc. Combined extracts were washed with saturated NaHCO$_3$ solution and brine, dried over MgSO$_4$, filtered and concentrated to provide the title compound as a light yellow oil: TLC (hexane-EtOAc 1:1): Rf=0.70; HPLC Rt$_{H3}$=1.115 min; $^1$H NMR (360 MHz, CDCl$_3$): δ 7.72 (dd, 1H), 7.32 (m, 1H), 6.85 (dd, 1H), 3.73 (d, 1H), 3.51 (d, 1H), 2.44 (s, 1H), 1.50 (s, 3H).

f) (S)-1-Amino-2-(5-bromo-2-fluoro-phenyl)-propan-2-ol

To a suspension of LiAlH$_4$ (4.65 g, 122 mmol) in THF (250 ml) was added under argon at 0-5° C. a solution of (S)-1-azido-2-(5-bromo-2-fluoro-phenyl)-propan-2-ol (33.4 g, 122 mmol) dissolved in THF (150 ml) over a period of 30 min. After stirring for 1 h at 0-5° C., the reaction was quenched by careful addition of water (4.7 ml), 4 N NaOH (4.7 ml) and water (14.1 ml) and stirred again for 3 h at 25° C. The white suspension was dried with MgSO$_4$, filtered and concentrated. The solidified product was re-crystallized from TBME-hexane to provide the title compound as beige crystals: 98% ee (Chiralpak AD-H hexane-EtOH 75-25+0.05% NEt$_3$); TLC (CH$_2$Cl$_2$-MeOH 10:1) Rf=0.10; HPLC Rt$_{H5}$=0.558 min; ESIMS: 248, 250 [(M+H)$^+$]; $^1$H NMR (360 MHz, CDCl$_3$): δ 7.76 (dd, 1H), 7.25 (m, 1H), 6.82 (dd, 1H), 4.16 (br s, 1H), 3.19 (d, 1H), 2.72 (d, 1H), 1.44 (s, 3H), 0.95 (br s, 2H).

g) N—[(S)-2-(5-Bromo-2-fluoro-phenyl)-2-hydroxypropyl]-2-nitro-benzenesulfonamide To a solution of (S)-1-amino-2-(5-bromo-2-fluoro-phenyl)-propan-2-ol (34.7 g, 140 mmol) in THF (400 ml) was added 2-nitro-benzenesulfonyl chloride (34.9 g, 154 mmol) at 0-5° C. and afterwards 1N aqueous NaOH over a period of 0.5 h. The reaction mixture was stirred for 2 h at 20° C. The reaction mixture was diluted with TBME and washed with water and NaH$_2$PO$_4$ solution and brine, dried over MgSO$_4$, filtered and concentrated to provide the title compound after crystallization from TBME-hexane as beige crystals: TLC (toluene-EtOAc 3:1): Rf=0.51; HPLC Rt$_{H5}$=1.118 min; ESIMS: 450, 452 [(M+NH$_4$)$^+$]; $^1$H NMR (360 MHz, CDCl$_3$): δ 7.98 (m, 1H), 7.81 (m, 1H), 7.65 (m, 2H), 7.59 (dd, 1H), 7.24 (m, 1H), 6.79 (dd, 1H), 5.60 (t, 1H), 4.16 (br s, 1H), 3.55 (dd, 1H), 3.44 (dd, 1H), 2.51 (s, 1H), 1.51 (s, 3H).

h) (R)-2-(5-Bromo-2-fluoro-phenyl)-2-methyl-1-(2-nitro-benzenesulfonyl)-aziridine To a solution of N—[(S)-2-(5-bromo-2-fluoro-phenyl)-2-hydroxy-propyl]-2-nitro-benzenesulfonamide (20.8 g, 48 mmol) in CH$_2$Cl$_2$ (400 ml) was added PPh$_3$ (19.2 g, 72.4 mmol) at 0-5° C. and diethyl azodicarboxylate (11.6 ml, 72.4 mmol). The reaction mixture was stirred for 24 h at 25° C. and concentrated. The title compound was obtained after chromatographic purification over silica gel (hexane-EtOAc 20:1 to 2:1) as yellow crystals: TLC (toluene-EtOAc 3:1): Rf=0.69; HPLC Rt$_{H5}$=1.308 min; $^1$H NMR (360 MHz, CDCl$_3$): δ 8.31 (m, 1H), 7.28 (m, 3H), 7.60 (dd, 1H), 7.42 (m, 1H), 6.91 (dd, 1H), 3.24 (s, 1H), 2.81 (s, 1H), 2.06 (s, 3H).

i) (R)-2-[(R)-2-(5-Bromo-2-fluoro-phenyl)-2-(2-nitro-benzenesulfonylamino)-propoxy]-3,3,3-trifluoro-2-methyl-propionic acid ethyl ester To a suspension of NaH (2.53 g 60% in mineral oil, 63 mmol) in DMF (160 ml) was added drop-wise under argon (R)-3,3,3-trifluoro-2-hydroxy-2-methyl-propionic acid ethyl ester (11.99 g, 63 mmol) and after stirring for 0.5 h at 20° C. (R)-2-(5-bromo-2-fluoro-phenyl)-2-methyl-1-(2-nitro-benzenesulfonyl)-aziridine (21.85 g, 52.6 mmol). The reaction was kept at 25° C. for 16 h. The mixture was added to cold aqueous 2N HCl and the product extracted with TBME. Combined organic layers were washed with saturated NaHCO$_3$ solution and brine, dried over MgSO$_4$, filtered and concentrated. The residual solid was re-crystallized from TBME-hexane to provide the title compound as yellow crystals: TLC (hexane-EtOAc 1:1): Rf=0.59; HPLC Rt$_{H5}$=1.444 min; ESIMS: 618, 620 [(M+NH$_4$)$^+$]; $^1$H NMR (360 MHz, CDCl$_3$): δ 7.83 (dd, 1H), 7.61 (m, 3H), 7.48 (dd, 1H), 7.27 (m, 1H), 6.73 (s, 1H), 6.60 (dd, 1H), 4.33 (m, 2H), 3.84 (s, 2H), 1.84 (s, 3H), 1.57 (s, 3H), 1.33 (t, 3H).

j) (R)-2-[(R)-2-(5-Bromo-2-fluoro-pheyl)-2-(2-nitro-benzenesulfonylamino)-propoxy]-3,3,3-trifluoro-2-methyl-propionamide A solution of (R)-2-[(R)-2-(5-bromo-2-fluoro-phenyl)-2-(2-nitro-benzenesulfonylamino)-propoxy]-3,3,3-trifluoro-2-methyl-propionic acid ethyl ester (26.6 g, 44.2 mmol) in 7N NH$_3$ in MeOH (75 ml) was stirred for 16 h at 50° C. The solvent was removed under reduced pressure and the residual solid re-crystallized from Et$_2$O to give the title compound as yellow crystals: TLC (hexane-EtOAc 1:1): Rf=0.35; HPLC Rt$_{H5}$=1.184 min; ESIMS: 589, 591 [(M+NH$_4$)$^+$]; $^1$H NMR (360 MHz, CDCl$_3$): δ 7.85 (d, 1H), 7.64 (m, 3H), 7.44 (d, 1H), 7.41 (dd, 1H), 7.26 (m, 1H), 6.68 (br s, 1H), 6.57 (dd, 1H), 6.19 (s, 1H), 5.54 (br s, 1H), 4.24 (d, 1H), 3.93 (d, 1H), 1.79 (s, 3H), 1.67 (s, 3H).

k) N—[(R)-1-(5-Bromo-2-fluoro-phenyl)-2-(R)-1-cyano-2,2,2-trifluoro-1-methyl-ethoxy)-1-methyl-ethyl]-2-nitro-benzenesulfonamide To a solution of (R)-2-[(R)-2-(5-bromo-2-fluoro-pheyl)-2-(2-nitro-benzenesulfonylamino)-propoxy]-3,3,3-trifluoro-2-methyl-propionamide (20.83 g, 35.6 mmol) in CH$_2$Cl$_2$ (300 ml) was added under argon NEt$_3$ (12.5 ml, 89 mmol) and at 0-5° C. trifluoroacetic anhydride (6.15 ml, 42.7 mmol). After stirring for 4 h at 25° C. the reaction mixture was added to a cold NaHCO$_3$ solution and the product was extracted with CH$_2$Cl$_2$. Combined extracts were washed with cold 0.1 N aqueous HCl, water and saturated NaHCO$_3$ solution, dried over MgSO$_4$, filtered and concentrated to provide the title compound as a yellow oil, which was used as such for the next step: TLC (hexane-EtOAc 1:1): Rf=0.73; HPLC Rt$_{H5}$=1.364 min; ESIMS: 571, 573 [(M+NH$_4$)$^+$]; $^1$H NMR (360 MHz, CDCl$_3$): δ 7.89 (d, 1H), 7.62 (ddd, 1H), 7.57 (ddd, 1H), 7.52 (m, 2H), 7.29 (m, 1H), 6.58 (dd, 1H), 6.19 (s, 1H), 4.17 (s, 2H), 1.81 (s, 3H), 1.72 (s, 3H).

l) (2R,5R)-5-(5-Bromo-2-fluoro-phenyl)-2,5-dimethyl-2-trifluoromethyl-5,6-dihydro-2H-[1,4]oxazin-3-ylamine To a solution of N—[(R)-1-(5-bromo-2-fluoro-phenyl)-2-((R)-1-cyano-2,2,2-trifluoro-1-methyl-ethoxy)-1-methyl-ethyl]-2-nitro-benzenesulfonamide (6.54 g, 11.8 mmol) and N-acetyl-cysteine (2.4 g, 26.0 mmol) in MeOH (80 ml) was added K$_2$CO$_3$ (3.62 g, 26.0 mmol) and the reaction mixture was heated at 80° C. for 16 h. After removal of the solvent the residue was dissolved in water and extracted with EtOAc. Combined extracts were washed with saturated NaHCO$_3$ solution and brine, dried over MgSO$_4$, filtered and concentrated to provide the title compound after chromatographic purification over silica gel (hexane-EtOAc 10:1 to 1:2 containing 0.03% NEt$_3$) as a yellow oil: TLC (hexane-EtOAc 1:1): Rf=0.58; HPLC R$_{H5}$=0.843 min; ESIMS: 369, 371 [(M+H)$^+$]; $^1$H NMR (360 MHz, CDCl$_3$): δ 7.66 (dd, 1H), 7.35 (m, 1H), 6.91 (dd, 1H), 3.97 (m, 2H), 1.53 (s, 3H), 1.49 (s, 3H).

m) (2R,5R)-6-(2-Fluoro-phenyl)-2,5-dimethyl-2-trifluoromethyl-5,6-dihydro-2H-[1,4]oxazin-3-ylamine A solution of (2R,5R)-5-(5-bromo-2-fluoro-phenyl)-2,5-dimethyl-2-trifluoromethyl-5,6-dihydro-2H-[1,4]oxazin-3-ylamine (1.66 g, 4.5 mmol) and sodium acetate (0.369 g, 4.5 mmol) in MeOH (50 ml) was hydrogenated over 10% Pd—C for 6 h at 50° C. The catalyst was filtered off over Celite and the filtrate was concentrated. The residue was dissolved in saturated NaHCO$_3$ solution and extracted with EtOAc. Combined extracts were washed with brine, dried over MgSO$_4$, filtered and concentrated to provide the title compound as a colorless oil: TLC (hexane-EtOAc 1:1): Rf=0.19; HPLC Rt$_{H5}$=0.777 min; ESIMS: 291 [(M+H)$^+$]; $^1$H NMR (360 MHz, CDCl$_3$): δ 7.41 (dt, 1H), 7.26 (m, 1H), 7.11 (t, 1H), 7.05 (dd, 1H), 4.11 (dd, 1H), 3.94 (dd, 1H), 1.54 (s, 3H), 1.49 (s, 3H).

n) (2R,5R)-5-(2-Fluoro-5-nitro-phenyl)-2,5-dimethyl-2-trifluoromethyl-6,6-dihydro-2H-[1,4]oxazin-3-ylamine To a solution of (2R,5R)-5-(2-fluoro-phenyl)-2,5-dimethyl-2-trifluoromethyl-5,6-dihydro-2H-[1,4]oxazin-3- ylamine (1.035 g, 3.57 mmol) in H$_2$SO$_4$ (6 ml) was added in portions KNO$_3$ (0.379 g, 3.74 mmol) under ice-water cooling. The reaction mixture was stirred for 2 h at 25° C., diluted with water and basified with K$_2$CO$_3$ under cooling. The product was extracted with EtOAc. Combined extracts were washed with saturated NaHCO$_3$ solution and brine, dried over MgSO$_4$, filtered and concentrated. Purification via chromatography on silica gel (hexane-EtOAc 4:1 to 1:1 containing 0.05% NEt$_3$) gave the title compound as a light yellow oil: TLC (hexane-EtOAc 1:1): Rf=0.50; HPLC Rt$_{H5}$=0.749 min; ESIMS: 336 [(M+H)$^+$]; $^1$H NMR (360 MHz, CDCl$_3$): δ 8.48 (dd, 1H), 8.14 (m, 1H), 7.15 (dd, 1H), 4.20 (br s, 2H), 4.04 (dd, 1H), 3.91 (dd, 1H), 1.54 (s, 3H), 1.49 (s, 3H).

o) [(2R,5R)-(2-Fluoro-5-nitro-phenyl)-2,5-dimethyl-2-trifluoromethyl-5,6-dihydro-2H-[1,4]oxazin-3-yl]-carbamic acid tert-butyl ester To a solution of (2R,5R)-5-(2-fluoro-5-nitro-phenyl)-2,5-dimethyl-2-trifluoromethyl-5,6-dihydro-2H-[1,4]oxazin-3-ylamine (1.14 g, 3.4 mmol) in ACN (20 ml) was added Boc$_2$O (0.891 g, 4.08 mmol) and NEt$_3$ (0.72 ml, 5.1 mmol) and the mixture was stirred for 16 h at 25° C. The reaction mixture was evaporated and the residual oil purified by chromatography on silica gel (hexane-EtOAc 20:1 to 7:3) to give the title compound after crystallization from Et$_2$O-hexane as beige crystals: TLC (hexane-EtOAc 3:1): Rf=0.37; HPLC Rt$_{H5}$=1.355 min; ESIMS: 436 [(M+H)$^+$]; $^1$H NMR (360 MHz, CDCl$_3$): δ 11.04 (br s, 1H), 8.24 (m, 2H), 7.30 (dd, 1H), 4.41 (dd, 1H), 4.11 (dd, 1H), 1.68 (s, 3H), 1.51 (s, 9H), 1.49 (s, 3H).

p) [(2R,5R)-5-(5-Amino-2-fluoro-phenyl)-2,5-dimethyl-2-trifluoromethyl-6,6-dihydro-2H-[1,4]oxazin-3-yl]-carbamic acid tert-butyl ester A solution of [(2R,5R)-5-(2-fluoro-5-nitro-phenyl)-2,5-dimethyl-2-trifluoromethyl-5,6-dihydro-2H-[1,4]oxazin-3-yl]-carbamic acid tert-butyl ester (0.98 g, 2.25 mmol) in iso-propanol-THF 2:1 (24 ml) was hydrogenated over 5% Pd—C for 4 h at 50° C. The catalyst was filtered off over Celite and the filtrate was concentrated to provide the title compound after crystallization from TBME-hexane as beige crystals: TLC (hexane-EtOAc 1:1): Rf=0.42; HPLC Rt$_{H5}$=0.955 min; ESIMS: 406 [(M+H)$^+$]; $^1$H NMR (360 MHz, CDCl$_3$): δ 6.82 (dd, 1H), 6.52 (m, 2H), 4.30 (dd, 1H), 3.97 (dd, 1H), 3.06 (br s, 2H), 1.58 (s, 3H), 1.48 (s, 3H), 1.46 (s, 9H).

q) ((2R,5R)-6-{5-[(5-Bromo-pyrimidine-2-carbonyl)-amino]-2-fluoro-phenyl}-2,5-di-methyl-2-trifluoromethyl-5,6-dihydro-2H-[1,4]oxazin-3-yl)-carbamic acid tert-butyl ester To a solution of [(2R,5R)-5-(5-amino-2-fluoro-phenyl)-2,5-dimethyl-2-trifluoromethyl-5,6-di-hydro-2H-[1,4]oxazin-3-yl]-carbamic acid tert-butyl ester (76 mg, 0.187 mmol) in DMF (2 ml) was added 5-bromopyridine-2-carboxylic acid (47 mg, 0.225 mmol), EDC.HCl (48 mg, 0.244 mmol), HOAt (29 mg, 0.206 mmol) and DIPEA (0.08 ml, 0.469 mmol) and the reaction mixture was kept at 25° C. for 16 h. The mixture was concentrated, the residue dissolved in EtOAc and washed with saturated NaHCO$_3$ solution and brine, dried over MgSO$_4$, filtered and purified by chromatography on silica gel (hexane-EtOAc 20:1 to 1:1) to provide the title compound as a light yellow foam: HPLC Rt$_{H5}$=1.297 min); ESIMS: 590, 592 [(M+H)$^+$]; $^1$H NMR (360 MHz, CDCl$_3$): δ 10.98 (br s, 1H), 9.71 (br s, 1H), 8.94 (s, 2H), 7.89 (m, 1H), 7.49 (dd, 1H), 7.12 (dd, 1H), 4.38 (d, 1H), 4.04 (d, 1H), 1.66 (s, 3H), 1.56 (s, 3H), 1.52 (s, 9H).

r) 5-Bromo-pyrimidine-2-carboxylic acid [3-((3R,6R)-5-amino-3,6-dimethyl-6-trifluoro-methyl-3,6-dihydro-2H-[1,4]oxazin-3-yl)-4-fluoro-phenyl]-amide hydrochloride A solution of ((2R,5R)-5-{5-[(5-bromo-pyrimidine-2-carbonyl)-amino]-2-fluoro-phenyl}-2,5-di-methyl-2-trifluoromethyl-5,6-dihydro-2H-[1,4]oxazin-3-yl)-carbamic acid tert-butyl ester (90 mg, 0.153 mmol) in 4N HCl in dioxane (1 ml) was stirred at 40-45° C. for 6 h. The mixture was concentrated and the residue crystallized from Et$_2$O to yield the title compound as a beige solid: HPLC Rt$_{H5}$=0.837 min); ESIMS: 490,492 [(M+H)$^+$]; $^1$H NMR (600 MHz, DMSO-d$_6$): 11.61 (br s, 1H), 11.14 (br s, 1H), 9.61 (br s, 2H), 9.26 (s, 2H), 7.98 (d, 1H), 7.90 (d, 1H), 7.32 (dd, 1H), 4.31 (d, 1H), 4.10 (d, 1H), 1.72 (s, 3H), 1.62 (s, 3H).

Examples 72 to 74

The compounds listed in Table 9 can be prepared by procedures analogous to those used in examples 71 and 72.

TABLE 9

| Example | Compound | $^1$H-NMR (δ; DMSO-d$_6$) | MS [m/z; (M + 1)$^+$] |
|---|---|---|---|
| 72 | 5-Cyano-3-methyl-pyridine-2-carboxylic acid [3-((3R,6R)-5-amino-3,6-dimethyl-6-trifluoro-methyl-3,6-dihydro-2H-[1,4]oxazin-3-yl)-4-fluoro-phenyl]-amide hydrochloride | 11.0 (s, 1H), 9.60 (d, 2H), 9.04 (s, 1H), 8.41 (s, 1H), 7.96 (m, 1H), 7.83 (dd, 1H), 7.33 (dd, 1H), 4.37 (d, 1H), 4.11 (d, 1H), 2.56 (s, 3H), 1.73 (s, 3H), 1.70 (s, 3H) | 450 |

TABLE 9-continued

| Example | Compound | ¹H-NMR (δ; DMSO-d₆) | MS [m/z; (M + 1)⁺] |
|---|---|---|---|
| 73 | 5-Cyano-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide hydrochloride | 9.65 (d, 2H), 9.22 (s, 1H), 8.60 (d, 1H), 8.29 (d, 1H), 8.07 (m, 1H), 7.98 (m, 1H), 7.35 (dd, 1H), 4.34 (d, 1H), 4.10 (d, 1H), 1.75 (s, 3H), 1.71 (s, 3H) | 436 |
| 74 | 5-(2-Methoxy-ethoxy)-pyrazine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide hydrochloride | 10.82 (br s, 1H), 9.58 (br s, 2H), 8.86 (s, 1H), 8.46 (s, 1H), 8.00 (m, 2H), 7.28 (m, 1H), 4.52 (br s, 2H), 4.31 (m, 1H), 4.08 (m, 1H), 3.72 (br s, 2H), 3.33 (s, 3H), 1.70 (s, 3H), 1.66 (s, 3H) | 486 |

More Detailed Description of Preparation of Example 72

5-Cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide hydrochloride a) ((2R,5R)-6-{5-[(5-Cyano-3-methyl-pyridine-2-carbonyl)-amino]-2-fluoro-phenyl}-2,5-dimethyl-2-trifluoromethyl-5,6-dihydro-2H-[1,4]oxazin-3-yl)-carbamic acid tert-butyl ester To a solution of [(2R,5R)-5-(5-amino-2-fluoro-phenyl)-2,5-dimethyl-2-trifluoromethyl-5,6-di-hydro-2H-[1,4]oxazin-3-yl]-carbamic acid tert-butyl ester (82 mg, 0.20 mmol) in DMF (2 ml) was added 5-cyano-3-methyl-pyridine-2-carboxylic acid [Acid-3](42 mg, 0.26 mmol), EDC.HCl (51 mg, 0.26 mmol), HOAt (31 mg, 0.22 mmol) and DIPEA (0.09 ml, 0.52 mmol) and the reaction mixture was kept at 25° C. for 16 h. The mixture was concentrated, the residue dissolved in EtOAc and washed with saturated NaHCO₃ solution and brine, dried over MgSO₄, filtered and purified by chromatography on silica gel (hexane-EtOAc 20:1 to 1:1) to provide the title compound as a light yellow foam: TLC (hexane-EtOAc 1:1): Rf=0.81; HPLC Rt$_{H5}$=1.437 min; ESIMS: 550 [(M+H)⁺]; ¹H NMR (360 MHz, CDCl₃): δ 10.96 (br s, 1H), 9.95 (br s, 1H), 8.63 (s, 2H), 7.88 (m, 1H), 7.71 (m, 1H), 7.54 (dd, 1H), 7.08 (dd, 1H), 4.34 (d, 1H), 4.02 (d, 1H), 2.77 (s, 3H), 1.63 (s, 3H), 1.47 (m, 12H).

b) 5-Cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide hydrochloride To a solution of ((2R,5R)-5-{5-[(5-cyano-3-methyl-pyridine-2-carbonyl)-amino]-2-fluoro-phenyl}-2,5-dimethyl-2-trifluoromethyl-5,6-dihydro-2H-[1,4]oxazin-3-yl)-carbamic acid tert-butyl ester in CH₂Cl₂ (0.3 ml) was added TFA (0.6 ml) and the reaction mixture was kept at 25° C. for 2 h. The reaction was added to cold 10% aqueous K₂CO₃ solution and the product extracted with EtOAc. Combined organic layers were washed with brine, dried over MgSO₄, filtered and concentrated to provide 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide as a colorless foam. The title compound was converted into its hydrochloride salt by dissolving the free base in CH₂Cl₂, adding 1 eq of 2N HCl in Et₂O, evaporation to dryness, followed by crystallization from CH₂Cl₂-Et₂O to provide the title compound as a white solid: HPLC Rt$_{H5}$=0.957 min; ESIMS: 450 [(M+H)⁺]; ¹H NMR (600 MHz, DMSO-d₆): 11.0 (s, 1H), 9.60 (d, 2H), 9.04 (s, 1H), 8.41 (s, 1H), 7.96 (m, 1H), 7.83 (dd, 1H), 7.33 (dd, 1H), 4.37 (d, 1H), 4.11 (d, 1H), 2.56 (s, 3H), 1.73 (s, 3H), 1.70 (s, 3H).

Example 75

5-Cyano-pyridine-2-carboxylic acid [3(3R*,6R*)-5-amino-3-difluoromethyl-6-methyl-3,6-dihydro-2H-[1,4]oxazin-3-yl)-4-fluoro-phenyl]-amide hydrochloride

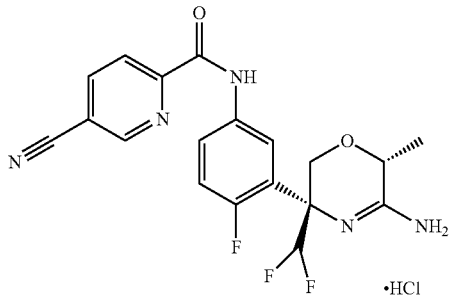 [SMILES: C[C@H]1OC[C@](c2cc(NC(=O)c3ccc(C#N)cn3)ccc2F)(C(F)F)N=C1N ; Cl]

a) N-[1-(5-Bromo-2-fluoro-phenyl)-2,2-difluoro-1-hydroxymethyl-ethyl]-2-chloro-propionamide

[1-(5-Bromo-2-fluoro-phenyl)-2,2-difluoro-1-hydroxymethyl-ethyl]-carbamic acid tert-butyl ester [Example 42 step c)](2.21 g, 5.75 mmol) was dissolved in 20 mL HCl solution 4 mol/L in dioxane and stirred at room temperature for 60 minutes. The reaction mixture was evaporated to give a white solid which was directly taken up in 15 mL dichloromethane. 20 mL aqueous $Na_2CO_3$ solution (10% w/w) was added and the emulsion was cooled to 0-5° C. Racemic 2-chloro-propionyl chloride (787 mg, 6.20 mmol) was added dropwise and the reaction mixture was slowly warmed to room temperature. After 30 minutes, the layers were separated and washed with dichloromethane. The organic layers were combined, dried over $Na_2SO_4$ and evaporated. The crude product was purified on a silica gel column by eluting with heptanes/EtOAc 3/1->2/1 to give 632 mg of the first eluting and 619 mg of the second eluting diastereomer.

Analytical Data of First Eluting Diastereomer:
HPLC $Rt_{H1}$=2.403 min; ESIMS [M+H]$^+$=374, 376 (1 Br);
$^1$H-NMR (CDCl$_3$, 360 MHz): 7.56-7.46 (m, 2H), 7.39 (dd, 1H), 7.06 (dd, 1H), 6.35 (t, J=54 Hz, 1H), 4.64-4.56 (dd, 1H), 4.40-4.29 (m, 1H), 4.21-4.14 (m, 1H), 4.07-4.00 (dd, 1H), 1.86 (d, 3H).

Analytical Data of Second Eluting Diastereomer:
HPLC $Rt_{H1}$=2.409 min; ESIMS [M+H]$^+$=374, 376 (1 Br)
$^1$H-NMR (CDCl$_3$, 360 MHz): 7.46-7.38 (m, 1H), 7.36 (s, 1H), 7.31 (dd, 1H), 6.95 (dd, 1H), 6.23 (t, J=54 Hz, 1H), 4.53-4.44 (dd, 1H), 4.30-4.20 (m, 1H), 4.11-4.03 (m, 1H), 4.01-3.95 (dd, 1H), 1.77 (d, 3H).

b) 5-(5-Bromo-2-fluoro-phenyl)-6-difluoromethyl-2-methyl-morpholin-3-one

A solution of N-[1-(5-bromo-2-fluoro-phenyl)-2,2-difluoro-1-hydroxymethyl-ethyl]-2-chloro-propionamide first eluting diastereomer (442 mg, 1.180 mmol) in 4.4 mL acetonitrile was treated with potassium hydroxide (86 mg, 1.298 mmol) and stirred over night. Additional potassium hydroxide (26 mg, 0.472 mmol) was added and the reaction mixture was stirred for another night. Eventually, the reaction mixture was partitioned between 1N HCl and EtOAc. The layers were separated, washed with brine and EtOAc. The combined organic layers were dried over $MgSO_4.H_2O$ and evaporated. The crude product was crystallized from TBME to give 251 mg of the title compound as white crystals.

HPLC: $Rt_{H1}$=2.221 min; ESIMS [M+H]$^+$=338, 340 (1 Br);
$^1$H-NMR (DMSO-d6, 360 MHz): 8.96 (s, 1H), 7.82 (m, 1H), 7.73-7.65 (m, 1H), 7.30 (dd, 1H), 6.59 (t, J=54 Hz, 1H), 4.46 (d, 1H), 4.23-4.15 (dd, 1H), 3.89-3.80 (m, 1H), 1.33 (d, 3H).

c) 5-(5-Bromo-2-fluoro-phenyl)-6-difluoromethyl-2-methyl-morpholine-3-thione To a solution of 5-(5-bromo-2-fluoro-phenyl)-5-difluoromethyl-2-methyl-morpholin-3-one (659 mg, 1.949 mmol) in 6.6 mL pyridine was added phosphorus pentasulfide (433 mg, 1.949 mmol) and the mixture was heated to 80° C. for 120 minutes. The reaction mixture was cooled to room temperature and partitioned between 0.1 N NaOH and EtOAc. The layers were separated, washed with brine and EtOAc. The combined organic layers were dried over $MgSO_4.H_2O$ and evaporated to give 704 mg of the title compound as a diastereomeric mixture.

HPLC: $Rt_{H1}$=2.961 min; ESIMS [M+H]$^+$=354, 356 (1 Br), $Rt_{H1}$=3.007 min; ESIMS [M+H]$^+$=354, 356 (1 Br);
$^1$H-NMR of diastereomeric mixture (DMSO-d6, 360 MHz): 11.32 and 11.26 (s, 1H), 7.82-7.71 and 7.59 (m, 2H), 7.45-7.33 (m, 1H), 6.72 and 6.63 (t, J=54 Hz, 1H), 4.62-4.41 and 4.04-3.95 (m, 3H), 1.62 and 1.51 (d, 3H).

d) [5-(5-Amino-2-fluoro-phenyl)-5-difluoromethyl-2-methyl-5,6-dihydro-2H-[1,4]oxazin-3-yl]-carbamic acid tert-butyl ester This compound was obtained from 5-(5-bromo-2-fluoro-phenyl)-5-difluoromethyl-2-methyl-morpholine-3-thione by a similar sequence as described for example 42 steps g) to j) as a diastereomeric mixture (white foam).

HPLC: $Rt_{H3}$=2.793 min; ESIMS [M+H]$^+$=374;
Rf (hexane/EtOAc 1/1): 0.40 (isomer 1, major spot), 0.47 (isomer 2, minor spot);
$^1$H-NMR of diastereomeric mixture (CDCl$_3$, 360 MHz, broad signals due to rotamers): 11.00 and 11.96 (s, 1H), 7.01-7.89 (m, 1H), 6.76-6.62 (m, 2H), 6.32 (t, J=54 Hz, 1H), 4.66-3.92 (m, 3H), 3.70 (s, 2H), 1.59-1.56 (s, 12H).

e) (5-{5-[(5-Cyano-pyridine-2-carbonyl)-amino]-2-fluoro-phenyl}-5-difluoromethyl-2-methyl-5,6-dihydro-2H-[1,4]oxazin-3-yl)-carbamic acid tert-butyl ester A solution of [5-(5-amino-2-fluoro-phenyl)-5-difluoromethyl-2-methyl-5,6-dihydro-2H-[1,4]oxazin-3-yl]-carbamic acid tert-butyl ester (140 mg, 0.375 mmol), 5-cyano-2-pyridinecarboxylic acid (83 mg, 0.562 mmol) and HOAT (92 mg, 0.675 mmol) in 2 mL DMF was cooled to 0-5° C. EDC (108 mg, 0.562 mmol) followed by DIPEA (97 mg, 0.750 mmol) was added. The reaction mixture was allowed to warm up to room temperature. After 135 minutes, the mixture was partitioned between saturated aqueous $NaHCO_3$ solution and EtOAc. The layers were separated, washed with saturated aqueous $NaHCO_3$ solution, brine and EtOAc. The combined organic layers were dried over $MgSO_4.H_2O$ and evaporated. The crude product was purified on a silica gel column by eluting with hexane/EtOAc 3/1->2/1 to give the title compound as a diastereomeric mixture (white foam).

Rf (hexane/EtOAc 2/1): 0.36 (isomer 1), 0.30 (isomer 2);
HPLC: $Rt_{H3}$=2.870 min; ESIMS [M+H]$^+$=504;

$^1$H-NMR of diastereomeric mixture (CDCl$_3$, 360 MHz, broad signals due to rotamers): 11.14 and 11.07 (s, 1H), 9.93 (s, 1H), 8.95 and 8.92 (s, 1H), 8.50-8.42 (m, 1H), 8.26 and 8.24 (d, 1H), 8.16-7.97 (m, 1H), 7.79-7.74 (m, 1H), 7.28-7.12 (m, 1H), 6.36 (t, J=54 Hz, 1H), 4.72-3.94 (m, 3H), 1.67-1.43 (m, 12H).

f) 5-Cyano-pyridine-2-carboxylic acid [3-((3R*,6R*)-6-amino-3-difluoromethyl-6-methyl-3,6-dihydro-2H-[1,4]oxazin-3-yl)-4-fluoro-phenyl]-amide hydrochloride To a solution of (5-{5-[(5-cyano-pyridine-2-carbonyl)-amino]-2-fluoro-phenyl}-5-difluoromethyl-2-methyl-5,6-dihydro-2H-[1,4]oxazin-3-yl)-carbamic acid tert-butyl ester (170 mg, 0.338 mmol) in 1.95 mL dichloromethane was added 0.65 mL TFA. After the solution had been stirring for 45 minutes it was evaporated at room temperature. The residue was taken up in EtOAc and extracted with saturated aqueous NaHCO$_3$ solution. The layers were separated, washed with brine and EtOAc. The combined organic layers were evaporated. The crude product was purified on a silica gel column by eluting with CH$_2$Cl$_2$/0.5-3% EtOH:NH$_3$ 9:1 to give a first and a second eluting isomer. Each isomer was individually dissolved in THF and 0.1 mL 1N HCl in diethyl ether was added. The mixtures were evaporated to give 35.8 mg of the first eluting and 43.5 mg of the second eluting isomer as their corresponding hydrochlorides.

Analytical data of first eluting isomer, 5-cyano-pyridine-2-carboxylic acid [3-((3R*,6R*)-5-amino-3-difluoromethyl-6-methyl-3,6-dihydro-2H-[1,4]oxazin-3-yl)-4-fluoro-phenyl]-amide hydrochloride:

HPLC: Rt$_{H3}$=2.774 min; ESIMS [M+H]$^+$=404;
$^1$H-NMR (DMSO, 600 MHz): 11.06 (s, 1H), 10.90 (s, 1H), 9.57 (s, 1H), 9.22 (s, 1H), 8.85 (s, 1H), 8.61 (d, 1H), 8.30 (d, 1H), 8.17-8.13 (m, 1H), 8.09-8.04 (m, 1H), 7.41 (t, 1H), 6.81 (t, J=54 Hz, 1H), 4.81 (d, 1H), 4.46 (d, 1H), 4.04 (d, 1H), 1.57 (d, 3H).

Example 76

5-Cyano-pyridine-2-carboxylic acid [3-((3R*,6S*)-5-amino-3-difluoromethyl-6-methyl-3,6-dihydro-2H-[1,4]oxazin-3-yl)-4-fluoro-phenyl]-amide hydrochloride

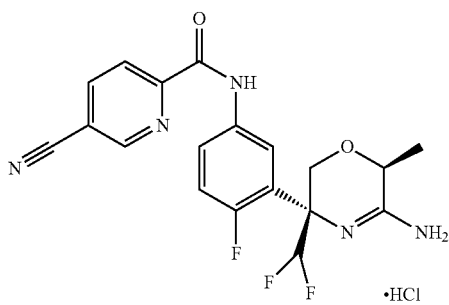 [SMILES: C[C@@H]1OC[C@](c2cc(NC(=O)c3ccc(C#N)cn3)ccc2F)(C(F)F)N=C1N ; Cl]

To a solution of (5-{5-[(5-cyano-pyridine-2-carbonyl)-amino]-2-fluoro-phenyl}-5-difluoromethyl-2-methyl-5,6-dihydro-2H-[1,4]oxazin-3-yl)-carbamic acid tert-butyl ester [example 75 step e)](170 mg, 0.338 mmol) in 1.95 mL dichloromethane was added 0.65 mL TFA. After the solution had been stirring for 45 minutes it was evaporated at room temperature. The residue was taken up in EtOAc and extracted with saturated aqueous NaHCO$_3$ solution. The layers were separated, washed with brine and EtOAc. The combined organic layers were evaporated. The crude product was purified on a silica gel column by eluting with CH2Cl2/0.5-3% EtOH:NH$_3$ 9:1 to give a first and a second eluting isomer. Each isomer was individually dissolved in THF and 0.1 mL 1N HCl in diethyl ether was added. The mixtures were evaporated to give 35.8 mg of the first eluting and 43.5 mg of the second eluting isomer as their corresponding hydrochlorides.

Analytical data of second eluting isomer, 5-cyano-pyridine-2-carboxylic acid [3-((3R*,6S*)-5-amino-3-difluoromethyl-6-methyl-3,6-dihydro-2H-[1,4]oxazin-3-yl)-4-fluoro-phenyl]-amide hydrochloride:

HPLC: Rt$_{H3}$=2.746 min; ESIMS [M+H]$^+$=404;
$^1$H-NMR (DMSO, 600 MHz): 11.17 (s, 1H), 11.05 (s, 1H), 9.71 (s, 1H), 9.22 (s, 1H), 8.92 (s, 1H), 8.60 (d, 1H), 8.31 (d, 1H), 8.16-8.10 (m, 1H), 8.08-8.02 (m, 1H), 7.40 (t, 1H), 6.77 (t, J=54 Hz, 1H), 4.86 (d, 1H), 4.34 (d, 1H), 4.13 (d, 1H), 1.50 (d, 3H).

Example 77

5-Bromo-pyridine-2-carboxylic acid [3-((3R*,6R*)-5-amino-3-difluoromethyl-6-methyl-3,6-dihydro-2H-[1,4]oxazin-3-yl)-4-fluoro-phenyl]-amide hydrochloride

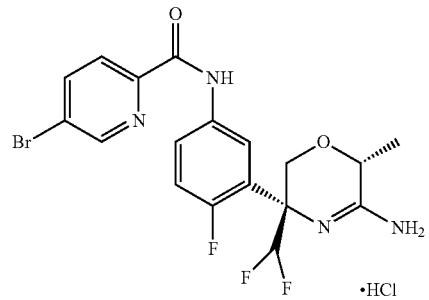 [SMILES: C[C@H]1OC[C@](c2cc(NC(=O)c3ccc(Br)cn3)ccc2F)(C(F)F)N=C1N ; Cl]

a) (5-{5-[(5-Bromo-pyridine-2-carbonyl)-amino]-2-fluoro-phenyl}-5-difluoromethyl-2-methyl-5,6-dihydro-2H-[1,4]oxazin-3-yl)-carbamic acid tert-butyl ester This compound was prepared from 5-(5-amino-2-fluoro-phenyl)-5-difluoromethyl-2-methyl-5,6-dihydro-2H-[1,4] oxazin-3-yl]-carbamic acid tert-butyl ester [example 75 step d)] in an analogous manner as described for example 75 step e).

Rf (hexane/EtOAc 3/1): 0.26 (isomer 1), 0.22 (isomer 2);
HPLC: Rt$_{H3}$=3.137 min; ESIMS [M+H]$^+$=557/559;
$^1$H-NMR of diastereomeric mixture (CDCl$_3$, 360 MHz, broad signals due to rotamers): 11.04 and 10.97 (s, 1H), 9.79 (s, 1H), 8.63-8.57 (m, 1H), 8.13-8.06 (m, 1H), 8.03-7.45 (m, 3H), 7.16-7.00 (m, 1H), 6.24 (t, J=54 Hz, 1H), 4.62-3.86 (m, 3H), 1.56-1.34 (m, 12H).

b) 5-Bromo-pyridine-2-carboxylic acid[3-((3R*,6R*)-5-amino-3-difluoromethyl-6-methyl-3,6-dihydro-2H-[1,4]oxazin-3-yl)-4-fluoro-phenyl]-amide hydrochloride (5-{5-[(5-Bromo-pyridine-2-carbonyl)-amino]-2-fluoro-phenyl}-5-difluoromethyl-2-methyl-5,6-dihydro-2H-[1,4]

oxazin-3-yl)-carbamic acid tert-butyl ester (179 mg, 0.321 mmol) was dissolved in HCl solution 4 mol/L in dioxane (2.4 mL, 9.63 mmol) and 0.1 mL HCl solution 3 mol/L in methanol was added as a co-solvent. The sealed reaction vessel was heated to 50° C. for 120 minutes. The mixture was evaporated; its residue was taken up in EtOAc and extracted with saturated aqueous NaHCO$_3$ solution. The layers were separated, washed with brine and EtOAc. The combined organic layers were evaporated. The crude product was purified on a silica gel column by eluting with CH$_2$Cl$_2$/0.5-2% EtOH:NH$_3$ 9:1 to give a first and a second eluting isomer. Each isomer was individually dissolved in THF and 0.1 mL 1N HCl in diethyl ether was added. The mixtures were evaporated to give 37.0 mg of the first eluting and 54.3 mg of the second eluting isomer as their corresponding hydrochlorides.

Analytical data of first eluting isomer, 5-bromo-pyridine-2-carboxylic acid [3-((3R*,6R*)-5-amino-3-difluoromethyl-6-methyl-3,6-dihydro-2H-[1,4]oxazin-3-yl)-4-fluoro-phenyl]-amide hydrochloride:

HPLC: Rt$_{H3}$=2.910 min; ESIMS [M+H]$^+$=457/459;
$^1$H-NMR (DMSO, 600 MHz): 10.93 (s, 1H), 10.91 (s, 1H), 9.63 (s, 1H), 8.94 (s, 1H), 8.88 (s, 1H), 8.35 (d, 1H), 8.15-8.04 (m, 3H), 7.39 (dd, 1H), 6.81 (t, J=54 Hz, 1H), 4.81 (d, 1H), 4.48 (d, 1H), 4.05 (d, 1H), 1.58 (d, 3H).

Example 78

5-Bromo-pyridine-2-carboxylic acid [3-((3R*,6S*)-5-amino-3-difluoromethyl-6-methyl-3,6-dihydro-2H-[1,4]oxazin-3-yl)-4-fluoro-phenyl]-amide hydrochloride

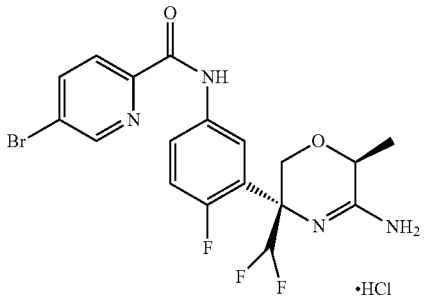 [SMILES: C[C@@H]1OC[C@](c2cc(NC(=O)c3ccc(Br)cn3)ccc2F)(C(F)F)N=C1N ; Cl]

(5-{5-[(5-Bromo-pyridine-2-carbonyl)-amino]-2-fluoro-phenyl}-5-difluoromethyl-2-methyl-5,6-dihydro-2H-[1,4]oxazin-3-yl)-carbamic acid tert-butyl ester [example 77 step a)](179 mg, 0.321 mmol) was dissolved in HCl solution 4 mol/L in dioxane (2.4 mL, 9.63 mmol) and 0.1 mL HCl solution 3 mol/L in methanol was added as a co-solvent. The sealed reaction vessel was heated to 50° C. for 120 minutes. The mixture was evaporated; its residue was taken up in EtOAc and extracted with saturated aqueous NaHCO$_3$ solution. The layers were separated, washed with brine and EtOAc. The combined organic layers were evaporated. The crude product was purified on a silica gel column by eluting with CH$_2$Cl$_2$/0.5-2% EtOH:NH$_3$ 9:1 to give a first and a second eluting isomer. Each isomer was individually dissolved in THF and 0.1 mL 1N HCl in diethyl ether was added. The mixtures were evaporated to give 37.0 mg of the first eluting and 54.3 mg of the second eluting isomer as their corresponding hydrochlorides.

Analytical data of second eluting isomer, 5-bromo-pyridine-2-carboxylic acid [3-((3R*,6S*)-5-amino-3-difluoromethyl-6-methyl-3,6-dihydro-2H-[1,4]oxazin-3-yl)-4-fluoro-phenyl]-amide hydrochloride:

HPLC: Rt$_{H3}$=2.916 min; ESIMS [M+H]$^+$=457/459;
$^1$H-NMR (DMSO, 600 MHz): 11.03 (s, 2H), 9.70 (s, 1H), 8.91 (s, 1H), 8.88 (s, 1H), 8.34 (d, 1H), 8.13-8.08 (m, 2H), 8.04-8.00 (m, 1H), 7.38 (dd, 1H), 6.77 (t, J=54 Hz, 1H), 4.86 (d, 1H), 4.34 (d, 1H), 4.13 (d, 1H), 1.50 (d, 3H).

Example 79

5-Cyano-pyridine-2-carboxylic acid[3-(5-amino-3-difluoromethyl-6,6-dimethyl-3,6-dihydro-2H-[1,4]oxazin-3-yl)-4-fluoro-phenyl]-amide

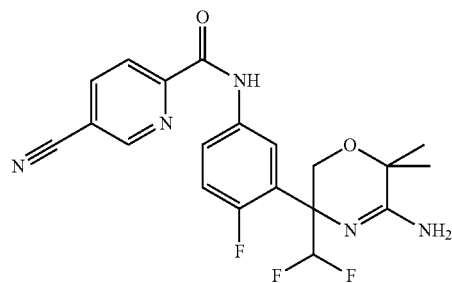 [SMILES: CC1(C)OCC(c2cc(NC(=O)c3ccc(C#N)cn3)ccc2F)(C(F)F)N=C1N]

a) 2-(5-Bromo-2-fluoro-phenyl)-2-difluoromethyl-1-(2-nitro-benzenesulfonyl)-aziridine 2-Amino-2-(5-bromo-2-fluoro-phenyl)-3,3-difluoro-propan-1-ol (13.04 g, 45.9 mmol) [examples 42 step d)] was dissolved in 261 mL acetonitrile, 2-nitrobenzenesulfonyl chloride (22.38 g, 101 mmol) and potassium hydrogencarbonate (13.79 g, 138 mmol) were added. The mixture was heated to 80° C. and stirred over night. After this period, the reaction mixture was cooled down and partitioned between saturated aqueous NaHCO$_3$ solution and TBME. The layers were separated, washed with brine and TBME. The combined organic layers were dried over MgSO$_4$.H$_2$O and evaporated. The crude product was purified on a silica gel column by eluting with hexane/dichloromethane 2/1->1/2 to give 7.71 g of the title compound as white crystals.

HPLC: Rt$_{H1}$=3.309 min; ESIMS [M+Na]$^+$=473, 475 (1 Br);
$^1$H-NMR (CDCl$_3$, 360 MHz): 8.33-8.26 (m, 1H), 7.87-7.78 (m, 3H), 7.76 (dd, 1H), 7.60-7.53 (m, 1H), 7.05 (t, 1H), 6.22 (t, J=54 Hz, 1H), 3.42 (s, 1H), 3.28 (s, 1H).

b) 2-[2-(5-Bromo-2-fluoro-phenyl)-3,3-difluoro-2-(2-nitro-benzenesulfonylamino)-propoxy]-2-methyl-propionicacid tert-butyl ester To a solution of tert-butyl α-hydroxyisobutyrate (533 mg, 3.32 mmol) in 4.5 mL DMF and 0.75 mL THF was added portion wise (133 mg, 3.32 mmol) sodium hydride at room temperature. After the reaction mixture had been stirring for 15 minutes, a solution of 2-(5-bromo-2-fluoro-phenyl)-2-difluoromethyl-1-(2-nitro-benzenesulfonyl)-aziridine (1 g, 2.22 mmol) was added. The reaction mixture was stirred at rt for 150 minutes and quenched with aqueous NH$_4$Cl solution. TBME was added, the layers were separated, washed with brine and TBME. The combined organic layers were dried over MgSO$_4$.H$_2$O and evaporated. The crude product was purified on a silica gel column by eluting with hexane/EtOAc 6/1->5/1 to give 1.10 g of the title compound as a pale yellow resin.

HPLC: Rt$_{H7}$=3.471 min; ESIMS [M+Na]$^+$=633, 635 (1 Br);
$^1$H-NMR (CDCl$_3$, 360 MHz): 7.94 (dd, 1H), 7.82 (dd, 1H), 7.68 (t, 1H), 7.57 (d, 1H), 7.49 (t, 1H), 7.42 (s, 1H), 7.37-7.32 (m, 1H), 6.90 (dd, 1H), 6.72 (t, J=54 Hz, 1H), 4.02 (d, 1H), 3.94 (d, 1H), 1.58 (s, 9H), 1.47 (s, 3H), 1.45 (s, 3H).

c) 5-(5-Bromo-2-fluoro-phenyl)-5-difluoromethyl-2,2-dimethyl-4-(2-nitro-benzenesulfonyl)-morpholin-3-one To a solution of 2-[2-(5-bromo-2-fluoro-phenyl)-3,3-difluoro-2-(2-nitro-benzenesulfonylamino)-propoxy]-2-methyl-propionicacid tert-butyl ester (1.10 g, 1.80 mmol) in 8 mL dichloromethane was added 4 mL trifluoroacetic acid. After the reaction mixture had been stirring at room temperature for 60 minutes, it was evaporated to give 1.10 g of a white solid. This solid was directly dissolved in a mixture of 10 mL dichloromethane and N-methylmorpholine (546 mg, 5.40 mmol) followed by drop wise addition of ethyl chloroformate (293 mg, 2.70 mmol). After the reaction mixture had been stirring for 150 minutes at room temperature, the reaction mixture was partitioned between TBME and saturated aqueous NaHCO$_3$. The layers were separated, washed with 1N HCl, brine and TBME. The combined organic layers were dried over MgSO$_4$.H$_2$O and evaporated. The crude product was crystallized from TBME/hexane to give 822 mg of the title compound as white crystals.
HPLC: Rt$_{H6}$=3.087 min; ESIMS [M+H]$^+$=537, 539 (1 Br);
$^1$H-NMR (CDCl$_3$, 360 MHz): 8.15 (d, 1H), 7.82-7.70 (m, 2H), 7.65 (dd, 1H), 7.61-7.53 (m, 2H), 7.18 (t, J=54 Hz, 1H), 7.09 (dd, 1H), 4.49 (d, 1H), 4.25 (d, 1H), 1.56 (s, 3H), 1.40 (s, 3H)

d) 5-(5-Bromo-2-fluoro-phenyl)-6-difluoromethyl-2,2-dimethyl-morpholin-3-one

To a solution of 5-(5-bromo-2-fluoro-phenyl)-5-difluoromethyl-4-(2-nitro-benzenesulfonyl)-morpholin-3-one (6.29 g, 11.71 mmol) and thioglycolic acid (1.83 g, 19.90 mmol) in 63 mL DMF was added potassium carbonate (6.47 g, 46.8 mmol). The reaction mixture was heated to 60° C. After 120 minutes, additional thioglycolic acid (324 mg, 3.51 mmol) was added. 30 minutes later on, the reaction mixture was cooled to room temperature and partitioned between EtOAc and water. The layers were separated, washed with saturated aqueous NaHCO$_3$, brine and EtOAc. The combined organic layers were dried over MgSO$_4$.H$_2$O and evaporated. The crude product was crystallized from TBME/hexane to give 3.14 g of the title compound as white crystals.
HPLC: Rt$_{H1}$=2.476 min; ESIMS [M+H]$^+$=352, 354 (1 Br);
$^1$H-NMR (DMSO-d6, 360 MHz): 8.94 (s, 1H), 7.76-7.65 (m, 2H), 7.32 (dd, 1H), 6.55 (t, J=54 Hz, 1H), 4.20 (d, 1H), 4.08 (d, 1H), 1.37 (s, 3H), 1.28 (s, 3H).

e) 5-Difluoromethyl-6-(2-fluoro-phenyl)-2,2-dimethyl-morpholin-3-one 5-(5-Bromo-2-fluoro-phenyl)-5-difluoromethyl-2,2-dimethyl-morpholin-3-one (3.14 g, 8.92 mmol) and sodium acetate (1.46 g, 17.83 mmol) were suspended in 100 mL methanol and 10 mL THF. Eventually, 10% Pd on charcoal (315 mg) was added and the reaction mixture was treated with hydrogen (balloon) at rt. After 60 minutes the reaction mixture was filtered over celite and evaporated. The residue was partitioned between aqueous Na$_2$CO$_3$ solution and EtOAc. The layers were separated, washed with brine and EtOAc. The combined organic layers were dried over MgSO$_4$.H$_2$O and evaporated to give 2.42 g of the title compound as a white solid.
HPLC: Rt$_{H3}$=3.008 min; ESIMS [M+H]$^+$=274;
$^1$H-NMR (DMSO-d6, 360 MHz): 8.87 (s, 1H), 7.56 (t, 1H), 7.53-7.45 (m, 1H), 7.36-7.24 (m, 2H), 6.54 (t, J=54 Hz, 1H), 4.19 (d, 1H), 4.09 (d, 1H), 1.37 (s, 3H), 1.27 (s, 1H).

f) 5-Difluoromethyl-5-(2-fluoro-phenyl)-2,2-dimethyl-morpholine-3-thione

To a solution of 5-difluoromethyl-5-(2-fluoro-phenyl)-2,2-dimethyl-morpholin-3-one (2.41 g, 8.82 mmol) and hexamethyldisiloxane (2.58 g, 15.88 mmol) in toluene was added) phosphorous pentasulfide (2.35 g, 10.58 mmol). The reaction mixture was heated to 100° C. and stirred over night. After the reaction mixture had been cooled to room temperature, 23 mL Acetone and 33 mL aqueous K$_2$CO$_3$ solution (10% w/w) were added. This mixture was stirred for 90 minutes and then partitioned between water and EtOAc. The layers were separated, washed with 0.1 N NaOH, brine and EtOAc. The organic layers were combined, dried over MgSO$_4$.H$_2$O and evaporated. The crude product was crystallized from TBME/hexane to give 2.28 g of the title compound as white crystals
HPLC: Rt$_{H3}$=3.503 min; ESIMS [M+H]$^+$=290;
$^1$H-NMR (DMSO-d6, 360 MHz): 11.13 (s, 1H), 7.55-7.42 (m, 2H), 7.37-7.28 (m, 2H), 6.61 (t, J=54 Hz, 1H), 4.19 (dd, 2H), 1.60 (s, 3H), 1.48 (s, 3H).

g) 5-Difluoromethyl-5-(2-fluoro-phenyl)-2,2-dimethyl-5,6-dihydro-2H-[1,4]oxazin-3-ylamine 5-Difluoromethyl-5-(2-fluoro-phenyl)-2,2-dimethyl-morpholine-3-thione (2.50 g, 8.64 mmol) was dissolved in NH$_3$ solution 7 mol/L in methanol (40.7 mL, 285 mmol). The sealed reaction vessel was heated to 80° C. for 7 h, then the temperature was lowered to 70° C. and the reaction mixture was stirred over night. The reaction mixture was evaporated and purified on a silica gel column by eluting with CH$_2$Cl$_2$/1-4% EtOH:NH$_3$ 9:1 to give 2.09 g of the title compound as an off-white solid.
HPLC: Rt$_{H3}$=2.575 min; ESIMS [M+H]$^+$=273;
$^1$H-NMR (DMSO-d6, 360 MHz): 7.78 (t, 1H), 7.41-7.32 (m, 1H), 7.26-7.11 (m, 2H), 6.14 (s, 2H), 6.11 (t, J=54 Hz, 1H), 4.11 (dd, 1H), 3.87 (d, 1H), 1.39 (s, 3H), 1.24 (s, 3H).

h) 5-Cyano-pyridine-2-carboxylic acid[3-(5-amino-3-difluoromethyl-6,6-dimethyl-3,6-dihydro-2H-[1,4]oxazin-3-yl)-4-fluoro-phenyl]-amide This compound was obtained from 5-difluoromethyl-5-(2-fluoro-phenyl)-2,2-dimethyl-5,6-dihydro-2H-[1,4]oxazin-3-ylamine by a similar sequence as described for example 98 steps h) to I). With the exception that after the extraction, the base was not converted into a hydrochloride. The free base was crystallized from 2-propanol instead to give the title compound as white crystals.
HPLC: Rt$_{H3}$=2.818 min; ESIMS [M+H]$^+$=418;
$^1$H-NMR (DMSO, 600 MHz): 10.84 (s, 1H), 9.20 (s, 1H) 8.58 (d, 1H), 8.28 (d, 1H), 8.14-8.10 (m, 1H), 7.85-7.80 (m, 1H), 7.18 (t, 1H), 6.13 (s, 2H), 6.13 (t, J=54 Hz, 1H), 4.04 (d, 1H), 3.87 (d, 1H), 1.38 (s, 3H), 1.26 (s, 3H).

Example 80

The compounds listed in Table 10 can be prepared by a procedure analogous to that used in example 79, using 4N HCl in dioxane in the last step.

TABLE 10

| Example | Compound | ¹H-NMR (δ; DMSO-d₆) | MS [m/z; (M + 1)⁺] |
|---|---|---|---|
| 80 | 5-Bromo-pyridine-2-carboxylic acid [3-(5-amino-3-difluoromethyl-6,6-dimethyl-3,6-dihydro-2H-[1,4]oxazin-3-yl)-4-fluoro-phenyl]-amide hydrochloride | 11.01 (s, 2H), 9.76 (s, 1H) 8.97 (s, 1H), 8.88 (s, 1H), 8.35 (d, 1H), 8.10 (d, 2H), 8.06 (d, 1H), 7.39 (t, 1H), 6.79 (t, J = 54 Hz, 1H), 4.21 (dd, 2H), 1.61 (s, 3H), 1.55 (s, 3H) | 471, 473 |

Examples 81 to 84

The compounds listed in Table 11 can be prepared by a procedure analogous to that described in example 34, starting from 1,5-dibromo-2,4-difluoro-benzene.

TABLE 11

| Example | Compound | ¹H-NMR (δ; DMSO-d₆) | MS [m/z; (M + 1)⁺] |
|---|---|---|---|
| 81 | 5-Bromo-pyridine-2-carboxylic acid [5-(5-amino-3-difluoromethyl-3,6-dihydro-2H-[1,4]oxazin-3-yl)-2,4-difluoro-phenyl]-amide hydrochloride | 10.45 (s, 1 H), 8.88 (d, 1 H), 8.33 (dd, 1 H), 8.16 (t, 1 H), 8.06 (d, 1 H), 7.37 (t, 1 H), 6.21 (br. s., 2 H), 6.09 (t, 1 H, CHF2), 4.19 (dd, 1 H), 4.02 (d, 1 H), 3.91 (d, 1 H), 3.80 (d, 1 H) | 461, 463 |
| 82 | 5-Cyano-pyridine-2-carboxylic acid [5-(5-amino-3-difluoromethyl-3,6-dihydro-2H-[1,4]oxazin-3-yl)-2,4-difluoro-phenyl]-amide hydrochloride | 11.06 (s, 1 H), 10.76 (s, 1 H), 9.76 (s, 1 H), 9.24 (s, 1 H), 8.78 (s, 1 H), 8.61 (dd, 1 H), 8.28 (d, 1 H), 7.94 (t, 1 H), 7.66 (t, 1 H), 6.76 (t, 1 H, CHF2), 4.77-4.58 (m, 2 H), 4.36 (d, 1 H), 4.21 (d, 1 H) | 408 |

TABLE 11-continued

| Example | Compound | $^1$H-NMR (δ; DMSO-$d_6$) | MS [m/z; $(M + 1)^+$] |
|---|---|---|---|
| 83 | 5-Bromo-3-methoxy-pyridine-2-carboxylic acid [5-(5-amino-3-difluoromethyl-3,6-dihydro-2H-[1,4]oxazin-3-yl)-2,4-difluoro-phenyl]-amide hydrochloride | 11.07 (s, 1 H), 10.37 (s, 1 H), 9.77 (s, 1 H), 8.78 (s, 1 H), 8.37 (s, 1 H), 8.06-7.98 (m, 2 H), 7.62 (t, 1 H), 6.76 (t, 1 H, CHF2), 4.76-4.59 (m, 2 H), 4.37 (d, 1 H), 4.19 (d, 1 H), 3.91 (s, 3 H) | 491, 493 |
| 84 | 5-Bromo-3-hydroxy-pyridine-2-carboxylic acid [5-(5-amino-3-difluoromethyl-3,6-dihydro-2H-[1,4]oxazin-3-yl)-2,4-fluoro-phenyl]-amide hydrochloride | 11.99 (br. s., 1 H), 11.03 (br. s., 1 H), 10.96 (br. s., 1 H), 9.74 (br. s., 1 H), 8.76 (br. s., 1 H), 8.39 (s, 1 H), 7.91 (s, 1 H), 7.82 (br. s., 1 H), 7.66 (br. s., 1 H), 6.75 (t, 1 H, CHF2), 4.70-4.61 (m, 2 H), 4.36 (d, 1 H), 4.20 (d, 1 H) | 477, 479 |

Example 85

5-Chloro-pyridine-2-carboxylic acid [3-((R)-5-amino-3-fluoromethyl-3,6-dihydro-2H-[1,4]oxazin-3-yl)-4-fluoro-phenyl]-amide hydrochloride

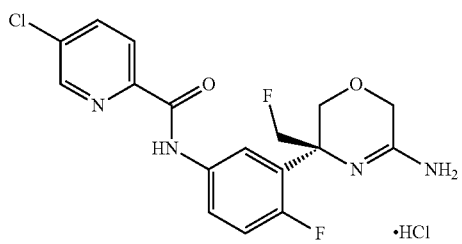 [SMILES: NC1=N[C@](CF)(c2cc(NC(=O)c3ccc(Cl)cn3)ccc2F)COC1 ; Cl]

a) 4-Bromo-1-fluoro-2-nitromethyl-benzene

A mixture of 4-bromo-1-fluoro-2-bromomethyl-benzene (5 g, 18.66 mmol) and AgNO$_2$ (3.45 g, 22.39 mmol) were stirred in 62 ml TBME for 7 h. The dark mixture was filtered over celite, washed with TBME and evaporated. The crude product was purified by chromatography on silica gel (heptane/EtOAc 20/1) to provide the title compound as a yellow oil.

TLC (Hex: EE/9:1) Rf 0.3

HPLC: Rt$_{H4}$=2.449 min;

$^1$H-NMR (CDCl$_3$, 360 MHz): 7.64-7.58 (m, 2H), 7.12 (t, 1H), 5.50 (s, 2H).

b) 2-(5-Bromo-2-fluoro-phenyl)-2-nitro-propane-1,3-diol

A solution of 4-bromo-1-fluoro-2-nitromethyl-benzene (7.75 g, 33.1 mmol), formaldehyde (35%, aqueous) (5.47 ml, 69.5 mmol) and Et$_3$N (2.3 ml, 16.56 mmol) were stirred in 66 ml dioxane for 3 h. The solution was diluted with brine and extracted with TBME. The organic layer was washed with brine, dried with Na$_2$SO$_4$ and evaporated. The crude product was purified by chromatography on silica gel (heptane/EtOAc 3/1) to provide the title compound as a white solid.

TLC (Hex: EE/2:1) Rf 0.24

HPLC: Rt$_{H4}$=2.070 min; ESIMS [M+Na]$^+$=316, 318 (1 Br);

$^1$H-NMR (DMSO, 360 MHz): 7.65-7.60 (m, 1H), 7.55 (dd, 1H), 7.75 (dd, 1H), 5.50 (s, 2H), 4.20 (br t, 4H).

c) 2-Amino-2-(5-bromo-2-fluoro-phenyl)-propane-1,3-diol

A solution of 2-(5-bromo-2-fluoro-phenyl)-2-nitro-propane-1,3-diol (7 g, 23.8 mmol) in 35 ml AcOH was added dropwise to a mixture of zinc (9.34 g, 143 mmol) in 35 ml AcOH while the temperature did not rise above 40° C. The mixture was stirred for 1 h, filtered over celite and washed with MeOH. The filtrate was evaporated, diluted with water and washed with TBME. The aqueous layer was basified with 2 N NaOH and NH$_3$ (25%, aqueous), saturated with NaCl and extracted with EtOAc. The organic layer was washed with brine, dried with Na$_2$SO$_4$ and evaporated to provide the title compound as an off-white solid.

TLC (EE: MeOH/19:1+1% NH3 (25%, aqueous)) Rf 0.38

HPLC: Rt$_{H2}$=2.332 min; ESIMS [M+H]$^+$=246, 266 (1 Br);

¹H-NMR (DMSO, 360 MHz): 7.82 (dd, 1H), 7.50-7.42 (m, 1H), 7.09 (dd, 1H), 4.71 (br s, 2H), 3.36 (dd, 4H), 2.20 (br s, 2H).

d) N-[1-(5-Bromo-2-fluoro-phenyl)-2-hydroxy-1-hydroxymethyl-ethyl]-2-chloro-acetamide A solution of chloro-acetyl chloride (6.39 ml, 80 mmol) in 10 ml ACN was added dropwise to a mixture of 2-amino-2-(5-bromo-2-fluoro-phenyl)-propane-1,3-diol (5.3 g, 20 mmol) and $K_2CO_3$ (11.1 g, 80 mmol) in 90 ml ACN while the temperature did not rise above 35° C. The mixture was stirred for 2 h. MeOH (40 ml, 99 mmol) were added and after 5 min stirring the mixture was filtered over celite and washed with MeOH. The filtrate was acidified with citric acid solution (10%, aqueous) (pH 4-5) and partly evaporated. The remaining aqueous layer was extracted with EtOAc. The organic layer was washed with $NaHCO_3$ solution (10%, aqueous) and brine, dried with $Na_2SO_4$ and evaporated to provide the title compound as an off-white solid.

TLC (Hex: EE/1:1) Rf 0.23
HPLC: $Rt_{H4}$=1.966 min; ESIMS [M+H]⁺=340, 342 (1 Br);
¹H-NMR (DMSO, 360 MHz): 8.19 (s, 1H), 7.47 (dd, 1H), 7.10 (dd, 1H), 5.00 (t, 2H), 4.19 (s, 2H), 3.98-3.81 (m, 4H).

e) 5-(5-Bromo-2-fluoro-phenyl)-6-hydroxymethyl-morpholin-3-one

A mixture of N-[1-(5-bromo-2-fluoro-phenyl)-2-hydroxy-1-ydroxymethyl-ethyl]-2-chloro-acetamide (6.34 g, 18.62 mmol) and potassium tert.-butoxide (2.09 g, 18.62 mmol) in 62 ml t-BuOH was refluxed for 30 min. 19 ml 1 N HCl and water were added and the aqueous layer was extracted with EtOAc. The organic layer was washed with brine, dried with $MgSO_4$ and evaporated. The crude product was recrystallized in Hex/EtOAc to provide the title compound as an off-white solid.

TLC (Hex: EE/1:2) Rf 0.25
HPLC: $Rt_{H4}$=1.885 min; ESIMS [M+H]⁺=304, 306 (1 Br);
¹H-NMR (DMSO, 360 MHz): 8.49 (s, 1H), 7.62-7.56 (m, 2H), 7.21 (dd, 1H), 5.25 (t, 1H), 4.15 (d, 1H), 4.02 (s, 2H), 3.91 (d, 1H), 3.79-3.62 (m, 2H).

f) 5-(5-Bromo-2-fluoro-phenyl)-5-fluoromethyl-morpholin-3-one

To a solution of 5-(5-bromo-2-fluoro-phenyl)-5-hydroxymethyl-morpholin-3-one (1.6 g, 5.26 mmol) in 30 ml THF was added dropwise diethylaminosulfur trifluoride (0.97 ml, 7.34 mmol) and stirred for 2 h. The colorless solution was slowly added to an ice cooled $Na_2CO_3$ solution (10%, aqueous) and extracted with TBME. The organic layer was washed with brine, dried with $MgSO_4$ and evaporated. The crude product was purified by chromatography on silica gel (heptane/EtOAc 3/1) to provide the title compound as a slightly yellow solid.

TLC (Hex: EE/1:1) Rf 0.43
HPLC: $Rt_{H4}$=2.136 min; ESIMS [M+H]⁺=306, 308 (1 Br);
¹H-NMR (CDCl₃, 360 MHz): 7.50-7.40 (m, 2H), 6.95 (dd, 1H), 6.55 (s, 1H), 4.86-4.58 (m, 2H), 4.22-4.11 (m, 2H), 4.07-3.98 (m, 2H).

g) [5-(5-Amino-2-fluoro-phenyl)-5-fluoromethyl-5,6-dihydro-2H-[1,4]oxazin-3-yl]-carbamic acid tert-butyl ester This compound was obtained from 5-(5-bromo-2-fluoro-phenyl)-5-fluoromethyl-morpholin-3-one by a similar sequence as described for example 42 steps g) to j).

TLC (Hex: EE/1:1) Rf 0.38
HPLC: $Rt_{H2}$=2.778 min; ESIMS [M+H]⁺=342;
¹H-NMR (DMSO, 360 MHz, broad signals due to rotamers): 9.79 (s, 1H), 6.82 (br t, 1H), 6.70-6.62 (m, 1H), 6.51-6.43 (m, 1H), 4.92 (s, 2H), 4.70-4.38 (m, 4H), 3.95-3.81 (m, 2H), 1.43 (s, 9H).

h) [(R)-5-(5-Amino-2-fluoro-phenyl)-5-fluoromethyl-5,6-dihydro-2H-[1,4]oxazin-3-yl]-carbamic acid tert-butyl ester The racemic product [5-(5-amino-2-fluoro-phenyl)-5-fluoromethyl-5,6-dihydro-2H-[1,4]oxazin-3-yl]-carbamic acid tert-butyl ester was separated via prep-HPLC on Chiralpak AD 20 μm 5×50×100 mm (5×SMB columns) (Flowrate: 65 mV min; Detection UV: 220 nm). The desired compound was the slower eluting (R)-enantiomer.

Purity: 99.0% ee
$[\alpha]_D$=−140° (c=1, CHCl₃).

i) ((R)-6-{5-[(5-Chloro-pyridine-2-carbonyl)-amino]-2-fluoro-phenyl}-5-fluoromethyl-6,6-dihydro-2H-[1,4]oxazin-3-yl)-carbamic acid tert-butyl ester

[(R)-5-(5-Amino-2-fluoro-phenyl)-5-fluoromethyl-5,6-dihydro-2H-[1,4]oxazin-3-yl]-carbamic acid tert-butyl ester (75 mg, 0.22 mmol), 5-chloro-pyridine-2-carboxylic acid (38.1 mg, 0.242 mmol), HOAt (38.9 mg, 0.286 mmol), EDC (63.2 mg, 0.33 mmol) and Et₃N (77 μl, 0.549 mmol) were dissolved in $CH_2Cl_2$ and stirred for 14 h. The solution was evaporated and the crude product was purified by chromatography on silica gel (heptane/EtOAc 6/1) to provide the title compound as a white solid.

TLC (Hex: EE/2:1) Rf 0.46
HPLC: $Rt_{H1}$=2.668 min; ESIMS [M+H]⁺=481, 483 (1 Cl);
¹H-NMR (DMSO, 360 MHz, broad signals due to rotamers): 9.79 (br s, 1H), 8.50 (s, 1H), 8.29 (d, 1H), 7.90-7.85 (m, 1H), 7.81 (dd, 1H), 7.65-7.55 (br m, 1H), 7.10-7.00 (m, 1H), 4.75-4.45 (br m, 4H), 4.19 (d, 1H), 3.91-3.81 (1H), 1.46 (br s, 9H).

j) 5-Chloro-pyridine-2-carboxylic acid [3-((R)-5-amino-3-fluoromethyl-3,6-dihydro-2H-[1,4]oxazin-3-yl)-4-fluoro-phenyl]-amide hydrochloride A solution of ((R)-5-{5-[(5-chloro-pyridine-2-carbonyl)-amino]-2-fluoro-phenyl}-5-fluoromethyl-5,6-dihydro-2H-[1,4]oxazin-3-yl)-carbamic acid tert-butyl ester (106 mg, 0.22 mmol), 4 N HCl/Dioxan (1.1 ml, 4.41 mmol) and 3 N HCl/MeOH in $CH_2Cl_2$ was stirred for 15 h at room temperature and for 2 h at 40° C. to complete the conversion. The yellow solution was evaporated and taken up in MeOH. TBME was added and the white precipitate was filtered off to provide the title compound.

HPLC: $Rt_{H2}$=3.033 min; ESIMS [M+H]⁺=381, 383 (1 Cl);
¹H-NMR (DMSO, 360 MHz): 11.90 (s, 1H), 11.85 (br s, 1H), 9.50 (br s, 1H), 8.83-8.80 (m, 1H), 8.25-8.15 (m, 2H), 8.10-8.01 (m, 2H), 7.40-7.32 (m, 2H), 5.08-4.97 (m, 1H), 4.95-4.82 (m, 1H), 4.71-4.60 (m, 1H), 4.20-4.10 (m, 1H).

Examples 86 to 95

The compounds listed in Table 12 can be prepared by a procedure analogous to that used in example 85, using the racemic [5-(5-amino-2-fluoro-phenyl)-5-fluoromethyl-5,6-dihydro-2H-[1,4]oxazin-3-yl]-carbamic acid tert-butyl ester [example 85 step g)] or [(R)-5-(5-amino-2-fluoro-phenyl)-5-fluoromethyl-5,6-dihydro-2H-[1,4]oxazin-3-yl]-carbamic acid tert-butyl ester [example 85 step g)].

TABLE 12

| Example | Compound | ¹H-NMR (δ; DMSO-d₆) | MS [m/z; (M + 1)⁺] |
|---|---|---|---|
| 86 | 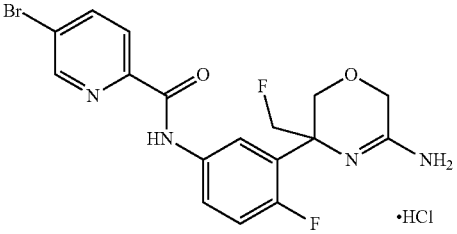 [SMILES: NC1=NC(CF)(c2cc(NC(=O)c3ccc(Cl)cn3)ccc2F)COC1 ; Cl]<br>5-Bromo-pyridine-2-carboxylic acid [3-(5-amino-3-fluoromethyl-3,6-dihydro-2H-[1,4]oxazin-3-yl)-4-fluoro-phenyl]-amide hydrochloride | 10.95-10.85 (m, 2H), 9.62-9.51 (m, 1H), 8.89 (s, 1H), 8.80-8.75 (m, 1H), 8.35 (dd, 1H), 8.30 (d, 1H), 8.08-8.05 (m, 1H), 8.04-8.02 (m, 1H), 7.37-7.31 (m, 1H), 5.00-4.85 (m, 1H), 4.70-4.59 (m, 1H), 4.18-4.05 (m, 1H) | 425, 427 |
| 87 | 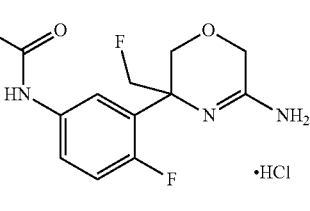<br>5-Chloro-pyridine-2-carboxylic acid [3-(5-amino-3-fluoromethyl-3,6-dihydro-2H-[1,4]oxazin-3-yl)-4-fluoro-phenyl]-amide hydrochloride | 10.95-10.90 (m, 2H), 9.60-9.55 (m, 1H), 8.81-8.78 (m, 2H), 8.23-8.21 (m, 1H), 8.18 (d, 1H), 8.08-8.05 (m, 1H), 8.04-8.02 (m, 1H), 7.37-7.32 (m, 1H), 5.00-4.70 (m, 2H), 4.69-4.59 (m, 2H), 4.19-4.09 (m, 2H) | 381, 383 |
| 88 | 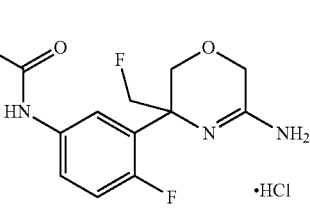<br>3,5-Dichloro-pyridine-2-carboxylic acid [3-(5-amino-3-fluoromethyl-3,6-dihydro-2H-[1,4]oxazin-3-yl)-4-fluoro-phenyl]-amide hydrochloride | 11.02-10.95 (m, 2H), 9.60 (s, 1H), 8.85 (s, 1H), 8.74 (s, 1H), 8.47 (s, 1H), 7.94-7.87 (m, 1H), 7.85-7.79 (m, 1H), 7.40-7.32 (m, 1H), 5.02-4.83 (m, 2H), 4.69-4.59 (m, 2H), 4.19-4.07 (m, 2H) | 415, 417 |
| 89 | 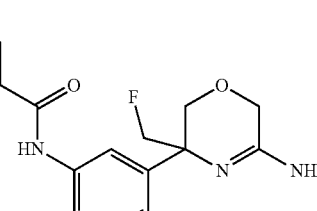<br>5-Cyano-pyridine-2-carboxylic acid [3-(5-amino-3-fluoromethyl-3,6-dihydro-2H-[1,4]oxazin-3-yl)-4-fluoro-phenyl]-amide hydrochloride | 11.07 (s, 1H), 10.88 (s, 1H), 9.53 (s, 1H), 9.21 (s, 1H), 8.74 (s, 1H), 8.60 (dd, 1H), 8.30 (d, 1H), 8.10-8.03 (m, 2H), 7.40-7.32 (m, 1H), 5.03-4.83 (m, 2H), 4.69-4.58 (m, 2H), 4.17-4.08 (m, 2H) | 372 |

TABLE 12-continued

| Example | Compound | ¹H-NMR (δ; DMSO-d₆) | MS [m/z; (M + 1)⁺] |
|---|---|---|---|
| 90 | 5-Bromo-3-methyl-pyridine-2-carboxylic acid [3-(5-amino-3-fluoromethyl-3,6-dihydro-2H-[1,4]oxazin-3-yl)-4-fluoro-phenyl]-amide hydrochloride | 10.89 (s, 1H), 10.78 (s, 1H), 9.54 (s, 1H), 8.77 (s, 1H), 8.67 (s, 1H), 8.18 (s, 1H), 8.00-7.96 (m, 1 H), 7.90 (dd, 1H), 7.37-7.29 (m, 1H), 5.01-4.82 (m, 2H), 4.69-4.58 (m, 2H), 4.17-4.08 (m, 2H), 2.55 (s, 3H) | 439, 441 |
| 91 | 5-Bromo-3-methyl-pyridine-2-carboxylic acid [3-((R)-5-amino-3-fluoromethyl-3,6-dihydro-2H-[1,4]oxazin-3-yl)-4-fluoro-phenyl]-amide hydrochloride | 10.84 (s, 1H), 10.78 (s, 1H), 9.54-9.46 (m, 1H), 8.73-8.66 (m, 2H), 8.22-8.19 (m, 1H), 8.03-7.96 (m, 1H), 7.96-7.90 (m, 1H), 7.40-7.30 (m, 1H), 5.08-4.95 (m, 1H), 4.95-4.82 (m, 1H), 4.72-4.59 (m, 2H), 4.20-4.10 (m, 2H), 2.58 (s, 3H) | 439, 441 |
| 92 | 5-Chloro-3-methyl-pyridine-2-carboxylic acid [3-((R)-5-amino-3-fluoromethyl-3,6-dihydro-2H-[1,4]oxazin-3-yl)-4-fluoro-phenyl]-amide | 10.51 (s, 1H), 8.55 (d, 1H), 8.00 (d, 1H), 7.91 (dd, 1H), 7.79-7.73 (m, 1H), 7.15-7.08 (m, 1H), 5.90 (s, 2H), 4.55-4.48 (m, 1H), 4.43-4.36 (m, 1H), 4.00-3.77 (m, 4H), 2.53 (s, 3H) | 395, 397 |
| 93 | 5-Chloro-4,6-dideutero-3-trideuteromethyl-pyridine-2-carboxylic acid [3-((R)-5-amino-3-fluoromethyl-3,6-dihydro-2H-[1,4]oxazin-3-yl)-4-fluoro-phenyl]-amide hydrochloride | 10.85 (d, 1H), 10.78 (s, 1H), 9.50 (d, 1H), 8.71 (d, 1H), 8.01-7.95 (m, 1H), 7.95-7.88 (m, 1H), 7.37-7.30 (m, 1H), 5.03-4.89 (m, 2H), 4.69-4.58 (m, 2H), 4.18-4.08 (m, 2H) | 400, 402 |

TABLE 12-continued

| Example | Compound | ¹H-NMR (δ; DMSO-d₆) | MS [m/z; (M + 1)⁺] |
|---|---|---|---|
| 94 | 5-Bromo-3-hydroxy-pyridine-2-carboxylic acid [3-((R)-5-amino-3-fluoromethyl-3,6-dihydro-2H-[1,4]oxazin-3-yl)-4-fluoro-phenyl]-amide hydrochloride | 12.25-12.12 (m, 1H), 11.14 (s, 1H), 10.92-10.83 (m, 1H), 9.58-9.47 (m, 1H), 8.79-8.68 (m, 1H), 8.39 (d, 1H), 8.04-7.93 (m, 2H), 7.91 (d, 1H), 7.45-7.34 (m, 1H), 5.08-4.95 (m, 1H), 4.95-4.81 (m, 1H), 4.72-4.58 (m, 2H), 4.21-4.09 (m, 2H) | 441, 443 |
| 95 | 5-Bromo-3-methoxy-pyridine-2-carboxylic acid [3-((R)-5-amino-3-fluoromethyl-3,6-dihydro-2H-[1,4]oxazin-3-yl)-4-fluoro-phenyl]-amide | 10.48 (s, 1H), 8.35 (d, 1H), 7.96 (d, 1H), 7.91-7.85 (m, 1H), 7.79-7.71 (m, 1H), 7.19-7.08 (m, 1H), 5.92 (s, 2H), 4.59-4.52 (m, 1H), 4.46-4.39 (m, 1H), 4.05-3.80 (m, 7H) | 455, 457 |

Example 96

5-Bromo-pyridine-2-carboxylic acid[3-((S)-3-amino-6-difluoromethyl-2,5,6,7-tetrahydro-[1,4]oxazepin-6-yl)-4-fluoro-phenyl]-amide hydrochloride

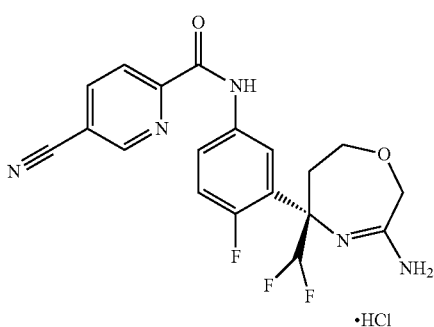 [SMILES: N#Cc1ccc(C(=O)Nc2ccc(F)c([C@]3(C(F)F)CCOCC(N)=N3)c2)nc1 ; Cl]

a) 1-5-Bromo-2-fluoro-phenyl)-2,2-difluoro-ethanone

A solution of diisopropyl amine (17.77 ml, 126 mmol) in 320 ml THF was cooled to −75° C. and brought under N₂ atmosphere. A 1.6 M solution of BuLi in hexane (79 ml, 126 mmol) was added. When the LDA solution had cooled down again, 1-fluoro-4-bromobenzene was added. The reaction temperature was kept below −60° C. After 2.5 h ethyl difluoro acetate (15.60 g, 126 mmol) was added rapidly and after 15 minutes, the reaction mixture was warmed to −40° C. After 15 minutes the mixture was quenched by pouring it on ice-cold 1N HCl. The mixture was extracted with petroleum ether (B.p. 40-60° C.) and the extract was dried with MgSO₄.H₂O. Chromatography on silica gel with hexane/TBME 9/1->6/1 gave 22.1 g yellow liquid.

Rf (hexanes/EtOAc 6/1)=0.28

¹H-NMR (CDCl₃, 360 MHz): 8.09 (dd, 1H), 7.79 (ddd, 1H), 7.17 (t, 1H), 6.44 (t, J=45 Hz, 1H).

b) [1-(5-Bromo-2-fluoro-phenyl)-2,2-difluoro-eth-(Z)-ylidene]-carbamic acid tert-butyl ester A suspension of 1-(5-bromo-2-fluoro-phenyl)-2,2-difluoro-ethanone (16.0 g, 63.2 mmol) and N-(triphenylphosphoranylidene)-carbamic acid 1,1-dimethylethyl ester (CAS 68014-21-1) (26.3 g, 69.6 mmol) in 12 ml toluene was stirred at 100° C. for 2 days. The suspension became clear. After being cooled down somewhat, hexane was added till crystallization of triphenylphosphine oxide started. The mixture was filtered and the filtrate was purified by chromatography on silica gel with hexane/TBME 1-5% to give 11.37 g of the title compound as a yellow liquid.

Rf (hexane/EtOAc 6/1)=0.65

¹H-NMR (DMSO-d6, 360 MHz): 7.88 (dd, 1H), 7.71 (br, 1H), 7.47 (t, 1H), 6.88 (br t, J=54 Hz, 1H), 1.29 (br s, 9H).

c) [1-(5-Bromo-2-fluoro-phenyl)-1-difluoromethyl-but-3-enyl]-carbamic acid tert-butyl ester To a solution of [1-(5-bromo-2-fluoro-phenyl)-2,2-difluoro-eth-(Z)-ylidene]-carbamic acid tert-butyl ester (9.61 g, 27.3 mmol) in 114 ml THF at −75° was added dropwise allylmagnesium chloride solution 2 mol/L in THF (15.0 ml, 30 mmol). The reaction temperature was not allowed to exceed −60° C. After 10 minutes the reaction was quenched with 10% aqueous NH$_4$Cl and extracted with TBME. The organic phase was washed with brine, dried with Na$_2$SO$_4$ and evaporated. The crude product was chromatographed on silica gel with 1-5% TBME/hexane to give 10.39 g of the title compound.

HPLC: Rt$_{H3}$=3.449 min; ESIMS [M+Na]$^+$=416, 418 (1 Br);
$^1$H-NMR (CDCl$_3$, 360 MHz): 7.45 (dd, 1H), 7.35 (ddd, 1H), 6.88 (dd, 1H), 6.28 (t, J=54 Hz), 1H), 5.72-5.60 (m, 1H), 5.13 (d, 1H), 5.12 (d, 1H), 5.00 (br s, 1H), 3.00-2.80 (m, 2H), 1.32 (br s, 9H).

d) [1-(5-Bromo-2-fluoro-phenyl)-1-difluoromethyl-3-hydroxy-propyl]-carbamic acid tert-butyl ester A suspension of [1-(5-bromo-2-fluoro-phenyl)-1-difluoromethyl-but-3-enyl]-carbamic acid tert-butyl ester (5.11 g, 12.96 mmol) and NaHCO$_3$ (1.63 g, 19.44 mmol) in 90 ml DCM and 30 ml MeOH was cooled to −75° C. A mixture of O$_3$ in oxygen gas was introduced till the blue color persisted. The excess ozone was removed by bubbling through oxygen gas for 10 minutes. NaBH$_4$ (0.981 g, 25.9 mmol) was added as a solid in three portions. The mixture was stirred 10 min at −75° C. and then allowed to warm to 0° C. After 30 min the mixture was poured onto ice-cold 1N HCl and extracted with TBME. The organic phase was washed with 1N HCl, brine, dried with MgSO$_4$.H$_2$O and evaporated. Chromatography on silica gel (hexanes/15-35% EtOAc) provided 4.75 g of the title compound as a colorless resin.

HPLC: Rt$_{H6}$=2.359 min; ESIMS [M+Na]$^+$=420, 422 (1 Br);
$^1$H-NMR (DMSO-d6, 360 MHz): 7.68 (br, 1H), 7.60-7.54 (m, 1H), 7.47 (dd, 1H), 7.20 (dd, 1H), 6.57 (t, J=54 Hz, 1H), 4.77 (t, 1H), 3.52-3.34 (m, 2H), 2.29 (br s, 2H), 1.36 (br, s, 9H).

e) N-[1-(5-Bromo-2-fluoro-phenyl)-1-difluoromethyl-3-hydroxy-propyl]-2-chloro-acetamide

[1-(5-Bromo-2-fluoro-phenyl)-1-difluoromethyl-3-hydroxy-propyl]-carbamic acid tert-butyl ester (4.75 g, 11.93 mmol) was dissolved in 89 ml 4N HCl in dioxane. The mixture was stirred 1 h and evaporated to give 4.2 g of a white solid. The solid was suspended in 60 ml ACN and K$_2$CO$_3$ (6.59 g, 7.7 mmol) was added. The stirred suspension was cooled to 0° C. and chloroacetyl chloride (4.04 g, 35.8 mmol) was added dropwise. The mixture was stirred at 25° C. overnight. The mixture was diluted with TBME, washed with water and brine, dried with MgSO$_4$.H$_2$O and evaporated to give 5.25 g of the crude diacylated product. This crude intermediate was dissolved in 60 mL of MeOH and K$_2$CO$_3$ (330 mg, 2.39 mmol) was added. After 30 minutes, the reaction mixture was partitioned between water and TBME. The layers were separated and washed with brine and TBME. The combined organic layers were dried over MgSO$_4$.H$_2$O and evaporated. The crude product was purified on a silica gel column by eluting with hexane/EtOAc 4/1->3/1->2/1. Pure fractions were combined and evaporated to give 3.81 g of the title compound as a colorless resin.

HPLC: Rt$_{H3}$=3.097 min; ESIMS [M+Na]$^+$=374, 376 (1 Br);
$^1$H-NMR (CDCl$_3$, 360 MHz): 8.56 (br, s, 1H), 7.53 (dd, 1H), 7.49-7.43 (m, 1H), 6.99 (dd, 1H), 6.79 (t, J=54 Hz, 1H), 4.14-4.02 (m, 3H), 3.88-3.79 (m, 1H), 2.45 (t, 2H), 1.19 (d, 1H).

f) 5-(5-Bromo-2-fluoro-phenyl)-5-difluoromethyl-[1,4]oxazepan-3-one

To a refluxing solution of potassium tert-butylate (1.63 g, 14.52 mmol) in 555 ml t-BuOH was added dropwise a solution of) N-[1-(5-bromo-2-fluoro-phenyl)-1-difluoromethyl-3-hydroxy-propyl]-2-chloro-acetamide (2.72 g, 7.26 mmol) in 45 ml THF over a period of 40 minutes. The reaction mixture was cooled down and quenched with 1N HCl. EtOAc was added and the organic layer was washed with brine, dried with Na$_2$SO$_4$ and evaporated. The crude product was crystalized from DCM/TBME to provide the title compound as white crystals.

HPLC: Rt$_{H3}$=2.989 min; ESIMS [M+H]$^+$=338, 340 (1 Br);
$^1$H-NMR (DMSO-d6, 360 MHz): 8.38 (s, 1H), 7.70-7.63 (m, 2H), 7.29 (dd, 1H), 6.20 (t, J=54 Hz, 1H), 4.17 (d, 1H), 4.04 (d, 1H), 3.80-3.73 (m, 1H), 3.45-3.34 (m, 1H), 2.73-2.56 (m, 2H).

g) [5-(5-Amino-2-fluoro-phenyl)-5-difluoromethyl-2,5,6,7-tetrahydro-[1,4]oxazepin-3-yl]-carbamic acid tert-butyl ester This compound was obtained from 5-(5-bromo-2-fluoro-phenyl)-5-difluoromethyl-[1,4]oxazepan-3-one by a similar sequence as described for example n75 step c) and example 42 steps g) to j) as a colorless foam.

HPLC: Rt$_{H3}$=2.410 min; ESIMS [MH+H$_2$O]$^+$=392, Rt$_{H3}$=2.595 min; ESIMS [MH]$^+$=374;
$^1$H-NMR (CDCl$_3$, 360 MHz, broad signals due to rotamers): 11.09 (s, 1H), 6.96-6.88 (dd, 1H), 6.71-6.62 (m, 2H), 6.11 (t, J=54 Hz, 1H), 4.47-4.25 (m, 2H), 3.89-3.80 (m, 1H), 3.74-3.55 (m, 3H), 2.79-2.69 (m, 1H), 2.65-2.50 (m, 1H), 1.58 (s, 9H).

h) [(S)-5-(5-Amino-2-fluoro-phenyl)-5-difluoromethyl-2,5,6,7-tetrahydro-[1,4]oxazepin-3-yl]-carbamic acid tert-butyl ester Racemic [5-(5-amino-2-fluoro-phenyl)-5-difluoromethyl-2,5,6,7-tetrahydro-[1,4]oxazepin-3-yl]-carbamic acid tert-butyl ester (1.62 g, 4.04 mmol) was separated via a VWR prep HPLC System on a Chiralpak AD 20 um 4×50×100 (4×SMB columns) column; eluent: heptane/ethanol 70/30; flow=65 ml/min; UV detection at 220 nm. As a result, 754 mg of the desired title compound ((S)-isomer) was obtained as the first eluting isomer. Purity: >99.5% ee.

$^1$H-NMR (CDCl$_3$, 360 MHz, broad signals due to rotamers): 11.08 (s, 1H), 6.96-6.88 (dd, 1H), 6.71-6.63 (m, 2H), 6.11 (t, J=54 Hz, 1H), 4.47-4.26 (m, 2H), 3.89-3.81 (m, 1H), 3.80-3.56 (m, 3H), 2.78-2.70 (m, 1H), 2.64-2.51 (m, 1H), 1.58 (s, 9H). α$_D$=−166.5° (c=1, solvent=CHCl$_3$)

i) ((S)-5-{5-[(5-Cyano-pyridine-2-carbonyl)-amino]-2-fluoro-phenyl}-5-difluoromethyl-2,5,6,7-tetrahydro-[1,4]oxazepin-3-yl)-carbamic acid tert-butyl ester A solution of [(S)-5-(5-amino-2-fluoro-phenyl)-5-difluoromethyl-2,5,6,7-tetrahydro-[1,4]oxazepin-3-yl]-carbamic acid tert-butyl ester (51.2 mg, 0.137 mmol), 5-cyano-2-pyridinecarboxylic acid (30.5 mg, 0.206 mmol) and HOAT (33.6 mg, 0.247 mmol) in 0.6 mL DMF was cooled to 0-5° C. EDC (39.4 mg, 0.206 mmol) and DIPEA (35.4 mg, 0.274 mmol) were added. The resulting solution was allowed to warm up to rt over night. The reaction mixture was then partitioned between saturated aqueous NaHCO₃ solution and EtOAc. The layers were separated, washed with saturated aqueous NaHCO₃ solution, brine and EtOAc. The combined 6.55 (t, J=54 Hz, 1H), 4.77 (d, 1H), 4.52 (d, 1H), 3.89-3.83 (m, 1H), 3.50-3.39 (m, 1H), 2.79-2.68 (m, 2H).

Example 97

The compound listed in Table 13 can be prepared by a procedure analogous to that used in example 96, using 4N HCl in dioxane in step j).

TABLE 13

| Example | Compound | $^1$H-NMR (δ; DMSO-d$_6$) | MS [m/z; (M + 1)$^+$] |
|---|---|---|---|
| 97 | 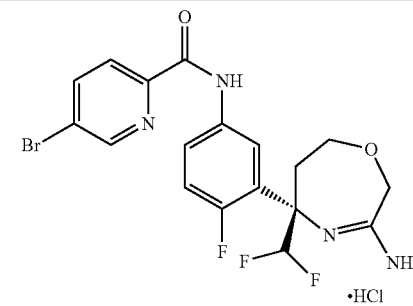<br>5-Bromo-pyridine-2-carboxylic acid[3-((S)-3-amino-5-difluoromethyl-2,5,6,7-tetrahydro-[1,4]oxazepin-5-yl)-4-fluoro-phenyl]-amide hydrochloride | 10.97 (s, 1H), 10.17 (s, 1H) 9.74 (s, 1H), 8.87 (s, 1H), 8.75 (s, 1H), 8.34 (d, 1H), 8.11-8.05 (m, 2H), 7.99-7.96 (m, 1H), 7.35 (dd, 1H), 6.54 (t, J = 54 Hz, 1H), 4.77 (d, 1H), 4.51 (d, 1H), 3.89-3.84 (m, 1H), 3.48-3.41 (m, 1H), 2.79-2.68 (m, 2H) | 457, 459 | organic layers were dried over MgSO₄.H₂O and evaporated. The crude product was purified on a silica gel column by eluting with hexane/EtOAc 3/1->1.5/1 to give 67.7 mg of the title compound as a colorless resin.

HPLC: Rt$_{H1}$=2.492 min; ESIMS=[M+H]+504;

$^1$H-NMR (CDCl₃, 360 MHz, broad signals due to rotamers): 11.10 (s, 1H), 9.85 (s, 1H), 8.86 (s, 1H), 8.35 (d, 1H), 8.28-8.19 (m, 1H), 8.14 (dd, 1H), 7.32-7.25 (m, 1H), 7.10 (t, 1H), 6.08 (t, J=54 Hz, 1H), 4.43-4.15 (m, 2H), 3.80-3.71 (m, 1H), 3.59-3.42 (m, 1H), 2.74-2.65 (m, 1H), 2.62-2.47 (m, 1H), 1.49 (s, 9H).

j) 5-Bromo-pyridine-2-carboxylic acid[3-((S)-3-amino-6-difluoromethyl-2,5,6,7-tetrahydro-[1,4]oxazepin-6-yl)-4-fluoro-phenyl]-amide hydrochloride ((S)-5-{5-[(5-Cyano-pyridine-2-carbonyl)-amino]-2-fluoro-phenyl}-5-difluoromethyl-2,5,6,7-tetrahydro-[1,4]oxazepin-3-yl)-carbamic acid tert-butyl ester (67.7 mg, 0.134 mmol) was dissolved in 0.75 mL dichloromethane and 0.25 mL trifluoroacetic acid. The solution was stirred at for 45 minutes and then evaporated at room temperature. The residue was dissolved in EtOAc and extracted with saturated aqueous NaHCO₃ solution. The layers were washed with brine and EtOAc. The combined organic layers were dried over Na₂SO₄ and evaporated. The crude product was dissolved in THF, 0.2 mL HCl solution 1 mol/L in diethyl ether was added and the mixture was evaporated. The residue was crystallized from ethanol and TBME to give 48 mg of the title compound as white crystals.

HPLC: Rt$_{H3}$=2.629 min; ESIMS [M+H]$^+$=404.0;

$^1$H-NMR (DMSO, 600 MHz): 11.11 (s, 1H), 10.20 (s, 1H) 9.75 (s, 1H), 9.22 (s, 1H), 8.78 (s, 1H), 8.60 (d, 1H), 8.30 (d, 1H), 8.12-8.07 (m, 1H), 8.01-7.97 (m, 1H), 7.35 (dd, 1H),

Example 98

5-Cyano-pyridine-2-carboxylic acid [3-3-amino-5-trifluoromethyl-2,5,6,7-tetrahydro-[1,4]oxazepin-5-yl)-4-fluoro-phenyl]-amide hydrochloride

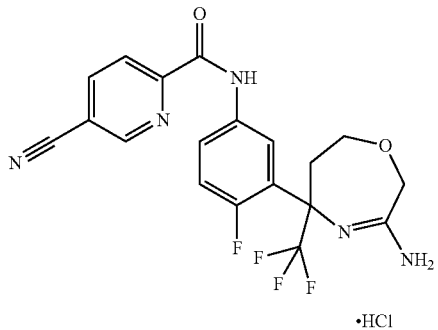 [SMILES: N#Cc1ccc(C(=O)Nc2ccc(F)c(C3(C(F)(F)F)CCOCC(N)=N3)c2)nc1 ; Cl]

a) [2,2,2-Trifluoro-1-(2-fluoro-phenyl)-eth-(Z)-ylidene]-carbamic acid tert-butyl ester A suspension of 1-(2-fluoro-phenyl)-2,2,2-trifluoro-ethanone (CAS 124004-75-7) (17.0 g, 88 mmol) and N-(triphenylphosphoranylidene)-carbamic acid 1,1-dimethylethyl ester (CAS 68014-21-1) (36.7 g, 97 mmol) in 17 ml toluene was stirred at 120° C. for 18 h. The suspension became clear. After being cooled down hexane was added till crystallization of triphenylphosphine oxide started. The mixture was filtered and the filtrate was purified by chromatography on silica gel with 1-5% TBME/hexanes to yield 11.37 g of a yellow liquid.

Rf (Hex/TBME 95/5)=0.18

HPLC: Rt$_{H6}$=3.168 min; ESIMS [M+Na]$^+$=314,
$^1$H-NMR (CDCl3, 360 MHz): 7.59-7.52 (m, 1H), 7.42-7.35 (m, 1H), 7.30-7.18 (m, 2H), 1.31 (s, 9H).

b) [1-(2-Fluoro-phenyl)-1-trifluoromethyl-but-3-enyl]-carbamic acid tert-butyl ester To a solution of [2,2,2-Trifluoro-1-(2-fluoro-phenyl)-eth-(Z)-ylidene]-carbamic acid tert-butyl ester (16.63 g, 57.1 mmol) in 170 mL THF at −75° was added dropwise allylmagnesium chloride solution 2 mol/L in THF (31.4 ml, 62.8 mmol). The reaction temperature was not allowed to exceed −60° C. After 30 minutes, the reaction was quenched with 10% aqueous NH$_4$Cl and extracted with TBME. The organic phase was washed with brine, dried with MgSO$_4$.H$_2$O and evaporated. The crude product was chromatographed on silica gel with hexane/TBME 95/5 to give 18.52 g of the title compound.

HPLC: Rt$_{H3}$=3.296 min; ESIMS [M+Na]$^+$=356;
$^1$H-NMR (CDCl$_3$, 360 MHz): 7.49 (t, 1H), 7.41-7.33 (m, 1H), 7.19 (t, 1H), 7.14-7.06 (dd, 1H), 5.92-5.78 (m, 2H), 5.30-5.19 (m, 2H), 3.37-3.18 (br, m, 2H), 1.40 (br, s, 9H).

c) [1-(2-Fluoro-phenyl)-3-hydroxy-1-trifluoromethyl-propyl]-carbamic acid tert-butyl ester A suspension of [[1-(2-fluoro-phenyl)-1-trifluoromethyl-but-3-enyl]-carbamic acid tert-butyl ester (9.27 g, 27.8 mmol) and NaHCO$_3$ (3.50 g, 41.7 mmol) in 168 ml DCM and 56 ml MeOH was cooled to −75° C. A mixture of O$_3$ in oxygen gas was introduced till the blue color persisted. The excess ozone was removed by bubbling through oxygen gas for 10 minutes. Solid NaBH$_4$ (2.10 g, 55.6 mmol) was added in two portions. The mixture was stirred 10 min at −75° C. and then allowed to warm to 0° C. After 30 minutes, the mixture was poured onto ice-cold 1N HCl and extracted with TBME. The organic phase is washed with 1N HCl, brine, dried with MgSO$_4$.H$_2$O and evaporated. Crystallization from hexane provided 7.83 g of the title compound as white crystals.

HPLC: Rt$_{H1}$=2.738 min; ESIMS [M+Na]$^+$=360;
$^1$H-NMR (DMSO-d6, 360 MHz): 7.82 (br, s, 1H), 7.46-7.35 (m, 2H), 7.27-7.17 (m, 2H), 4.79 (t, 1H), 3.51-3.36 (m, 2H), 2.48-2.31 (m, 2H), 1.32 (br, s, 9H).

d) 2-Chloro-N-[1-(2-fluoro-phenyl)-3-hydroxy-1-trifluoromethyl-propyl]-acetamide

[1-(2-Fluoro-phenyl)-3-hydroxy-1-trifluoromethyl-propyl]-carbamic acid tert-butyl ester (7.83 g, 23.21 mmol) was dissolved in 116 ml 4N HCl in dioxane. The mixture was stirred 1 h and evaporated to give 6.42 g of a white solid. The solid was dissolved in 65 ml dichloromethane and pyridine (11.3 mL, 139 mmol). The solution was cooled to −15° C. and chloroacetyl chloride (5.50 g, 48.7 mmol) was added dropwise. The temperature was kept below −5° C. Afterwards, the mixture was allowed to warm up to room temperature. After 40 minutes, the reaction mixture was partitioned between 1N HCl and TBME. The layers were separated, washed with brine and TBME. The combined organic layers were dried over MgSO$_4$.H$_2$O and evaporated. The crude product was purified on silica gel by eluting with hexane/EtOAc 3/1->2/1 to give 5.46 g of a mixture of diacylated and O-acylated product. This mixture was dissolved in 80 mL dichloromethane. DIPEA (15.8 mL, 90.70 mmol) was added and the reaction mixture was cooled to −75° C. and chloroacetyl chloride (9.89 g, 87.57 mmol) was added dropwise. Afterwards, the mixture was stirred without cooling bath for 15'. The reaction mixture was partitioned between 1N HCl and TBME. The layers were separated, washed with brine and TBME. The combined organic layers were dried over MgSO$_4$.H$_2$O and evaporated. The crude product was purified on a silica gel column by eluting with hexane/EtOAc 3/1 to give 3.71 g of the diacylated compound.

In order to get the title compound, the diacylated compound was dissolved in 50 mL of MeOH and K$_2$CO$_3$ (657 mg, 4.76 mmol) was added. After 45 minutes, the reaction mixture was partitioned between water and TBME. The layers were separated, washed with brine and TBME. The combined organic layers were dried over MgSO$_4$.H$_2$O and evaporated. The crude product was purified on a silica gel column by eluting with hexane/EtOAc 3/1->2/1->1.5/1 to give 1.77 g of the title compound as a yellow resin.

HPLC: Rt$_{H3}$=2.889 min; ESIMS [M+H]$^+$=314;
$^1$H-NMR (DMSO-d6, 360 MHz): 9.10 (br, s, 1H), 7.48-7.39 (m, 2H), 7.27-7.17 (m, 2H), 4.77 (br, t, 1H), 4.25 (dd, 2H), 3.54-3.40 (m, 2H), 2.72-2.61 (m, 1H), 2.58-2.48 (m, 1H)

e) 5-(2-Fluoro-phenyl)-5-trifluoromethyl-[1,4]oxazepan-3-one

To a refluxing solution of potassium tert-butylate (1.31 g, 11.29 mmol) in 43 ml t-BuOH was added dropwise a solution of 2-chloro-N-[1-(2-fluoro-phenyl)-3-hydroxy-1-trifluoromethyl-propyl]-acetamide (1.77 g, 5.64 mmol) in 35 ml THF over a period of 60 minutes. The reaction mixture was cooled down and quenched with 1N HCl. EtOAc was added and the organic layer was washed with brine, dried with MgSO$_4$.H$_2$O and evaporated. The crude product was purified on a silica gel column by eluting with hexane/EtOAc 3/1->2.5/1 to give 1.19 g of the title compound as white crystals.

HPLC: Rt$_{H3}$=2.943 min; ESIMS [M+H]$^+$=278;
$^1$H-NMR (CDCl3, 360 MHz): 7.58 (t, 1H), 7.51-7.44 (m, 1H), 7.33-7.27 (m, 1H), 7.18 (dd, 1H), 6.47 (br, s, 1H), 4.16 (dd, 2H), 4.00-3.91 (m, 1H), 3.82-3.72 (m, 1H), 3.19-3.11 (m, 1H), 2.81-2.68 (m, 1H).

f) 5-(2-Fluoro-phenyl)-5-trifluoromethyl-[1,4]oxazepane-3-thione

To a solution of 5-(2-fluoro-phenyl)-5-trifluoromethyl-[1,4]oxazepan-3-one (1.19 g, 4.29 mmol) in 15 mL THF was added Lawesson's reagent (955 mg, 2.36 mmol). The reaction mixture was stirred at room temperature over night. The mixture was then partitioned between aqueous Na$_2$CO$_3$ solution (2 mol/L) and TBME. The layers were separated, washed with aqueous Na$_2$CO$_3$ solution (2 mol/L), brine and TBME. The combined organic layers were dried over MgSO$_4$.H$_2$O and evaporated. The crude product was purified on a silica gel column by eluting with hexane/EtOAc 95/5->90/10 to give 1.25 g of the title compound as a yellow resin.

HPLC: Rt$_{H3}$=2.620 min; ESIMS [M+H]$^+$=294;
$^1$H-NMR (CDCl3, 360 MHz): 8.42 (br, s, 1H), 7.54-7.45 (m, 2H), 7.35-7.27 (m, 1H), 7.20 (dd, 1H), 4.54 (dd, 2H), 4.05-3.97 (m, 1H), 3.84-3.74 (m, 1H), 3.17-3.08 (m, 1H), 2.85-2.73 (m, 1H).

g) 5-(2-Fluoro-phenyl)-5-trifluoromethyl-2,5,6,7-tetrahydro-[1,4]oxazepin-3-ylamine 5-(2-Fluoro-phenyl)-5-trifluoromethyl-[1,4]oxazepane-3-thione (1.25 g, 4.26 mmol) was dissolved in NH$_3$ solution 7 mol/L in methanol (27 mL, 128 mmol). The sealed reaction vessel was stirred over night at rt. The reaction mixture was evaporated, dissolved in TBME and extracted with 1N HCl.

The layers were separated, washed with water and TBME. The aqueous layers were combined, basified by addition of solid $K_2CO_3$ and extracted with dichloromethane four times. The combined $CH_2Cl_2$ layers were dried over $MgSO_4 \cdot H_2O$ and evaporated to give 1.12 g of the title compound as white crystals.

HPLC: $Rt_{H3}$=2.475 min; ESIMS [M+H]$^+$=277;

$^1$H-NMR (CDCl3, 360 MHz): 7.50 (t, 1H), 7.32-7.23 (m, 1H), 7.09 (t, 1H), 7.04-6.96 (m, 1H), 4.62 (br, s, 2H), 3.95 (m, 2H), 3.76 (d, 1H), 3.73-3.63 (m, 1H), 2.92-2.84 (m, 1H), 2.46-2.34 (m, 1H).

h) 5-(2-Fluoro-5-nitro-phenyl-5-trifluoromethyl-2,5,6,7-tetrahydro-[1,4]oxazepin-3-ylamine To a solution of 5-(2-fluoro-phenyl)-5-trifluoromethyl-2,5,6,7-tetrahydro-[1,4]oxazepin-3-ylamine (1.12 g, 4.05 mmol) in 12 mL concentrated sulfuric acid (95%) was added potassium nitrate (533 mg, 5.27 mmol) in two portions. The reaction mixture was stirred at rt for 30 minutes, it was then poured onto ice water and TBME was added. The layers were separated, washed with water and TBME. The combined aqueous layers were basified with solid $Na_2CO_3$ and extracted with EtOAc. The EtOAc layers were dried over $MgSO_4 \cdot H_2O$ and evaporated to give 1.29 g of the title compound was a white solid.

HPLC: $Rt_{H3}$=2.433 min; ESIMS [M+H]$^+$=322;

$^1$H-NMR (DMSO-d6, 360 MHz): 8.47 (dd, 1H), 8.39-8.31 (m, 1H), 7.58 (dd, 1H), 6.48 (br, s, 2H), 4.23 (d, 1H), 3.96 (d, 1H), 3.93-3.85 (m, 1H), 3.55-3.45 (m, 1H), 2.85-2.76 (m, 1H), 2.61-2.53 (m, 1H).

i) [5-(2-Fluoro-6-nitro-phenyl)-5-trifluoromethyl-2,5,6,7-tetrahydro-[1,4]oxazepin-3-yl]-carbamic acid tert-butyl ester To a suspension of 5-(2-fluoro-5-nitro-phenyl)-5-trifluoromethyl-2,5,6,7-tetrahydro-[1,4]oxazepin-3-ylamine (1.29 g, 4.02 mmol) in 10 mL dichlormethane and 15 mL THF were added DIPEA (779 mg, 6.02 mmol) and di-tert-butyldicarbonate (1.14 g, 5.22 mmol). The reaction mixture was stirred over night and then heated to 40° C. for 24 h. Additional DIPEA (104 mg, 0.8 mmol) and di-tert-butyldicarbonate (175 mg, 0.8 mmol) were added. The mixture was stirred at 40° C. for another 8 h. The reaction mixture was then evaporated and purified on a silica gel column by eluting with hexane/TBME 9/1->7/1 to give 1.69 g of the title compound as a white foam.

HPLC: $Rt_{H1}$=3.445 min; ESIMS=[M-tBu]$^+$ 366;

$^1$H-NMR (CDCl$_3$, 360 MHz): 8.41-8.34 (m, 1H), 8.30-8.24 (m, 1H), 7.39 (br, s, 1H), 7.28 (t, 1H), 5.12 (d, 1H), 4.52 (d, 1H), 3.90-3.78, (m, 2H), 3.05-2.97 (m, 1H), 2.71-2.59 (m, 1H), 1.53 (s, 9H).

j) [5-(5-Amino-2-fluoro-phenyl)-6-trifluoromethyl-2,5,6,7-tetrahydro-[1,4]oxazepin-3-yl]-carbamic acid tert-butyl ester A solution of [5-(2-fluoro-5-nitro-phenyl)-5-trifluoromethyl-2,5,6,7-tetrahydro-[1,4]oxazepin-3-yl]-carbamic acid tert-butyl ester (1.69 g, 4.01 mmol) in 10 mL ethanol and 10 mL THF was brought under nitrogen atmosphere and 500 mg of 5% Pd on charcoal was added. The reaction mixture was then stirred under a hydrogen atmosphere (balloon) for 6 hours. Then it was filtered over celite and evaporated. The crude product was crystallized from hexane/TBME to give 1.38 g of the title compound as white crystals.

HPLC: $Rt_{H3}$=3.006 min; ESIMS=[M+H]$^+$ 392;

$^1$H-NMR (CDCl$_3$, 360 MHz, broad signals due to rotamers): 7.01-6.86 (m, 1H), 6.76-6.62 (m, 2H), 4.96 (d, 1H), 4.58 (d, 1H), 4.31-4.18 (dd, 1H), 4.03-3.73 (m, 2H), 3.69 (s, 1H), 3.57 (s, 1H), 3.13-2.90 (dd, 1H), 2.70-2.46 (m, 1H), 1.58 (s, 9H).

k) (5-{5-[(5-Cyano-pyridine-2-carbonyl)-amino]-2-fluoro-phenyl}-6-trifluoromethyl-2,5,6,7-tetrahydro-[1,4]oxazepin-3-yl)-carbamic acid tert-butyl ester A solution of [5-(5-amino-2-fluoro-phenyl)-5-trifluoromethyl-2,5,6,7-tetrahydro-[1,4]oxazepin-3-yl]-carbamic acid tert-butyl ester (50 mg, 0.128 mmol), 5-cyano-2-pyridinecarboxylic acid (28.4 mg, 0.192 mmol) and HOAT (31.3 mg, 0.230 mmol) in 0.5 mL DMF was cooled to 0-5° C. EDC (36.7 mg, 0.192 mmol) and DIPEA (33 mg, 0.256 mmol) were added. The resulting solution was allowed to warm up to rt over night. The reaction mixture was then partitioned between saturated aqueous NaHCO$_3$ solution and EtOAc. The layers were washed with saturated aqueous NaHCO$_3$ solution, brine and EtOAc. The combined organic layers were dried over MgSO$_4$·H$_2$O and evaporated. The crude product was purified on a silica gel column by eluting with hexane/EtOAc 4/1->3/1 to give 63.3 mg of the title compound as a white solid.

HPLC: $Rt_{H1}$=2.426 min; ESIMS=[M+H$_2$O]$^+$ 540, $Rt_{H1}$=3.177 min; ESIMS=[M+H]$^+$ 522;

$^1$H-NMR (CDCl$_3$, 360 MHz, broad signals due to rotamers): 9.75 (s, 1H), 8.83 (s, 1H), 8.35 (d, 1H), 8.14 (dd, 1H), 8.03-7.95 (m, 1H), 7.48-7.39 (m, 1H), 7.06 (t, 1H), 4.94 (d, 1H), 4.46 (d, 1H), 4.19 (s, 1H), 3.92-3.63 (m, 2H), 3.08-2.85 (m, 1H), 2.69-2.43 (m, 1H), 1.42 (s, 9H).

l) 5-Cyano-pyridine-2-carboxylic acid [3-(3-amino-6-trifluoromethyl-2,5,6,7-tetrahydro-[1,4]oxazepin-6-yl)-4-fluoro-phenyl]-amide hydrochloride (5-{5-[(5-Cyano-pyridine-2-carbonyl)-amino]-2-fluoro-phenyl}-5-trifluoromethyl-2,5,6,7-tetrahydro-[1,4]oxazepin-3-yl)-carbamic acid tert-butyl ester (63.3, 0.121 mmol) was dissolved in 0.68 mL dichloromethane and 0.23 mL trifluoroacetic acid. The solution was stirred at for 45 minutes and then evaporated at room temperature. The residue was dissolved in EtOAc and extracted with saturated aqueous NaHCO$_3$ solution. The layers were washed with brine and EtOAc. The combined organic layers were dried over Na$_2$SO$_4$ and evaporated. The crude product was dissolved in THF, 0.3 mL HCl solution 1 mol/L in diethyl ether was added and the mixture was evaporated. The residue was crystallized from wet ethanol and TBME to give 52.4 mg of the title compound as white crystals.

HPLC: $Rt_{H3}$=2.814 min; ESIMS [M+H]$^+$=422;

$^1$H-NMR (DMSO, 600 MHz): 11.15 (s, 1H), 10.73 (s, 1H) 9.95 (s, 1H), 9.22 (s, 1H), 8.95 (s, 1H), 8.60 (d, 1H), 8.29 (d, 1H), 8.12-8.06 (m, 2H), 7.40 (dd, 1H), 4.76 (d, 1H), 4.49 (d, 1H), 3.98-3.93 (m, 1H), 3.69-3.62 (m, 1H), 2.99-2.92 (s, broad, 2H).

Example 99

The compound listed in Table 14 can be prepared by a procedure analogous to that used in example 98, using 4N HCl in dioxane in step I).

TABLE 14

| Example | Compound | $^1$H-NMR (δ; DMSO-$d_6$) | MS [m/z; $(M+1)^+$] |
|---|---|---|---|
| 99 | ![structure] 5-Bromo-pyridine-2-carboxylic acid [3-(3-amino-5-trifluoromethyl-2,5,6,7-tetrahydro-[1,4]oxazepin-5-yl)-4-fluoro-phenyl]-amide hydrochloride | 11.01 (s, 1H), 10.71 (s, 1H) 9.93 (s, 1H), 8.93 (s, 1H), 8.88 (s, 1H), 8.34 (d, 1H), 8.11-8.05 (m, 3H), 7.39 (dd, 1H), 4.76 (d, 1H), 4.48 (d, 1H), 3.98-3.93 (m, 1H), 3.69-3.61 (m, 1H), 2.97-2.92 (s, broad, 2H) | 475, 477 |

Example 100

N-(3-(3-amino-6,6-difluoro-6-methyl-2,5,6,7-tetrahydro-1,4-oxazepin-6-yl)-4-fluorophenyl)-6-chloropicolinamide

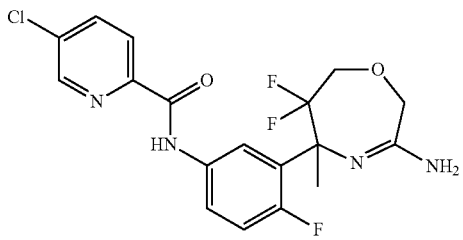 [SMILES: CC1(c2cc(NC(=O)c3ccc(Cl)cn3)ccc2F)N=C(N)COCC1(F)F]

a) Ethyl 3-(5-bromo-2-fluorophenyl)-2,2-difluoro-3-hydroxyproxypropanoate

To an ice cooled solution of 5-bromo-2-fluorobenzaldehyde (10.0 g, 49.2 mmol) in dry DMF (14 mL), Indium powder (8.48 g, 73.7 mmol) was added and stirred for 15 min. ethylbromodifluoroacetate (9.48 ml [14.98 g], 73.7 mmol) in dry DMF (10 mL) was added to the resultant reaction mixture and temperature of the reaction mixture was allowed to warm to rt (30° C.). Stirring continued for 24 h. TLC analysis of the reaction mixture indicated the product formation. Reaction mixture was treated with aqueous saturated NH$_4$Cl solution and the crude product was extracted with ethyl acetate (500 mL) by washing with water, brine and the organic layer was dried over anhydrous Na$_2$SO$_4$. The organic layer was concentrated and the crude product was purified by column chromatography on silica gel using 4% Ethyl acetate in Hexane to obtain title compound as a colorless thick liquid. Yield=12.0 g (75%).

TLC (5% ethyl acetate in Hexane: Rf=0.2), $^1$H NMR (400 MHz, CDCl$_3$) δ 7.75-7.68 (m, 1H), 7.52-7.45 (m, 1H), 6.98 (t, 1H, J=7 Hz), 5.52 (dt, 1H, J=10 Hz, 4 Hz), 4.37 (q, 2H, J=5 Hz), 2.9 (d, 1H), 1.35 (t, 3H).

b) 1-(5-bromo-2-fluorophenyl)-2,2-difluoropropane-1,3-diol

To a solution of ethyl 3-(5-bromo-2-fluorophenyl)-2,2-difluoro-3-hydroxypropanoate (20.0 g, 61.3 mmol) in MeOH (160 mL), NaBH$_4$ (7.0 g, 184.2 mmol) was added portion wise over a period of 30 min. at 0° C. Stirring was continued for 1 h at 0° C. and reaction was monitored by TLC. Upon complete consumption of the starting material, reaction mass was concentrated under reduced pressure and treated with saturated ammonium chloride solution. The crude reaction mass was dissolved in ethyl acetate and organic layer was washed with brine (15 mL) followed by drying over anhydrous Na$_2$SO$_4$. The organic layer was concentrated under reduced pressure to furnish title compound with sufficient purity. Yield=17 g (97%). TLC (50% ethyl acetate in Hexane): Rf=0.32), LCMS: Rt$_{H8}$=0.665, [M−H]$^+$=283.0, 283.9, $^1$H NMR (400 MHz, CDCl$_3$) δ 7.76-7.70 (m, 1H), 7.51-7.42 (m, 1H), 6.90 (t, 1H, J=8.0 Hz), 5.42 (dd, 1H J=8.2 Hz, 4.0 Hz), 4.15-3.81 (m, 2H), 3.0 (s; 1H), 2.26 (s, 1H).

c) 1-(5-bromo-2-fluorophenyl)-3-tert-butyldimethylsilyloxy)-2,2-difluoropropan-1-ol To an ice cooled solution of 1-(5-bromo-2-fluorophenyl)-2,2-difluoropropane-1,3-diol (17.0 g, 59.8 mmol) in dry DCM (200 mL) was added imidazole (12.2 g, 179.2 mmol) at 0° C. and stirred for 15 min. tert-butyldimethylsilylchloride (13.5 g, 89.5 mmol) was added to the resultant reaction mixture portion wise for a period of 30 min. and stirring continued for 2 h. Reaction was monitored by TLC analysis. The solids formed in the reaction mixture were separated by filtration and filtrate was concentrated under reduced pressure to obtain crude product which was purified by column chromatography on silica gel with 2% Ethylacetate in Hexane as eluent to furnish title compound as a colorless liquid. Yield=19 g (80%). TLC (20% ethyl acetate in Hexane): Rf=0.75), LCMS: Rt$_{H8}$=2.09, [M+H]$^+$=399.0, ¹H NMR (300 MHz, CDCl₃) δ 7.77-7.69 (m, 1H), 7.48-7.39 (m, 1H), 6.96 (t, 1H, J=9 Hz), 5.41 (dt, 1H, J=14 Hz, 3.4 Hz), 4.1-3.8 (m, 2H), 3.22 (d, 1H, J=5.2 Hz), 0.93 (s, 9.1 H), 0.16 (s, 6H).

d) 1-(5-bromo-2-fluorophenyl)-3-(tert-butyldimethylsilyloxy)-2,2-difluoropropan-1-one A mixture of 1-(5-bromo-2-fluorophenyl)-3-(tert-butyldimethylsilyloxy)-2,2-difluoropropan-1-ol (19.0 g, mmol) and Pyridinium dichromate (90.0 g, 239.2 mmol) in Dichloromethane (200 mL) was refluxed for 16 h under constant stirring. The catalyst was filtered through a pad of celite and the filtrate was concentrated under reduced pressure to obtain brown colored thick mass. Crude product was purified by column chromatography on silica gel with 1% ethyl acetate in Hexane to obtain title compound as colorless oil. Yield=17.0 g (90%). TLC (10% ethyl acetate in Hexane): Rf=0.56), LCMS: $Rt_{H8}$=1.917, [M+H]⁺=396.7, 398.6, ¹H NMR (300 MHz, CDCl₃) δ 7.91-7.85 (m, 2H), 7.71-7.62 (m, 1H), 7.08 (t, 1H, J=8.5 Hz), 4.12 (t, 1H, J=11.5 Hz), 0.83 (s, 9H), 0.4 (6H).

e) N-(1-(5-bromo-2-fluorophenyl)-3-(tert-butyldimethylsilyloxy)-2,2-difluoropropylidene)-2-methylpropane-2-sulfinamide To a solution of 1-(5-bromo-2-fluorophenyl)-3-(tert-butyldimethylsilyloxy)-2,2-difluoropropan-1-one (16.0 g, 40.4 mmol) in dry THF (350 mL) was added Ti(OEt)₄ (16.7 mL, 80.4 mmol) and 2-Methyl-2-propane sulfonamide (5.8 g, 48.4 mmol) and refluxed for 16 h. Reaction mixture was concentrated under reduced pressure and the crude residue was directly purified by column chromatography on silica gel with 3% ethyl acetate in Hexane to furnish title compound as a colorless liquid. Yield=13.1 g (65.5%). TLC (10% ethyl acetate in Hexane): Rf=0.2), LCMS $Rt_{H8}$=2.29 [M+H]⁺=499.9, 501.8, ¹H NMR (300 MHz, CDCl₃) δ 7.48-7.29 (m, 2H, 6.98 (m, 1H), 4.10 (t, 1H), 1.23 (d, 9H), 0.96 (d, 9H), 0.5 (d, 6H).

f) N-(2-(5-bromo-2-fluorophenyl)-4-(tert-butyldimethylsilyloxy)-3,3-difluorobutan-2-yl)-2-methylpropane-2-sulfinamide To a solution of N-(1-(5-bromo-2-fluorophenyl)-3-(tert-butyldimethylsilyloxy)-2,2-difluoropropylidene)-2-methylpropane-2-sulfinamide (12 g, 24.04 mmol) in diethyl ether (120 mL) was added CH₃MgBr (3M in Diethyl ether) (41 mL, 120 mmol) at −25° C. The reaction mixture was brought to 0° C. and maintained for 30 min. Reaction mixture was again cooled to −35° C. and quenched by drop wise addition of saturated ammonium chloride solution. Organic layer was separated and washed with brine and dried over anhydrous sodium sulphate. Crude compound was purified by column chromatography on silica gel with 8% ethyl acetate in Hexane to furnish title compound as a colorless liquid. Yield=8.8 g (71%). TLC (20% ethyl acetate in Hexane): Rf=0.33), LCMS: $Rt_{H8}$=2.161 [M+H]⁺=516.1, 519.0, ¹H NMR (300 MHz, CDCl₃) δ 7.71-7.62 (m, 1H), 7.44-7.38 (m, 1H), 7.0-6.84 (m, 1H), 4.82 (d, 1H), 4.05-3.9 (m, 2H), 2.06 (s, 3H), 1.25 (s, 9H), 0.9 (s, 9H), 0.11 (s, 6H).

g) 3-amino-3-(5-bromo-2-fluorophenyl)-2,2-difluorobutan-1-ol

To a solution of N-(2-(5-bromo-2-fluorophenyl)-4-(tert-butyldimethylsilyloxy)-3,3-difluorobutan-2-yl)-2-methylpropane-2-sulfinamide (8.8 g, 17.08 mmol) in dry MeOH (60 mL), dry HCl gas was purged for 30 min at −22° C. Reaction mixture was concentrated under reduced pressure and basified with NH₄OH solution under cooling. Product was extracted with dichloromethane, washed with brine, dried over anhydrous Na₂SO₄ and concentrated under reduced pressure to furnish title compound as a color less thick liquid. Yield=4.4 g (88%).

TLC (50% ethyl acetate in Hexane): Rf=0.35),

LCMS: $Rt_{H8}$=0.118 [M+H]⁺=298.0, 299.9,

¹H NMR (300 MHz, CDCl₃) δ 7.68-7.59 (m, 1H), 7.48-7.39 (m, 1H), 6.99 (dd, 1H, J=9 Hz, 4.5 Hz), 4.1-3.69 (m, 3H), 1.8 (s, 3H).

h) N-(2-(5-bromo-2-fluorophenyl)-3,3-difluoro-4-hydroxybutan-2-yl)-2-chloroacetamide To an ice cooled solution of 3-amino-3-(5-bromo-2-fluorophenyl)-2,2-difluorobutan-1-ol (3.1 g, 10.4 mmol), in DCM (60 ml) was added aqueous Na₂CO₃ (2.74 g, 25.8 mmol in 7.0 mL H₂O) and stirred for 10 min. Chloroacetyl chloride (0.986 ml, 11.4 mmol) was then added to the resultant reaction mixture and stirring continued for 30 min at 0° C. Upon formation of the new product by TLC analysis, K₂CO₃ (1.5 g, 10.4 mmol) in MeOH (17 mL) was added to the reaction mixture and stirred at rt for 30 min. The reaction mixture was diluted with DCM, separated the organic layer and washed successively with water and brine solution, dried over anhydrous Na₂SO₄ and concentrated under reduced pressure to furnish title compound as a colorless gum. Yield=3.3 g (78.5%).

TLC (50% ethyl acetate in Hexane): Rf=0.55),

LCMS: $Rt_{H9}$=1.287 [M+H]⁺=374.0, 375.9,

¹H NMR (300 MHz, CDCl₃) δ 8.28 (s, 1H), 7.53-7.38 (m, 2H), 6.92 (dd, 1H, J=11 Hz, 7.5 Hz), 4.11-3.78 (m, 2H), 2.49 (t, 1H, J=7.4 Hz), 2.08 (d, 3H).

i) 5-(5-bromo-2-fluorophenyl)-6,6-difluoro-5-methyl-1,4-oxazepan-3-one

To a solution of t-BuOK (0.36 g, 3.2 mmol) in t-BuOH (10 mL) was added N-(2-(5-bromo-2-fluorophenyl)-3,3-difluoro-4-hydroxybutan-2-yl)-2-chloroacetamide (1.0 g, 2.6 mmol) t-BuOH (10 mL) at rt and heated to reflux temperature for 1 h 30 min. Reaction mixture was monitored by TLC analysis. Reaction mixture was concentrated under reduced pressure and adjusted pH to −2 using 2 N HCl. Ethyl acetate was added to extract the product, organic layer was washed with water, brine solution followed by drying over anhy. Na₂SO₄ and concentrated under reduced pressure. The crude compound (0.9 g) was carried forward for the next step without purification. LCMS: $Rt_{H8}$=1.616 [M+H]⁺=337.8, 339.9 (56%); 1.482 [M+H]⁺=675.1, 676.8 (34%).

j) 5-(5-bromo-2-fluorophenyl)-6,6-difluoro-6-methyl-1,4-oxazepane-3-thione

To a solution of 5-(5-bromo-2-fluorophenyl)-6,6-difluoro-5-methyl-1,4-oxazepan-3-one (2.0 g, 5.93 mmol) in THF (25 mL) was added Lawesson's reagent (2.87 g, 7.1 mmol) at rt and heated to reflux temperature for 16 h. Reaction mixture was concentrated under reduced pressure and directly purified by column chromatography on silica gel using 4% ethyl acetate in Hexane to furnish title compound as colorless gum. Yield=1.0 g (50%). LCMS: $Rt_{H8}$=1.75 [M+H]$^+$=354.8, 355.7, $^1$H NMR (300 MHz, CDCl$_3$) δ 7.86 (s, 1H), 7.59-7.41 (m, 2H), 7.02 (m, 1H), 4.81 (dt, J=3 Hz, 16 Hz), 4.55 (d, 1H), 4.1-3.95 (m, 2H), 1.92 (s, 3H).

k) 5-(5-bromo-2-fluorophenyl)-6,6-difluoro-5-methyl-1,4-oxazepan-3-imine

A mixture of 5-(5-bromo-2-fluorophenyl)-6,6-difluoro-5-methyl-1,4-oxazepane-3-thione (1.0 g, 2.83 mmol) and 10% NH$_3$/MeOH (25 mL) was stirred in a sealed tube at rt for 24 h. Reaction mixture was concentrated and purified by column chromatography on silica gel with 5% MeOH, 2% NH$_3$ in chloroform to furnish the title compound as a pale brown gum. Yield=1.1 g ( ). LCMS: $Rt_{H8}$=0.146 [M+H]$^+$=337.0, 339.0, $^1$H NMR (300 MHz, DMSO-d$_6$) δ 7.87 (dd, 1H, J=2.5 Hz, 6.4 Hz), 7.53-7.45 (m, 1H), 7.09 (dd, 1H, J=5.1 Hz, 9.2 Hz), 6.08 (s, 2H), 4.32-4.11 (m, 3H), 3.97-3.83 (m, 1H), 1.88 (d, 3H).

l) tert-butyl 5-(5-bromo-2-fluorophenyl)-6,6-difluoro-5-methyl-1,4-oxazepan-3-ylidenecarbamate To a solution of 5-(5-bromo-2-fluorophenyl)-6,6-difluoro-5-methyl-1,4-oxazepan-3-imine (1.1 g, 3.2 mmol) in dry THF (15 mL) was added diisopropyl ethyl amine (0.84 mL, 4.8 eq) at 0° C. and stirred for 15 min. di-tertiarybutyl pyrocarbonate (0.98 mL, 4.2 eq) was added to the reaction mixture and stirred 2 h. Reaction mixture was concentrated and the crude product was purified by column chromatography on silica gel with 8% ethyl acetate in Hexane. Yield=950 mg (67%). TLC (20% ethyl acetate in Hexane): Rf=0.75), LCMS: $Rt_{H8}$=1.781 [M+H-Boc]$^+$=337.0, 339.0, $^1$H NMR (300 MHz, CDCl$_3$) δ 10.9 (s, 1H), 7.61-7.39 (m, 2H), 7.03-6.95 (m, 1H), 4.42-4.21 (m, 2H), 4.03-3.81 (m, 2H), 1.93 (s, 3H), 1.51 (s, 9H).

m) tert-butyl 5-(5-azido-2-fluorophenyl)-6,6-difluoro-5-methyl-2,5,6,7-tetrahydro-1,4-oxazepin-3-ylcarbamate To a solution of tert-butyl 5-(5-bromo-2-fluorophenyl)-6,6-difluoro-5-methyl-1,4-oxazepan-3-ylidenecarbamate (1.72 g, 3.94 mmol) and trans-N,N'-dimethylcyclohexane1,2-diamine (0.62 mL, 3.94 mmol), in ethanol (60 mL) was added a solution of NaN$_3$ (2.05 g, 31.5 mmol), (+)-sodium-L-ascorbate (0.312 g, 1.57 mmol) in water (16 mL). The reaction mixture was degassed with argon for 15 min. Cu(1) (0.3 g, 1.57 mmol) was added to the reaction mixture and heated to 70° C. for 5 min.

The reaction mixture was concentrated under reduced pressure, diluted with ethyl acetate, washed with brine and organic layer was dried over anhydrous sodium sulphate and concentrated under reduced pressure. The crude reaction mass was purified by column chromatography on silica gel with 8%-40% ethyl acetate in hexane to furnish title compound along with the corresponding amine. Yield=Amine (0.62 g, 36%); Azide (0.32 g, 22%). TLC (10% ethyl acetate in Hexane for azide): Rf=0.5; (50% ethyl acetate in Hexane for amine; Rf=0.4). The azide (620 mg, 1.5 mmol) was hydrogenated with H$_2$ gas under balloon pressure in the presence of 10% Pd/C (50 mg) in ethyl acetate (10 mL) for 1 h at rt. Catalyst was filtered using a short bed of celite and the filtrate was concentrated under reduced pressure to furnish amine product as color less gum. Yield=575 mg, (99%).

Azide: LCMS: $Rt_{H8}$=1.683 [M+H]$^+$=399.9, $^1$H NMR (400 MHz, CDCl$_3$) δ 10.89 (s, 1H), 7.21-6:95 (m, 3H), 4.41-4.22 (m, 2H), 4.05-3.80 (m, 2H), 1.98 (s, 3H), 1.25 (s, 9H);

Amine: LCMS: $Rt_{H8}$=0.38 [M+H-Boc]$^+$=374.2, 274.2, $^1$H NMR (400 MHz, CDCl$_3$) δ 10.62 (s, 1H), 6.91-6.83 (m, 1H), 6.72-6.6.67 (m, 1H), 6.64-6.59 (m, 1H), 4.41-4.4.15 (m, 2H), 4.03-3.85 (m, 4H), 1.90 (s, 3H), 1.49 (s, 9H).

n) tert-butyl 5-(5-(5-chloropicolinamido)-2-fluorophenyl)-6,6-difluoro-6-methyl-2,5,6,7-tetrahydro-1,4-oxazepin-3-ylcarbamate To a solution of 5-Chloro-pyridine-2-carboxylic acid (0.085 g, 0.54 mmol) in dry DMF (3.0 mL), Et$_3$N (0.22 mL, 1.6 mmol) and EDCI (0.128 mg, 0.81 mmol) and HOAt (0.11 g, 0.81 mmol) and tert-butyl 5-(5-amino-2-fluorophenyl)-6,6-difluoro-5-methyl-2,5,6,7-tetrahydro-1,4-oxazepin-3-yl-carbamate (0.201 g, 0.54 mmol) were added and stirred at rt for 24 h. upon completion of the reaction, reaction mixture was poured into a rapidly stirred ice cold water to obtain precipitate. Yield=220 mg, (80%). TLC (30% ethyl acetate in Hexane): Rf=0.4, LCMS: $Rt_{H8}$=1.78 [M+H-Boc]$^+$=413.0, 414.8, $^1$H NMR (400 MHz, CDCl$_3$) δ 10.89 (s, 1H), 9.91 (s, 1H), 8.6 (s, 1H), 8.22 (d, 1H, J=9.3 Hz), 7.90 (dd, 2H, J=10.2 Hz, 3.1 Hz), 7.69 (d, 1H), 7.11 (t, 1H), 4.44-4.21 (m, 2H), 3.93-4.18 (m, 2H), 1.98 (s, 3H), 1.49 (s, 9H).

o) N-(3-(3-amino-6,6-difluoro-5-methyl-2,5,6,7-tetrahydro-1,4-oxazepin-6-yl)-4-fluorophenyl)-5-chloropicolinamide A solution of tert-butyl 5-(5-(5-chloropicolinamido)-2-fluorophenyl)-6,6-difluoro-5-methyl-2,5,6,7-tetrahydro-1,4-oxazepin-3-ylcarbamate (0.210 g, 0.41 mmol) in 10% dioxane in HCl was heated in a sealed tube at 55° C. for 5 h. Reaction mixture was concentrated under reduced pressure, basified with 2% methanolic ammonia and purified by column chromatography on silica gel with MeOH/DCM (3:97) to obtain the title compound as an off white solid. Yield=0.08 g (50%). TLC (20% methanol in chloroform): Rf=0.35, m.p.=190-193° C., LCMS: $Rt_{H8}$=0.39 [M+H]$^+$=412.8, 415.0, $^1$H NMR (400 MHz, DMSO-d$_6$) δ 8.79 (d, 1H), 8.23-8.12 (m, 2H), 8.07-8.02 (dd, 1H, J=9.6 Hz, 3.4 Hz), 7.85 (dt, 1H, J=8.5 Hz, 2.6 Hz), 7.10 (dd, 1H, J=12.2 Hz, 7.6 Hz), 5.98 (s, 2H), 4.29-4.08 (m, 3H), 3.98-3.85 (m, 1H), 1.76 (s, 3H).

Example 101

The compound listed in Table 15 can be prepared by a procedure analogous to that used in example 100.

TABLE 15

| Example | Compound | ¹H-NMR (δ) | MS [m/z; (M + 1)⁺] |
|---|---|---|---|
| 101 | 5-Bromo-pyridine-2-carboxylic acid [3-(3-amino-6,6-dihydro-5-methyl-2,5,6,7-tetrahydro-[1,4]oxazin-5-yl)-4-fluoro-phenyl]-amide | ¹H NMR (400 MHz, DMSO-$d_6$) δ 10.57 (s, 1H), 8.85 (d, 1H), 8.32 (d, 1H), 8.12-8.01 (m, 2H), 7.90-7.81 (m, 1H), 7.16-7.05 (m, 1H), 6.17 (s, 1H), 4.32-4.05 (m, 3H), 4.01-3.85 (m 1H), 1.76 (s, 3H) | 456, 458 |

Examples 102 to 110

The compounds listed in Table 16 were prepared by a procedure analogous to that used in Example 34

TABLE 16

| Example | Compound | ¹H-NMR (δ; DMSO-$d_6$) | MS [m/z; (M + 1)⁺] |
|---|---|---|---|
| 102 | 4-Bromo-furan-2-carboxylic acid [3-(5-amino-3-difluoromethyl-3,6-dihydro-2H-[1,4]oxazin-3-yl)-phenyl]-amide hydrochloride | 11.09-10.96 (m, 1 H), 10.50 (s, 1 H), 9.65 (d, 1 H), 8.67 (d, 1 H), 8.25 (s, 1 H), 7.91 (s, 1 H), 7.77 (d, 1 H), 7.57 (s, 1 H), 7.52-7.43 (m, 1 H), 7.30 (d, 1 H), 6.71 (t, 1 H, CHF2), 4.73-4.57 (m, 2 H), 4.37 (d, 1 H), 4.04 (d, 1 H) | 414, 416 |
| 103 | 6-Hydroxy-pyridazine-3-carboxylic acid [3-(5-amino-3-difluoromethyl-3,6-dihydro-2H-[1,4]oxazin-3-yl)-phenyl]-amide hydrochloride | 10.15 (s, 1 H), 7.90 (s, 1 H), 7.83 (s, 1 H), 7.49 (d, 1 H), 7.31-7.16 (m, 2 H), 6.06-5.76 (m, 5 H), 4.08 (d, 1 H), 4.04-3.96 (m, 1 H), 3.95-3.87 (m, 1 H), 3.71 (d, 1 H) | 364 |
| 104 | 2-Methyl-oxazole-4-carboxylic acid [3-(5-amino-3-difluoromethyl-3,6-dihydro-2H-[1,4]oxazin-3-yl)-phenyl]-amide hydrochloride | 11.09 (s, 1 H), 10.24 (s, 1 H), 9.71 (s, 1 H), 8.83 (s, 1 H), 8.67 (s, 1 H), 7.96 (s, 1 H), 7.90 (d, 1 H), 7.46 (t, 1 H), 7.30 (d, 1 H), 6.69 (t, 1 H, CHF2), 4.72-4.55 (m, 2 H), 4.38 (d, 1 H), 4.03 (d, 1 H), 2.52 (s, 3 H) | 351 |

TABLE 16-continued

| Example | Compound | ¹H-NMR (δ; DMSO-d₆) | MS [m/z; (M + 1)⁺] |
|---|---|---|---|
| 105 | 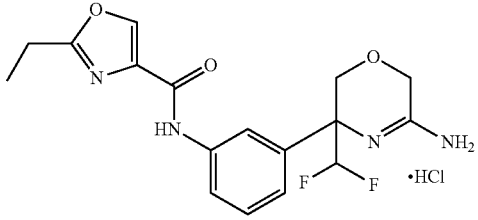<br>2-Ethyl-oxazole-4-carboxylic acid [3-(5-amino-3-difluoromethyl-3,6-dihydro-2H-[1,4]oxazin-3-yl)-phenyl]-amide hydrochloride | 11.06 (s, 1 H), 10.18 (s, 1 H), 9.68 (s, 1 H), 8.77 (s, 1 H), 8.69 (s, 1 H), 8.00-7.83 (m, 2 H), 7.46 (t, 1 H), 7.30 (d, 1 H), 6.70 (t, 1 H, CHF2), 4.73-4.56 (m, 2 H), 4.38 (d, 1 H), 4.03 (d, 1 H), 2.86 (q, 2 H), 1.30 (t, 3 H) | 365 |
| 106 | 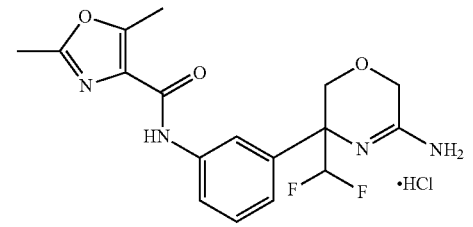 [SMILES: Cc1nc(C(=O)Nc2cccc(C3(C(F)F)COCC(N)=N3)c2)c(C)o1 ; Cl]<br>2,5-Dimethyl-oxazole-4-carboxylic acid [3-(5-amino-3-difluoromethyl-3,6-dihydro-2H-[1,4]oxazin-3-yl)-phenyl]-amide hydrochloride | 11.05 (s, 1 H), 10.04 (s, 1 H), 9.69 (s, 1 H), 8.79 (s, 1 H), 7.95 (s, 1 H), 7.90 (d, 1 H), 7.44 (t, 1 H), 7.28 (d, 1 H), 6.69 (t, 1 H, CHF2), 4.72-4.57 (m, 2 H), 4.38 (d, 1 H), 4.02 (d, 1 H), 2.59 (s, 3 H), 2.46 (s, 3 H) | 365 |
| 107 | 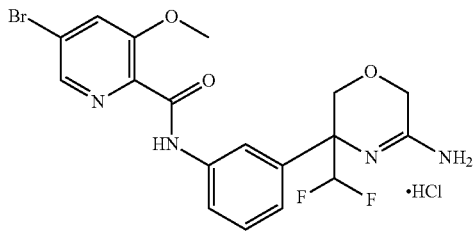 [SMILES: NC1=NC(c2cccc(NC(=O)c3ncc(Br)cc3O)c2)(C(F)F)COC1 ; Cl]<br>5-Bromo-3-methoxy-pyridine-2-carboxylic acid [3-(5-amino-3-difluoromethyl-3,6-dihydro-2H-[1,4]oxazin-3-yl)-phenyl]-amide hydrochloride | 11.11 (s, 1 H), 10.61 (s, 1 H), 9.72 (s, 1 H), 8.84 (s, 1 H), 8.39-8.27 (m, 1 H), 7.98 (s, 1 H), 7.90 (s, 1 H), 7.77 (d, 1 H), 7.47 (t, 1 H), 7.31 (d, 1 H), 6.71 (t, 1 H, CHF2), 4.72-4.55 (m, 2 H), 4.38 (d, 1 H), 4.04 (d, 1 H), 3.89 (s, 3 H) | 455, 457 |
| 108 | 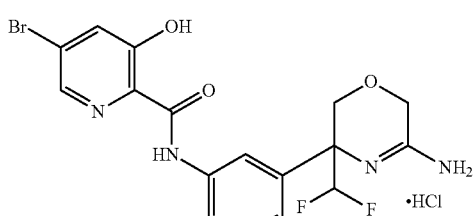<br>5-Bromo-3-hydroxy-pyridine-2-carboxylic acid [3-(5-amino-3-difluoromethyl-3,6-dihydro-2H-[1,4]oxazin-3-yl)-phenyl]-amide hydrochloride | 12.20 (br. s., 1 H), 11.13 (s, 1 H), 11.02 (s, 1 H), 9.72 (s, 1 H), 8.85 (s, 1 H), 8.37 (s, 1 H), 8.00-7.84 (m, 3 H), 7.53 (t, 1 H), 7.39 (d, 1 H), 6.71 (t, 1 H, CHF2), 4.74-4.54 (m, 2 H), 4.40 (d, 1 H), 4.06 (d, 1 H) | 441, 443 |

TABLE 16-continued

| Example | Compound | $^1$H-NMR (δ; DMSO-$d_6$) | MS [m/z; (M + 1)$^+$] |
|---|---|---|---|
| 109 | 5-(2-Methoxy-ethoxy)-pyridine-2-carboxylic acid [3-(5-amino-3-difluoromethyl-3,6-dihydro-2H-[1,4]oxazin-3-yl)-phenyl]-amide hydrochloride | 10.40 (s, 1 H), 8.87 (s, 1 H), 8.44 (s, 1 H), 8.00 (br. s., 1 H), 7.81 (br. s., 1 H), 7.32 (d, 2 H), 6.06-5.88 (m, 3 H), 4.53 (dd, 2 H), 4.08-3.97 (m, 2 H), 3.97-3.84 (m, 1 H), 3.65-3.80 (m, 3 H), 3.31 (s, 3 H) | 422 |
| 110 | 5-Difluoromethyl-pyrazine-2-carboxylic acid [3-(5-amino-3-difluoromethyl-3,6-dihydro-2H-[1,4]oxazin-3-yl)-phenyl]-amide hydrochloride | 11.07 (s, 1 H), 11.01 (s, 1 H), 9.68 (s, 1 H), 9.41 (s, 1 H), 9.11 (s, 1 H), 8.74 (br. s., 1 H), 8.08 (br. s., 1 H), 7.99 (d, 1 H), 7.53 (t, 1 H), 7.36 (s, 1 H), 7.27 (t, 1 H, CHF2), 6.72 (t, 1 H, CHF2), 4.73-4.55 (m, 2 H), 4.39 (d, 1 H), 4.06 (d, 1 H) | 398 |

Examples 111 to 151

The compounds listed in Table 17 were prepared by procedures analogous to those used in Examples 42 or 112.

For enantiomerically pure compounds the racemic precursor [5-(5-amino-2-fluoro-phenyl)-5-difluoromethyl-5,6-dihydro-2H-[1,4]oxazin-3-yl]-carbamic acid tert-butyl ester (example 42j)) was separated via prep-HPLC on Chiralpak AD-H 250×4.6 mm column using supercritical CO2/EtOH 9:1 as an eluent. The desired compound was the slower eluting (R)-enantiomer. Enantiomeric excess=99.7%; [α]$_D$=−109.7° (c=1, CHCl$_3$).

TABLE 17

| Example | Compound | $^1$H-NMR (δ; DMSO-$d_6$) | MS [m/z; (M + 1)$^+$] |
|---|---|---|---|
| 111 | 3,5-Dichloro-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.06 (s, 1H), 10.99 (s, 1H), 9.76 (s, 1H), 8.75 (s, 1H), 8.73 (s 1H), 8.48 (d, 1H), 7.93-7.86 (m, 2H), 7.41 (t, 1H), 6.79 (t, J = 54 Hz, 1H), 4.71 (d, 1H), 4.65 (d, 1H), 4.34 (d, 1H), 4.18 (d, 1H) | 433 |

TABLE 17-continued

| Example | Compound | $^1$H-NMR (δ; DMSO-$d_6$) | MS [m/z; $(M + 1)^+$] |
|---|---|---|---|
| 112 | 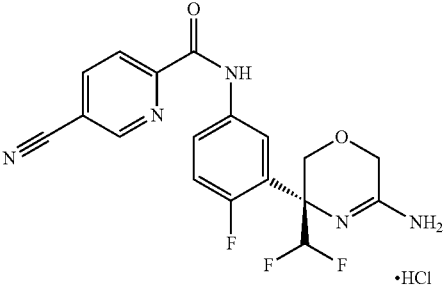 [SMILES: N#Cc1ccc(C(=O)Nc2ccc(F)c([C@]3(C(F)F)COCC(N)=N3)c2)nc1 ; Cl]<br>5-Cyano-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.09 (s, 1H), 11.01 (s, 1H) 9.76 (s, 1H), 9.22 (s, 1H), 8.75 (s, 1H), 8.61 (d, 1H), 8.30 (d, 1H), 8.12-8.06 (m, 2H), 7.41 (dd, 1H), 6.79 (t, J = 54 Hz, 1H), 4.71 (d, 1H), 4.65 (d, 1H), 4.34 (d, 1H), 4.18 (d, 1H) | 390 |
| 113 | 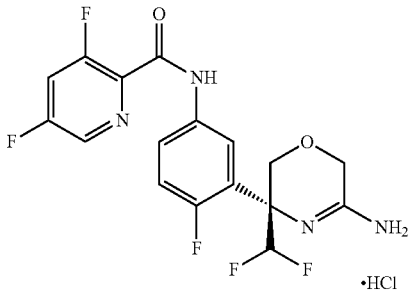 [SMILES: NC1=N[C@@](c2cc(NC(=O)c3ncc(F)cc3F)ccc2F)(C(F)F)COC1 ; Cl]<br>3,5-Difluoro-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.00 (s, 1H), 10.85 (s, 1H) 9.74 (s, 1H), 8.72-8.67 (m, 2H), 8.23-8.18 (m, 1H), 8.04-8.00 (m, 1H), 7.96-7.92 (m, 1H), 7.40 (dd, 1H), 6.79 (t, J = 54 Hz, 1H), 4.71 (d, 1H), 4.65 (d, 1H), 4.34 (d, 1H), 4.18 (d, 1H) | 401 |
| 114 | 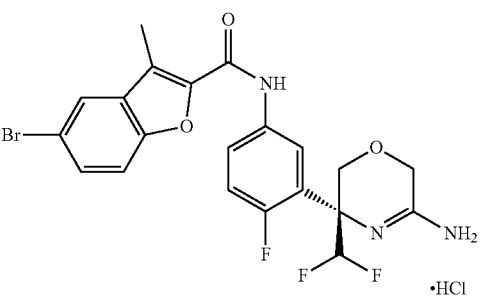 [SMILES: Cc1c(C(=O)Nc2ccc(F)c([C@]3(C(F)F)COCC(N)=N3)c2)oc2ccc(Br)cc12 ; Cl]<br>5-Bromo-3-methyl-benzofuran-2-carboxylic acid [3-((R)-5-amino-3-difluoromethyl-3,6-dihydro-2H-[1,4]oxazin-3-yl)-4-fluoro-phenyl]-amide hydrochloride | 11.01 (s, 1H), 10.74 (s, 1H), 9.76 (s, 1H), 8.74 (s, 1H), 8.08 (s, 1H), 8.03-7.99 (m, 1H), 7.98-7.93 (m, 1H), 7.69-7.64 (m, 2H), 7.39 (dd, 1H), 6.79 (t, J = 54 Hz, 1H), 4.71 (d, 1H), 4.65 (d, 1H), 4.34 (d, 1H), 4.18 (d, 1H), 2.57 (s, 3H) | 496, 498 |

TABLE 17-continued

| Example | Compound | $^1$H-NMR (δ; DMSO-$d_6$) | MS [m/z; (M + 1)$^+$] |
|---|---|---|---|
| 115 | 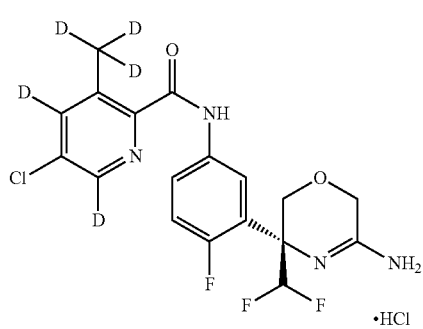 [SMILES: [2H]c1nc(C(=O)Nc2ccc(F)c([C@]3(C(F)F)COCC(N)=N3)c2)c(C([2H])([2H])[2H])c([2H])c1Cl ; Cl]<br>5-Chloro-4,6-dideutero-3-trideuteromethyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.02 (s, 1H), 10.79 (s, 1H) 9.77 (s, 1H), 8.76 (s, 1H), 8.01-7.94 (m, 2H), 7.38 (dd, 1H), 6.78 (t, J = 54 Hz, 1H), 4.71 (d, 1H), 4.65 (d, 1H), 4.34 (d, 1H), 4.18 (d, 1H) | 418 |
| 116 | 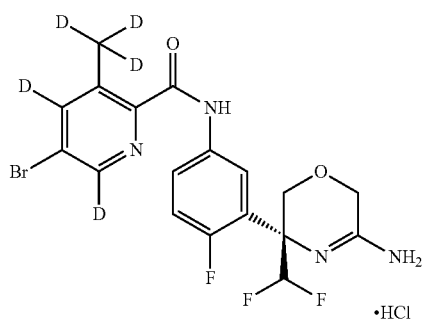 [SMILES: [2H]c1nc(C(=O)Nc2ccc(F)c([C@]3(C(F)F)COCC(N)=N3)c2)c(C([2H])([2H])[2H])c([2H])c1Br ; Cl]<br>5-Bromo-4,6-dideutero-3-trideuteromethyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.00 (s, 1H), 10.79 (s, 1H) 9.76 (s, 1H), 8.73 (s, 1H), 8.01-7.94 (m, 2H), 7.38 (dd, 1H), 6.78 (t, J = 54 Hz, 1H), 4.71 (d, 1H), 4.65 (d, 1H), 4.34 (d, 1H), 4.18 (d, 1H) | 462, 464 |
| 117 | 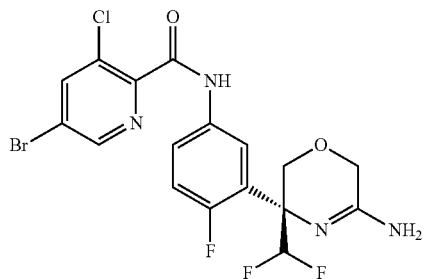<br>5-Bromo-3-chloro-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.08 (s, 1H), 10.99 (s, 1H), 9.78 (s, 1H), 8.81 (s, 1H), 8.77 (s, 1H), 8.58 (s, 1H), 7.92-7.85 (m, 2H), 7.40 (dd, 1H), 6.79 (t, J = 54 Hz, 1H), 4.71 (d, 1H), 4.65 (d, 1H), 4.34 (d, 1H), 4.18 (d, 1H) | 478 |

TABLE 17-continued

| Example | Compound | ¹H-NMR (δ; DMSO-d₆) | MS [m/z; (M + 1)⁺] |
|---|---|---|---|
| 118 | 5-Bromo-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.08 (s, 1H), 10.99 (s, 1H), 9.78 (s, 1H), 8.81 (s, 1H), 8.77 (s, 1H), 8.35 (d, 1H), 8.12-8.05 (m, 3H), 7.39 (t, 1H), 6.78 (t, J = 54 Hz, 1H), 4.72 (d, 1H), 4.64 (d, 1H), 4.33 (d, 1H), 4.18 (d, 1H) | 443, 445 |
| 119 | 5-Bromo-3-hydroxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 12.17 (s, 1H), 11.16 (s, 1H), 11.02 (s,1H), 9.78 (s, 1H), 8.78 (s, 1H), 8.37 (s, 1H), 8.03-7.96 (m, 2H), 7.90 (s, 1H), 7.42 (t, 1H), 6.78 (t, J = 54 Hz, 1H), 4.72 (d, 1H), 4.64 (d, 1H), 4.33 (d, 1H), 4.18 (d, 1H) | 459, 461 |
| 120 | 5-Ethoxy-pyridine-2-carboxylic acid [3-((R)-5-amino-3-difluoromethyl-3,6-dihydro-2H-[1,4]oxazin-3-yl)-4-fluoro-phenyl]-amide | 10.42 (s, 1H), 8.37 (s, 1H), 8.13-8.08 (m, 2H), 7.86-7.80 (m, 1H), 7.59 (d, 1H), 7.16 (t, 1H), 6.16 (s, 2H), 6.14 (t, J = 54 Hz, 1H), 4.21 (q, 2H), 4.12 (d, 1H), 4.01 (d, 1H), 3.90 (d, 1H), 3.82 (d, 1H), 1.38 (t, 3H) | 409 |
| 121 | 5-Bromo-pyrimidine-2-carboxylic acid [3-((R)-5-amino-3-difluoromethyl-3,6-dihydro-2H-[1,4]oxazin-3-yl)-4-fluoro-phenyl]-amide hydrochloride | 11.17-11.00 (m, 2 H), 9.79 (br. s., 1 H), 9.24 (s, 2 H), 8.80 (br. s., 1 H), 8.15-7.98 (m, 2 H), 7.40 (dd, 1 H), 6.79 (t, 1 H, CHF2), 4.82-4.68 (m, 1 H), 4.68-4.55 (m, 1 H), 4.33 (d, 1 H), 4.18 (d, 1 H) | 488, 490 |

TABLE 17-continued

| Example | Compound | ¹H-NMR (δ; DMSO-d₆) | MS [m/z; (M + 1)⁺] |
|---|---|---|---|
| 122 | 5-Difluoromethyl-pyrazine-2-carboxylic acid [3-((R)-5-amino-3-difluoromethyl-3,6-dihydro-2H-[1,4]oxazin-3-yl)-4-fluoro-phenyl]-amide hydrochloride | 11.15 (s, 1 H), 11.06 (s, 1 H), 9.80 (s, 1 H), 9.41 (s, 1 H), 9.11 (s, 1 H), 8.81 (br. s., 1 H), 8.19-8.01 (m, 2 H), 7.42 (dd, 1 H), 7.32-7.21 (m, 1 H), 7.21-7.09 (m, 1 H), 6.79 (t, 1 H, CHF2), 4.78-4.69 (m, 1 H), 4.69-4.58 (m, 1 H), 4.33 (d, 1 H), 4.19 (d, 1 H) | 416 |
| 123 | 5-(2,2-Difluoro-ethoxy)-pyrazine-2-carboxylic acid [3-((R)-5-amino-3-difluoromethyl-3,6-dihydro-2H-[1,4]oxazin-3-yl)-4-fluoro-phenyl]-amide hydrochloride | 11.05 (s, 1 H), 10.82 (s, 1 H), 9.82 (br. s., 1 H), 8.92 (s, 1 H), 8.85 (br. s., 1 H), 8.56 (s, 1 H), 8.14-7.99 (m, 2 H), 7.39 (dd, 1 H), 7.24 (t, 1 H), 7.19-7.10 (m, 1 H), 6.78 (t, 1 H, CHF2), 6.57-6.38 (m, 1 H), 4.81-4.68 (m, 3 H), 4.68-4.58 (m, 1 H), 4.33 (d, 1 H), 4.18 (d, 1 H) | 446 |
| 124 | 5-(2,2,2-Trifluoro-ethoxy)-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.97 (s, 1 H), 10.86 (s, 1 H), 9.72 (br. s., 1 H), 8.94 (s, 1 H), 8.68 (br. s., 1 H), 8.64 (s, 1 H), 8.15-8.07 (m, 1 H), 8.04 (d, 1 H), 7.39 (dd, 1 H), 6.79 (t, 1 H, CHF2), 5.17 (q, 2 H), 4.76-4.68 (m, 1 H), 4.68-4.59 (m, 1 H), 4.33 (d, 1 H), 4.18 (d, 1 H) | 464 |
| 125 | 4-Bromo-furan-2-carboxylic acid [3-((R)-5-amino-3-difluoromethyl-3,6-dihydro-2H-[1,4]oxazin-3-yl)-4-fluoro-phenyl]-amide hydrochloride | 11.04 (s, 1 H), 10.64 (s, 1 H), 9.78 (s, 1 H), 8.79 (s, 1 H), 8.25 (s, 1 H), 7.95 (dd, 1 H), 7.86 (dd, 1 H), 7.60 (s, 1 H), 7.37 (dd, 1 H), 6.77 (t, 1 H, CHF2), 4.76-4.68 (m, 1 H), 4.68-4.59 (m, 1 H), 4.32 (d, 1 H), 4.17 (d, 1 H) | 432, 434 |

| Example | Compound | $^1$H-NMR (δ; DMSO-d$_6$) | MS [m/z; (M + 1)$^+$] |
|---|---|---|---|
| 126 | Pyrazolo[1,5-a]pyridine-2-carboxylic [3-((R)-5-amino-3 difluoromethyl-3,6-dihydro-2H [1,4]oxazin-3-yl)-4-fluoro-phenyl]-amide hydrochloride | 11.00 (s, 1 H), 10.65 (s, 1 H), 9.77 (s, 1 H), 8.78 (s, 1 H), 8.73 (d, 1 H), 8.07 (d, 1 H), 7.99 (d, 1 H), 7.82 (d, 1 H), 7.33 (m, 2 H), 7.13 (s, 1 H), 7.08 (t, 1 H), 6.77 (t, 1H, CHF2), 4.71 (d, 1H), 4.64 (d, 1H), 4.32 (d, 1H), 4.17(d, 1H) | 404 |
| 127 | 2-Methyl-oxazole-4-carboxylic acid [3-((R)-5-amino-3-difluoromethyl-3,6-dihydro-2H-[1,4]oxazin-3-yl)-4-fluoro-phenyl]-amide hydrochloride | 11.01 (s, 1 H), 10.41 (s, 1 H), 9.77 (s, 1 H), 8.77 (s, 1 H), 8.68 (s, 1 H), 8.08-7.99 (m, 1 H), 7.99-7.89 (m, 1 H), 7.35 (dd, 1 H), 6.77 (t, 1 H, CHF2), 4.76-4.67 (m, 1 H), 4.67-4.57 (m, 1 H), 4.31 (d, 1 H), 4.16 (d, 1 H), 2.52 (s, 3 H) | 369 |
| 128 | 2,5-Dimethyl-oxazole-4-carboxylic acid [3-((R)-5-amino-3-difluoromethyl-3,6-dihydro-2H-[1,4]oxazin-3-yl)-4-fluoro-phenyl]-amide | 10.97 (s, 1 H), 10.22 (s, 1 H), 9.76 (s, 1 H), 8.75 (br. s., 1 H), 8.05-7.90 (m, 2 H), 7.33 (dd, 1 H), 6.76 (t, 1 H, CHF2), 4.77-4.67 (m, 1 H), 4.67-4.58 (m, 1 H), 4.32 (d, 1 H), 4.15 (d, 1 H), 2.58 (s, 3 H), 2.46 (s, 3 H) | 383 |
| 129 | Imidazo[1,2-a]pyridine-2-carboxylic acid [3-((R)-5-amino-3-difluoromethyl-3,6-dihydro-2H-[1,4]oxazin-3-yl)-4-fluoro-phenyl]-amide hydrochloride | 1.07 (s, 1 H), 10.80 (s, 1 H), 9.85 (s, 1 H), 8.90 (s, 1 H), 8.49 (d, 1 H), 8.39 (d, 1 H), 7.87 (m, 2 H), 7.63 (d, 1 H), 7.41 (m, 1 H), 7.14 (dd, 1 H), 6.99 (t, 1 H), 6.25 (t, 1H, CHF2), 4.14 (m, 3 H), 3.96 (d, 1H) | 404 |

TABLE 17-continued

| Example | Compound | $^1$H-NMR ($\delta$; DMSO-$d_6$) | MS [m/z; (M + 1)$^+$] |
|---|---|---|---|
| 130 | 5-Bromo-3-methoxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.04 (s, 1 H), 10.71 (s, 1 H), 9.76 (s, 1 H), 8.75 (s, 1 H), 8.36 (s, 1 H), 7.99 (s, 1 H), 7.94 (d, 1 H), 7.86-7.84 (m, 1 H), 7.37 (dd, 1 H), 6.78 (t, 1 H, CHF2), 4.68 (q, 2 H), 4.33 (d, 1 H), 4.17 (d, 1 H), 3.89 (s, 3 H) | 473, 475 |
| 131 | 2-Ethyl-oxazole-4-carboxylic acid [3-((R)-5-amino-3-difluoromethyl-3,6-dihydro-2H-[1,4]oxazin-3-yl)-4-fluoro-phenyl]-amide hydrochloride | 11.01 (s, 1 H), 10.35 (s, 1 H), 9.77 (s, 1 H), 8.83-8.73 (m, 1 H), 8.70 (s, 1 H), 8.06-7.90 (m, 2 H), 7.35 (dd, 1 H), 6.77 (t, 1 H, CHF2), 4.76-4.67 (m, 1 H), 4.67-4.57 (m, 1 H), 4.32 (d, 1 H), 4.17 (d, 1 H), 2.86 (q, 2 H), 1.30 (t, 3 H) | 383 |
| 132 | 5-Difluoromethyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.03 (s, 1H), 10.97 (s, 1H), 9.71 (s, 1H), 8.95 (s, 1H), 8.66 (br. s., 1H), 8.31-8.27 (m, 2H), 8.14-8.07 (m, 2H), 7.45-7.38 (m, 1H), 7.28 (t, 1H), 6.79 (t, 1H), 4.71 (d, 1H), 4.63 (d, 1H), 4.33 (d, 1H), 4.18 (d, 1H) | 415 |
| 133 | 1-Methyl-1H-imidazole-2 carboxylic acid [3-((R)-5-amino-3 difluoromethyl-3,6-dihydro-2H [1,4]oxazin-3-yl)-4-fluoro-phenyl]-amide hydrochloride | 11.04 (s, 1 H), 10.77 (s, 1 H), 9.82 (s, 1 H), 8.88 (s, 1 H), 7.97 (d, 1 H), 7.54 (d, 1 H), 7.35 (t, 1 H), 7.23 (s, 1 H), 6.75 (t, 1H, CHF$_2$), 4.70 (d, 1H), 4.62 (d, 1H), 4.31 (d, 1H), 4.16 (d, 1H) | 368 |

TABLE 17-continued

| Example | Compound | ¹H-NMR (δ; DMSO-d₆) | MS [m/z; (M + 1)⁺] |
|---|---|---|---|
| 134 | 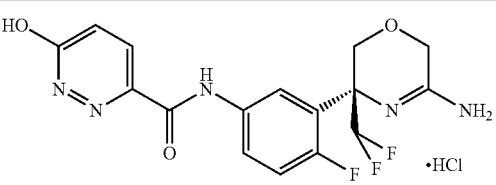<br>6-Hydroxy-pyridazine-3-carboxylic acid [3-((R)-5-amino-3-difluoromethyl-3,6-dihydro-2H-[1,4]oxazin-3-yl)-4-fluoro-phenyl]-amide hydrochloride | 13.61 (s, 1 H), 11.04 (s, 1 H), 10.57 (s, 1 H), 9.80 (s, 1 H), 8.88-8.74 (m, 1 H), 8.01-7.83 (m, 3 H), 7.37 (dd, 1 H), 7.03 (dd, 1 H), 6.77 (t, 1 H, CHF2), 4.79-4.67 (m, 1 H), 4.67-4.58 (m, 1 H), 4.32 (d, 1 H), 4.17 (d, 1 H) | 382 |
| 135 | 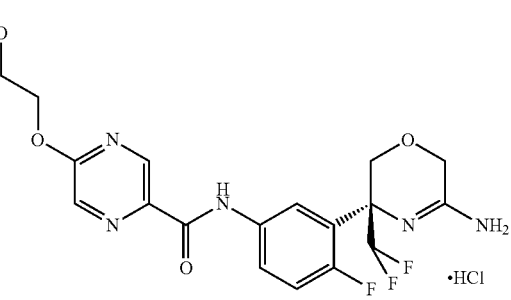<br>5-(2-Methoxy-ethoxy)-pyrazine-2-carboxylic acid [3-((R)-5-amino-3-difluoromethyl-3,6-dihydro-2H-[1,4]oxazin-3-yl)-4-fluoro-phenyl]-amide hydrochloride | 11.01 (s, 1 H), 10.77 (s, 1 H), 9.77 (br. s., 1 H), 8.92 (d, 1 H), 8.77 (br. s., 1 H), 8.48 (d, 1 H), 8.17-7.98 (m, 2 H), 7.40 (dd, 1 H), 6.80 (t, 1 H, CHF2), 4.83-4.60 (m, 2 H), 4.60-4.51 (m, 2 H), 4.36 (d, 1 H), 4.20 (d, 1 H), 3.75 (dd, 2 H), 3.34 (s, 3 H) | 440 |
| 136 | 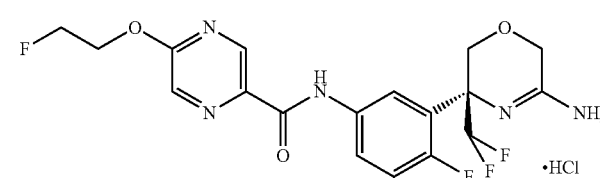<br>5-(2-Fluoro-ethoxy)-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.52 (br. s., 1 H), 8.87 (s, 1 H), 8.48 (s, 1 H), 8.13 (d, 1 H), 7.80 (br. s., 1 H), 7.17 (br. s., 1 H), 6.23-6.05 (m, 2 H), 4.92-4.82 (m, 1 H), 4.82-4.73 (m, 1 H), 4.73-4.67 (m, 1 H), 4.67-4.57 (m, 1 H), 4.11 (d, 1 H), 4.06-3.96 (m, 1 H), 3.91 (d, 1 H), 3.84 (d, 1 H) | 428 |
| 137 | 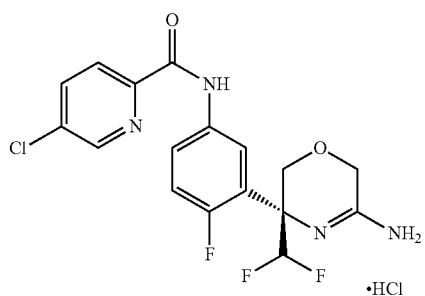 [SMILES: NC1=N[C@@](c2cc(NC(=O)c3ccc(Cl)cn3)ccc2F)(C(F)F)COC1 ; Cl]<br>5-Chloro-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.01 (s, 1H), 10.93 (s, 1H), 9.77 (s, 1H), 8.80 (s, 1H), 8.75 (s, 1H), 8.22 (d, 1H), 8.16 (d, 1H), 8.11-8.04 (m, 2H), 7.38 (t, 1H), 6.78 (t, J = 54 Hz, 1H), 4.72 (d, 1H), 4.64 (d, 1H), 4.33 (d, 1H), 4.18 (d, 1H) | 399 |

TABLE 17-continued

| Example | Compound | ¹H-NMR (δ; DMSO-d₆) | MS [m/z; (M + 1)⁺] |
|---|---|---|---|
| 138 | 5-Difluoromethoxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.02 (br. s., 1H), 10.89 (s, 1H), 9.78 (br. s., 1H), 8.77 (br. s., 1 H), 8.63 (d, 1H), 8.24 (d, 1H), 8.05-8.12 (m, 2H), 7.93 (dd, 1H), 7.52 (t, 1H), 7.39 (dd, 1H), 6.79 (t, 1H), 4.72 (d, 1H), 4.64 (d, 1H), 4.34 (d, 1H), 4.18 (d, 1H) | 431 |
| 139 | 5-Fluoromethoxy-pyridine-2-carboxylic acid [3-((R)-5-amino-3-difluoromethyl-3,6-dihydro-2H-[1,4]oxazin-3-yl)-4-fluoro-phenyl]-amide | 11.02 (s, 1H), 10.82 (s, 1H), 9.78 (br. s., 1H), 8.78 (br. s., 1H), 8.55 (d, 1H), 8.20 (d, 1H), 8.12-8.05 (m, 2H), 7.83 (dd, 1H), 7.38 (dd, 1H), 6.79 (t, 1H), 6.06 (d, 2H), 4.72 (d, 1H), 4.64 (d, 1H), 4.34 (d, 1H), 4.18 (d, 1H) | 413 |
| 140 | 5-Chloro-3-fluoro-pyridine-2-carboxylic acid [3-((R)-5-amino-3-difluoromethyl-3,6-dihydro-2H-[1,4]oxazin-3-yl)-4-fluoro-phenyl]-amide | 10.96 (br. s., 1H), 10.91 (s, 1H), 9.67 (br. s., 1H), 8.68 (s, 1H), 8.59 (br. s., 1H), 8.37 (dd, 1H), 8.02 (dd, 1H), 7.97-7.90 (m, 1H), 7.40 (dd, 1H), 6.79 (t, 1H), 4.71 (d, 1H), 4.64 (d, 1H), 4.33 (d, 1H), 4.18 (d, 1H) | 417 |
| 141 | 5-Chloro-pyrazine-2-carboxylic acid [3-((R)-5-amino-3-difluoromethyl-3,6-dihydro-2H-[1,4]oxazin-3-yl)-4-fluoro-phenyl]-amide | 11.03 (s, 1H), 10.99 (s, 1H), 9.65 (br. s., 1H), 9.13 (s, 1H), 8.95 (s, 1H), 8.71 (br. s., 1H), 8.09 (dd, 1H), 8.06-7.96 (m, 1H), 7.40 (dd, 1H), 6.78 (t, 1H), 4.70 (d, 1H), 4.63 (d, 1H), 4.32 (d, 1H), 4.18 (d, 1H) | 400 |

TABLE 17-continued

| Example | Compound | ¹H-NMR (δ; DMSO-d₆) | MS [m/z; (M + 1)⁺] |
|---|---|---|---|
| 142 | 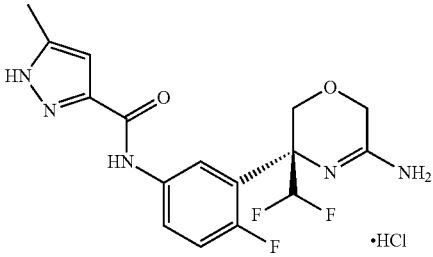 [SMILES: Cc1cc(C(=O)Nc2ccc(F)c([C@]3(C(F)F)COCC(N)=N3)c2)n[nH]1 ; Cl]<br>5-Methyl-1H-pyrazole-3-carboxylic acid [3-((R)-5-amino-3-difluoromethyl-3,6-dihydro-2H-[1,4]oxazin-3-yl)-4-fluoro-phenyl]-amide hydrochloride | 11.02 (br. s., 1 H), 10.25 (s, 1 H), 9.81 (br. s., 1 H), 8.83 (br. s., 1 H), 8.04 (d, 1 H), 7.95 (d, 1 H), 7.33 (dd, 1 H), 6.76 (t, 1 H, CHF2), 6.54 (s, 1 H), 4.76-4.67 (m, 1 H), 4.67-4.58 (m, 1 H), 4.33 (d, 1 H), 4.15 (d, 1 H), 2.29 (s, 3 H) | 368 |
| 143 | 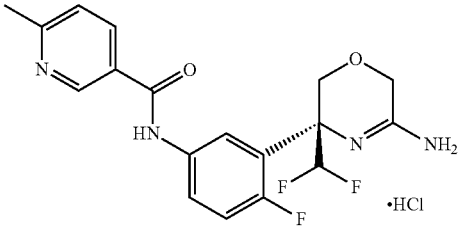 [SMILES: Cc1ccc(C(=O)Nc2ccc(F)c([C@]3(C(F)F)COCC(N)=N3)c2)cn1 ; Cl]<br>5-Methyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.07 (s, 1 H), 10.84 (s, 1 H), 9.86 (s, 1H), 8.91 (br. s., 1 H), 8.59 (s, 1 H), 8.16-8.02 (m, 3 H), 7.89 (d, 1 H), 7.37 (dd, 1 H), 6.78 (t, 1 H, CHF2), 4.78-4.68 (m, 1 H), 4.68-4.57 (m, 1 H), 4.34 (d, 1 H), 4.17 (d, 1 H), 2.43 (s, 3 H) | 379 |
| 144 | 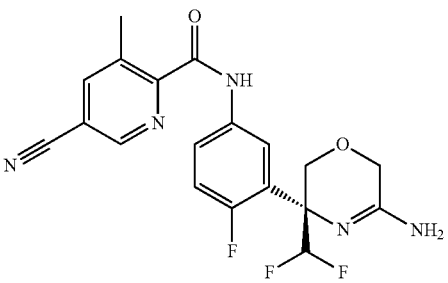 [SMILES: Cc1cc(C#N)cnc1C(=O)Nc1ccc(F)c([C@]2(C(F)F)COCC(N)=N2)c1]<br>5-Cyano-3-methyl-pyridine-2-carboxylic acid [3-((R)-5-amino-3-difluoromethyl-3,6-dihydro-2H-[1,4]oxazin-3-yl)-4-fluoro-phenyl]-amide | 10.72 (s, 1H), 8.97 (s, 1H) 8.39 (s, 1H), 8.02-7.97 (m, 1H), 7.83-7.78 (m, 1H), 7.18 (dd, 1H), 6.14 (s, 2H), 6.14 (t, J = 54 Hz, 1H), 4.10 (d, 1H), 4.01 (d, 1H), 3.91 (d, 1H), 3.84 (d, 1H), 2.54 (s, 3H) | 404 |
| 145 | 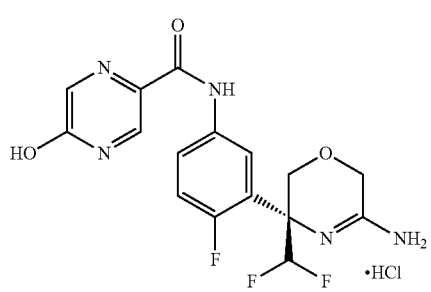 [SMILES: NC1=N[C@@](c2cc(NC(=O)c3cnc(O)cn3)ccc2F)(C(F)F)COC1 ; Cl]<br>5-Hydroxy-pyrazine-2-carboxylic acid [3-((R)-5-amino-3-difluoromethyl-3,6-dihydro-2H-[1,4]oxazin-3-yl)-4-fluoro-phenyl]-amide hydrochloride | 11.01 (s, 1H), 10.42 (s, 1H), 9.31 (s, 1H) 8.82 (s, 1H), 9.2-7.9 (m, 4H), 7.36 (dd, 1H), 6.29 (t, J = 54 Hz, 1H), 4.68 (m, 2H), 4.36 (d, 1H), 4.18 (d, 1H) | 382 |

TABLE 17-continued

| Example | Compound | $^1$H-NMR (δ; DMSO-d$_6$) | MS [m/z; (M + 1)$^+$] |
|---|---|---|---|
| 146 | 5-Methoxy-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.77 (s, 1H), 9.65 (s, 1H), 8.85 (s, 1H), 8.78 (s, 1H), 8.40 (s, 1H), 8.11 (d, 1H), 8.03 (m, 1H), 7.37 (dd, 1H), 6.77 (t, 1H), 4.71 (m, 2H), 4.32 (d, 1H), 4.22 (d, 1H) | 396 |
| 147 | 5-Cyano-4,6-dideutero-3-trideuteromethyl-pyridine-2-carboxylic acid [3-((R)-5-amino-3-difluoromethyl-3,6-dihydro-2H-[1,4]oxazin-3-yl)-4-fluoro-phenyl]-amide | 10.72 (s, 1H), 8.02-7.97 (m, 1H), 7.83-778 (m, 1H), 7.18 (t, 1H), 6.14 (t, J = 54 Hz, 1H), 6.14 (s, 2H), 4.10 (d, 1H), 4.01 (d, 1H), 3.91 (d, 1H), 3.83 (d, 1H) | 409 |
| 148 | 2-Methyl-thiazole-4-carboxylic acid [3-((R)-5-amino-3-difluoromethyl-3,6-dihydro-2H-[1,4]oxazin-3-yl)-4-fluoro-phenyl]-amide hydrochloride | 11.1 (s, 1H), 10.45 (s, 1H), 9.91 (s, 1H), 9.02 (s, 1H), 8.32 (s, 1H), 8.04-8.0 (m, 2H), 7.35 (t, 1H), 6.77 (t, 1H, CHF$_2$), 4.72 (d, 1H, AB-system), 4.65 (d, 1H, AB-system), 4.32 (d, 1H, AB-system), 4.18 (d, 1H, AB-system)), 2.77 (s, 3H) | 385 |
| 149 | 5-Methyl-thiazole-2-carboxylic acid [3-((R)-5-amino-3-difluoromethyl-3,6-dihydro-2H-[1,4]oxazin-3-yl)-4-fluoro- | 11.1 (s, 1H), 10.92 (s, 1H), 9.88 (s, 1H), 8.95 (s, 1H), 8.08-8.04 (m, 1H), 8.0-7.98 (m, 1H), 7.82 (s, 1H), 7.40-7.36 (m, 1H), 6.77 (t, 1H, CHF$_2$), 4.72 (d, 1H, AB-system), 4.65 (d, 1H, AB-system), 4.32 (d, 1H, AB-system), 4.18 (d, 1H, AB-system)), 2.58 (s, 3H) | 385 |

TABLE 17-continued

| Example | Compound | ¹H-NMR (δ; DMSO-d₆) | MS [m/z; (M + 1)⁺] |
|---|---|---|---|
| 150 | 1-Methyl-1H-pyrazole-3-carboxylic acid [3-((R)-5-amino-3-difluoromethyl-3,6-dihydro-2H-[1,4]oxazin-3-yl)-4-fluoro-phenyl]-amide hydrochloride | 11.04 (s, 1 H), 10.32 (s, 1 H), 9.84 (s, 1 H), 8.87 (br. s., 1 H), 8.02 (d, 1 H), 7.96 (dd, 1 H), 7.87 (d, 1 H), 7.33 (dd, 1 H), 6.77 (t, 1 H, CHF2), 4.78-4.68 (m, 1 H), 4.68-4.58 (m, 1 H), 4.32 (d, 1 H), 4.16 (d, 1 H), 3.97 (s, 3 H) | 368 |
| 151 | 1-Methyl-4-nitro-1H-pyrazole-3-carboxylic acid [3-((R)-5-amino-3-difluoromethyl-3,6-dihydro-2H-[1,4]oxazin-3-yl)-4-fluoro-phenyl]-amide hydrochloride | 11.08 (s, 1 H), 10.98 (s, 1 H), 9.77 (s, 1 H), 8.97 (s, 1 H), 8.76 (s, 1 H), 7.91-7.76 (m, 2 H), 7.40 (dd, 1 H), 6.79 (t, 1 H, CHF2), 4.78-4.59 (m, 2 H), 4.33 (d, 1 H), 4.18 (d, 1 H), 3.96 (s, 3 H) | 413 |

More Detailed Description of Preparation of Example 112

5-Cyano-pyridine-2-carboxylic acid [3-((R)-5-amino-3-difluoromethyl-3,6-dihydro-2H-[1,4]oxazin-3-yl)-4-fluoro-phenyl]-amide hydrochloride a) 5-Difluoromethyl-6-(2-fluoro-phenyl)-morpholin-3-one 5-(5-Bromo-2-fluoro-phenyl)-5-difluoromethyl-morpholin-3-one (190 g, 586 mmol) [example 42 step e)] and sodium acetate (57.7 g, 703 mmol) were suspended in 1850 mL methanol. 10% Pd on charcoal (18.7 g) was then added and the reaction mixture was shaken in a Parr apparatus in an atmosphere of hydrogen at rt. After 60 minutes the reaction mixture was filtered over celite and evaporated. The residue was dissolved in 2 L TBME and washed with aqueous NaHCO₃ and brine. The organic layer was dried over MgSO₄.H₂O and evaporated to give 143.2 g of the title compound as a white solid.

HPLC: Rt$_{H1}$=0.792 min; ESIMS [M+H]⁺=246;
¹H-NMR (CDCl₃, 360 MHz): 7.50-7.43 (m, 2H), 7.32-7.27 (m, 1H), 7.19 (dd, 1H), 6.62 (br, 1H), 6.37 (t, J=54 Hz, 1H), 4.34 (d, 1H), 4.31 (d, 1H), 4.22 (d, 1H), 4.20 (d, 1H).

b) 5-Difluoromethyl-6-(2-fluoro-phenyl)-morpholine-3-thione

A mixture of 5-difluoromethyl-5-(2-fluoro-phenyl)-morpholin-3-one (141 g, 575 mmol) and Lawesson's reagent (132 g, 316 mmol) in 1400 ml of THF was heated at 68° C. for 1 h, cooled down and then evaporated. The residue was dissolved in 1 L DCM and filtered over 2 Kg silica gel with 10 L DCM to give 161 g of the title compound in the form of a greenish resin that slowly crystallized. The compound was used without further purification.

HPLC: Rt$_{H1}$=1.799 min; ESIMS [M+H]⁺=262; ¹H-NMR (360 MHz, CDCl₃): 7.42-7.35 (m, 1H), 7.28 (t, 1H), 7.19 (t, 1H), 7.11 (dd, 1H), 6.29 (t, J=54 Hz, 1H), 4.57 (d, 1H), 4.47 (d, 1H), 4.21 (d, 1H), 4.18 (d, 1H).

c) 5-Difluoromethyl-5-(2-fluoro-phenyl)-6,6-dihydro-2H-[1,4]oxazin-3-ylamine 5-Difluoromethyl-5-(2-fluoro-phenyl)-morpholine-3-thione (160 g, 570 mmol) was dissolved in 2.4 L of a NH₃ solution 7 mol/L in methanol for 6.5 h and afterwards left standing overnight. The reaction mixture was evaporated and taken up in 2 L 1N aqueous HCl and 2 L TBME. The aqueous phase was washed with TBME and made basic by the addition of 300 ml 30% aqueous NaOH and some ice. The mixture was extracted with DCM three times and the combined organic layers were dried with $Na_2SO_4$ and concentrated in vacuo. The title compound was obtained by crystallization from DCM/heptanes (128.45 g).

HPLC: $Rt_{H3}$=2.059 min; ESIMS [M+H]$^+$=245;

$^1$H-NMR (CDCl$_3$, 360 MHz): 7.77 (t, 1H), 7.38-7.30 (m, 1H), 7.21 (t, 1H), 7.09 (dd, 1H), 6.19 (t, J=54 Hz, 1H), 4.51 (br, 2H), 4.32, (d, 1H), 4.18 (d, 1H), 4.05 (d, 1H), 3.96 (d, 1H), 1.39 (s, 3H), 1.24 (s, 3H).

d) 5-Difluoromethyl-5-(2-fluoro-6-nitro-phenyl)-5,6-dihydro-2H-[1,4]oxazin-3-ylamine Potassium nitrate (60.3 g, 596 mmol) was added portionwise to 600 ml sulfuric acid (Temperature<20° C.). This solution was added dropwise to a solution of 5-difluoromethyl-5-(2-fluoro-phenyl)-5,6-dihydro-2H-[1,4]oxazin-3-ylamine (112 g, 459 mmol) in 600 ml sulfuric acid, while keeping the reaction temperature<22° C. with an ice bath. After stirring for 1 h, the mixture was poured onto 10 Kg ice. TBME (6 L) was added and the pH was adjusted to 12-14 by the addition of about 5 L 30% aqueous NaOH. The phases were separated and the aqueous phase was extracted twice with TBME. The combined organic layers were dried with sodium sulfate and evaporated to give 130 g of a yellow solid that was used further without purification.

HPLC: $Rt_{H3}$=2.063 min; ESIMS [M+H]$^+$=290;

$^1$H-NMR (CDCl$_3$, 360 MHz): 8.71 (dd, 1H), 8.13 (dt, 1H), 7.13 (dd, 1H), 5.99 (t, J=54 Hz, 1H), 4.55 (br, 2H), 4.33 (dd, 1H), 4.10 (d, 1H), 3.97 (d, 1H), 3.82 (dt, 1H).

e) [5-Difluoromethyl-5-(2-fluoro-5-nitro-phenyl)-5,6-dihydro-2H-[1,4]oxazin-3-yl]-carbamic acid tert-butyl ester A solution of 5-Difluoromethyl-5-(2-fluoro-5-nitro-phenyl)-5,6-dihydro-2H-[1,4]oxazin-3-ylamine (144.5 g, 500 mmol), Boc anhydride (142 g, 650 mmol) and DIPEA (131 ml, 749 mmol) in 2500 ml THF was stirred for 3 days at rt, after which there was still starting material remaining. Boc anhydride (56 g, 325 mmol) was added, the mixture heated to 60° C. and stirred for 10 h until the reaction was complete. The mixture was evaporated, dissolved in TBME, washed with ice-cold 1N aqueous HCl, water, 10% aqueous NaHCO$_3$ and brine. The organic phase was dried with sodium sulfate, filtered and evaporated. The product was purified by crystallization from DCM/heptanes. Yield 182.8 g white crystals.

HPLC: $Rt_{H1}$=3.259 min; ESIMS [M+Na]$^+$=412;

$^1$H-NMR (CDCl$_3$, 360 MHz): 8.70 (dd, 1H), 8.27 (dt, 1H), 7.34 (br, 1H), 7.25 (dd, 1H), 6.09 (t, J=54 Hz, 1H), 4.85 (d, 1H), 4.58 (d, 1H), 4.49 (dd, 1H), 3.94 (dt, 1H).

f) [5-(5-Amino-2-fluoro-phenyl)-6-difluoromethyl-5,6-dihydro-2H-[1,4]oxazin-3-yl]-carbamic acid tert-butyl ester

[5-Difluoromethyl-5-(2-fluoro-5-nitro-phenyl)-5,6-dihydro-2H-[1,4]oxazin-3-yl]-carbamic acid tert-butyl ester (180 g, 462 mmol) and 17.61 g Pd—C 10% were suspended in 1760 mL THF. The mixture was shaken in a Parr apparatus in an atmosphere of hydrogen at rt. After 6 h the reaction mixture was filtered over celite and evaporated. The residue was crystallized from DCM/heptanes to provide 157.6 g of the title compound as beige crystals.

HPLC: $Rt_{H3}$=2.748 min; ESIMS [M+H]$^+$=360;

$^1$H-NMR (CDCl$_3$, 360 MHz): Spectrum uninterpretable due to the presence of a complex mixture of rotamers.

g) [(R)-6-(5-Amino-2-fluoro-phenyl)-5-difluoromethyl-5,6-dihydro-2H-[1,4]oxazin-3-yl]-carbamic acid tert-butyl ester The racemic product ((rac)[5-(5-Amino-2-fluoro-phenyl)-5-difluoromethyl-5,6-dihydro-2H-[1,4]oxazin-3-yl]-carbamic acid tert-butyl ester) was separated via prep-HPLC on Chiralpak AD-H 20 um (8×100×48 mm HPLC columns), on a Bayer SMB CC50 instrument using SMB technology with heptane/EtOH/MeOH 70:20:10 as eluent. The desired compound was the slower eluting (R)-enantiomer. Yielding 72.29 g of the title compound as a colourless foam. ee=99.3%; Opt. rotation: [α]$_D$ −97.5° (c=1, CHCl$_3$)

HPLC: $Rt_{H3}$=2.748 min; ESIMS [M+H]$^+$=360;

$^1$H-NMR (CDCl$_3$, 360 MHz): Spectrum uninterpretable due to the presence of a complex mixture of rotamers.

h) ((R)-6-{5-[(5-Cyano-pyridine-2-carbonyl)-amino]-2-fluoro-phenyl}-6-difluoromethyl-5,6-dihydro-2H-[1,4]oxazin-3-yl)-carbamic acid tert-butyl ester

[(R)-5-(5-Amino-2-fluoro-phenyl)-5-difluoromethyl-5,6-dihydro-2H-[1,4]oxazin-3-yl]-carbamic acid tert-butyl ester (35 g, 97.4 mmol), 5-cyano-pyridine-2-carboxylic acid (15.87 g, 107.14 mmol) and HOBt hydrate (22.35 g, 146.1 mmol) were dissolved in 185 ml DMF and stirred with ice cooling. When the temperature had reached 0-5° C. EDC (22.33 ml, 126.62 mmol) was added dropwise. The mixture was stirred for 2 h. The ice bath was taken away and stirring was continued for 2 h. The mixture was taken up in EtOAc and water. The phases were separated and the organic phase was washed with 5% aqueous NaHCO$_3$ and brine. The organic phase was dried with MgSO$_4$.H$_2$O and evaporated to provide a beige solid. Crystallisation from EtOAc/hexane gave the title compound as colorless crystals. Yield 44.47 g.

HPLC: $Rt_{H1}$=2.888 min; ESIMS [M+Na]$^+$=512;

$^1$H-NMR (CDCl$_3$, 360 MHz, signals broadened due to rotamers): 8.95 (s, 1H), 8.48 (d, 1H), 8.25 (d, 1H), 8.08-8.03 (m, 1H), 7.84-7.80 (m, 1H), 7.37 (s, 1H), 7.17 (t, 1H), 6.18 (t, J=54 Hz, 1H), 4.83 (d, 1H), 4.60 (d, 1H), 4.42 (d, 1H), 4.4-4.3 (br, 1H), 3.97 (d, 1H), 1.53 (s, 9H).

i) 5-Cyano-pyridine-2-carboxylic acid [3-((R)-5-amino-3-difluoromethyl-3,6-dihydro-2H-[1,4]oxazin-3-yl)-4-fluoro-phenyl]-amide ((R)-5-{5-[(5-Cyano-pyridine-2-carbonyl)-amino]-2-fluoro-phenyl}-5-difluoromethyl-5,6-dihydro-2H-[1,4]oxazin-3-yl)-carbamic acid tert-butyl ester (44.47 g, 91.0 mmol) was dissolved in 450 ml DCM and mildly chilled with a rt water bath. TFA (150 ml) was added. The reaction was slightly exothermic. The mixture was stirred for 1.5 h at it. The volatiles were removed with vacuum at rt. The residue was taken up in DCM and the procedure repeated twice. The residue was taken up in 3 L EtOAc and washed with 10% aqueous $Na_2CO_3$ and brine. The organic phase was dried with sodium sulfate and partially evaporated. iPrOH was added and the mixture chilled. The title compound was collected as snow-white crystals. Yield 30.56 g.

HPLC: $Rt_{H3}$=2.605 min; ESIMS $[M+H]^+$=390;

$^1$H-NMR (dmso-d6, 600 MHz): 10.85 (s, 1H), 9.22 (s, 1H), 8.58 (d, 1H), 8.27 (d, 1H), 8.18-8.14 (m, 1H), 7.85-7.80 (m, 1H), 7.19 (t, 1H), 6.16 (br s, 2H), 6.14 (t, J=54 Hz, 1H), 4.12 (d, 1H), 4.01 (d, 1H), 3.92 (d, 1H), 3.88 (d, 1H).

j) 5-Cyano-pyridine-2-carboxylic acid [3-((R)-5-amino-3-difluoro-methyl-3,6-dihydro-2H-[1,4]oxazin-3-yl)-4-fluoro-phenyl]-amide, hydrochloride A solution of 5-cyano-pyridine-2-carboxylic acid [3-((R)-5-amino-3-difluoro-methyl-3,6-dihydro-2H-[1,4]oxazin-3-yl)-4-fluoro-phenyl]-amide (277 mg, 0.71 mmol) in 5 ml THF was triturated with 0.9 ml of 1M HCl in $Et_2O$. The mixture was partially evaporated, diluted with TBME and partially evaporated (3×), finally to dryness. The hydrochloride salt contained a significant amount of THF. It was taken up in EtOH and evaporated to dryness twice. The product was finally lyophilized with 15 ml water. Yield 261 mg white lyophilisate.

$^1$H-NMR (dmso-d6, 600 MHz): 11.05 (s, 1H), 11.01 (s, 1H), 9.75 (s, 1H), 9.25 (s, 1H), 8.73 (br s, 1H), 8.61 (d, 1H), 8.10 (d, 1H), 8.12-8.07 (m, 2H), 7.41 (dd, 1H), 6.79 (t, J=54 Hz, 1H), 4.70 (d, 1H), 4.65 (d, 1H), 4.36 (d, 1H), 4.18 (d, 1H).

Example 152

Crystalline 5-cyano-pyridine-2-carboxylic acid [3-((R)-5-amino-3-difluoromethyl-3,6-dihydro-2H-[1,4]oxazin-3-yl)-4-fluoro-phenyl]-amide 5-cyano-pyridine-2-carboxylic acid [3-((R)-5-amino-3-difluoromethyl-3,6-dihydro-2H-[1,4]oxazin-3-yl)-4-fluoro-phenyl]-amide was dissolved in EtOAc, isopropanol added and the resulting solution concentrated at reduced pressure. This procedure was repeated until most of the product had crystallised.

The resultant crystalline material was analysed by XRPD and the ten most characteristic peaks are shown in Table 18 (see also FIG. 1).

TABLE 18

| Degrees 2-Θ | d-spacing (Å) | Intensity (counts) | Relative Intensity % |
| --- | --- | --- | --- |
| 8.29 | 10.65649 | 9840 | High |
| 10.813 | 8.17512 | 5198 | Medium |
| 14.077 | 6.28645 | 1911 | Low |
| 14.525 | 6.09337 | 2446 | Low |
| 16.624 | 5.32842 | 19854 | High |
| 18.919 | 4.68693 | 3766 | Medium |
| 21.453 | 4.13863 | 3862 | Medium |
| 22.244 | 3.99323 | 6947 | Medium |
| 23.327 | 3.81033 | 4257 | Medium |
| 25.436 | 3.49889 | 3672 | Medium |
| 28.495 | 3.12985 | 5558 | Medium |

X-ray powder diffraction (XRPD) analysis was performed using a Brucker D8 Advance x-ray diffractometer. Measurements were taken at about 30 kV and 40 mA under the following conditions:

Scan rate (continuous scan): 0.3 s/step (equals 107.1 s step time)
Step size: 0.017° (2Theta)
Soller slit 2.5°
Slits (from left to right): V12 (variable), 6 mm antiscatter slit
The X-ray diffraction pattern was recorded between 2° and 40° (2 theta) with $CuK_\alpha$ radiation for identification of the whole pattern.

The crystalline material was also analysed by differential scanning calorimetry using a PerkinElmer DSC7 and was found to have an onset of melting at about 227° C. (227.46° C.).

Example 153

The compound in Table 19 can be prepared by procedures analogous to those used in Examples 71 and 72.

TABLE 19

| Example | Compound | $^1$H-NMR (δ; DMSO-$d_6$) | MS [m/z; $(M + 1)^+$] |
| --- | --- | --- | --- |
| 153 | 3-Amino-5-chloro-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide hydrochloride | 11.84 (s, 1H), 10.71 (s, 1H), 9.71 (d, 2H), 7.99 (m, 1H), 7.87 (m, 2H), 7.38 (s, 1H), 7.29 (dd, 1H), 7.19 (br s, 2H), 4.31 (d, 1H), 4.06 (d, 1H), 1.75 (s, 3H), 1.71 (s, 3H) | 460, 462 |

Examples 154 to 156

The compounds listed in Table 20 were prepared by a procedure analogous to that used in Example 100.

TABLE 20

| Example | Compound | ¹H-NMR (δ; DMSO-d₆) | MS [m/z; (M + 1)⁺] |
|---|---|---|---|
| 154 | 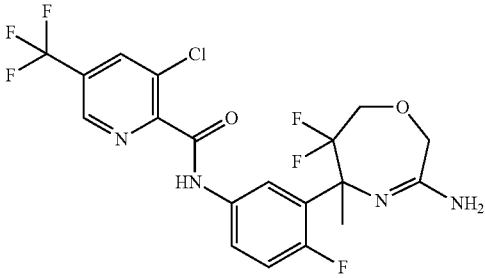 [SMILES: CC1(c2cc(NC(=O)c3ncc(C(F)(F)F)cc3Cl)ccc2F)N=C(N)COCC1(F)F]<br>3-Chloro-5-trifluoromethyl-pyridine-2-carboxylic acid [3-(3-amino-6,6-difluoro-5-methyl-2,5,6,7-tetrahydro-[1,4]oxazepin-5-yl)-4-fluoro-phenyl]-amide | 11.93 (s, 1H), 9.08 (s, 1H), 8.72 (s, 1H), 7.85 (m, 2H), 7.23 (s, 1H), 4.68-3.93 (m, 4H), 1.82 (s, 3H) | 481, 483 |
| 155 | 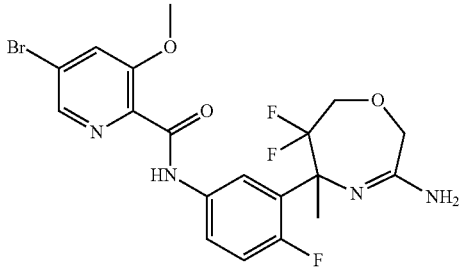 [SMILES: COc1cc(Br)cnc1C(=O)Nc1ccc(F)c(C2(C)N=C(N)COCC2(F)F)c1]<br>5-Bromo-3-methoxy-pyridine-2-carboxylic acid [3-(3-amino-6,6 difluoro-5-methyl-2,5,6,7 tetrahydro-[1,4]oxazepin-5-yl)-4 fluoro-phenyl]-amide | 10.49 (s, 1H), 8.33 (s, 1H), 7.95 (s, 1H), 7.86-7.87 (m, 2H), 7.08 (dd, 1H, J = 11.0 Hz, 8.4 Hz), 5.98 (s, 1H), 4.32-4.05 (m, 3H), 3.96-3.81 (m, 4H), 3.53-3.45 (m, 1H), 1.74 (s, 3H) | 487 |
| 156 | 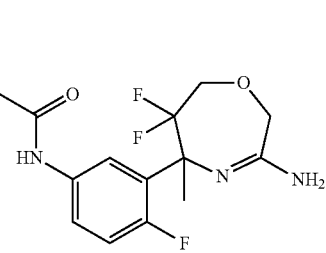<br>5-Cyano-pyridine-2-carboxylic acid [3-(3-amino-6,6-difluoro-5 methyl-2,5,6,7-tetrahydro[1,4]oxazepin-5-yl)-4 fluoro-phenyl]-amide | 10.8 (s, 1H), 9.19 (d, 1H, J = 3.5 Hz), 8.58 (dd, 1H, J = 10.3 Hz, 3.2 Hz), 8.27 (dd, 1H, J = 10.5 Hz, 2.7 Hz), 8.07 (dd, 1H, J = 9.5 Hz, 3.6 Hz), 7.85 (m, 1H), 7.12 (dd, 1H, J = 14 Hz, 10.5 Hz), 7.95 (s, 2 H), 4.31-4.08 (m, 3H), 3.96-3.84 (m, 1H), 1.75 (s, 3H) | 404 |

(Note: For example 156 the deprotection of the Boc group was carried out using TFA/DCM (in an analogous manner as for example 112) instead of HCl/dioxane.

Examples 157 to 185

The compounds listed in Table 21 were prepared by procedures analogous to those used in Example 42 or Example 112.

For enantiomerically pure compounds the racemic precursor [5-(5-amino-2-fluoro-phenyl)-5-difluoromethyl-5,6-dihydro-2H-[1,4]oxazin-3-yl]-carbamic acid tert-butyl ester (example 42j)) was separated via prep-HPLC on Chiralpak AD-H 250×4.6 mm column using supercritical CO2/EtOH 9:1 as an eluent. The desired compound was the slower eluting (R)-enantiomer. Enantiomeric excess=99.7%; [α]$_D$=−109.7° (c=1, CHCl₃).

TABLE 21

| Example | Compound | ¹H-NMR (δ; DMSO-d₆) | MS [m/z; (M + 1)⁺] |
|---|---|---|---|
| 157 | 7H-Pyrrolo[2,3-d]pyrimidine-6-carboxylic acid [3-((R)-5-amino-3-difluoromethyl-3,6-dihydro-2H-[1,4]oxazin-3-yl)-4-fluoro-phenyl]-amide hydrochloride | 13.85 (s, 1H), 11.2 (s, 1H), 11.15 (s, 1H), 9.88 (s, 1H), 9.55 (s, 1H), 9.25 (s, 1H), 8.91 (s, 1H), 8.1 (m, 1H), 8.00 (m, 1H), 7.95 (s, 1H), 7.45-7.40 (dd, 1H), 6.80 (t, 1H, CHF2), 4.72 (d, 1H, AB-system), 4.67 (d, 1H, AB-system), 4.35 (d, 1H, AB-system), 4.20 (d, 1H, AB-system) | 405 |
| 158 | 3-Amino-5-(2-methoxy-ethoxy)-pyrazine-2-carboxylic acid [3-((R)-5-amino-3-difluoromethyl-3,6-dihydro-2H-[1,4]oxazin-3-yl)-4-fluoro-phenyl]-amide | 10.14 (br s, 1 H), 8.03 (d, 1 H), 7.75 (br s, 1 H), 7.53 (s, 1 H), 7.14 (t, 1 H), 6.16 (br s, 2 H), 4.41 (br. s., 2 H), 4.14 (d, 1 H), 4.01 (d, 1 H), 3.91 (d, 1 H), 3.81 (d, 1 H), 3.72-3.66 (m, 3 H), 3.50 (s, 1 H), 3.30 (s, 3 H) | 455 |
| 159 | ((R)-5-Difluoromethyl-5-{5-[(5-ethyl-pyridine-2-carbonyl)-amino]-2-fluoro-phenyl}-5,6-dihydro-2H-[1,4]oxazin-3-yl)-carbamic acid tert-butyl ester, hydrochloride | 10.85 (s, 1H), 9.80 (s, 1H), 8.84 (s, 1H), 8.64 (s, 1H), 8.13-8.08 (m, 3H), 7.94 (d, 1H), 7.38 (dd, 1H), 6.78 (t, J = 54 Hz, 1H), 4.73 (d, 1H), 4.61 (d, 1H), 4.36 (d, 1H), 4.18 (d, 1H), 2.78 (q, 2H), 1.24 (t, 3H) | 393 |
| 160 | 3-Amino-5-chloro-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.99 (s, 1 H), 10.60 (s, 1 H), 9.78 (br s, 1 H), 8.80 (br s, 1 H), 8.05 (d, 1 H), 7.93 (d, 1 H), 7.86 (s, 1 H), 7.42-7.30 (m, 2 H), 7.17 (br s, 2 H), 6.77 (t, 1 H, CHF2), 4.78-4.67 (m, 1 H), 4.67-4.57 (m, 1 H), 4.34 (d, 1 H), 4.16 (d, 1 H) | 414, 416 |

TABLE 21-continued

| Example | Compound | $^1$H-NMR (δ; DMSO-d$_6$) | MS [m/z; (M + 1)$^+$] |
|---|---|---|---|
| 161 | 3-Chloro-5-methoxy-pyridine-2-carboxylic acid [3-((R)-5-amino-3-difluoromethyl-3,6-dihydro-2H-[1,4]oxazin-3-yl)-4-fluoro-phenyl]-amide | 10.6 (s, 1H), 8.33 (s, 1H), 7.97 (m, 1H), 7.78 (m, 1H), 7.72 (s, 1H), 7.17 (dd, 1H), 6.14 (t, 1H), 6.13 (br s, 2H), 4.15 (d, 1H), 4.02 (d, 1H), 3.93 (s, 3H), 3.91 (d, 1H), 3.83 (d, 1H) | 429, 431 |
| 162 | 6-Oxo-1,6-dihydro-pyridine-3-carboxylic acid [3-((R)-5-amino-3-difluoromethyl-3,6-dihydro-2H-[1,4]oxazin-3-yl)-4-fluoro-phenyl]-amide hydrochloride | 12.20 (s, 1H), 11.02 (s, 1H), 10.32 (s, 1H), 9.78 (s, 1H), 8.79 (s, 1H), 8.24 (s, 1H), 7.97 (dd, 1H), 7.92 (dd, 1H), 7.79 (m, 1H), 7.35 (t, 1H), 6.77 (t, 1H, CHF2), 6.41 (d, 1H), 4.72 (d, 1H, AB-system), 4.65 (d, 1H, AB-system), 4.32 (d, 1H, AB-system), 4.18 (d, 1H, AB-system) | 381 |
| 163 | Pyrrolo[1,2-c]pyrimidine-3-carboxylic acid [3-((R)-5-amino-3-difluoromethyl-3,6-dihydro-2H-[1,4]oxazin-3-yl)-4-fluoro-phenyl]-amide | 10.30 (s, 1H), 9.30 (s, 1H), 8.21 (s, 1H), 8.09 (m, 1H), 7.90 (s, 1H), 7.87 (m, 1H), 7.18 (dd, 1H), 7.05 (t, 1H), 6.83 (d, 1H), 6.18 (s, NH2), 6.14 (t, 1H, CHF2), 4.12 (d, 1H, AB-system), 4.02 (d, 1H, AB-system), 3.93 (d, 1H, AB-system), 3.82 (d, 1H, AB-system) | 404 |
| 164 | 5-But-2-ynyloxy-pyrazine-2-carboxylic acid [3-((R)-5-amino-3-difluoromethyl-3,6-dihydro-2H-[1,4]oxazin-3-yl)-4-fluoro-phenyl]-amide hydrochloride | 11.02 (s, 1 H), 10.78 (s, 1 H), 9.66 (s, 1 H), 8.91 (s, 1 H), 8.78 (s, 1 H), 8.46 (s, 1 H), 8.11 (d, 1 H), 8.03 (dd, 1 H), 7.37 (dd, 1 H), 6.77 (t, 1 H, CHF2), 5.08 (d, 2 H), 4.76-4.67 (m, 1 H), 4.67-4.58 (m, 1 H), 4.33 (d, 1 H), 4.17 (d, 1 H), 1.84 (s, 3 H) | 434 |

TABLE 21-continued

| Example | Compound | ¹H-NMR (δ; DMSO-d₆) | MS [m/z; (M + 1)⁺] |
|---|---|---|---|
| 165 | 3-Amino-5-bromo-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.98 (s, 1H), 10.13 (s, 1H), 9.74 (s, 1H), 8.72 (s, 1H), 8.04 (d, 1H), 7.95-7.91 (m, 2H), 7.52 (s, 1H), 7.36 (dd, 1H), 7.12 (br, 2H), 6.78 (t, J = 54 Hz, 1H), 4.72 (d, 1H), 4.64 (d, 1H), 4.32 (d, 1H), 4.15 (d, 1H) | 458, 460 |
| 166 | 1-Ethyl-1H-imidazole-2-carboxylic acid [3-((R)-5-amino-3-difluoromethyl-3,6-dihydro-2H-[1,4]oxazin-3-yl)-4-fluoro-phenyl]-amide hydrochloride | 11.15 (s, 1H), 11.07 (s, 1H), 9.98 (s, 1H), 9.09 (s, 1H), 7.96 (m, 2H), 7.73 (s, 1H), 7.37 (m, 2H), 6.74 (t, 1H, CHF2), 4.71 (d, 1H), 4.63 (d, 1H), 4.47 (q, 2H), 4.31 (d, 1H), 4.14(d, 1H), 1.37 (t, 2H) | 382 |
| 167 | 5-Prop-2-ynyloxy-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.54 (br s, 1 H), 8.90 (s, 1 H), 8.49 (s, 1 H), 8.14 (dd, 1 H), 7.81 (br s, 1 H), 7.19 (t, 1 H), 6.24-6.06 (m, 3 H), 5.14 (d, 2 H), 4.12 (d, 1 H), 4.03-4.01 (m, 1 H), 3.94-3.91 (m, 1 H), 3.84 (d, 1 H), 3.66 (s, 1H) | 420 |
| 168 | 5-Amino-2-methyl-oxazole-4-carboxylic acid [3-((R)-5-amino-3-difluoromethyl-3,6-dihydro-2H-[1,4]oxazin-3-yl)-4-fluoro-phenyl]-amide hydrochloride | 10.96 (s, 1 H), 9.79 (s, 1 H), 9.62 (s, 1 H), 8.80 (s, 1 H), 8.00-7.96 (m, 1 H), 7.92 (d, 1 H), 7.33-7.20 (m, 1 H), 7.00 (br s, 1 H), 6.76 (t, 1 H, CHF2), 4.76-4.56 (m, 2 H), 4.32 (d, 1 H), 4.14 (d, 1 H), 2.31 (s, 3 H) | 384 |

TABLE 21-continued

| Example | Compound | ¹H-NMR (δ; DMSO-d₆) | MS [m/z; (M + 1)⁺] |
|---|---|---|---|
| 169 | 5-Chloro-3-hydroxy-pyridine-2-carboxylic acid [3-((R)-5-amino-3-difluoromethyl-3,6-dihydro-2H-[1,4]oxazin-3-yl)-4-fluoro-phenyl]-amide | 11.1 (d, 1H), 9.68 (s, 1H), 8.84 (s, 1H), 8.28 (s, 1H), 8.0 (m, 2H), 7.73 (s, 1H), 7.40 (dd, 1H), 6.77 (t, 1H), 4.67 (d, 1H), 4.63 (d, 1H), 4.34 (d, 1H), 4.17 (d, 1H) | 415, 417 |
| 170 | 5-Isopropoxy-pyrazine-2-carboxylic acid [3-((R)-5-amino-3-difluoromethyl-3,6-dihydro-2H-[1,4]oxazin-3-yl)-4-fluoro-phenyl]-amide | 10.49 (br s, 1H), 8.85 (s, 1H), 8.33 (s, 1H), 8.13 (d, 1H), 7.80 (br s, 1H), 7.19 (dd, 1H), 6.15 (br s, 2H), 6.13 (t, 1H), 5.34 (m, 1H), 4.16 (d, 1H), 4.02 (d, 1H), 3.87 (d, 1H), 3.71 (d, 1H), 1.35 (d, 6H) | 424 |
| 171 | 5-Ethoxy-pyrazine-2-carboxylic acid [3-((R)-5-amino-3-difluoromethyl-3,6-dihydro-2H-[1,4]oxazin-3-yl)-4-fluoro-phenyl]-amide | 10.49 (br s, 1H), 8.87 (s, 1H), 8.37 (s, 1H), 8.17 (d, 1H), 7.81 (br s, 1H), 7.18 (dd, 1H), 6.16 (br s, 2H), 6.14 (t, 1H), 4.43 (t, 2H), 3.7-4.2 (m, 4H), 1.35 (t, 3H) | 410 |
| 172 | 5-Dimethylaminomethyl-3-methyl-benzofuran-2-carboxylic acid [3-((R)-5-amino-3-difluoromethyl-3,6-dihydro-2H-[1,4]oxazin-3-yl)-4-fluoro-phenyl]-amide hydrochloride | 11.07 (s, 1 H), 10.80 (br s, 1 H), 10.75 (s, 1 H), 9.84 (s, 1 H), 8.88 (s, 1 H), 8.09-7.94 (m, 3 H), 7.84-7.70 (m, 2 H), 7.40 (dd, 1 H), 6.79 (t, 1 H, CHF2), 4.80-4.70 (m, 2 H), 4.41-4.30 (m, 3 H), 4.19 (d, 1 H), 2.72 (s, 3 H), 2.71 (s, 3 H), 2.61 (s, 3 H) | 475 |

TABLE 21-continued

| Example | Compound | ¹H-NMR (δ; DMSO-d₆) | MS [m/z; (M + 1)⁺] |
|---|---|---|---|
| 173 | 1,5-Dimethyl-1H-[1,2,3]triazole-4-carboxylic acid [3-((R)-5-amino-3-difluoromethyl-3,6-dihydro-2H-[1,4]oxazin-3-yl)-4-fluoro-phenyl]-amide hydrochloride | 11.04 (s, 1H), 10.57 (s, 1H), 9.87 (s, 1H), 8.93 (s, 1H), 7.99 (m, 2H), 7.31 (m, 2H), 6.74 (t, 1H, CHF2), 4.70 (d, 1H), 4.62 (d, 1H), 4.31 (d, 1H), 4.14 (d, 1H), 3.98 (s, 3H), 2.54 (s, 3H) | 383 |
| 174 | 5-Methoxy-3-methyl-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.99 (s, 1 H), 10.68 (s, 1 H), 9.75 (s, 1 H), 8.74 (s, 1 H), 8.26 (s, 1 H), 8.06-7.92 (m, 2 H), 7.44-7.32 (m, 1 H), 6.78 (t, 1 H, CHF2), 4.78-4.68 (m, 2 H), 4.34 (d, 1 H), 4.18 (d, 1 H), 4.00 (s, 3 H), 2.77 (s, 3 H) | 410 |
| 175 | 3-Amino-5-methoxy-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.98 (s, 1 H), 10.41 (s, 1 H), 9.76 (s, 1 H), 8.77 (s, 1 H), 8.14-7.98 (m, 1 H), 7.98-7.82 (m, 1 H), 7.54 (s, 1 H), 7.34 (dd, 1 H), 4.80-4.67 (m, 1 H), 4.67-4.53 (m, 1 H), 4.34 (d, 1 H), 4.16 (d, 1 H), 3.91 (s, 3 H) | 411 |
| 176 | 5-Difluoromethoxy-3-methyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.91 (br s, 1H), 10.75 (s, 1H), 9.66 (br s, 1H), 8.59 (br s, 1H), 8.44 (d, 1H), 8.00-7.98 (m, 2H), 7.75 (d, 1H), 7.45 (t, 1H), 7.41-7.35 (m, 1H), 6.79 (t, 1H), 4.71 (d, 1H), 4.64 (d, 1H), 4.34 (d, 1H), 4.18 (d, 1H), 2.61 (s, 3H) | 445 |

TABLE 21-continued

| Example | Compound | ¹H-NMR (δ; DMSO-d₆) | MS [m/z; (M + 1)⁺] |
|---|---|---|---|
| 177 | 5-Fluoromethoxy-3-methyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.92 (br s, 1H), 10.70 (s, 1H), 9.67 (br s, 1H), 8.61 (br s, 1H), 8.38 (d, 1H), 8.00-7.98 (m, 2H), 7.65 (d, 1H), 7.41-7.35 (m, 1H), 6.79 (t, 1H), 6.03 (d, 2H), 4.71 (d, 1H), 4.65 (d, 1H), 4.35 (d, 1H), 4.18 (d, 1H), 2.63 (s, 3H) | 427 |
| 178 | 5-Methoxy-ethoxy)-3-methyl-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.98 (s, 1 H), 10.68 (s, 1 H), 9.74 (s, 1 H), 8.72 (br s, 1 H), 8.28 (s, 1 H), 8.06-7.91 (m, 2 H), 7.37 (dd, 1 H), 6.78 (t, 1 H, CHF2), 4.72-4.63 (m, 2 H), 4.57-4.48 (m, 2 H), 4.34 (d, 1 H), 4.18 (d, 1 H), 3.79-3.63 (m, 2 H), 3.31 (s, 3 H), 2.76 (s, 3 H) | 454 |
| 179 | 3,5-Dimethoxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.00 (s, 1H), 10.48 (s, 1H), 9.77 (s, 1H), 8.75 (s, 1H), 8.01 (d, 1H), 7.97 (s, 1H), 7.91-7.87 (m, 1H), 7.34 (t, 1H), 7.22 (br, 2H), 6.78 (t, J = 54 Hz, 1H), 4.69 (d, 1H), 4.65 (d, 1H), 4.33 (d, 1H), 3.94 (s, 3H), 3.89 (s, 3H) | 425 |
| 180 | 5-(2-Methoxy-ethoxy)-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.98 (br s, 1H), 10.74 (s, 1H), 9.76 (br s, 1H), 8.74 (br s, 1H), 8.42 (d, 1H), 8.13 (d, 1H), 8.10-8.05 (m, 2H), 7.65 (dd, 1H), 7.37 (dd, 1H), 6.79 (t, 1H), 4.72 (d, 1H), 4.64 (d, 1H), 4.34 (d, 1H), 4.31-4.28 (m, 2H), 4.17 (d, 1H), 3.73-3.69 (m, 2H), 3.32 (s, 3H) | 439 |

TABLE 21-continued

| Example | Compound | ¹H-NMR (δ; DMSO-d₆) | MS [m/z; (M + 1)⁺] |
|---|---|---|---|
| 181 | 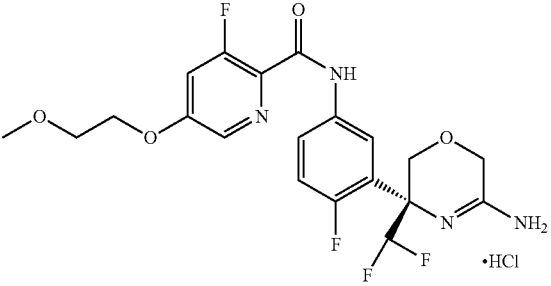<br>3-Fluoro-5-(2-methoxy-ethoxy)-pyridine-2-carboxylic acid [3-((R)-5-amino-3-difluoromethyl-3,6-dihydro-2H-[1,4]oxazin-3-yl)-4-fluoro-phenyl]-amide hydrochloride | 10.99 (br s, 1H), 10.67 (s, 1H), 9.75 (br s, 1H), 8.72 (br s, 1H), 8.31 (d, 1H), 8.03 (d, 1H), 8.00-7.94 (m, 1H), 7.66 (dd, 1H), 7.37 (dd, 1H), 6.79 (t, 1H), 4.71 (d, 1H), 4.64 (d, 1H), 4.37-4.29 (m, 3H), 4.18 (d, 1H), 3.72-3.69 (m, 2H), 3.32 (s, 3H) | 457 |
| 182 | 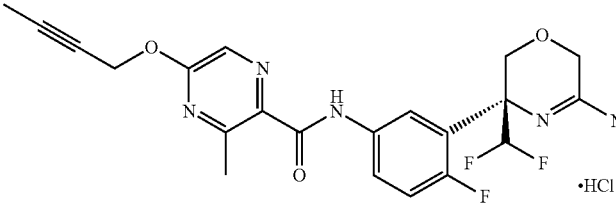<br>5-But-2-ynyloxy-3-methyl-pyrazine-2-carboxylic acid [3-((R)-5-amino-3-difluoromethyl-3,6-dihydro-2H-[1,4]oxazin-3-yl)-4-fluoro-phenyl]-amide hydrochloride | 10.94 (s, 1 H), 10.70 (s, 1 H), 9.69 (s, 1 H), 8.64 (s, 1 H), 8.30 (s, 1 H), 7.98 (d, 2 H), 7.38 (t, 1 H), 6.79 (t, 1 H, CHF2), 5.08 (br s, 2 H), 4.75-4.59 (m, 2 H), 4.34 (d, 1 H), 4.18 (d, 1 H), 2.76 (s, 3 H), 1.86 (s, 3 H) | 448 |
| 183 | 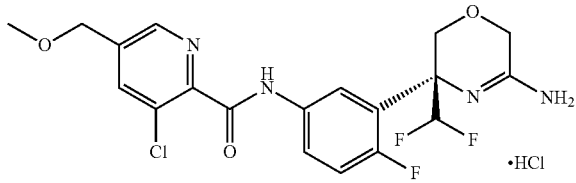 [SMILES: CCOc1cnc(C(=O)Nc2ccc(F)c([C@]3(C(F)F)COCC(N)=N3)c2)cn1]<br>3-Chloro-5-methoxymethyl-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.21 (s, 1H), 10.96 (s, 1H), 9.95 (s, 1H), 9.09 (s, 1H), 8.59 (s, 1H), 8.04 (s, 1H), 7.94 (m, 1H), 7.90 (d, 1H), 7.40 (dd, 1H), 6.79 (t, 1H), 4.71 (m, 2H), 4.55 (s, 2H), 4.33 (d, 1H), 4.44 (d, 1H), 3.37 (s, 3H) | 443, 445 |
| 184 | 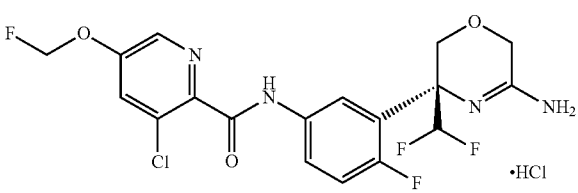 [SMILES: NC1=N[C@@](c2cc(NC(=O)c3ncc(CC(F)F)cc3Cl)ccc2F)(C(F)F)COC1 ; Cl]<br>3-Chloro-5-fluoromethoxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.06 (s, 1H). 10.89 (s, 1H), 9.78 (s, 1H), 8.79 (s, 1H), 8.52 (s, 1H), 7.99 (s, 1H), 7.95 (d, 1H), 7.91 (m, 1H), 7.40 (dd, 1H), 6.79 (t, 1H), 6.08 (d, 2H), 4.71 (m, 2H), 4.34 (d, 1H), 4.23 (d, 1H) | 447, 449 |

TABLE 21-continued

| Example | Compound | $^1$H-NMR (δ; DMSO-d$_6$) | MS [m/z; (M + 1)$^+$] |
|---|---|---|---|
| 185 | 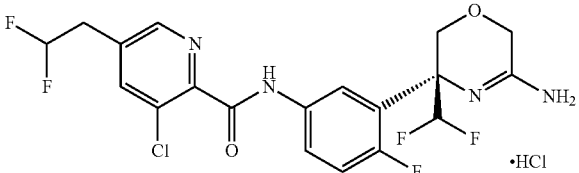<br>3-Chloro-5-difluoromethoxy-pyridine-2-carboxylic acid [3-((R)-5-amino-3-difluoromethyl-3,6-dihydro-2H-[1,4]oxazin-3-yl)-4-fluoro-phenyl]-amide hydrochloride | 11.07 (s, 1H), 10.93 (s, 1H), 9.76 (s, 1H), 8.82 (s, 1H), 8.60 (s, 1H), 8.16 (s, 1H), 7.91 (m, 2H), 7.51 (t, 1H), 7.40 (m, 1H), 6.79 (t, 1H), 4.73 (m, 2H), 4.33 (d, 1H), 4.23 (d, 1H) | 465, 467 |

Preparation of Intermediates

The substituted acid building blocks were either commercially available or can be prepared as described in the literature or in an analogous manner, e.g. WO 2005063738, WO 2009091016, WO 2010047372, Bioorg. Med. Chem. 2001, 9, 2061-2071, or can be prepared as described hereafter or in an analogous manner.

Acid-1: 5-Cyano-4,6-dideutero-3-trideuteromethyl-pyridine-2-carboxylic acid a) 5-Bromo-4,6-dideutero-3-trideuteromethyl-pyridine-2-carboxylic acid A suspension of 2.16 g (0.00 mmol) 5-bromo-3-methyl-pyridine-2-carboxylic acid in 36 ml of D2O (99.96% D) was treated with 4 ml of a 40% solution of NaOD in D2O. The homogeneous solution was heated in a 100 ml Teflon vessel with a Synthos 3000 Microwave apparatus. The mixture was heated at 160° C. for 5 h and cooled down. $^1$H-NMR and MS analises of the product showed that deuteration had progressed to a high degree. Only minor amounts of tetradeutero derivatives were present. The reaction mixture was acidified to pH3 with 2N HCl and extracted with EtOAc. The organic phase was dried with MgSO4.H2O and evaporated to give the title compound as a white solid, pure enough for further transformations.

HPLC: Rt$_{H2}$=2.829 min; ESIMS [M+H]$^+$=221, 223 (1 Br, 5D);

b) 5-Bromo-4,6-dideutero-3-trideuteromethyl-pyridine-2-carboxylic acid tert-butyl ester A solution of 1.65 g (7.46 mmol) 5-bromo-4,6-dideutero-3-trideuteromethyl-pyridine-2-carboxylic acid and two drops of DMF were dissolved in 17 ml DCM. Oxalyl chloride (1.3 ml, 14.9 mmol) was added dropwise. The development of gas started immediately. After stirring for 2 h at 25° C. the mixture was evaporated, taken up in toluene and evaporated again. The residual brownish resin was dissolved in 3 ml THF and added to a stirred solution of 14 ml (22.39 mmol) BuLi (1.6 M in hexane) in 24 ml t-BuOH. After 1 h the mixture was poured onto 10% aqueous NH4Cl and extracted wth TBME. The organic layer was washed with brine, dried with MgSO4.H2O and evaporated. Chromatography on silica gel (hexane/EtOAc 9:1) provided the title compound as a colorless liquid.

HPLC: Rt$_{H1}$=3.002 min; ESIMS [M+H]$^+$=277, 279 (1 Br, 5D);
$^1$H-NMR (360 MHz, CDCl$_3$): 1.65 (s, 9H).

c) 5-Cyano-4,6-dideutero-3-trideuteromethyl-pyridine-2-carboxylic acid tert-butyl ester A mixture of 1.41 g (5.09 mmol) 5-bromo-4,6-dideutero-3-trideuteromethyl-pyridine-2-carboxylic acid tert-butyl ester, 0.418 g (3.56 mmol) Zn(CN)2, 0.033 g Zn powder (0.509 mmol) and 0.265 g (0.254 mmol) Pd2(dba)3.CHCl3 were suspended in 14 ml DMF under nitrogen atmosfere. A 0.25 M solution of tBu3P in dioxane (4.0 ml, 1.02 mmol) was added and the mixture was stirred for 16 h at 60° C. After being cooled down the mixture was diluted with TBME, filtered over celite and washed with brine three times. The crude product was purified by column chromatography on silica gel (hexane/EtOAc 5-15%) to give the title compound as an off white solid.

HPLC: Rt$_{H3}$=3.275 min; ESIMS [M+Na]$^+$=246 (5D);
$^1$H-NMR (360 MHz, CDCl$_3$): 1.68 (s, 9H);
Ft-IR: 2231 cm$^{-1}$ (CN).

d) 5-Cyano-4,6-dideutero-3-trideuteromethyl-pyridine-2-carboxylic acid

To a solution of 825 mg (3.69 mmol) 5-cyano-4,6-dideutero-3-trideuteromethyl-pyridine-2-carboxylic acid tert-butyl ester in 5.1 g (37 mmol) 1,3-dimethoxybenzene were added 8.3 ml TFA and stirred for 6.5 h. The reaction mixture was diluted with toluene and evaporated. The residue was taken up in toluene and evaporated (2x). The product was crystallized from TBME/hexane to give the title compound as a white powder.

HPLC: Rt$_{H2}$=2.397 min; ESIMS [M+H]$^+$=168 (5D);
$^1$H-NMR (360 MHz, CDCl$_3$): non-deuterated impurities.

Acid-2: 5-Chloro-4,6-dideutero-3-trideuteromethyl-pyridine-2-carboxylic acid

The title compound was prepared by an analogous procedure as Acid-1 steps a) to b).

HPLC: Rt$_{H2}$=2.820 min; ESIMS [M+H]$^+$=177 (5D);
$^1$H-NMR (360 MHz, D2O): non deuterated impurities.

Acid-3: 5-Cyano-3-methyl-pyridine-2-carboxylic acid

The title compound was prepared by an analogous procedure to Acid-1 starting with 5-bromo-3-methyl-pyridine-2-carboxylic acid instead of the deuterated derivative [Acid-1 step a)].

Rf (hexanes/EtOAc 6:1)=0.28
$^1$H-NMR (360 MHz, CDCl$_3$): 8.09 (dd, 1H), 7.79 (ddd, 1H), 7.17 (t, 1H), 6.44 (t, J=45 Hz, 1H).

Acid-4: 3,5-Dimethoxy-pyridine-2-carboxylic acid

A suspension of 3,5-dimethoxy-pyridine-2-carbonitrile (CAS: 36057-45-1, 2.71 g, 16.51 mmol) in 45 ml MeOH and 65 ml 30% aq NaOH was refluxed for 6 h. MeOH was removed by evaporation and the residue was washed with TBME. The aq phase was acidified with conc. HCl till the pH was 3. The mixture was extracted with EtOAc and THF. The combined org layers were dried with sodium sulfate and evaporated. The brown solid was crystallized from EtOH to provide the title compound as pale brown crystals.
HPLC: Rt$_{H2}$=2.183 min; ESIMS [M+H]$^+$=184;
$^1$H-NMR (360 MHz, DMSO-d6): 12.61 (s, 1H), 3.93 (s, 3H), 3.88 (s, 3H).

Acid-5: 5-Difluoromethoxy-3-methyl-pyridine-2-carboxylic acid a) 5-Difluoromethoxy-3-methyl-pyridine-2-carbonitrile A solution of 5-hydroxy-3-methyl-pyridine-2-carbonitrile (CAS registry 228867-86-5) (228 mg, 1.70 mmol), sodium chlorodifluoroacetate (CAS registry 1895-39-2) (518 mg, 3.40 mmol) and K$_2$CO$_3$ (705 mg, 5.10 mmol) in DMF (7 ml) was stirred for 0.5 h at 100° C. The reaction mixture was diluted with EtOAc and washed with saturated aqueous NH$_4$Cl soln. and brine. The aqueous layers were reextracted with EtOAc, the combined organic layers dried over Na$_2$SO$_4$, filtrated and the filtrate was concentrated. The title compound was obtained as a colourless oil after flash chromatography on silica gel (cyclohexane/EtOAc gradient 0-3 min 95:5, 3-35 min 95:5 to 60:40).
HPLC Rt$_{H10}$=0.87 min; ESIMS: 185 [(M+H)$^+$];
$^1$H NMR (400 MHz, CDCl$_3$): 8.40 (d, 1H), 7.45 (d, 1H), 6.64 (t, 1H), 2.61 (s, 3H).

b) 5-Difluoromethoxy-3-methyl-pyridine-2-carboxylic acid

To a solution of 5-difluoromethoxy-3-methyl-pyridine-2-carbonitrile (145 mg, 0.787 mmol) in EtOH (5 ml) was added 1M aqueous NaOH soln. (2.5 ml). The reaction mixture was stirred for 7 h at 70° C., then for 9 h at room temperature. It was diluted with Et$_2$O and twice extracted with water. The combined aqueous layers were reextracted with Et$_2$O, acidified to pH 2 with 1M aqueous HCl and twice extracted with TBME. The combined organic layers were dried over Na$_2$SO$_4$, filtrated and the filtrate was concentrated to yield the title compound as a white solid which was used for the next step without further purification.
HPLC Rt$_{H10}$=0.61 min; ESIMS: 204 [(M+H)$^+$];
$^1$H NMR (400 MHz, MeOD): 8.32 (d, 1H), 7.61 (d, 1H), 7.06 (t, 1H), 2.64 (s, 3H).

Acid-6: 5-Fluoromethoxy-3-methyl-pyridine-2-carboxylic acid a) 5-Fluoromethoxy-3-methyl-pyridine-2-carbonitrile To a solution of 5-hydroxy-3-methyl-pyridine-2-carbonitrile (CAS registry 228867-86-5) (228 mg, 1.70 mmol) in DMF (10 ml) was added a solution of toluene-4-sulfonic acid fluoromethyl ester (CAS registry 114435-86-8) (521 mg, 2.55 mmol) and Cs$_2$CO$_3$ (1.386 g, 4.26 mmol) in DMF (4 ml). The reaction mixture was stirred for 1 h at 100° C., then for 1 h at 70° C., diluted with EtOAc and washed with saturated aqueous NH$_4$Cl soln. and brine. The aqueous layers were reextracted with EtOAc, the combined organic layers dried over Na$_2$SO$_4$, filtrated and the filtrate was concentrated. The title compound was obtained as a white solid after flash chromatography on silica gel (cyclohexane/EtOAc gradient 0-3 min 95:5, 3-30 min 95:5 to 65:35).
HPLC Rt$_{H10}$=0.77 min; ESIMS: 167 [(M+H)$^+$];
$^1$H NMR (400 MHz, CDCl$_3$): 8.36 (d, 1H), 7.34 (d, 1H), 5.79 (d, 2H), 2.59 (s, 3H).

b) 5-Fluoromethoxy-3-methyl-pyridine-2-carboxylic acid

To a solution of 5-fluoromethoxy-3-methyl-pyridine-2-carbonitrile (118 mg, 0.71 mmol) in EtOH (4 ml) was added 1M aqueous NaOH soln. (2 ml). The reaction mixture was stirred for 7 h at 70° C., then for 9 h at room temperature. It was diluted with TBME and twice washed with water. The combined aqueous layers were reextracted with TBME, acidified to pH 2 with 1M aqueous HCl and twice extracted with TBME. The combined organic layers were dried over Na$_2$SO$_4$, filtrated and the filtrate was concentrated to yield the title compound as a white solid which was used for the next step without further purification.
HPLC Rt$_{H10}$=0.50 min; ESIMS: 186 [(M+H)$^+$]
$^1$H NMR (400 MHz, MeOD): 8.28 (d, 1H), 7.55 (d, 1H), 5.88 (d, 2H), 2.66 (s, 3H).

Acid-7: 5-(2-Methoxy-ethoxy)-pyridine-2-carboxylic acid a) 5-(2-Methoxy-ethoxy)-pyridine-2-carboxylic acid methyl ester To a precooled solution of 5-hydroxy-pyridine-2-carboxylic acid methyl ester (CAS registry 30766-12-2) (150 mg, 0.980 mmol) and 2-methoxyethanol (82 mg, 0.085 ml, 1.077 mmol) in THF (10 ml) was added at 0° C. triphenylphosphine (397 mg, 1.469 mmol) and the reaction mixture was stirred for 10 min at 0° C. A solution of DIAD (316 mg, 1.469 mmol) in THF (5 ml) was added and the mixture was stirred at room temperature for 19.5 h. After dilution with EtOAc, the crude mixture was extracted with water and brine, the aqueous layers were reextracted with EtOAc, the combined organic extracts dried over Na$_2$SO$_4$, filtered and the filtrate concentrated to yield the title compound after flash chromatography on silica gel (DCM/EtOAc gradient 0-3 min 60:40; 3-35 min 60:40 to 25:75).
HPLC Rt$_{H10}$=0.63 min; ESIMS: 212 [(M+H)$^+$];
$^1$H NMR (400 MHz, CDCl$_3$): 8.47 (d, 1H), 8.14 (d, 1H), 7.35 (dd, 1H), 4.27-4.24 (m, 2H), 4.00 (s, 3H), 3.82-3.79 (m, 2H), 3.47 (s, 3H).

b) 5-(2-Methoxy-ethoxy)-pyridine-2-carboxylic acid

To a solution of 5-(2-methoxy-ethoxy)-pyridine-2-carboxylic acid methyl ester (390 mg, 0.489 mmol) in THF (3 ml) was added 1M aqueous NaOH (0.538 ml). The reaction mixture was stirred at room temperature for 2.5 h, concentrated, the residue was dissolved in EtOAc and washed twice with water. The aqueous layers were acidified with 1M aqueous HCl (0.538 ml) and the title compound was isolated by lyophilisation.

HPLC Rt$_{H10}$=0.42 min; ESIMS: 198 [(M+H)$^+$];
$^1$H NMR (400 MHz, DMSO-d$_6$): 8.37 (d, 1H), 8.01 (d, 1H), 7.52 (dd, 1H), 4.28-4.24 (m, 2H), 3.71-3.67 (m, 2H), 3.31 (s, 3H).

Acid-8: 3-Fluoro-5-(2-methoxy-ethoxy)-pyridine-2-carboxylic acid a) 2-Chloro-3-fluoro-5-(2-methoxy-ethoxy)-pyridine

To a solution of 6-chloro-5-fluoro-pyridin-3-ol (CAS registry 870062-76-3) (800 mg, 5.42 mmol), 2-methoxy-ethanol (454 mg, 0.471 ml, 5.96 mmol) and triphenylphosphine (2.199 g, 8.13 mmol) in THF (40 ml) was added dropwise a solution of DIAD (1.731 g, 8.13 mmol) in THF (20 ml) while keeping the temperature at 0-5° C. The reaction mixture was stirred for 20 h at room temperature, water and brine were added and the mixture was diluted with EtOAc. The aqueous layer was twice extracted with EtOAc, the combined organic layers were dried over Na$_2$SO$_4$, filtered, the filtrate was concentrated and yielded after trituration with Et$_2$O and filtration, the title compound as a white solid. The filtrate yielded another batch of the product after purification by prep. NP HPLC using an Alltech Grom Saphir 65 Si 10 μM 250×50 mm column (heptane/EtOAc, gradient 0-1.7 min 15% EtOAc, 1.7-17 min 15-100% EtOAc, 17-24.3 min 100% EtOAc, 24.3-27.8 min 0% EtOAc).

HPLC Rt$_{H10}$=0.86 min; ESIMS: 206 [(M+H)$^+$];
$^1$H NMR (400 MHz, CDCl$_3$): 7.97 (d, 1H), 7.12 (dd, 1H), 4.25-4.08 (m, 2H), 3.83-3.68 (m, 2H), 3.46 (s, 3H).

b) 3-Fluoro-6-(2-methoxy-ethoxy)-pyridine-2-carbonitrile

To a solution of 2-chloro-3-fluoro-5-(2-methoxy-ethoxy)-pyridine (806 mg, 3.92 mmol) and Zn(CN)$_2$ (486 mg, 4.12 mmol) was added under a N$_2$ atmosphere Pd(PPh$_3$)$_4$ (362 mg, 0.314 mmol). The reaction mixture was stirred for 20 min at 120° C. in a microwave, diluted with water and TBME. The insolubles were filtered, the phases were separated and the aqueous layer was extracted twice with TBME. The combined organic layers were washed with brine, dried over Na$_2$SO$_4$, filtered and the solvent was removed to leave the title compound as a pale brown oil that was purified by prep. NP HPLC using an Alltech Grom Saphir 65 Si 10 μM 250×50 mm column (heptane/EtOAc, gradient 0-1.7 min 25% EtOAc, 1.7-17 min 25-100% EtOAc, 17-24.3 min 100% EtOAc, 24.3-27.8 min 0% EtOAc).

HPLC Rt$_{H10}$=0.78 min; ESIMS: 197 [(M+H)$^+$];
$^1$H NMR (400 MHz, CDCl$_3$): 8.27 (dd, 1H), 7.10 (dd, 1H), 4.34-4.17 (m, 2H), 3.87-3.71 (m, 2H), 3.45 (s, 3H).

c) 3-Fluoro-6-(2-methoxy-ethoxy)-pyridine-2-carboxylic acid

A solution of 3-fluoro-5-(2-methoxy-ethoxy)-pyridine-2-carbonitrile in 5 ml aqueous 2M NaOH was stirred at 120° C. for 20 min in a microwave. The reaction mixture was diluted with H$_2$O and the pH was adjusted to 1-1.5. The mixture was extracted with DCM three times and the combined organic phases were dried over Na$_2$SO$_4$, filtered and the solvent was removed to yield the crude title compound that was purified by prep. RP HPLC using a Waters SunFire C18 OBD 5 μM 19×150 mm column (A/B: water/ACN+0.1% TFA, gradient 0-1 min 5% B, 1-7 min 5 to 90% B, 7-7.5 min 90% B, 7.5-8 min 90 to 5% B, 8-10 min 5% B) to yield its TFA salt.

HPLC Rt$_{H10}$=0.50 min; ESIMS: 216 [(M+H)$^+$];
$^1$H NMR (400 MHz, CDCl$_3$): 8.22 (br s, 1H), 7.15 (dd, 1H), 6.29 (br s, 2H), 4.38-4.19 (m, 2H), 3.89-3.74 (m, 2H), 3.47 (s, 3H).

The TFA salt was converted to the corresponding HCl salt by trituration with HCl/dioxane and subsequent evaporation.

Acid-9: 5-Methoxy-3-methyl-pyrazine-2-carboxylic acid a) 3-Methyl-4-oxy-pyrazine-2-carboxylic acid methyl ester

To a solution of 2.0 g (13.14 mmol) 3-methyl-pyrazine-2-carboxylic acid methyl ester in 40 ml CHCl$_3$ was added 3.24 g (13.14 mmol) meta-chlorperoxybenzoic acid and the resulting mixture was heated to reflux for 1.5 h. The reaction mixture was basified with saturated aqueous NaHCO$_3$ and extraced with CHCl$_3$, the combined organic layers were dried with Na$_2$SO$_4$ and evaporated. The residue was purified by chromatography on silica gel (DCM to DCM/MeOH 9:1) to provide the title compound as colorless solid.

HPLC: Rt$_{H11}$=0.40 min; ESIMS [M+H]$^+$=169;
$^1$H NMR (600 MHz, DMSO-d$_6$): 8.56 (d, 1H), 8.48 (d, 1H), 3.33 (s, 3H).

b) 5-Chloro-3-methyl-pyrazine-2-carboxylic acid methyl ester

To a solution of 575 mg (3.4 mmol) 3-methyl-4-oxy-pyrazine-2-carboxylic acid methyl ester in 6.8 ml DMF was added 1.141 ml (1.88 g, 12.24 mmol) phosphoryl trichloride and the resulting mixture was heated to 120° C. for 15 min. After cooling to room temperature ice was added and the mixture was extracted with toluene. The combined organic layers were washed with halfsaturated aqueous NaCl, dried with Na$_2$SO$_4$ and evaporated to provide the title compound as brownish solid in a ~3:2 mixture with the undesired 6-chloro-3-methyl-pyrazine-2-carboxylic acid methyl ester. The mixture was used in the next step without further purification.

HPLC: Rt$_{H10}$=0.70 min; ESIMS [M+H]$^+$=187.1;
$^1$H NMR (600 MHz, DMSO-d$_6$. 5—Cl isomer): 8.74 (s, 1H), 3.90 (s, 3H), 2.71 (s, 3H).

c) 5-Methoxy-3-methyl-pyrazine-2-carboxylic acid methyl ester

At 0° C. 58 mg (1.458 mmol) 60% sodium hydride in oil was added in portions to 7.3 ml MeOH and the mixture was stirred at room temperature for 30 min. After re-cooling to 0° C. 272 mg (1.458 mmol) of the crude product of the previous step was added as a suspension in 1.7 ml MeOH and the mixture was heated to 50° C. for 1 h. At 0° C. halfsaturated aqueous NH$_4$Cl was added and the mixture was extracted with EtOAc. The combined organic layers were washed with halfsaturated aqueous NaCl, dried with Na$_2$SO$_4$ and evaporated. The residue was purified by chromatography on silica gel (cyclohexane to cyclohexane/EtOAc 4:1) to provide the title compound as brownish solid.

HPLC: Rt$_{H10}$=0.69 min; ESIMS [M+H]$^+$=183.1;
$^1$H NMR (600 MHz, DMSO-d$_6$): 8.21 (s, 1H), 3.97 (s, 3H), 3.84 (s, 3H), 2.67 (s, 3H).

d) 5-Methoxy-3-methyl-pyrazine-2-carboxylic acid

A solution of 105 mg (0.577 mmol) 5-methoxy-3-methyl-pyrazine-2-carboxylic acid methyl ester in 2.6 ml THF was cooled to O. °C., 0.635 ml (0.635 mmol) 1N sodium hydroxide was added dropwise and the mixture was stirred at room temperature for 1.5 h.

After re-cooling to 0° C. 0.635 ml (0.635 mmol) 1N HCl and 1.2 ml toluene were added and the solvents were evaporated to provide the title compound together with sodium chloride as brownish solid. The mixture was used for coupling reactions without further purification.

HPLC: $Rt_{H10}$=0.50 min; ESIMS $[M+H]^+$=169.1;
$^1$H NMR (600 MHz, DMSO-$d_6$): 13.04 (br s, 1H), 8.19 (s, 1H), 3.96 (s, 3H), 2.67 (s, 3H).

Acid-10: 5-(2-Methoxy-ethoxy)-3-methyl-pyrazine-2-carboxylic acid

The title compound was prepared by an analogous procedure to Acid-9 using 2-methoxy-ethanol instead of methanol [Acid-9 step c)].

HPLC: $Rt_{H10}$=0.54 min; ESIMS $[M+H]^+$=213.1;
$^1$H NMR (600 MHz, DMSO-$d_6$): 13.04 (br. s., 1H), 8.20 (s, 1H), 4.54-4.40 (m, 2H), 3.80-3.61 (m, 2H), 3.30 (s, 3H), 2.66 (s, 3H).

Acid-11: 5-But-2-ynyloxy-3-methyl-pyrazine-2-carboxylic acid

The title compound was prepared by an analogous procedure to Acid-9 using but-2-yn-1-ol instead of methanol [Acid-9 step c)].

HPLC: $Rt_{H10}$=0.78 min; ESIMS $[M+H]^+$=207.0;
$^1$H NMR (360 MHz, DMSO-$d_6$): 8.23 (s, 1H), 5.06 (d, 2H), 2.68 (s, 3H), 1.87 (t, 3H).

Acid-12: 3-Amino-5-methoxy-pyrazine-2-carboxylic acid a) 3-Amino-1-methoxy-pyrazine-2-carboxylic acid methyl ester At 0° C. 75 mg (1.866 mmol) 60% sodium hydride in oil was added in portions to 5 ml MeOH and the mixture was stirred at room temperature for 30 min. After re-cooling to 0° C. 350 mg (1.866 mmol) 3-amino-5-chloro-pyrazine-2-carboxylic acid methyl ester (GB 1248146) was added and the mixture was allowed to warm to room temperature and stirred over night. Saturated aqueous NH$_4$Cl was added and the mixture was extracted with DCM and EtOAc, the combined organic layers were washed with saturated aqueous sodium chloride, dried with Na$_2$SO$_4$ and evaporated. The residue was purified by chromatography on silica gel (cyclohexane to EtOAc) to provide the title compound as colorless solid.

HPLC: $Rt_{H10}$=0.61 min; ESIMS $[M+H]^+$=184.2;
$^1$H-NMR (360 MHz, DMSO-$d_6$): 7.52 (s, 1H), 7.49 (br s, 2H), 3.91 (s, 3H), 3.81 (s, 3H).

b) 3-Amino-6-methoxy-pyrazine-2-carboxylic acid

To a solution of 200 mg (1.092 mmol) 3-amino-5-methoxy-pyrazine-2-carboxylic acid methyl ester in 4 ml THF was added 1.20 ml (1.20 mmol) i N sodium hydroxide and the mixture was stirred at room temperature for 29 h. To the mixture were added 1.09 ml (1.09 mmol) 1N HCl after stirring for 5 min toluene was added and the solvents were evaporated to provide the title compound together with sodium chloride as colorless solid. The mixture was used for coupling reactions without further purification.

HPLC: $Rt_{H11}$=0.52 min; ESIMS $[M+H]^+$=170.0;
$^1$H NMR (600 MHz, DMSO-$d_6$): 12.48 (br s, 1H), 7.57 (br s, 2H), 7.48 (s, 1H), 3.88 (s, 3H).

Acid-13: 5-tert-Butoxycarbonylamino-2-methyl-oxazole-4-carboxylic acid a) 5-tert-Butoxycarbonylamino-2-methyl-oxazole-4-carboxylic acid ethyl ester To a solution of 221 mg (1.3 mmol) 5-amino-2-methyl-oxazole-4-carboxylic acid ethyl ester in 6.5 ml acetonitrile was added at 0° C. 0.795 ml (4.55 mmol) DIPEA, 31.8 mg (0.26 mmol) DMAP and 709 mg (3.25 mmol) Boc$_2$O and the mixture was stirred at 45° C. for 2 days. After cooling to room temperature water was added and the mixture was extracted with DCM. The combined organic layers were washed with 1N HCl and halfsaturated aqueous NaCl, dried with Na$_2$SO$_4$ and evaporated. The residue was purified by chromatography on silica gel (cyclohexane to cyclohexane/EtOAc 1:1) to provide the title compound as pinkish solid.

HPLC: $Rt_{H10}$=1.21 min; ESIMS $[M+H]^+$=271.1.

b) 5-tert-Butoxycarbonylamino-2-methyl-oxazole-4-carboxylic acid

To a solution of 314 mg (1.163 mmol) 5-tert-butoxycarbonylamino-2-methyl-oxazole-4-carboxylic acid ethyl ester in 1.16 ml THF was added at 0° C. 5.82 ml (5.82 mmol) 1N sodium hydroxide, the mixture was allowed to warm to room temperature and stirring was continued for 6 days. At 0° C. 5.82 ml (5.82 mmol) 1N HCl was added and the solvents were evaporated. The residue was suspended in DCM and filtered, the solvent was evaporated to provide the title compound as colorless solid.

HPLC: $Rt_{H10}$=0.62 min; ESIMS $[M-H]^-$=241.0;
$^1$H NMR (600 MHz, DMSO-$d_6$): 12.80 (br s, 1H), 9.56 (br s, 1H), 2.35 (s, 3H), 1.42 (s, 9H).

Acid-14: 3-Chloro-6-fluoromethoxy-pyridine-2-carboxylic acid a) 3-Chloro-6-hydroxy-pyridine-2-carbonitrile To a solution of acetic acid 5,6-dichloro-pyridin-3-yl ester (CA 110861-18-2, Synthesis, 1990, 499) (4.88 g, 23.6 mmol) in anhydrous DMF (45 ml) was added after degasing with argon Zn-dust (70 mg, 1.07 mmol), Zn(CN)$_2$ (1.28 g, 10.9 mmol) and DPPF PdCl$_2$ (966 mg, 1.18 mmol) and the reaction mixture was heated for 6 h at 130° C. and 18 h at 150° C. The reaction mixture was diluted with TBME and H$_2$O, filtered over Celite, and the product was extracted with TBME. Combined extracts were washed with water and brine, dried over MgSO$_4$, filtered and concentrated. The title compound was obtained as a beige solid after crystallization from EtOAc-hexane: TLC (CH$_2$Cl$_2$-MeOH 19:1): Rf=0.22;

HPLC $Rt_{H5}$=0.677 min; ESIMS: 153 and 155 $[(M-H)^-]$;
$^1$H NMR (360 MHz, CD$_3$OD): 8.19 (d, 1H), 7.41 (d, 1H).

b) 3-Chloro-6-fluoromethoxy-pyridine-2-carbonitrile

To a solution of 3-chloro-5-hydroxy-pyridine-2-carbonitrile (315 mg, 2.03 mmol) in DMF (16 ml) was added Cs$_2$CO$_3$ (1.652 g, 5.07 mmol) und toluene-4-sulfonic acid fluoromethyl ester (CAS registry 114435-86-8) (621 mg, 3.04 mmol) and the reaction mixture was heated at 80° C. for 24 h. The solvent was removed under reduced pressure and the residue taken up in TBME, washed with water and brine, dried over MgSO$_4$, filtered and concentrated. The title compound was obtained as a yellow oil after chromatography on silica gel (hexane-EtOAc 10:1 to 2:1) to provide the title compound as a light yellow oil: TLC (hexane-EtOAc 1:1): Rf=0.62;
HPLC Rt$_{H5}$=0.872 min; ESIMS: 185 and 187 [(M−H)$^−$];
$^1$H NMR (360 MHz, CDCl$_3$): 8.35 (s, 1H), 7.47 (s, 1H), 5.72 (d, 2H).

c) 3-Chloro-5-fluoromethoxy-pyridine-2-carboxylic acid

To a solution of 3-chloro-5-fluoromethoxy-pyridine-2-carbonitrile (76 mg, 0.4 mmol) in dioxane (3 ml) was added 1N NaOH (1.4 ml) and the reaction mixture was heated for 30 h at 70° C. The reaction mixture was acidified with 4N HCl to pH 3 and evaporated to dryness. The residue was suspended in CH$_2$Cl$_2$-MeOH 8:1, filtered over Celite and concentrated to provide the title compound as a yellow oil.
HPLC Rt$_{H5}$=0.549 min; ESIMS: 204 and 206 [(M−H)$^−$];
$^1$H NMR (360 MHz, CD$_3$OD): 8.39 (s, 1H), 7.76 (s, 1H), 5.90 (d, 2H).

Acid-15:
3-Chloro-5-difluoromethoxy-pyridine-2-carboxylic acid a) 3-Chloro-5-difluoromethoxy-pyridine-2-carbonitrile To a solution of 3-chloro-5-hydroxy-pyridine-2-carbonitrile (314 mg, 2.03 mmol) in DMF (10 ml) was added K$_2$CO$_3$ (841 mg, 6.09 mmol) and sodium chlorodifluoroacetate (1.29 g, 8.11 mmol) and the reaction mixture was heated at 100° C. for 10 min. The reaction mixture was diluted with H$_2$O and extracted with TBME. Combined extracts were washed with brine, dried over MgSO$_4$, filtered and concentrated. The title compound was obtained as a yellow oil after chromatography on silica gel (hexane-EtOAc 20:1 to 1:1) to provide the title compound as a light yellow oil: TLC (hexane-EtOAc 2:1): Rf=0.54;
HPLC Rt$_{H5}$=0.968 min; ESIMS: 203 and 205 [(M−H)$^−$];
$^1$H NMR (360 MHz, CDCl$_3$): 8.41 (d, 1H), 7.59 (d, 1H), 6.61 (t, 1H).

b) 3-Chloro-5-difluoromethoxy-pyridine-2-carboxylic acid

To a solution of 3-chloro-5-hydroxy-pyridine-2-carbonitrile (90 mg, 0.44 mmol) in dioxane (2 ml) was added 1N NaOH (1.5 ml) and the reaction mixture was heated for 14 h at 70° C. The reaction mixture was extracted with EtOAc, the aqueous layer acidified to pH 3 with 4N HCl and evaporated to dryness. The residue was suspended in CH$_2$Cl$_2$-MeOH 10:1, filtered over Celite and concentrated to provide the title compound as beige solid.
HPLC Rt$_{H5}$=0.667 min; ESIMS: 222 and 224 [(M−H)$^−$];
$^1$H NMR (360 MHz, CD$_3$OD): 8.46 (s, 1H), 7.87 (s, 1H), 7.12 (t, 1H).

Acid-16: 3-Chloro-6-methoxymethyl-pyridine-2-carboxylic acid a) 3-Chloro-6-methoxymethyl-pyridine-2-carbonitrile To a solution of 2,3-dichloro-5-methoxymethyl-pyridine (CA registry 202395-72-0) (7.5 g, 38 mmol) in DMF (100 ml) was added after degasing with argon Zn-dust (126 mg, 1.91 mmol), Zn(CN)$_2$ (2.27 g, 19.1 mmol) and DPPF PdCl$_2$ (0.997 g, 1.15 mmol) and the reaction mixture was heated for 2 h at 145° C. The reaction mixture was concentrated, the residue redissolved in TBME and 5% aqueous NaHCO$_3$ solution and extracted with TBME. Combined extracts were washed with water and brine, dried over MgSO$_4$, filtered and concentrated. The title compound was obtained after chromatography on silica gel (hexane-EtOAc 20:1 to EtOAc) as beige crystals: TLC (hexane-EtOAc 1:1): Rf=0.47; HPLC Rt$_{H5}$=0.854 min; ESIMS: 183 and 185 [(M+H)$^+$];
$^1$H NMR (360 MHz, CDCl$_3$): 8.46 (s, 1H), 7.80 (s, 1H), 4.49 (s, 2H), 3.41 (s, 3H).

b) 3-Chloro-5-methoxymethyl-pyridine-2-carboxylic acid

To a solution of 3-chloro-5-methoxymethyl-pyridine-2-carbonitrile (2.75 g, 15 mmol) in dioxane (30 ml) was added 2N NaOH (30 ml) and the reaction mixture was heated for 8 h at 75° C. The reaction mixture was acidified to pH 3 with 4N HCl and evaporated to dryness. The residue was suspended in EtOH-THF 1:1, filtered and concentrated. The title compound was obtained after recrystallization from EtOH-TBME as beige crystals.
HPLC Rt$_{H5}$=0.480 min; ESIMS: 169 and 170 [(M—CH3OH)$^+$];
$^1$H NMR (360 MHz, CD$_3$OD): 8.37 (s, 1H), 7.81 (s, 1H), 4.48 (s, 2H), 3.39 (s, 3H).

Example 186

Biological Activity of Compounds of the Formula I

The compounds of the Examples hereinbefore show the following IC$_{50}$ values in Test 1 described hereinbefore:

TABLE 22

| Example | Bace IC50 [µM] | Example | Bace IC50 [µM] |
|---|---|---|---|
| 1 | 1.3 | 2 | 0.14 |
| 3 | 0.070 | 4 | >10 |
| 5 | 0.64 | 6 | 4.7 |
| 7 | 0.54 | 8 | >10 |
| 9 | 2.3 | 10 | 0.59 |
| 11 | 3.8 | 12 | 0.85 |
| 13 | 3.4 | 14 | 0.16 |
| 15 | 9.1 | 16 | 9.2 |
| 17 | 0.4 | 18 | 0.56 |
| 19 | 2.0 | 20 | 0.35 |
| 21 | 0.24 | 22 | 0.42 |
| 23 | 11 | 24 | 0.97 |
| 25 | >130 | 26 | >130 |
| 27 | 1.4 | 28 | 60 |
| 29 | 0.056 | 30 | 0.33 |
| 31 | 0.16 | 32 | 1.4 |
| 33 | 0.13 | 34 | 0.56 |
| 35 | 0.30 | 36 | 0.35 |
| 37 | 0.12 | 38 | >10 |
| 39 | 0.78 | 40 | 1.0 |
| 41 | 0.35 | 42 | 0.056 |
| 43 | 0.062 | 44 | 0.019 |
| 45 | 0.016 | 46 | 0.071 |
| 47 | 0.056 | 48 | 0.55 |
| 49 | 0.050 | 50 | 0.42 |
| 51 | 0.23 | 52 | 0.18 |
| 53 | 0.38 | 54 | 0.44 |
| 55 | 0.084 | 56 | 0.101 |
| 57 | 1.7 | 58 | 0.78 |
| 59 | 0.24 | 60 | 0.058 |
| 61 | 1.97 | 62 | 0.095 |
| 63 | 0.11 | 64 | 0.040 |

TABLE 22-continued

| Example | Bace IC50 [μM] | Example | Bace IC50 [μM] |
|---|---|---|---|
| 65 | 1.2 | 66 | 0.020 |
| 67 | 0.10 | 68 | 0.011 |
| 69 | 0.009 | 70 | 0.034 |
| 71 | 0.016 | 72 | 0.010 |
| 73 | 0.026 | 74 | 0.079 |
| 75 | 0.13 | 76 | 0.046 |
| 77 | 0.092 | 78 | 0.038 |
| 79 | 0.12 | 80 | 0.074 |
| 81 | 1.1 | 82 | 3.0 |
| 83 | 2.9 | 84 | 0.93 |
| 85 | 0.026 | 86 | 0.044 |
| 87 | 0.057 | 88 | 0.033 |
| 89 | 0.094 | 90 | 0.039 |
| 91 | 0.015 | 92 | 0.005 |
| 93 | 0.008 | 94 | 0.022 |
| 95 | 0.39 | 96 | 0.027 |
| 97 | 0.018 | 98 | 0.24 |
| 99 | 0.14 | 100 | 0.034 |
| 101 | 0.030 | 102 | 0.89 |
| 103 | 7.8 | 104 | 1.5 |
| 105 | 5.2 | 106 | 4.0 |
| 107 | 0.82 | 108 | 0.028 |
| 109 | 1.2 | 110 | 1.9 |
| 111 | 0.025 | 112 | 0.042 |
| 113 | 0.12 | 114 | 0.006 |
| 115 | 0.006 | 116 | 0.018 |
| 117 | 0.018 | 118 | 0.014 |
| 119 | 0.010 | 120 | 0.18 |
| 121 | 0.036 | 122 | 0.20 |
| 123 | 0.097 | 124 | 0.025 |
| 125 | 0.078 | 126 | 0.74 |
| 127 | 0.098 | 128 | 0.17 |
| 129 | 2.2 | 130 | 0.093 |
| 131 | 0.33 | 132 | 0.087 |
| 133 | 1.0 | 134 | 0.26 |
| 135 | 0.045 | 136 | 0.13 |
| 137 | 0.030 | 138 | 0.042 |
| 139 | 0.075 | 140 | 0.043 |
| 141 | 0.033 | 142 | 0.82 |
| 143 | 0.11 | 144 | 0.017 |
| 145 | 0.34 | 146 | 0.10 |
| 147 | 0.079 | 148 | 0.94 |
| 149 | 0.70 | 150 | 0.29 |
| 151 | 1.2 | 152 | |
| 153 | 0.008 | 154 | 0.12 |
| 155 | 0.18 | 156 | 0.034 |
| 157 | 5.2 | 158 | 0.018 |
| 159 | 0.13 | 160 | 0.012 |
| 161 | 0.066 | 162 | 8.5 |
| 163 | 0.68 | 164 | 0.001 |
| 165 | 0.008 | 166 | 1.2 |
| 167 | 0.003 | 168 | 0.26 |
| 169 | 0.012 | 170 | 0.34 |
| 171 | 0.049 | 172 | 0.009 |
| 173 | >10 | 174 | 0.21 |
| 175 | 0.016 | 176 | 0.018 |
| 177 | 0.029 | 178 | 0.17 |
| 179 | 0.92 | 180 | 0.34 |
| 181 | 0.34 | 182 | 0.004 |
| 183 | 0.70 | 184 | 0.059 |
| 185 | 0.05 | | |

Certain compounds of the Examples hereinbefore show the following $IC_{50}$ values in Test 4 described hereinbefore:

TABLE 20

| Example | Bace IC50 [μM] |
|---|---|
| 1 | 1.7 |
| 3 | 0.017 |
| 4 | 5.8 |
| 16 | 3.1 |
| 38 | 1.1 |
| 54 | 0.061 |
| 64 | 0.004 |

TABLE 20-continued

| Example | Bace IC50 [μM] |
|---|---|
| 71 | 0.004 |
| 72 | 0.003 |
| 99 | 0.10 |
| 104 | 0.15 |
| 112 | 0.007 |
| 116 | 0.004 |
| 129 | 1.2 |
| 144 | 0.006 |
| 147 | 0.008 |
| 164 | 0.001 |
| 175 | 0.004 |

FIGURE DESCRIPTION

FIG. 1 shows the X-ray powder diffraction pattern for a crystalline form of 5-cyano-pyridine-2-carboxylic acid [3-((R)-5-amino-3-difluoromethyl-3,6-dihydro-2H-[1,4]oxazin-3-yl)-4-fluoro-phenyl]-amide when measured using $CuK_\alpha$ radiation. For details see Example 152.

What is claimed is:

1. A compound 5-cyano-3-methyl-pyridine-2-carboxylic acid [3-(5-amino-3-difluoromethyl-3,6-dihydro-2H-[1,4]oxazin-3-yl)-4-fluoro-phenyl]-amide of the following formula

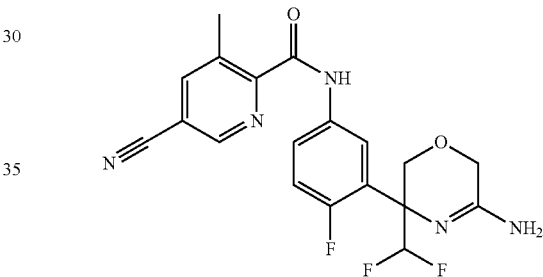

or a pharmaceutically acceptable salt thereof.

2. The compound of claim 1 in free form.

3. The compound of claim 1 in hydrochloride salt form.

4. A pharmaceutical composition comprising a compound of claim 1, or a pharmaceutically acceptable salt thereof, as active ingredient and a pharmaceutical carrier or diluent.

5. A compound 5-cyano-3-methyl-pyridine-2-carboxylic acid [3-((R)-5-amino-3-difluoromethyl-3,6-dihydro-2H-[1,4]oxazin-3-yl)-4-fluoro-phenyl]-amide of the following formula

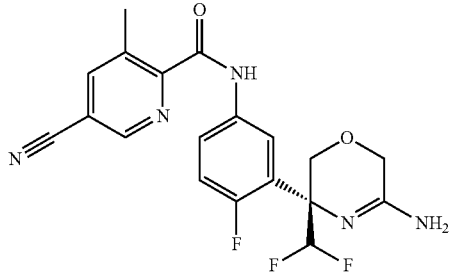 [SMILES: Cc1cc(C#N)cnc1C(=O)Nc1ccc(F)c([C@]2(C(F)F)COCC(N)=N2)c1]

or a pharmaceutically acceptable salt thereof.

6. The compound of claim 5 in free form.

7. The compound of claim 5 in hydrochloride salt form.

8. A pharmaceutical composition comprising a compound of claim 5, or a pharmaceutically acceptable salt thereof, as active ingredient and a pharmaceutical carrier or diluent.

\* \* \* \* \*